US012626826B2

(12) United States Patent
Ronen et al.

(10) Patent No.: US 12,626,826 B2
(45) Date of Patent: May 12, 2026

(54) INFORMATION MANAGEMENT SYSTEM AND METHOD

(71) Applicant: CalmWave, Inc., Seattle, WA (US)

(72) Inventors: Ophir Ronen, Seattle, WA (US); Justin Kearns, Lexington, KY (US); Michael Gruzynski, Seattle, WA (US); Christian Bauer, Frisco, TX (US); Margaret Pilon, Maple Grove, MN (US); Seth Falcon, Minneapolis, MN (US); Thomas Dziedzic, Elmwood Park, IL (US); Cees de Groot, Berkeley (CA); Kurt Eulau, San Francisco, CA (US); Keith Boudreau, Durham, NC (US); Daven Casia, Saskatoon (CA)

(73) Assignee: CALMWAVE, INC., Seattle, WA (US)

( * ) Notice: Subject to any disclaimer, the term of this patent is extended or adjusted under 35 U.S.C. 154(b) by 0 days.

(21) Appl. No.: 18/798,700

(22) Filed: Aug. 8, 2024

(65) Prior Publication Data

US 2025/0054613 A1     Feb. 13, 2025

Related U.S. Application Data

(60) Provisional application No. 63/518,241, filed on Aug. 8, 2023.

(51) Int. Cl.
*G16H 80/00* (2018.01)
*A61B 5/00* (2006.01)
(Continued)

(52) U.S. Cl.
CPC ............. *G16H 80/00* (2018.01); *A61B 5/746* (2013.01); *G16H 10/60* (2018.01); *G16H 15/00* (2018.01);
(Continued)

(58) Field of Classification Search
USPC ........................................................ 705/2–3
See application file for complete search history.

(56) References Cited

U.S. PATENT DOCUMENTS 6,241,661 B1     6/2001   Schluess et al.
7,079,035 B2 *   7/2006   Bock ................. A61B 5/02405
                                                          600/301
(Continued)

FOREIGN PATENT DOCUMENTS

WO          2010/102069 A2      9/2010

OTHER PUBLICATIONS

Non-Final Office Action issued in related U.S. Appl. No. 18/798,613 on Nov. 22, 2024.
(Continued)

*Primary Examiner* — Michael Tomaszewski
(74) *Attorney, Agent, or Firm* — Brian J. Colandreo; Jeffrey T. Placker; Holland & Knight LLP

(57) ABSTRACT

A computer-implemented method, computer program product and computing system for: monitoring a plurality of data signals associated with a plurality of patients within a medical environment over a defined period of time; calculating an acuity score for each of the plurality of patients, wherein the acuity score defines the overall care needs of each of the plurality of patients; and generating a rounding list that prioritizes the plurality of patients based, at least in part, upon the acuity scores.

30 Claims, 46 Drawing Sheets

(51) Int. Cl.

| | | |
|---|---|---|
| *G16H 10/60* | (2018.01) | |
| *G16H 15/00* | (2018.01) | |
| *G16H 40/20* | (2018.01) | |
| *G16H 40/40* | (2018.01) | |
| *G16H 40/60* | (2018.01) | |
| *G16H 40/67* | (2018.01) | |
| *G16H 50/20* | (2018.01) | |
| *G16H 50/70* | (2018.01) | |

(52) U.S. Cl.
CPC ............. *G16H 40/20* (2018.01); *G16H 40/40* (2018.01); *G16H 40/60* (2018.01); *G16H 40/67* (2018.01); *G16H 50/20* (2018.01); *G16H 50/70* (2018.01)

(56) References Cited

U.S. PATENT DOCUMENTS

| | | | |
|---|---|---|---|
| 7,664,657 B1 | 2/2010 | Letzt et al. | |
| 8,090,592 B1* | 1/2012 | Goodall | G06Q 10/063 |
| | | | 705/2 |
| 8,645,164 B2 | 2/2014 | Faiola et al. | |
| 8,666,774 B1 | 3/2014 | Gonzales et al. | |
| 10,943,407 B1* | 3/2021 | Morgan | G16H 15/00 |
| 11,257,587 B1* | 2/2022 | D'Angelo | A61B 5/0022 |
| 11,830,623 B1* | 11/2023 | Aranke | G16H 50/70 |
| 11,971,914 B1 | 4/2024 | Watson et al. | |
| 2002/0095077 A1 | 7/2002 | Swedlow et al. | |
| 2003/0125983 A1 | 7/2003 | Flack et al. | |
| 2003/0130873 A1 | 7/2003 | Nevin et al. | |
| 2004/0236187 A1* | 11/2004 | Bock | G16H 40/63 |
| | | | 600/300 |
| 2004/0249249 A1 | 12/2004 | Lawson et al. | |
| 2004/0249674 A1 | 12/2004 | Eisenberg et al. | |
| 2005/0055242 A1 | 3/2005 | Bello et al. | |
| 2005/0060193 A1 | 3/2005 | Lancaster et al. | |
| 2005/0192844 A1 | 9/2005 | Esler et al. | |
| 2006/0036619 A1 | 2/2006 | Fuerst et al. | |
| 2006/0242293 A1* | 10/2006 | Russ | A61B 5/00 |
| | | | 709/224 |
| 2006/0252999 A1* | 11/2006 | Devaul | A61B 5/0024 |
| | | | 128/920 |
| 2007/0043590 A1 | 2/2007 | Lee | |
| 2007/0180140 A1 | 8/2007 | Welch et al. | |
| 2007/0185739 A1* | 8/2007 | Ober | G16H 50/20 |
| | | | 600/301 |
| 2007/0239484 A1 | 10/2007 | Arond et al. | |
| 2007/0265533 A1* | 11/2007 | Tran | A61B 5/0006 |
| | | | 600/528 |
| 2008/0275722 A1* | 11/2008 | Newell | G16H 20/00 |
| | | | 705/2 |
| 2008/0281639 A1 | 11/2008 | Quinn et al. | |
| 2009/0033505 A1 | 2/2009 | Jones et al. | |
| 2009/0093686 A1* | 4/2009 | Hu | G16Z 99/00 |
| | | | 600/300 |
| 2009/0171167 A1 | 7/2009 | Baker, Jr. | |
| 2010/0185463 A1 | 7/2010 | Noland et al. | |
| 2011/0001605 A1 | 1/2011 | Kiani et al. | |
| 2011/0004071 A1 | 1/2011 | Faiola et al. | |
| 2011/0004126 A1* | 1/2011 | Einav | G16H 15/00 |
| | | | 600/595 |
| 2011/0172504 A1* | 7/2011 | Wegerich | A61B 5/6898 |
| | | | 600/301 |
| 2012/0095300 A1* | 4/2012 | McNair | G16H 50/30 |
| | | | 600/300 |
| 2012/0109243 A1* | 5/2012 | Hettrick | A61B 5/686 |
| | | | 600/509 |
| 2012/0293323 A1 | 11/2012 | Kaib et al. | |
| 2013/0191158 A1* | 7/2013 | Fillmore | G16H 50/30 |
| | | | 705/3 |
| 2013/0231949 A1 | 9/2013 | Baronov et al. | |
| 2013/0311201 A1 | 11/2013 | Chatfield et al. | |
| 2014/0019162 A1* | 1/2014 | Skowronski | G16H 40/20 |
| | | | 705/3 |

| | | | |
|---|---|---|---|
| 2014/0032242 A1 | 1/2014 | Laborde et al. | |
| 2014/0046674 A1 | 2/2014 | Rosenfeld et al. | |
| 2014/0113263 A1 | 4/2014 | Jarrell et al. | |
| 2014/0121473 A1 | 5/2014 | Banet et al. | |
| 2014/0266736 A1 | 9/2014 | Cretu-Petra | |
| 2014/0316804 A1 | 10/2014 | Tran et al. | |
| 2015/0106121 A1* | 4/2015 | Muhsin | G16H 10/60 |
| | | | 705/2 |
| 2015/0137968 A1 | 5/2015 | Rusin et al. | |
| 2015/0186602 A1* | 7/2015 | Pipke | G16H 40/63 |
| | | | 705/3 |
| 2015/0213224 A1* | 7/2015 | Amarasingham | G16H 40/30 |
| | | | 705/2 |
| 2015/0213225 A1* | 7/2015 | Amarasingham | G16H 50/30 |
| | | | 705/2 |
| 2015/0221045 A1 | 8/2015 | Heckler et al. | |
| 2015/0227710 A1 | 8/2015 | Pappada | |
| 2016/0012189 A1 | 1/2016 | Farha et al. | |
| 2016/0132653 A1 | 5/2016 | Baralay | |
| 2016/0143598 A1 | 5/2016 | Rusin et al. | |
| 2016/0171865 A1* | 6/2016 | Fuller | G16H 40/67 |
| | | | 340/573.1 |
| 2017/0076052 A1* | 3/2017 | Phillips | G16H 70/20 |
| 2017/0095217 A1 | 4/2017 | Hubert et al. | |
| 2017/0124279 A1* | 5/2017 | Rothman | G16H 50/30 |
| 2017/0181825 A1 | 6/2017 | Hunter | |
| 2017/0262614 A1 | 9/2017 | Vishnubhatla et al. | |
| 2017/0372020 A1* | 12/2017 | Govro | G16H 40/20 |
| 2017/0372029 A1* | 12/2017 | Saliman | G16H 10/60 |
| 2018/0025116 A1 | 1/2018 | Carrington et al. | |
| 2018/0052655 A1 | 2/2018 | Hannibal et al. | |
| 2018/0358114 A1 | 12/2018 | Schecter | |
| 2018/0358126 A1* | 12/2018 | Edmonson, III | G16H 50/30 |
| 2019/0073615 A1 | 3/2019 | Ronen et al. | |
| 2019/0180868 A1* | 6/2019 | Makram | G06N 20/00 |
| 2020/0111578 A1 | 4/2020 | Koblick et al. | |
| 2020/0185088 A1* | 6/2020 | Kaliraman | G06N 5/048 |
| 2020/0211692 A1* | 7/2020 | Kalafut | G16H 50/20 |
| 2020/0303067 A1* | 9/2020 | Gilham | A61B 5/02 |
| 2020/0357513 A1 | 11/2020 | Katra et al. | |
| 2021/0052217 A1* | 2/2021 | Zhao | A61B 5/7264 |
| 2021/0069390 A1 | 3/2021 | Gross | |
| 2021/0077035 A1 | 3/2021 | Kayser et al. | |
| 2021/0121060 A1* | 4/2021 | Wojciechowski | G16H 10/60 |
| 2021/0169417 A1* | 6/2021 | Burton | A61B 5/4815 |
| 2021/0287806 A1* | 9/2021 | Rajasekhar | A61B 5/7275 |
| 2021/0398236 A1 | 12/2021 | Nesarikar et al. | |
| 2022/0189628 A1 | 6/2022 | Kaethner | |
| 2022/0310241 A1* | 9/2022 | Atallah | G16H 40/20 |
| 2023/0104655 A1 | 4/2023 | Amarasingham et al. | |
| 2023/0130914 A1 | 4/2023 | Kaliraman et al. | |
| 2023/0207125 A1* | 6/2023 | Tgavalekos | G16H 10/60 |
| | | | 705/2 |
| 2023/0368284 A1 | 11/2023 | Sheikh et al. | |
| 2024/0029848 A1 | 1/2024 | Gupta et al. | |
| 2024/0070585 A1 | 2/2024 | Galusha et al. | |
| 2024/0221878 A1 | 7/2024 | Shelton et al. | |
| 2024/0242040 A1 | 7/2024 | Cogswell et al. | |
| 2024/0289560 A1 | 8/2024 | Kelly et al. | |
| 2024/0395392 A1 | 11/2024 | Lima et al. | |
| 2024/0411994 A1 | 12/2024 | Siracusano et al. | |
| 2024/0412866 A1 | 12/2024 | Wen et al. | |
| 2024/0427813 A1 | 12/2024 | Spuck et al. | |
| 2025/0021548 A1 | 1/2025 | Petersen et al. | |
| 2025/0022595 A1 | 1/2025 | Rezaeian et al. | |
| 2025/0054588 A1 | 2/2025 | Ronen et al. | |
| 2025/0054613 A1* | 2/2025 | Ronen | G16H 50/30 |
| 2025/0054643 A1 | 2/2025 | Ronen et al. | |
| 2025/0061351 A1 | 2/2025 | Domeniconi | |

OTHER PUBLICATIONS

Non-Final Office Action issued in related U.S. Appl. No. 18/798,632 on Nov. 7, 2024.
International Search Report and Written Opinion issued in related Application Serial No. PCT/US2024/041546 on Oct. 24, 2024.
International Search Report and Written Opinion issued in related Application Serial No. PCT/US2024/041549 on Oct. 25, 2024.

(56) References Cited

OTHER PUBLICATIONS

International Search Report and Written Opinion issued in related Application Serial No. PCT/US2024/041554 on Oct. 24, 2024.

International Search Report and Written Opinion issued in related Application Serial No. PCT/US2024/041557 on Oct. 24, 2024.

International Search Report and Written Opinion issued in related Application Serial No. PCT/US2024/041558 on Oct. 25, 2024.

International Search Report and Written Opinion issued in related Application Serial No. PCT/US2024/041564 on Oct. 25, 2024.

Non-Final Office Action issued in related Application Serial No. U.S. Appl. No. 18/798,670 on Oct. 18, 2024.

Non-Final Office Action issued in related Application Serial No. U.S. Appl. No. 18/798,686 on Oct. 23, 2024.

Final Office Action issued in related U.S. Appl. No. 18/798,670 on issue Jan. 31, 2025.

Non-Final Office Action issued in related U.S. Appl. No. 18/798,632 on Mar. 19, 2025.

"An Evidence based Approach to Reduce Nuisance Alarms and Alarm fatigue"; Welch, James; 2011 (Year: 2011).

"Incorporating Observed Physiological Data to Personalize Pediatric Vital sign Alarm thresholds"; Poole et al.; Oct. 16, 2019. (Year: 2019).

Final Office Action issued in related U.S. Appl. No. 18/798,613 on Jun. 30, 2025.

Final Office Action issued in related U.S. Appl. No. 18/798,686 on Jun. 27, 2025.

Non-Final Office Action issued in related U.S. Appl. No. 18/798,670 on Aug. 6, 2025.

Non-Final Office Action issued in related U.S. Appl. No. 18/798,613 on Dec. 1, 2025.

Non-Final Office Action issued in related U.S. Appl. No. 18/798,716 on Dec. 18, 2025.

Non-Final Office Action issued in related U.S. Appl. No. 18/798,721 on Dec. 11, 2025.

Singh, D., Celik, A., Zhang, E. W., Liu, E., & Rosenfield, D. (2025). AI-Driven Injury Reporting in Pediatric Emergency Departments. JAMA Network Open, 8(7), e2524154-e2524154. (Year: 2025).

Non-Final Office Action issued in related U.S. Appl. No. 18/798,686 on Oct. 22, 2025.

Non-Final Office Action issued in related U.S. Appl. No. 18/798,706 on Sep. 9, 2025.

Non-Final Office Action issued in related U.S. Appl. No. 18/798,710 on Sep. 30, 2025.

Weenk, Mariska et al: Continuous Monitoring of Vital Signs in the General Ward Using Wearable Devices: Randomized Controlled Trial. J Med Internet Res. Jun. 10, 2020; 22(6):e15471. doi: 10.2196/15471. PMID: 32519972; PMCID: PMC7315364. (Year: 2020).

Yoon Dukyong, et al: Discovering hidden information in biosignals from patients using artificial intelligence. Korean J Anesthesiol. Aug. 2020; 73(4):275-284. doi: 10.4097/kja.19475. Epub Jan. 16, 2020. PMID: 31955546; PMCID: PMC7403115. (Year: 2020)

Final Office Action issued in related U.S. Appl. No. 18/798,670 on Jan. 21, 2026.

Non-Final Office Action issued in related U.S. Appl. No. 18/798,632 on Jan. 20, 2026.

Final Office Action issued in related U.S. Appl. No. 18/798,706 on Mar. 30, 2026.

Final Office Action issued in related U.S. Appl. No. 18/798,716 on Apr. 8, 2026.

Notice of Allowance issued in related U.S. Appl. No. 18/798,686 on Apr. 10, 2026.

* cited by examiner

10

10

10

10

10

10

10

10

10

10

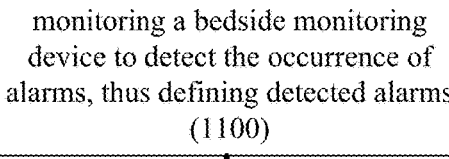

monitoring a bedside monitoring device to detect the occurrence of alarms, thus defining detected alarms (1100)

defining volume information for the detected (1104)

utilizing the volume information to determine the authenticity of the detected alarms (1106)

defining volatility information for the detected alarms (1108)

utilizing the volatility information to determine the authenticity of the detected alarms (1110)

defining bias information for the detected alarms (1112)

processing the detected alarms to determine their authenticity (1102)

utilizing the bias information to determine the authenticity of the detected alarms (1114)

defining persistence information for the detected alarms (1116)

utilizing the persistence information to determine the authenticity of the detected alarms (1118)

defining stationary information for the detected alarms (1120)

utilizing the stationary information to determine the authenticity of the detected alarms (1122)

if a detected alarm is determined to be non-authentic, adjusting one or more monitoring criteria that was instrumental in producing the non-authentic detected alarm (1124)

defining bespoke monitoring criteria for the bedside monitoring device (1126)

if a detected alarm is determined to be authentic, effectuating an appropriate medical response to the authentic detected alarm (1128)

FIG. 12

Figure 13A:
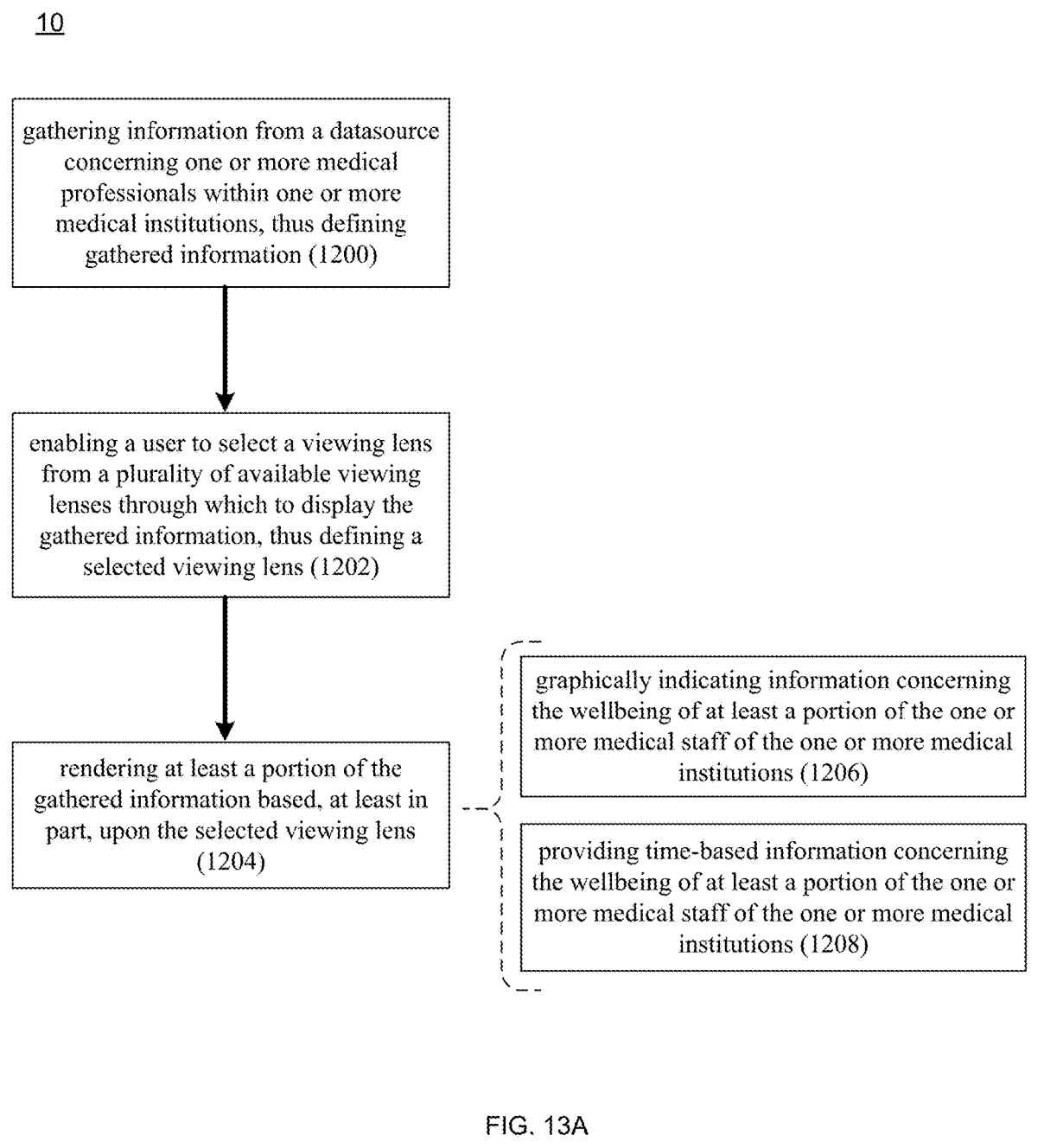

10 gathering information from a datasource
concerning one or more medical
professionals within one or more
medical institutions, thus defining
gathered information (1200)

↓ enabling a user to select a viewing lens
from a plurality of available viewing
lenses through which to display the
gathered information, thus defining a
selected viewing lens (1202)

↓ rendering at least a portion of the
gathered information based, at least in
part, upon the selected viewing lens
(1204)

graphically indicating information concerning
the wellbeing of at least a portion of the one or
more medical staff of the one or more medical
institutions (1206)

providing time-based information concerning
the wellbeing of at least a portion of the one or
more medical staff of the one or more medical
institutions (1208)

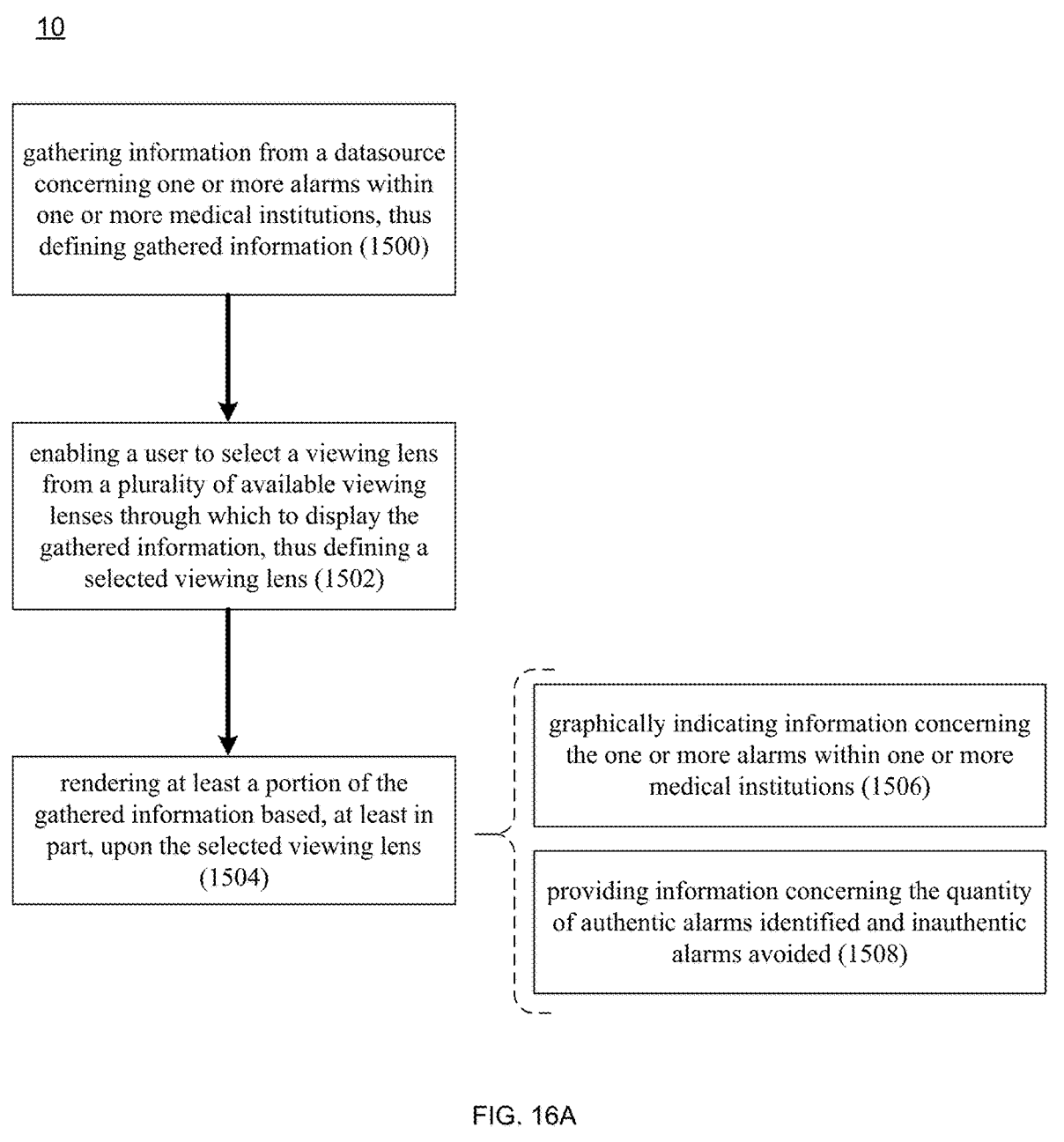

10 gathering information from a datasource
concerning one or more alarms within
one or more medical institutions, thus
defining gathered information (1500)

↓ enabling a user to select a viewing lens
from a plurality of available viewing
lenses through which to display the
gathered information, thus defining a
selected viewing lens (1502)

↓ rendering at least a portion of the
gathered information based, at least in
part, upon the selected viewing lens
(1504)

graphically indicating information concerning
the one or more alarms within one or more
medical institutions (1506)

providing information concerning the quantity
of authentic alarms identified and inauthentic
alarms avoided (1508)

FIG. 16A

10 utilizing prompt engineering and the generative AI model to produce the recommendation based upon the one or more incidents so that the user may gain more incite into these one or more incidents (1812)

Figure 19A:
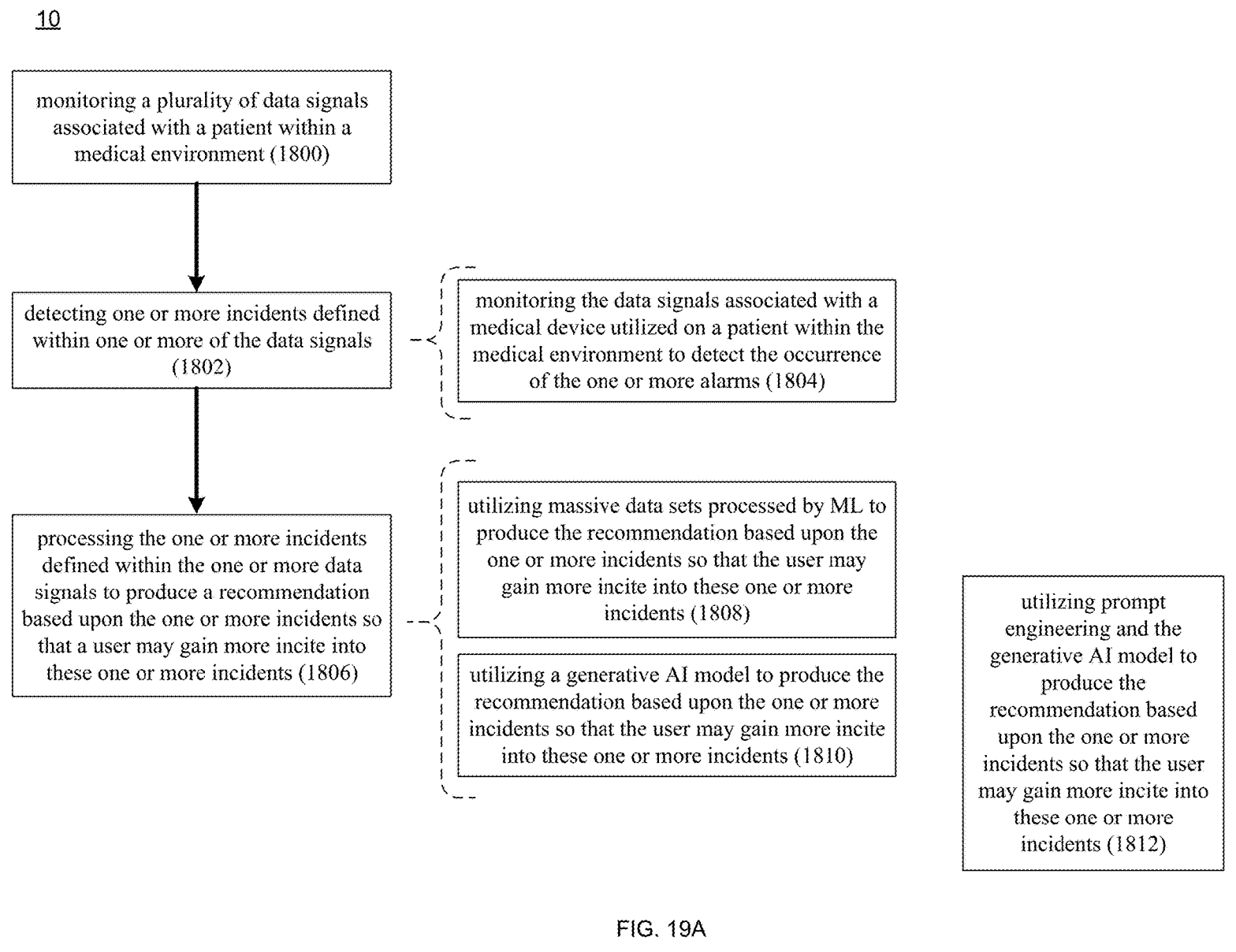

monitoring the data signals associated with a medical device utilized on a patient within the medical environment to detect the occurrence of the one or more alarms (1804)

utilizing massive data sets processed by ML to produce the recommendation based upon the one or more incidents so that the user may gain more incite into these one or more incidents (1808)

utilizing a generative AI model to produce the recommendation based upon the one or more incidents so that the user may gain more incite into these one or more incidents (1810)

monitoring a plurality of data signals associated with a patient within a medical environment (1800)

detecting one or more incidents defined within one or more of the data signals (1802)

processing the one or more incidents defined within the one or more data signals to produce a recommendation based upon the one or more incidents so that a user may gain more incite into these one or more incidents (1806)

302
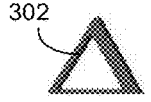
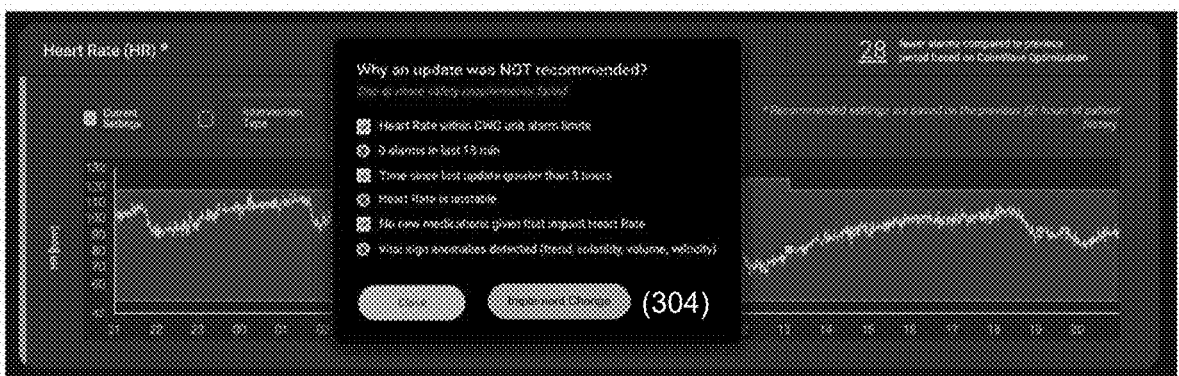
FIG. 20B

10

302

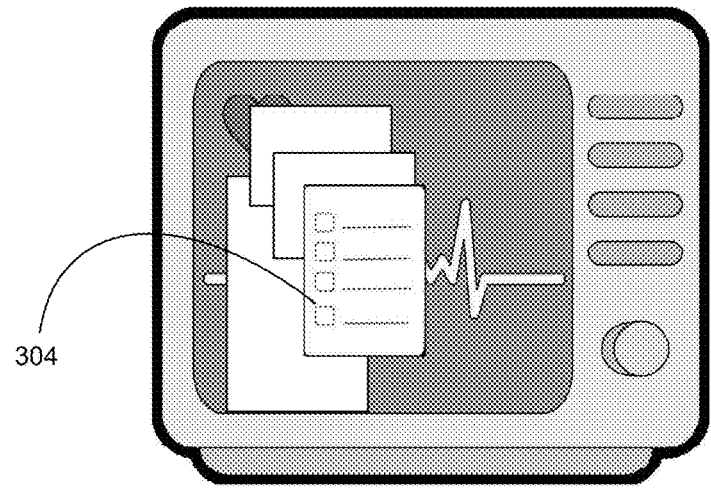
304
FIG. 22B
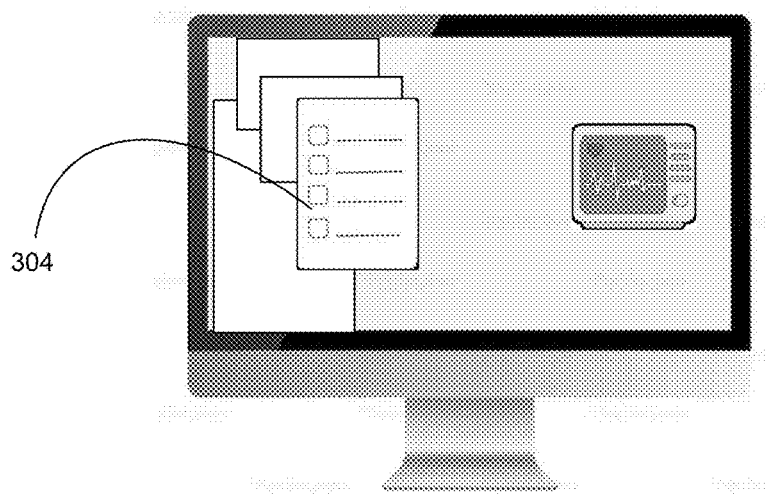
304
FIG. 22C
304
FIG. 22D

306

Summary
(308)

Recommendations
(310)

Justification
(312)

| Rounding List for Dr. Smith | | |
| --- | --- | --- |
| Patient | Room | Acuity Score |
| John Smith | 302 | 97 |
| Mary Jones | 126 | 91 |
| Alan Clark | 233 | 82 |
| Jim Roberts | 716 | 72 |
| Cindy Paul | 552 | 60 |
| Lenny Briscoe | 477 | 51 |
| Jack Smith | 300 | 41 |

FIG. 24B

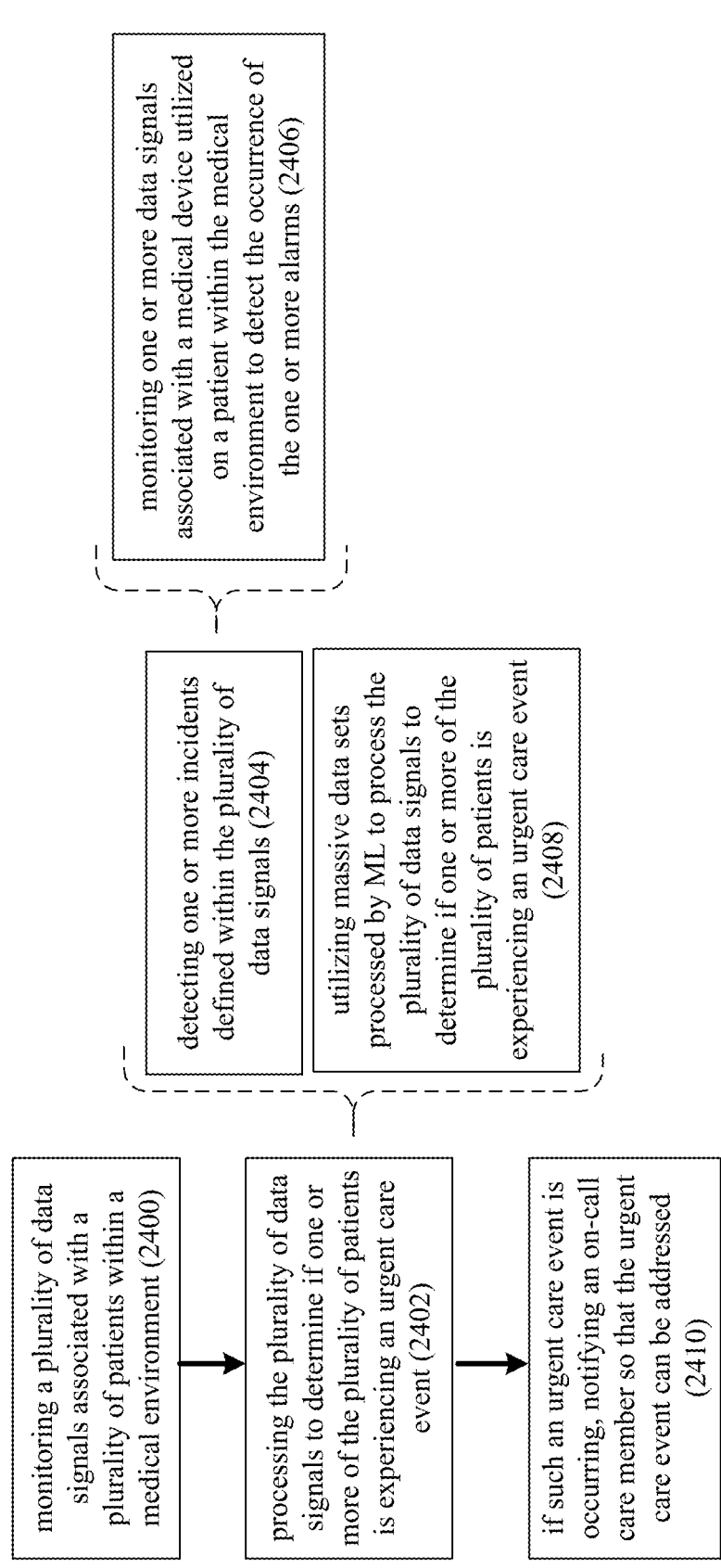

FIG. 25A monitoring one or more data signals associated with a medical device utilized on a patient within the medical environment to detect the occurrence of the one or more alarms (2406)

detecting one or more incidents defined within the plurality of data signals (2404)

utilizing massive data sets processed by ML to process the plurality of data signals to determine if one or more of the plurality of patients is experiencing an urgent care event (2408)

monitoring a plurality of data signals associated with a plurality of patients within a medical environment (2400)

processing the plurality of data signals to determine if one or more of the plurality of patients is experiencing an urgent care event (2402)

if such an urgent care event is occurring, notifying an on-call care member so that the urgent care event can be addressed (2410)

10

318

10

326

Operations Management Score
(328)

89%

Explanation
(330)

Justification
(332)

FIG. 27B

INFORMATION MANAGEMENT SYSTEM AND METHOD

RELATED APPLICATION(S)

This application claims the benefit of the following U.S. Provisional Application No. 63/518,241, filed on 8 Aug. 2023; the entire contents of which are incorporated herein by reference.

TECHNICAL FIELD

This disclosure relates to information systems and methods and, more particularly, to information systems and methods that enable a plurality of devices to communicate and/or be managed.

BACKGROUND

The lack of communication between medical devices can lead to significant problems in managing alarms on those devices. Alarms play a critical role in patient care, alerting healthcare providers to changes in a patient's condition or potential issues with medical devices. However, when devices are not able to communicate effectively with each other, several challenges arise in managing alarms:

Lack of Context and Situational Awareness: Without communication between devices, alarms may lack important context and situational information. For example, a patient's vital signs monitored by one device may trigger an alarm, but this alarm may not be synchronized with alarms from other devices, such as infusion pumps or ventilators. This lack of context can make it challenging for healthcare providers to assess the urgency and priority of each alarm.

Alarm Fatigue and Desensitization: Healthcare providers are frequently exposed to a large number of alarms from various devices. When alarms are not coordinated or synchronized, it can result in an overwhelming number of alarms, leading to alarm fatigue. Alarm fatigue occurs when healthcare providers become desensitized to alarms due to their frequency, leading to delayed or missed responses to critical alarms.

Inefficient Alarm Prioritization and Response: When alarms from different devices are not communicated or integrated, it becomes difficult to prioritize and respond to alarms effectively. Without a centralized system for managing alarms, healthcare providers may need to manually assess and prioritize each alarm separately, potentially leading to delays in responding to critical situations.

Increased Risk of Missed or Delayed Alarms: When devices do not communicate, there is an increased risk of missed or delayed alarms. For example, if a patient's oxygen saturation level is dropping, an alarm from a pulse oximeter may not trigger an alarm on other devices, such as a bedside monitor or nurse call system, potentially delaying the necessary intervention.

The consequences of these problems can be severe, including compromised patient safety, adverse events, and suboptimal clinical outcomes. Moreover, the lack of communication between medical devices adds complexity to healthcare provider workflows and can lead to increased stress and burden on the clinical staff.

SUMMARY OF DISCLOSURE

Rounding List Generation:

In one implementation, a computer-implemented method is executed on a computing device and includes: monitoring a plurality of data signals associated with a plurality of patients within a medical environment over a defined period of time; calculating an acuity score for each of the plurality of patients, wherein the acuity score defines the overall care needs of each of the plurality of patients; and generating a rounding list that prioritizes the plurality of patients based, at least in part, upon the acuity scores.

One or more of the following features may be included. The defined period of time may include one or more of: a shift within the medical environment; a plurality of shifts within the medical environment; and a history of the one or more patients within the medical environment. The plurality of patients may include one or more of: a plurality of patients assigned to an on-call nurse; a plurality of patients assigned to an on-call manager; and a plurality of patients assigned to an on-call physician. The acuity score may be recalculated for each of the plurality of patients, thus defining a plurality of updated acuity scores. The rounding list may be updated based, at least in part, upon the updated acuity scores. Calculating an acuity score for each of the plurality of patients may include: utilizing massive data sets processed by ML to calculate the acuity score for each of the plurality of patients. Generating a rounding list that prioritizes the plurality of patients may include: utilizing a generative AI model to generate the rounding list that prioritizes the plurality of patients. Utilizing a generative AI model to generate the rounding list that prioritizes the plurality of patients may include: utilizing prompt engineering and the generative AI model to generate the rounding list that prioritizes the plurality of patients. The plurality of data signals may include one or more of: one or more data signals associated with a medical device utilized on a patient within the medical environment; one or more data signals associated with drugs administered to the patient within the medical environment; one or more data signals associated with lab work performed on the patient within the medical environment; one or more data signals associated with clinical assessments performed on the patient within the medical environment; one or more data signals associated with clinical procedures performed on the patient within the medical environment; one or more data signals associated with electronic health records and/or electronic medical records of the patient within the medical environment; and one or more data signals associated with a medical history of the patient within the medical environment. The one or more data signals associated with a medical device utilized on a patient within the medical environment may concern one or more details of the medical device and/or uses of the medical device. The medical device may include one or more sub-medical devices.

In another implementation, a computer program product resides on a computer readable medium and has a plurality of instructions stored on it. When executed by a processor, the instructions cause the processor to perform operations including: monitoring a plurality of data signals associated with a plurality of patients within a medical environment over a defined period of time; calculating an acuity score for each of the plurality of patients, wherein the acuity score defines the overall care needs of each of the plurality of patients; and generating a rounding list that prioritizes the plurality of patients based, at least in part, upon the acuity scores.

One or more of the following features may be included. The defined period of time may include one or more of: a shift within the medical environment; a plurality of shifts within the medical environment; and a history of the one or more patients within the medical environment. The plurality of patients may include one or more of: a plurality of patients assigned to an on-call nurse; a plurality of patients assigned to an on-call manager; and a plurality of patients assigned to an on-call physician. The acuity score may be recalculated for each of the plurality of patients, thus defining a plurality of updated acuity scores. The rounding list may be updated based, at least in part, upon the updated acuity scores. Calculating an acuity score for each of the plurality of patients may include: utilizing massive data sets processed by ML to calculate the acuity score for each of the plurality of patients. Generating a rounding list that prioritizes the plurality of patients may include: utilizing a generative AI model to generate the rounding list that prioritizes the plurality of patients. Utilizing a generative AI model to generate the rounding list that prioritizes the plurality of patients may include: utilizing prompt engineering and the generative AI model to generate the rounding list that prioritizes the plurality of patients. The plurality of data signals may include one or more of: one or more data signals associated with a medical device utilized on a patient within the medical environment; one or more data signals associated with drugs administered to the patient within the medical environment; one or more data signals associated with lab work performed on the patient within the medical environment; one or more data signals associated with clinical assessments performed on the patient within the medical environment; one or more data signals associated with clinical procedures performed on the patient within the medical environment; one or more data signals associated with electronic health records and/or electronic medical records of the patient within the medical environment; and one or more data signals associated with a medical history of the patient within the medical environment. The one or more data signals associated with a medical device utilized on a patient within the medical environment may concern one or more details of the medical device and/or uses of the medical device. The medical device may include one or more sub-medical devices.

In another implementation, a computing system includes a processor and a memory system configured to perform operations including: monitoring a plurality of data signals associated with a plurality of patients within a medical environment over a defined period of time; calculating an acuity score for each of the plurality of patients, wherein the acuity score defines the overall care needs of each of the plurality of patients; and generating a rounding list that prioritizes the plurality of patients based, at least in part, upon the acuity scores.

One or more of the following features may be included. The defined period of time may include one or more of: a shift within the medical environment; a plurality of shifts within the medical environment; and a history of the one or more patients within the medical environment. The plurality of patients may include one or more of: a plurality of patients assigned to an on-call nurse; a plurality of patients assigned to an on-call manager; and a plurality of patients assigned to an on-call physician. The acuity score may be recalculated for each of the plurality of patients, thus defining a plurality of updated acuity scores. The rounding list may be updated based, at least in part, upon the updated acuity scores. Calculating an acuity score for each of the plurality of patients may include: utilizing massive data sets processed by ML to calculate the acuity score for each of the plurality of patients. Generating a rounding list that prioritizes the plurality of patients may include: utilizing a generative AI model to generate the rounding list that prioritizes the plurality of patients. Utilizing a generative AI model to generate the rounding list that prioritizes the plurality of patients may include: utilizing prompt engineering and the generative AI model to generate the rounding list that prioritizes the plurality of patients. The plurality of data signals may include one or more of: one or more data signals associated with a medical device utilized on a patient within the medical environment; one or more data signals associated with drugs administered to the patient within the medical environment; one or more data signals associated with lab work performed on the patient within the medical environment; one or more data signals associated with clinical assessments performed on the patient within the medical environment; one or more data signals associated with clinical procedures performed on the patient within the medical environment; one or more data signals associated with electronic health records and/or electronic medical records of the patient within the medical environment; and one or more data signals associated with a medical history of the patient within the medical environment. The one or more data signals associated with a medical device utilized on a patient within the medical environment may concern one or more details of the medical device and/or uses of the medical device. The medical device may include one or more sub-medical devices.

The details of one or more implementations are set forth in the accompanying drawings and the description below. Other features and advantages will become apparent from the description, the drawings, and the claims.

BRIEF DESCRIPTION OF THE DRAWINGS

FIG. 12 is another flowchart of the information process of FIG. 1 according to an embodiment of the present disclosure;

FIG. 13A is another flowchart of the information process of FIG. 1 according to an embodiment of the present disclosure;

FIG. 16A is another flowchart of the information process of FIG. 1 according to an embodiment of the present disclosure;

FIG. 19A is another flowchart of the information process of FIG. 1 according to an embodiment of the present disclosure;

FIG. 20B is a diagrammatic view of a display screen/window rendered by the information process of FIG. 1 according to an embodiment of the present disclosure;

FIG. 22B-22D are diagrammatic views of user interfaces rendered by the information process of FIG. 1 according to an embodiment of the present disclosure;

FIG. 23B is a diagrammatic view of a summary rendered by the information process of FIG. 1 according to an embodiment of the present disclosure;

FIG. 24B is a diagrammatic view of a rounding list rendered by the information process of FIG. 1 according to an embodiment of the present disclosure;

FIG. 25A is another flowchart of the information process of FIG. 1 according to an embodiment of the present disclosure;

FIG. 27B is a diagrammatic view of a report rendered by the information process of FIG. 1 according to an embodiment of the present disclosure.

Like reference symbols in the various drawings indicate like elements.

DETAILED DESCRIPTION OF THE PREFERRED EMBODIMENTS

System Overview

Figure 1:
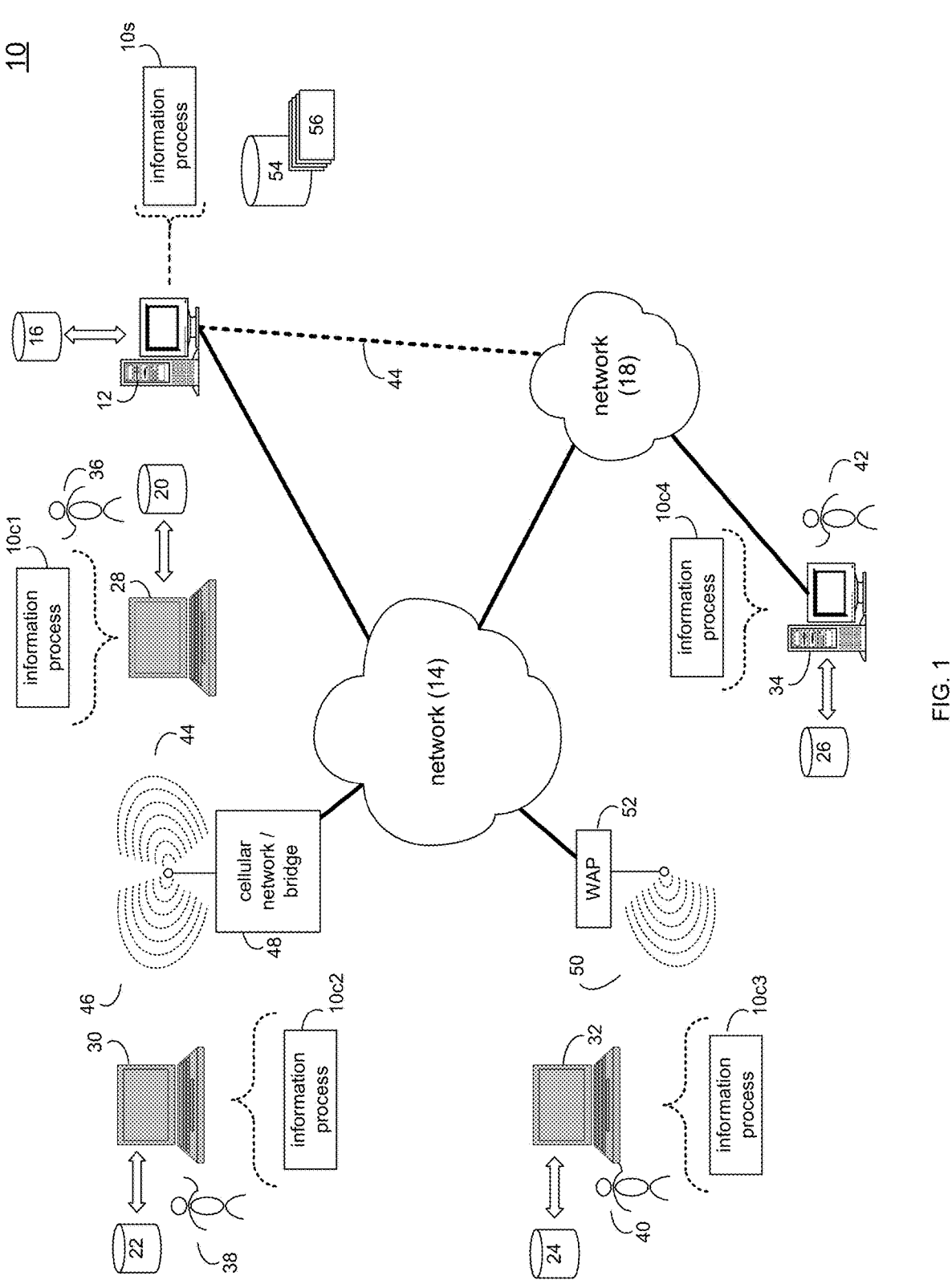
FIG. 1 is a diagrammatic view of a distributed computing network including a computing device that executes an information process according to an embodiment of the present disclosure.

Referring to FIG. 1, there is shown information process 10. Information process 10 may be implemented as a server-side process, a client-side process, or a hybrid server-side/client-side process. For example, information process 10 may be implemented as a purely server-side process via information process 10s. Alternatively, information process 10 may be implemented as a purely client-side process via one or more of information process 10c1, information process 10c2, information process 10c3, and information process 10c4. Alternatively still, information process 10 may be implemented as a hybrid server-side/client-side process via information process 10s in combination with one or more of information process 10c1, information process 10c2, information process 10c3, and information process 10c4. Accordingly, information process 10 as used in this disclosure may include any combination of information process 10s, information process 10c1, information process 10c2, information process 10c3, and information process 10c4.

Information process 10s may be a server application and may reside on and may be executed by computing device 12, which may be connected to network 14 (e.g., the Internet or a local area network). Examples of computing device 12 may include, but are not limited to: a personal computer, a server computer, a series of server computers, a mini computer, a mainframe computer, or a cloud-based computing platform.

The instruction sets and subroutines of information process 10s, which may be stored on storage device 16 coupled to computing device 12, may be executed by one or more processors (not shown) and one or more memory architectures (not shown) included within computing device 12. Examples of storage device 16 may include but are not limited to: a hard disk drive; a RAID device; a random-access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Examples of information processes 10c1, 10c2, 10c3, 10c4 may include but are not limited to a web browser, a game console user interface, a mobile device user interface, or a specialized application (e.g., an application running on e.g., the Android™ platform, the iOS™ platform, the Windows™ platform, the Linux™ platform or the UNIX™ platform). The instruction sets and subroutines of information processes 10c1, 10c2, 10c3, 10c4, which may be stored on storage devices 20, 22, 24, 26 (respectively) coupled to client electronic devices 28, 30, 32, 34 (respectively), may be executed by one or more processors (not shown) and one or more memory architectures (not shown) incorporated into client electronic devices 28, 30, 32, 34 (respectively). Examples of storage devices 20, 22, 24, 26 may include but are not limited to: hard disk drives; RAID devices; random access memories (RAM); read-only memories (ROM), and all forms of flash memory storage devices.

Examples of client electronic devices 28, 30, 32, 34 may include, but are not limited to, a smartphone (not shown), a personal digital assistant (not shown), a tablet computer (not shown), laptop computers 28, 30, 32, personal computer 34, a notebook computer (not shown), a server computer (not shown), a gaming console (not shown), and a dedicated network device (not shown). Client electronic devices 28, 30, 32, 34 may each execute an operating system, examples of which may include but are not limited to Microsoft Windows™, Android™, iOS™, Linux™, or a custom operating system.

Users 36, 38, 40, 42 may access information process 10 directly through network 14 or through secondary network 18. Further, information process 10 may be connected to network 14 through secondary network 18, as illustrated with link line 44.

The various client electronic devices (e.g., client electronic devices 28, 30, 32, 34) may be directly or indirectly coupled to network 14 (or network 18). For example, laptop computer 28 and laptop computer 30 are shown wirelessly coupled to network 14 via wireless communication channels 44, 46 (respectively) established between laptop computers 28, 30 (respectively) and cellular network/bridge 48, which is shown directly coupled to network 14. Further, laptop computer 32 is shown wirelessly coupled to network 14 via wireless communication channel 50 established between laptop computer 32 and wireless access point (i.e., WAP) 52, which is shown directly coupled to network 14. Additionally, personal computer 34 is shown directly coupled to network 18 via a hardwired network connection.

WAP 52 may be, for example, an IEEE 802.11a, 802.11b, 802.11g, 802.11n, Wi-Fi, and/or Bluetooth device that is capable of establishing wireless communication channel 50 between laptop computer 32 and WAP 52. As is known in the art, IEEE 802.11x specifications may use Ethernet protocol and carrier sense multiple access with collision avoidance (i.e., CSMA/CA) for path sharing. As is known in the art, Bluetooth is a telecommunications industry specification that allows e.g., mobile phones, computers, and personal digital assistants to be interconnected using a short-range wireless connection.

Information Process Overview

As will be discussed below in greater detail, information process 10 may be configured enable the analysis of working environments so that the working conditions within these working environments may be ascertained and defined . . . with specific attention being provided to minimizing worker attrition and maximizing worker wellbeing.

While many of the discussions below concern utilizing information process 10 on medical devices within a medical environments, this is for illustrative purposes only and is not intended to be a limitation of this disclosure, as other configurations are possible and are considered to be within the scope of this disclosure. For example, information process 10 may be equally applicable to process control devices, networking devices, computing devices, manufacturing devices, agricultural devices, energy/refining devices, aerospace devices, forestry devices, and defense devices.

Cross-Vendor Middleware:

The following discussion concerns the manner in which information process 10 may be utilized to function as an intermediary between devices that are offered by multiple vendors. As is often the case, individual vendors tend to produce devices that that can communicate amongst themselves but often have difficulties communicating with devices provided by other vendors. Accordingly and as will be discussed below, information process 10 may be configured to effectuate communication between devices produced by different vendors.

Figure 2:
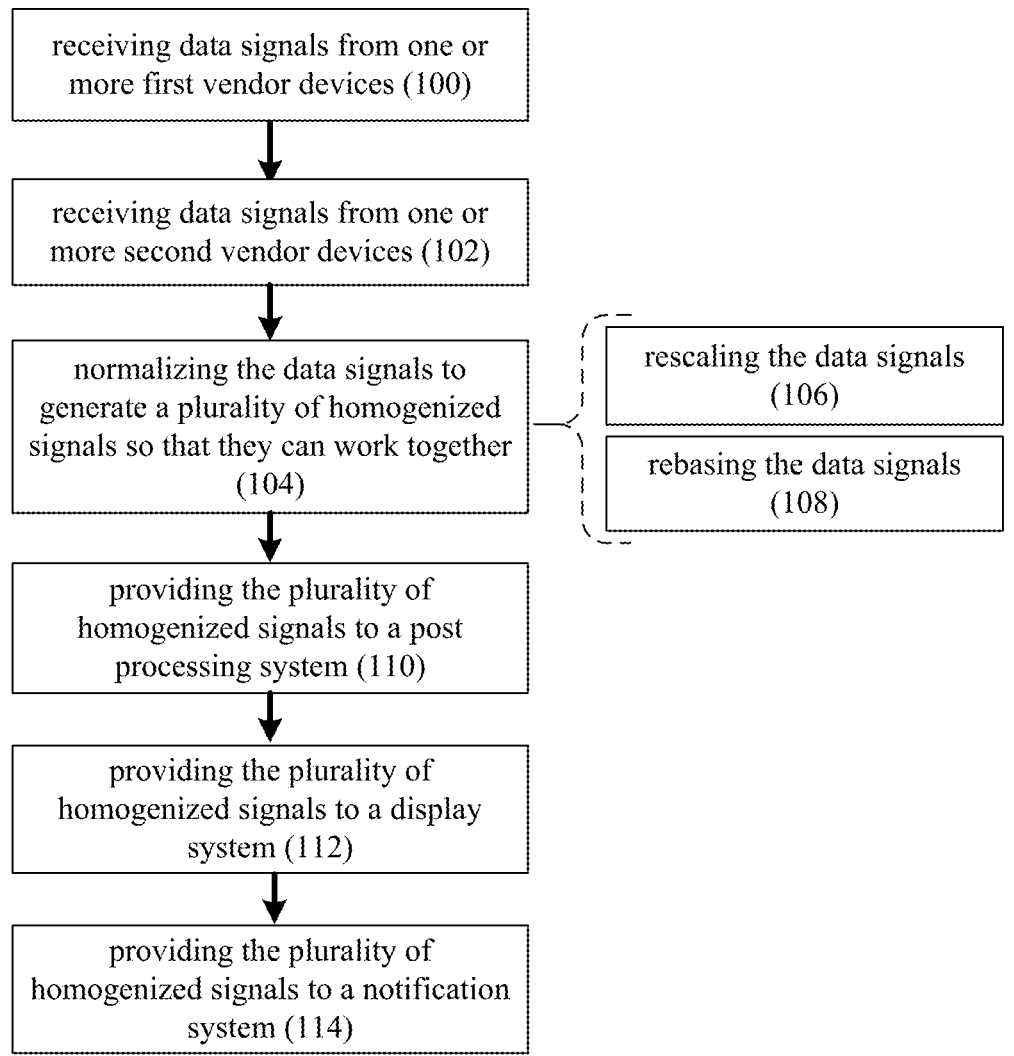
FIG. 2 is a flowchart of the information process of FIG. 1 according to an embodiment of the present disclosure.
Figure 3:
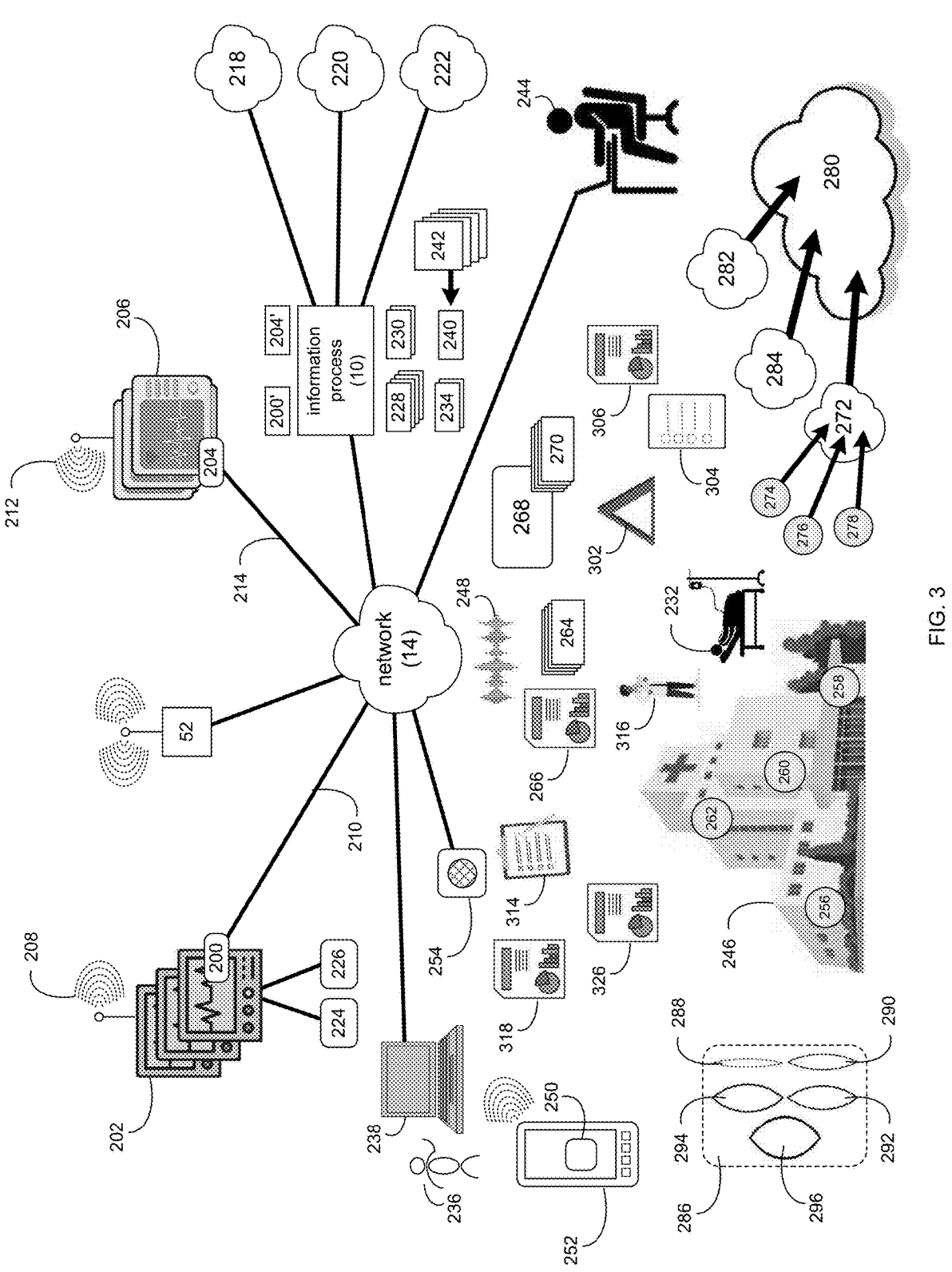
FIG. 3 is a diagrammatic view of multiple devices coupled to the information process of FIG. 1 according to an embodiment of the present disclosure.

Referring also to FIGS. 2-3, information process 10 may receive 100 data signals (e.g., data signals 200) from one or more first vendor devices (e.g., first vendor devices 202) and may receive 102 data signals (e.g., data signals 204) from one or more second vendor devices (e.g., second vendor devices 206). Generally speaking, the data signals (e.g., data signals 200, 204) may concern one or more details of the one or more first vendor devices (e.g., first vendor devices 202) and/or the one or more second vendor devices (e.g., second vendor devices 206). Additionally/alternatively, the data signals (e.g., data signals 200, 204) may concern one or more uses of the one or more first vendor devices (e.g., first vendor devices 202) and/or the one or more second vendor devices (e.g., second vendor devices 206).

The one or more first vendor devices (e.g., first vendor devices 202) may be coupled to information process 10 via e.g., wireless communication channel 208 established between the one or more first vendor devices (e.g., first vendor devices 202) and e.g., wireless access point (i.e., WAP) 52. Additionally/alternatively, the one or more first vendor devices (e.g., first vendor devices 202) may be coupled to information process 10 via e.g., wired connection 210 established between the one or more first vendor devices (e.g., first vendor devices 202) and e.g., network 14.

The one or more second vendor devices (e.g., second vendor devices 206) may be coupled to information process 10 via e.g., wireless communication channel 212 established between the one or more second vendor devices (e.g., second vendor devices 206) and e.g., wireless access point (i.e., WAP) 52. Additionally/alternatively, the one or more second vendor devices (e.g., second vendor devices 206) may be coupled to information process 10 via e.g., wired connection 214 established between the one or more second vendor devices (e.g., second vendor devices 206) and e.g., network 14.

The one or more first vendor devices (e.g., first vendor devices 202) and/or the one or more second vendor devices (e.g., second vendor devices 206) may include one or more of: a medical device, a process control device, a networking device, a computing device, a manufacturing device, an agricultural device, an energy/refining device, an aerospace device, a forestry device, and a defense device. Generally speaking, these vendor devices (e.g., first vendor devices 202 and/or second vendor devices 206) may be electrically coupled to information process 10 so that these vendor devices (e.g., first vendor devices 202 and/or second vendor devices 206) may provide the data signals (e.g., data signals 200 and/or data signals 204) to information process 10.

Examples of medical devices may include but are not limited to instruments, apparatuses, machines, implants, or any other similar items used in the diagnosis, prevention, monitoring, treatment, or alleviation of diseases, injuries, or disabilities in humans. These devices are specifically designed to serve medical purposes and are regulated by health authorities to ensure their safety and effectiveness.

Medical devices can range from simple tools such as thermometers and stethoscopes to more complex equipment like magnetic resonance imaging (MRI) machines, artificial organs, or robotic surgical systems. They are used by healthcare professionals, patients, or caregivers in various healthcare settings, including hospitals, clinics, laboratories, and even at home.

Examples of medical devices may include but are not limited to:

Diagnostic Devices: These devices are used to identify diseases or medical conditions. Examples include X-ray machines, ultrasound scanners, blood pressure monitors, and glucose meters.

Therapeutic Devices: These devices are used to treat or manage medical conditions. Examples include pacemakers, insulin pumps, dialysis machines, and prosthetic limbs.

Surgical Instruments: These devices are used during surgical procedures to perform specific tasks. Examples include scalpels, forceps, surgical lasers, and laparoscopic instruments.

Implants: These devices are surgically placed in the body to support or replace a specific function. Examples include artificial joints, dental implants, cardiac stents, and cochlear implants.

Assistive Devices: These devices help individuals with disabilities or limitations to improve their mobility or perform daily activities. Examples include wheelchairs, hearing aids, walkers, and canes.

Monitoring Devices: These devices are used to track and monitor vital signs or specific health parameters. Examples include electrocardiograms (ECGs), pulse oximeters, sleep apnea monitors, and continuous glucose monitors.

It's important to note that the classification and regulation of medical devices may vary by country or region. Regulatory agencies, such as the U.S. Food and Drug Administration (FDA) in the United States, oversee the approval, safety, and quality of medical devices to ensure they meet the necessary standards for patient care.

Examples of process control devices (also known as industrial control devices) may include but are not limited to instruments or equipment used to monitor and regulate industrial processes to achieve desired outcomes such as efficiency, quality, safety, and consistency. These devices are commonly employed in manufacturing, chemical processing, power generation, oil and gas refining, and other industrial sectors. They help automate and optimize processes, ensuring they operate within defined parameters and maintain desired conditions.

Examples of process control devices may include but are not limited to:

Programmable Logic Controllers (PLCs): PLCs are versatile digital computers that automate and control electromechanical processes. They receive input signals from sensors, make decisions based on pre-programmed logic, and send output signals to actuators to control machinery or equipment.

Distributed Control Systems (DCS): DCSs are comprehensive control systems used in large-scale industrial processes. They consist of multiple control units interconnected with sensors, actuators, and other devices. DCSs enable centralized monitoring and control of various process variables across a plant or facility.

Human-Machine Interface (HMI): HMIs provide a graphical interface for operators to interact with process control systems. They display real-time data, process status, alarms, and allow operators to input commands or adjust parameters. HMIs can be touchscreens, keypads, or other user-friendly interfaces.

Sensors and Transmitters: These devices are used to measure physical or chemical variables such as temperature, pressure, flow rate, level, pH, conductivity, and more. They convert these measurements into electrical signals that can be interpreted and used for control purposes.

Actuators: Actuators are devices responsible for converting control signals into physical action. They control valves, motors, pumps, and other equipment to adjust flow rates, pressures, positions, or other process parameters based on control system inputs.

Data Acquisition Systems: These systems collect and record data from sensors, devices, and instruments at various points in the process. They store this data for analysis, monitoring, and historical reference to optimize process performance and troubleshoot issues.

Control Valves: Control valves regulate fluid flow or pressure in a process. They receive signals from the control system and adjust their position or aperture to achieve the desired setpoint.

Analytical Instruments: These instruments measure and analyze chemical properties or composition in a process. Examples include pH meters, gas analyzers, spectrometers, and chromatographs.

Process control devices work together to enable real-time monitoring, analysis, and adjustment of industrial processes. They help improve efficiency, reduce errors, enhance safety, and ensure consistent product quality in a wide range of industries.

Examples of networking devices may include but are not limited to hardware or software components that facilitate communication and connectivity within a computer network. These devices enable the transmission, routing, and management of data across networks, allowing devices to communicate and share resources effectively. Networking devices play a crucial role in establishing and maintaining network infrastructure and connectivity.

Examples of networking devices may include but are not limited to:

Routers: Routers are essential devices that connect multiple networks and facilitate the transfer of data between them. They determine the optimal path for data packets to reach their destination based on network addressing and routing protocols.

Switches: Switches are used to connect devices within a local area network (LAN). They receive data packets and forward them to the appropriate destination device based on the device's MAC (Media Access Control) address. Switches help improve network performance by enabling efficient data transfer between connected devices.

Hubs: Hubs are simple network devices that operate at the physical layer of a network. They receive incoming data packets and broadcast them to all connected devices. However, unlike switches, hubs do not have the capability to selectively forward data to specific devices.

Modems: Modems are used to connect a network to an external network or the Internet. They convert digital data from a computer into analog signals suitable for transmission over telephone lines (in the case of dial-up modems) or digital signals for broadband connections.

Network Interface Cards (NICs): NICs are hardware components installed in computers or devices to connect them to a network. They provide the necessary interface for devices to transmit and receive data over the network.

Wireless Access Points (WAPs): WAPs enable wireless connectivity within a network. They serve as a central hub for wireless devices to connect to a wired network, providing wireless access and facilitating communication between wireless devices and the network.

Firewalls: Firewalls are security devices that monitor and control incoming and outgoing network traffic based on predetermined security rules. They help protect networks from unauthorized access, threats, and malicious activities.

Network Bridges: Bridges connect two or more LANs or network segments and facilitate communication between them. They operate at the data link layer of the network and can help extend network coverage or segment networks to improve performance and security.

Network Load Balancers: Load balancers distribute network traffic across multiple servers or network links to optimize resource usage, improve performance, and ensure high availability of network services.

Network Print Servers: Print servers enable network printers to be shared and accessed by multiple users within a network. They manage print jobs, print queues, and provide print services to network-connected devices.

These are just a few examples of networking devices commonly used in computer networks. The combination and configuration of these devices depend on the specific requirements of the network and the desired functionality.

Examples of computing devices may include but are not limited to electronic devices that process and manipulate data using computational capabilities. These devices are designed to perform various tasks, ranging from basic calculations to complex computations and data processing. Computing devices come in different forms and sizes, each tailored for specific purposes and user needs.

Examples of computing devices may include but are not limited to:

Personal Computers (PCs): Personal computers are general-purpose computing devices designed for individual use. They consist of a central processing unit (CPU), memory, storage devices, input/output peripherals (keyboard, mouse, display), and an operating system. PCs are versatile devices used for tasks such as browsing the web, word processing, gaming, multimedia, and more.

Laptops: Laptops are portable computing devices that provide the same functionality as personal computers. They incorporate a keyboard, display, and a built-in battery, allowing users to work or perform tasks on the go.

Tablets: Tablets are lightweight, portable devices with touchscreens and simplified user interfaces. They offer functionality similar to laptops but with a more compact and intuitive design. Tablets are commonly used for web browsing, media consumption, e-books, and mobile applications.

Smartphones: Smartphones are mobile computing devices that combine telephony capabilities with computing features. They offer advanced functionality, including internet access, email, multimedia, applications, and various sensors. Smartphones have become an essential part of modern life, providing communication, entertainment, and productivity features.

Servers: Servers are powerful computing devices designed to manage and process vast amounts of data and provide services to other devices or users. They are typically used in network environments to store and deliver data, host websites and applications, handle database management, and perform complex computations.

Workstations: Workstations are high-performance computing devices optimized for specialized tasks such as computer-aided design (CAD), video editing, 3D rendering, scientific simulations, and engineering. They typically have advanced processing power, enhanced graphics capabilities, and extensive memory capacity.

Embedded Systems: Embedded systems are specialized computing devices embedded within other systems or products. They are designed to perform specific functions and are often found in automobiles, appliances, medical equipment, industrial machinery, and other devices that require computing capabilities.

Wearable Devices: Wearable devices are computing devices worn on the body or integrated into clothing or accessories. Examples include smartwatches, fitness trackers, augmented reality glasses, and medical monitoring devices. These devices offer features such as health tracking, notifications, communication, and interaction with other devices.

Gaming Consoles: Gaming consoles are computing devices specifically designed for playing video games. They provide dedicated hardware and software platforms optimized for gaming, often with advanced graphics processing capabilities.

Internet of Things (IoT) Devices: IoT devices are computing devices embedded in everyday objects, connected to the internet, and capable of collecting and exchanging data. Examples include smart home devices, environmental sensors, industrial sensors, and connected appliances.

These are just a few examples of computing devices, each serving different purposes and catering to various computing needs. The computing landscape is continually evolving, with new devices and technologies being developed to meet changing user requirements.

Examples of manufacturing devices (also known as industrial manufacturing equipment) may include but are not limited to specialized machines, tools, and systems used in the production and manufacturing processes across various industries. These devices are designed to automate, optimize, and facilitate the manufacturing of products with efficiency, precision, and consistency. Manufacturing devices are employed in sectors such as automotive, electronics, pharmaceuticals, food processing, textiles, and more.

Examples of manufacturing devices may include but are not limited to:

CNC Machines: Computer Numerical Control (CNC) machines are automated machining tools that follow pre-programmed instructions to shape and cut materials with high precision. Examples include CNC milling machines, lathes, routers, and laser cutting machines.

Robotics and Automation Systems: Robotic devices and automation systems are used to automate repetitive tasks, assembly processes, material handling, and packaging. Industrial robots are programmable machines that perform tasks with speed, accuracy, and consistency, improving productivity and reducing human error.

Assembly Machines: These devices are specifically designed to automate assembly processes by joining and fastening components together. Examples include robotic arms, pick-and-place machines, and specialized assembly line systems.

3D Printers: Also known as additive manufacturing machines, 3D printers build three-dimensional objects by layering materials based on digital models. They enable the rapid prototyping, customization, and small-scale production of components or products.

Industrial Sewing Machines: These machines are used in textile and garment manufacturing to stitch fabrics and create finished products such as clothing, upholstery, and accessories. Industrial sewing machines offer enhanced speed, durability, and specialized stitching capabilities.

Injection Molding Machines: Injection molding machines melt and inject molten materials, typically plastics, into molds to produce a wide range of products and components. They are used in industries such as automotive, packaging, consumer goods, and medical devices.

Packaging Machines: Packaging machines automate the process of packaging products for distribution and sale. They can handle tasks like filling, sealing, labeling, and palletizing. Examples include form-fill-seal machines, blister packaging machines, and cartoning machines.

Inspection and Quality Control Devices: These devices are used to inspect and ensure the quality of manufactured products. They include tools like coordinate measuring machines (CMM), vision inspection systems, gauges, and sensors to detect defects, measure dimensions, and verify product specifications.

Material Handling Equipment: Material handling devices such as conveyor systems, automated guided vehicles (AGVs), forklifts, and robotic arms facilitate the movement, storage, and transportation of materials within the manufacturing facility.

Testing and Measurement Devices: Testing and measurement devices are used to assess the performance, functionality, and quality of manufactured products. Examples include hardness testers, spectrometers, oscilloscopes, and gauges.

These are just a few examples of manufacturing devices, and the specific devices used depend on the industry, production processes, and product requirements. Manufacturing devices help streamline production, increase efficiency, improve product quality, and reduce costs, contributing to the overall success and competitiveness of manufacturing operations.

Examples of agricultural devices (also known as farm equipment or agricultural machinery) may include but are not limited to specialized tools, machines, and equipment designed to assist in various tasks related to agricultural practices. These devices are used by farmers and agricultural workers to automate, enhance efficiency, and improve productivity in agricultural activities. Agricultural devices are utilized across different stages of farming, including land preparation, planting, cultivation, irrigation, harvesting, and post-harvest processing.

Examples of agricultural devices may include but are not limited to:

Tractors: Tractors are versatile vehicles used for multiple farming tasks. They are equipped with powerful engines and provide the necessary power and traction to perform tasks like plowing, tilling, planting, hauling, and spraying. Tractors can also be combined with various attachments and implements to carry out specific tasks.

Harvesters: Harvesters are machines designed to efficiently harvest crops such as grains, fruits, vegetables, and oilseeds. Different types of harvesters exist for specific crops, including combine harvesters for cereal crops, potato harvesters, grape harvesters, and cotton pickers.

Planters and Seeders: Planters and seeders are devices used to sow seeds in a controlled and efficient manner. They distribute seeds evenly at precise depths and spacing, ensuring optimal plant growth and yield. Planters and seeders can be manual, animal-drawn, or tractor-mounted, depending on the scale of farming operations.

Irrigation Systems: Irrigation devices are used to deliver water to crops in a controlled manner, ensuring proper moisture levels for growth. These systems include sprinklers, drip irrigation systems, center pivot irrigation systems, and furrow irrigation systems. They help conserve water, improve crop yield, and reduce labor requirements.

Sprayers: Sprayers are used to apply fertilizers, pesticides, herbicides, and other agricultural chemicals to crops. They can be handheld, backpack-mounted, or tractor-mounted, equipped with spray nozzles and tanks to evenly distribute the substances and protect crops from pests, diseases, and weeds.

Plows and Tillage Equipment: Plows and tillage equipment are used for primary tillage and land preparation. Plows break up and turn over the soil, while tillage equipment further cultivates the soil, preparing it for planting. Implements like moldboard plows, disc harrows, and cultivators fall under this category.

Livestock Equipment: Livestock equipment includes devices used in animal husbandry and management. Examples include feeding equipment, milking machines, animal handling systems, and barn ventilation systems. These devices contribute to the care, health, and productivity of livestock.

Grain Handling and Storage Equipment: Grain handling devices such as grain elevators, grain dryers, and silos are used to safely store, transport, and process harvested grains. They facilitate efficient storage, drying, and handling of grains to preserve their quality and prevent spoilage.

Hay and Forage Equipment: Hay and forage devices are used to harvest, process, and store animal feed. They include equipment such as hay balers, forage choppers, hay rakes, and bale wrappers.

Post-Harvest Processing Equipment: Post-harvest processing devices are used to clean, sort, grade, and process harvested agricultural products. Examples include threshers, sorters, graders, grain mills, and fruit and vegetable processing equipment.

These are just a few examples of agricultural devices. The specific devices used may vary depending on factors such as the type of crop, farming practices, scale of operations, and regional variations. Agricultural devices play a crucial role in modern farming, improving efficiency, productivity, and sustainability in the agricultural industry.

Examples of energy/refining devices may include but are not limited to specialized equipment and systems used in the energy industry, particularly in the refining and processing of various energy sources. These devices are crucial for extracting, converting, refining, and distributing energy resources in different forms, such as oil, natural gas, coal, and renewable energy sources. They are utilized in power plants, refineries, and other energy production and distribution facilities.

Examples of energy and refining devices may include but are not limited to:

Refining Equipment: Refining devices are used in oil refineries to process crude oil into various refined products such as gasoline, diesel, jet fuel, lubricants, and other petroleum-based products. Examples include distillation towers, catalytic converters, hydrotreaters, and fluid catalytic cracking units (FCCUs).

Boilers and Furnaces: Boilers and furnaces are devices used in power plants and industrial facilities to generate steam or heat. They burn fossil fuels or use other energy sources to produce high-pressure steam that drives turbines and generates electricity.

Turbines and Generators: Turbines, such as steam turbines, gas turbines, and wind turbines, convert the kinetic energy of a fluid or gas into mechanical energy. They are coupled with generators to produce electrical energy. Turbines and generators are key components in power generation systems.

Solar Panels: Solar panels, also known as photovoltaic panels, convert sunlight into electrical energy. They consist of interconnected solar cells that generate direct current (DC) electricity when exposed to sunlight. Solar panels are used in solar power systems to produce renewable energy.

Wind Turbines: Wind turbines capture the kinetic energy of the wind and convert it into electrical energy. They consist of large rotor blades that spin a generator when the wind blows. Wind turbines are used in wind farms and off-grid applications to generate clean and renewable energy.

Natural Gas Processing Equipment: Natural gas processing devices are used to extract and process natural gas from its sources. They include equipment such as compressors, separators, dehydrators, and gas sweetening units. These devices remove impurities and separate valuable components like methane, ethane, propane, and butane.

Power Distribution Equipment: Power distribution devices include transformers, switchgear, circuit breakers, and distribution panels. They are used to control and distribute electrical energy from power plants to various end-users, such as homes, businesses, and industrial facilities.

Energy Storage Systems: Energy storage devices store excess energy generated during periods of low demand and release it during peak demand or when renewable energy sources are unavailable. Examples include battery storage systems, pumped storage hydropower, and compressed air energy storage (CAES) systems.

Heat Exchangers: Heat exchangers transfer thermal energy between two or more fluids at different temperatures. They are used in various energy and refining processes to recover waste heat, facilitate heat exchange, and improve energy efficiency.

Pipelines and Storage Tanks: Pipelines and storage tanks are essential for transporting and storing energy resources like oil, natural gas, and petroleum products. Pipelines transport these resources over long distances, while storage tanks provide temporary storage and distribution hubs.

These are just a few examples of energy and refining devices. The energy industry is diverse, with a wide range of technologies and equipment used to produce, refine, and distribute different forms of energy. Advances in technology and the growing focus on renewable energy sources continue to drive innovation in this field.

Examples of aerospace devices may include but are not limited to specialized equipment, systems, and vehicles used in the aerospace industry, which encompasses the design, development, production, and operation of aircraft and spacecraft. These devices are designed to enable flight, exploration of space, and various aerospace-related activities. They include a wide range of components, instruments, and systems that are critical for aerospace operations.

Examples of aerospace devices may include but are not limited to:

Aircraft: Aircraft are vehicles designed to fly within the Earth's atmosphere. They include various types such as airplanes, helicopters, gliders, and unmanned aerial vehicles (UAVs). Aircraft devices encompass airframes, engines, avionics systems, landing gear, control surfaces, and onboard instruments necessary for navigation, control, and communication.

Spacecraft: Spacecraft are vehicles designed for space exploration and satellite deployment. They include crewed spacecraft, such as capsules and space shuttles, as well as robotic spacecraft, such as satellites, probes, and rovers. Spacecraft devices include propulsion systems, life support systems, communication systems, scientific instruments, solar panels, and heat shields.

Rocket Engines: Rocket engines are used to propel spacecraft and launch vehicles into space. They operate on the principle of expelling high-speed exhaust gases to generate thrust. Rocket engines include components such as combustion chambers, nozzles, propellant tanks, and turbopumps.

Avionics Systems: Avionics systems refer to the electronic systems used in aircraft for navigation, communication, flight control, and monitoring. They include devices such as flight computers, navigation systems (GPS), radar systems, communication systems, autopilots, and cockpit displays.

Aircraft Engines: Aircraft engines provide the necessary thrust to propel aircraft through the air. They include various types such as turbojet engines, turboprop engines, turbofan engines, and turboshaft engines. Aircraft engines are complex devices comprising components such as combustion chambers, turbines, compressors, and fuel systems.

Control Systems: Aerospace control systems are crucial for maneuvering, stability, and control of aircraft and spacecraft. They include flight control surfaces, such as ailerons, elevators, and rudders, as well as systems like fly-by-wire, autopilots, and attitude control thrusters for spacecraft.

Satellite Systems: Satellite systems consist of components and devices used for communication, navigation, remote sensing, and scientific research. They include satellite buses (platforms), payloads (instruments), antennas, solar panels, attitude control systems, and telemetry systems.

Parachutes: Parachutes are devices used for deceleration and landing of aircraft, spacecraft, or payloads. They are crucial for safe re-entry and recovery of crewed spacecraft, as well as for cargo or personnel airdrops.

Ground Support Equipment: Ground support equipment refers to the devices used on the ground to support aerospace operations. Examples include aircraft ground handling equipment, such as tugs, loaders, and fueling systems, as well as launch pad equipment for space-craft, such as umbilical towers, gantries, and fueling systems.

Flight Simulators: Flight simulators are devices used for pilot training, aircraft system testing, and research. They provide a simulated environment that replicates the experience of flying an aircraft, including the cock-pit controls, instruments, and visual displays.

These are just a few examples of aerospace devices, and the aerospace industry encompasses a vast array of tech-nologies and equipment. The development and utilization of these devices enable advancements in aviation, space explo-ration, satellite communication, and scientific research.

Examples of forestry devices may include but are not limited to specialized tools, equipment, and machinery used in the field of forestry for various tasks related to the management, harvesting, and processing of trees and forests. These devices are designed to improve efficiency, safety, and productivity in forestry operations. They are used by forest-ers, loggers, and other professionals involved in forest management and timber production.

Examples of forestry devices may include but are not limited to:

Chainsaws: Chainsaws are portable mechanical saws powered by either electricity, gasoline, or battery. They are used for felling trees, limbing, bucking (cutting felled trees into logs), and other tree-cutting operations in the forest.

Harvesters: Harvesters are specialized forestry machines designed for felling, delimbing, and processing trees in a single operation. They can fell, strip branches, and cut trees into logs, significantly reducing manual labor and increasing productivity.

Forwarders: Forwarders are purpose-built vehicles used to transport logs and other forest products from the cutting site to a central location, typically a log landing or a roadside collection point. They have a loading area and a crane for lifting and loading logs onto the vehicle.

Skidders: Skidders are heavy-duty machines used to extract logs from the forest and drag them to a landing or a loading area. They have large grapple arms or winches to grip and lift logs for transportation.

Logging Trucks: Logging trucks are specialized trucks used to transport logs from the forest to sawmills or other processing facilities. They are designed with trailers and secure load-holding structures to transport logs safely and efficiently.

Mulchers: Mulchers are machines used to clear vegeta-tion, shrubs, and small trees in forestry operations. They are equipped with rotating blades or hammers that shred vegetation, enabling land clearing and site prepa-ration.

Portable Sawmills: Portable sawmills are compact and transportable machines used for on-site processing of logs into lumber. They allow for immediate sawing of felled trees, reducing transportation costs and time to the sawmill.

Chippers: Chippers are devices used to process tree branches, limbs, and other forestry residues into wood chips. Wood chips are used for various purposes, including fuel, landscaping, and the production of pulp and paper.

Tree Planters: Tree planters are devices used for efficient tree planting in reforestation and afforestation projects. They can dig holes, place seedlings, and cover them with soil, improving the speed and accuracy of tree planting operations.

Forest Firefighting Equipment: Forest firefighting equip-ment includes devices like fire pumps, hoses, and fire suppression tools used to combat and control forest fires. They are crucial for protecting forests and mini-mizing the damage caused by wildfires.

These are just a few examples of forestry devices, and the specific devices used may vary depending on factors such as the type of forestry operation, terrain, tree species, and regional practices. Forestry devices play a vital role in sustainable forest management, timber production, and envi-ronmental conservation.

Examples of defense devices (also known as military devices or weapons systems) may include but are not limited to specialized equipment, technologies, and systems designed and utilized by military forces for defense and security purposes. These devices are designed to protect a country's interests, deter potential threats, and ensure the safety of military personnel and civilians. Defense devices encompass a wide range of technologies and equipment used for various defense applications.

Examples of defense devices may include but are not limited to:

Firearms: Firearms include various handheld weapons designed to launch projectiles using the force of expanding high-pressure gases. They encompass rifles, pistols, machine guns, and shotguns, which are used by military personnel for individual combat or close-quarters engagements.

Artillery: Artillery devices are heavy guns or cannons used for long-range indirect fire support. They can fire explosive projectiles or provide suppressive fire. Examples include howitzers, mortars, and rocket launchers.

Missiles: Missiles are self-propelled weapons that can be guided to specific targets. They can be launched from ground-based systems, ships, submarines, aircraft, or launched from portable platforms. Missiles include surface-to-air missiles (SAMs), surface-to-surface mis-siles (SSMs), anti-ship missiles, and air-to-air missiles (AAMs).

Tanks: Tanks are heavily armored tracked vehicles equipped with powerful cannons. They are used for ground combat and provide offensive and defensive capabilities on the battlefield. Tanks combine fire-power, mobility, and protection.

Fighter Aircraft: Fighter aircraft are high-performance military aircraft designed for air-to-air combat and ground attack missions. They are equipped with advanced avionics, radar systems, missiles, and guns for air superiority and tactical strikes.

Warships: Warships include naval vessels designed for combat operations at sea. They range from aircraft carriers, destroyers, and frigates to submarines and patrol boats. Warships are equipped with various weapon systems, including missiles, naval guns, torpedoes, and anti-aircraft systems.

Unmanned Aerial Vehicles (UAVs): UAVs, also known as drones, are remotely piloted or autonomous aircraft used for reconnaissance, surveillance, and targeted strikes. They provide real-time intelligence and can be armed with missiles or bombs.

Electronic Warfare Systems: Electronic warfare devices encompass a range of systems used to detect, deceive, disrupt, and counter enemy electronic systems. They include radar jammers, signal intelligence equipment, electronic countermeasures, and defensive systems to protect against cyber threats.

Ballistic Missile Defense Systems: Ballistic missile defense devices are designed to detect, track, and intercept incoming ballistic missiles. These systems employ sensors, radars, interceptor missiles, and command and control systems to protect against missile threats.

Protective Gear: Protective gear includes devices such as body armor, helmets, gas masks, and protective clothing worn by military personnel to provide protection against physical, ballistic, and chemical threats in combat situations.

These are just a few examples of defense devices. The defense industry is highly advanced and continuously evolving, driven by technological advancements and strategic needs. It encompasses a vast array of devices and systems tailored to meet the specific requirements of modern military forces.

Information process 10 may normalize 104 the data signals (e.g., data signals 200 and/or data signals 204) to generate a plurality of homogenized signals (e.g., data signals 200' and/or data signals 204') so that the data signals (e.g., data signals 200 and/or data signals 204) can work together.

For example and when normalizing data, information process 10 may transform data into a standardized format or range, which may involve adjusting the values of a dataset to a common scale, typically between 0 and 1 or −1 and 1, wherein the goal of data normalization is to eliminate the effects of varying scales, units, or distributions within the data, allowing for fairer comparisons and more accurate analysis.

Normalization is particularly useful when working with datasets that have different measurement units or widely varying ranges. By bringing all the data to a common scale, normalization enables meaningful comparisons and helps algorithms or models to better interpret and process the data, as it may prevent certain features from dominating the analysis or introducing bias due to their larger magnitude.

Examples of methods of normalizing data may include but are not limited to:

Min-Max Normalization (also known as feature scaling): This method scales the data linearly to a specific range, often between 0 and 1. It involves subtracting the minimum value of the feature and then dividing by the range (i.e., the difference between the maximum and minimum values). The formula for Min−Max normalization is: $normalized\_value = (x - min(x))/(max(x) - min(x))$ Z-Score Normalization (also known as standardization): This method transforms the data to have a mean of 0 and a standard deviation of 1. It involves subtracting the mean value of the feature and dividing by the standard deviation. The formula for Z-Score normalization is: $normalized\_value = (x - mean(x))/standard\_deviation(x)$ Decimal Scaling: In this method, the data is scaled by shifting the decimal point of each value. The number of decimal places to shift is determined based on the maximum absolute value in the dataset.

For example and when normalizing 104 the data signals (e.g., data signals 200 and/or data signals 204) to generate a plurality of homogenized signals (e.g., data signals 200' and/or data signals 204') so that the data signals (e.g., data signals 200 and/or data signals 204) can work together, information process 10 may: rescale 106 the data signals (e.g., data signals 200 and/or data signals 204); and/or rebase 108 the data signals (e.g., data signals 200 and/or data signals 204).

Rescaling data refers to the process of changing the scale or range of values in a dataset without necessarily transforming them into a specific standardized format. Unlike normalization, which typically aims to bring the data into a common scale, rescaling allows for adjustments that can be tailored to specific requirements or preferences. The goal of rescaling data is to manipulate the values in a way that preserves the relationships and distribution of the original data while fitting them into a desired range or scale. This can be useful for various reasons, such as enhancing visualization, improving algorithm performance, or accommodating specific constraints or preferences.

Examples of rescaling methods may include but are not limited to:

Min−Max Rescaling: Similar to min-max normalization, min-max rescaling scales the data to a specific range, often between 0 and 1 or any other desired minimum and maximum values. It involves subtracting the minimum value of the feature and then dividing by the range (i.e., the difference between the maximum and minimum values). The formula for min-max rescaling is the same as in normalization: $rescaled\_value = (x - min(x))/(max(x) - min(x))$ Feature Scaling: Feature scaling rescales each feature (column) in a dataset independently, without considering the range of the entire dataset. It can be done using various methods, such as standardization (Z-score normalization), range scaling, or decimal scaling.

Logarithmic Rescaling: Logarithmic rescaling involves applying a logarithmic function to the data values. This transformation can compress the scale of large values while expanding the scale of small values. Logarithmic rescaling is often useful when dealing with data that spans several orders of magnitude or has a skewed distribution.

Power Rescaling: Power rescaling applies a power function to the data values. It can be useful for adjusting the scale of values that are disproportionately large or small. By raising the values to a power, such as squaring or taking the square root, the scale can be modified accordingly.

Rescaling data allows for flexible adjustments to meet specific needs or preferences. However, it's important to note that rescaling does not necessarily eliminate the differences in distribution or units of measurement among features. The choice of rescaling method should be based on the characteristics of the data and the objectives of the analysis or modeling task.

Rebasing data refers to the process of recalculating or adjusting the values of a dataset with respect to a new base or reference point. It involves shifting the entire dataset by a certain amount or percentage to establish a different baseline or starting point for the data. The purpose of rebasing data is often to facilitate comparisons, identify trends, or analyze changes relative to a specific reference point. By rebasing the data, you can normalize it with respect to a chosen base and evaluate the relative changes or growth rates in the values.

The rebasing process may involve the following steps:

Selecting a Base Period: Choose a specific time period or reference point that will serve as the new base or starting point for the data. This period is often set to a specific date, such as the beginning of a year or a particular milestone.

Calculating the Rebased Values: Subtract or adjust the original values of the dataset by the difference between the chosen base period and the original base period. This adjustment aligns the data with the new base period and establishes the rebased values.

Expressing Rebased Values: Express the rebased values as indices or ratios relative to the base period. For example, if the base period has a rebased value of 100, other periods' values will be expressed relative to that base (e.g., 105 means a 5% increase from the base).

Rebasing can be useful in various scenarios, such as financial analysis, economic indicators, or market indices. It allows for a clearer understanding of relative changes over time and facilitates comparisons across different periods or entities.

As discussed above, information process 10 may be utilized to function as an intermediary between devices that are offered by multiple vendors, wherein information process 10 may be configured to effectuate communication between devices produced by different vendors. Accordingly and by performing the operations discussed aboe (e.g., normalizing, rescaling, rebasing), the various devices can now exchange information. Accordingly, information in the form of homogenized signals (e.g., data signals 200' and/or data signals 204') may be exchanged: between devices (e.g., first vendor devices 202 and/or second vendor devices 206), from devices (e.g., first vendor devices 202 and/or second vendor devices 206) to information process 10, and from information process 10 to devices (e.g., first vendor devices 202 and/or second vendor devices 206); thus enabling the free exchange of information/data, the remote control of such devices (e.g., first vendor devices 202 and/or second vendor devices 206), the remote adjustment of such devices (e.g., first vendor devices 202 and/or second vendor devices 206), and the remote configuration of such devices (e.g., first vendor devices 202 and/or second vendor devices 206).

Information process 10 may provide 110 the plurality of homogenized signals (e.g., data signals 200' and/or data signals 204') to a post processing system (e.g., post processing system 218).

A post-processing system (e.g., post processing system 218) refers to a set of activities, tools, or techniques that are applied to data or output after an initial process or operation has taken place. It involves analyzing, refining, and enhancing the data or results obtained from a primary process to derive additional insights or improve the quality and usability of the output.

Post-processing systems (e.g., post processing system 218) are commonly used in various fields, including scientific research, engineering, computer graphics, data analysis, and more. They are designed to perform tasks such as data filtering, noise reduction, data visualization, data integration, feature extraction, data transformation, and result interpretation.

Examples of post-processing systems may include but are not limited to:

Image and Video Processing: In image and video processing, post-processing systems are employed to enhance the quality, remove noise or artifacts, adjust brightness or contrast, apply filters or effects, and perform image or video stabilization. These systems help to improve visual perception, extract meaningful information, or prepare the data for further analysis or presentation.

Signal Processing: Post-processing systems in signal processing deal with analyzing and modifying signals obtained from various sources. They can involve techniques like noise filtering, frequency analysis, feature extraction, signal denoising, signal reconstruction, or signal normalization. These systems help to improve the accuracy, reliability, or interpretability of signals.

Computational Modeling and Simulation: Post-processing systems are used to analyze and interpret the results obtained from computational models and simulations. They involve tasks like data visualization, data analysis, statistical analysis, identifying trends or patterns, and extracting meaningful insights from the simulation outputs. These systems aid in understanding the behavior, performance, or impact of the modeled system or phenomenon.

Data Analysis and Machine Learning: In data analysis and machine learning, post-processing systems are employed to refine and interpret the results obtained from data mining, statistical analysis, or machine learning algorithms. They can involve tasks such as data visualization, outlier detection, error correction, feature selection, result validation, or model interpretation. These systems help to extract valuable knowledge, validate the findings, or make the results more understandable and actionable.

Natural Language Processing: Post-processing systems in natural language processing deal with refining and improving the output generated by language processing algorithms. They can involve tasks like grammatical error correction, language translation, sentiment analysis, information extraction, or summarization. These systems aim to enhance the accuracy, fluency, or coherence of the processed text.

Overall, post-processing systems (e.g., post processing system 218) play a crucial role in refining, enhancing, and interpreting the results obtained from various processes or algorithms. They contribute to improving the quality, usability, and understanding of the data or output, leading to more meaningful insights and informed decision-making.

Information process 10 may provide 112 the plurality of homogenized signals (e.g., data signals 200' and/or data signals 204') to a display system (e.g., display system 220).

A display system (e.g., display system 220) refers to a combination of hardware and software components designed to present visual information or output to users. It encompasses various devices and technologies used to display images, text, graphics, videos, or other visual content for human perception.

Display systems (e.g., display system 220) are widely used in a variety of applications, including computer systems, consumer electronics, entertainment, information display, medical imaging, advertising, and more. They provide a means to visually communicate information, enhance user experience, and facilitate interaction with digital content.

Examples of display systems may include but are not limited to:

Monitors: Monitors are the most common type of display system used in computers, laptops, and other electronic devices. They typically use liquid crystal display (LCD), light-emitting diode (LED), or organic light-emitting diode (OLED) technologies to present visual content on a flat screen.

Projectors: Projectors are display systems that project images or video onto a large screen or surface. They use light sources and optical systems to enlarge and project the content onto a surface for viewing by a larger audience. Projectors are commonly used in classrooms, conference rooms, theaters, and home entertainment systems.

Televisions: Televisions (TVs) are display systems specifically designed for broadcasting television programs and other video content. They come in various sizes and technologies, such as LCD, LED, OLED, or plasma, and often include additional features like smart capabilities and connectivity options.

Head-Mounted Displays (HMDs): HMDs are wearable display systems that immerse the user in a virtual or augmented reality environment. They typically consist of a headset or glasses with integrated display screens, sensors, and audio systems. HMDs are used in gaming, simulations, training, and other immersive experiences.

Digital Signage: Digital signage refers to display systems used for advertising, information dissemination, or wayfinding in public spaces, retail stores, transportation hubs, and other locations. These systems typically consist of large display panels or screens that can present dynamic content, including text, images, videos, and interactive elements.

Touchscreens: Touchscreen displays combine visual output with interactive input capabilities. They allow users to interact with the displayed content by directly touching the screen. Touchscreens are used in smartphones, tablets, kiosks, interactive displays, and other devices that require user input.

Wearable Displays: Wearable displays are integrated into wearable devices like smartwatches, fitness trackers, and smart glasses. They provide users with visual feedback, notifications, and information in a compact and portable form factor.

Display systems (e.g., display system 220) may also include additional features such as high-definition (HD) or 4K resolution, high refresh rates for smooth motion, color calibration, adjustable settings, and connectivity options to connect to various devices or networks.

Overall, display systems (e.g., display system 220) are essential components of modern technology, enabling the visual presentation of information and content in various applications, from personal devices to large-scale displays for public viewing.

Information process 10 may provide 114 the plurality of homogenized signals (e.g., data signals 200' and/or data signals 204') to a notification system (e.g., notification system 222).

A notification system (e.g., notification system 222) refers to a set of processes, tools, and technologies used to deliver alerts, messages, or updates to users or recipients. It enables the dissemination of information in a timely manner, ensuring that individuals are promptly notified about important events, changes, or actions that require their attention.

Notification systems (e.g., notification system 222) are commonly used in a wide range of contexts, including communication platforms, mobile applications, web services, enterprise systems, and more. They provide a means to notify users about various types of events, such as new messages, system status updates, reminders, alarms, security alerts, or workflow notifications.

Some key components and features of a notification system may include but are not limited to:

Trigger: A notification system is triggered by a specific event or condition that requires user awareness or action. Triggers can include incoming messages, updates to a system, time-based events, user interactions, data changes, or predefined rules.

Delivery Channels: Notification systems utilize various delivery channels to reach users effectively. These channels can include mobile push notifications, email, SMS text messages, in-app messages, pop-up alerts, browser notifications, voice calls, or even physical devices like pagers or smartwatches.

Personalization and Targeting: Notification systems often allow for personalization and targeting of notifications to specific users or user groups. This ensures that notifications are relevant to the recipient's preferences, interests, or context, increasing their effectiveness and reducing unnecessary noise.

Prioritization and Urgency: Notifications can be prioritized based on their importance or urgency. Critical alerts may require immediate attention, while less important notifications can be scheduled or displayed in a less intrusive manner.

Customization and Preferences: Users often have the ability to customize their notification preferences, including the types of events they want to be notified about, the delivery channels they prefer, and the frequency or timing of notifications. Customization options help users tailor the notification system to their specific needs and avoid notification overload.

Logging and History: Notification systems may maintain a log or history of sent notifications for reference or auditing purposes. This can include details such as the content, delivery time, recipient, and status of each notification.

Feedback and Interaction: Some notification systems allow users to interact with notifications, providing options to acknowledge, dismiss, or take action directly from the notification itself. This enhances user engagement and facilitates seamless workflows.

Notification systems (e.g., notification system 222) play a crucial role in keeping users informed, engaged, and up-to-date with relevant information. They are utilized in various domains, including messaging apps, social media platforms, customer support systems, IT infrastructure monitoring, task management tools, and more. The effectiveness of a notification system depends on careful design, appropriate targeting, and respect for user preferences and privacy.

Patient Onboarding Process to Establish Patient Norms:

The following discussion concerns the manner in which information process 10 may be utilized to establish norms for a patient while onboarding the patient within a hospital. As is often the case, when a patient is initially connected to e.g., various monitoring devices within a hospital room, it may be initially unclear as to where a patient's vital signs should be (e.g., What is their normal heart rate? What is their normal respiratory rate? What is their normal blood pressure? etc.). Accordingly and as will be discussed below, information process 10 may be configured to streamline such an onboarding process.

Figure 4:
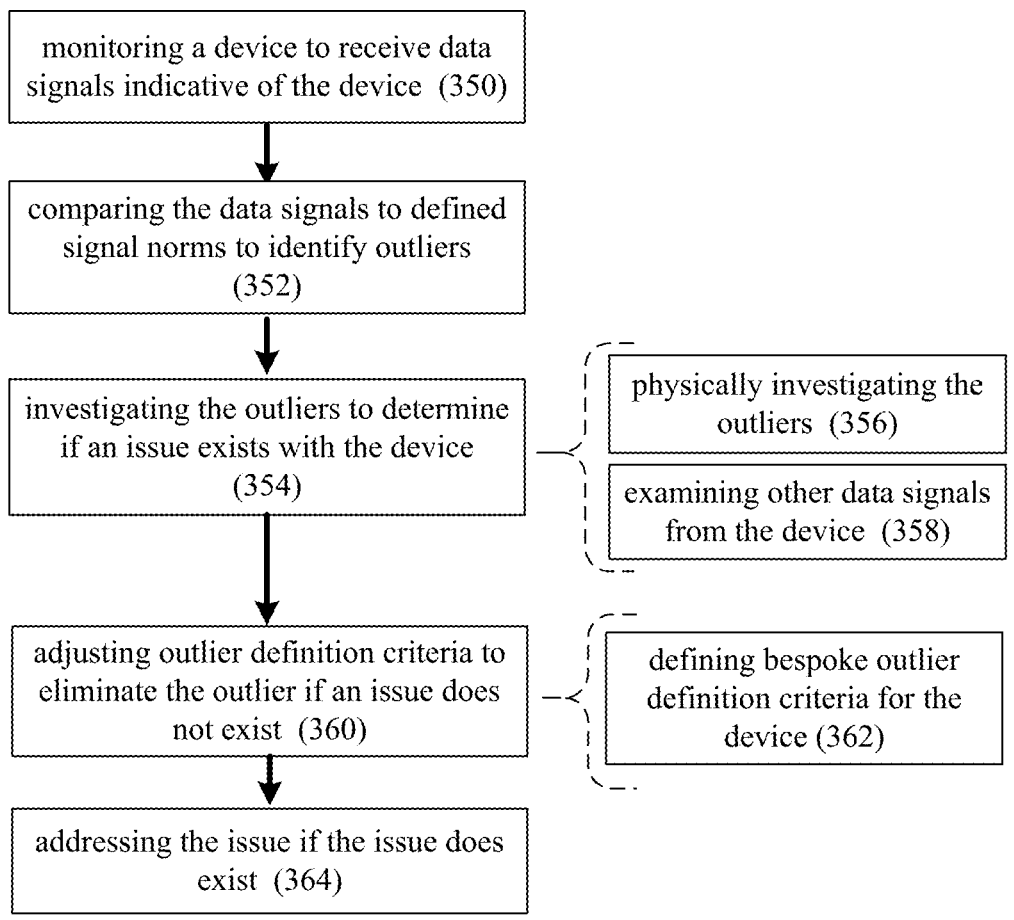
FIG. 4 is another flowchart of the information process of FIG. 1 according to an embodiment of the present disclosure.

Referring also to FIG. 4, information process 10 may monitor 350 a device (e.g., one or more of first vendor devices 202 and/or one or more of second vendor devices

206) to receive data signals (e.g., one or more of data signals 200 and/or one or more of data signals 204) indicative of the device (e.g., one or more of first vendor devices 202 and/or one or more of second vendor devices 206).

The data signals (e.g., one or more of data signals 200 and/or one or more of data signals 204) may concern one or more details of the device (e.g., one or more of first vendor devices 202 and/or one or more of second vendor devices 206) and/or uses of the device (e.g., one or more of first vendor devices 202 and/or one or more of second vendor devices 206).

Device Details: One or more details of the device (e.g., one or more of first vendor devices 202 and/or one or more of second vendor devices 206) may concern one or more readings, signals and/or alarms that are provided by the device and concern (in the example) the vital signs of a patient.

Device Uses: One or more uses of the device (e.g., one or more of first vendor devices 202 and/or one or more of second vendor devices 206) may concern the manner in which the device is being used (e.g., what is the device doing, what is the device being used for, who is the device assigned/connected to, etc.).

As discussed above, the device (e.g., one or more of first vendor devices 202 and/or one or more of second vendor devices 206) may include one or more of: a medical device, a process control device, a networking device, a computing device, a manufacturing device, an agricultural device, an energy/refining device, an aerospace device, a forestry device, and a defense device.

One or more of the devices (e.g., one or more of first vendor devices 202 and/or one or more of second vendor devices 206) may include one or more sub devices (e.g., sub devices 224, 226). Examples of such sub devices (e.g., sub devices 224, 226) may include any subordinate device that depends upon and/or interacts with a superior device. For example, a subordinate wireless blood gas monitor (e.g., sub device 224) and/or a subordinate wireless heart rate monitor (e.g., sub devices 226) may depend upon and/or interact with superior client vital sign monitoring device (e.g., first vendor device 202).

Information process 10 may compare 352 the data signals (e.g., one or more of data signals 200 and/or one or more of data signals 204) to defined signal norms (e.g., defined signal norms 228) to identify outliers (e.g., outliers 230).

In statistics, an outlier (e.g., outliers 230) is an observation or data point that significantly deviates from the other observations in a dataset. It is a value that lies an abnormal distance away from other data points and may be indicative of a rare or unusual occurrence, measurement error, or data entry mistake. Outliers can arise due to various reasons, such as natural variability, measurement errors, data corruption, or extreme events. Outliers can have a disproportionate impact on statistical analyses, leading to skewed results or inaccurate conclusions if not properly handled. Identifying and handling outliers is an important step in data analysis and statistical modeling. Outliers can be detected through various methods, including graphical techniques (e.g., scatter plots, box plots) or statistical tests (e.g., z-scores, modified z-scores, Mahalanobis distance).

For example, assume that the data signals (e.g., one or more of data signals 200 and/or one or more of data signals 204) concern the heart rate and respiratory rate of a patient (e.g., patient 232). Further, assuming that the patient (e.g., patient 232) is a 50-year-old male of average health, the defined signal norms (e.g., defined signal norms 228) would be a heart rate of 60-100 beats per minute and a respiratory rate of 12-20 breaths per minute. Accordingly, an outlier (e.g., outliers 230) may be a data signal (e.g., one or more of data signals 200 and/or one or more of data signals 204) that is above or below these defined signal norms (e.g., defined signal norms 228). So a heart rate of <60 beats per minute or >100 beats per minute may be considered outliers (e.g., outliers 230). Further, a respiratory rate of <12 breaths per minute or >20 breaths per minute may be considered outliers (e.g., outliers 230).

Additionally/alternatively, such defined signal norms (e.g., defined signal norms 228) may be more bespoke and individualized. So while the defined signal norms (e.g., defined signal norms 228) for a heart rate is 60-100 beats per minute and a respiratory rate is 12-20 breaths per minute; if the patient (e.g., patient 232) is a seasoned athlete of exceptional health, their "normal" heartrate may be 50-55 beats per minute and their "normal" respiratory rate may be 9-11 breaths per minute. Accordingly and in such a situation, the individual "norms" of the patient (e.g., patient 232) would consistently be outliers (e.g., outliers 230) if the societal heartrate norms and respiratory rate norms were applied to patient 232.

These defined signal norms (e.g., defined signal norms 228) may include user-defined signal norms and/or machine-defined signal norms. For example and with respect to user-defined signal norms, such user-defined signal norms may be the result of (in this example) medical studies, medical books, insurance charts, medical records, etc. Further and with respect to machine-defined signal norms, such machine-defined signal norms may be defined via massive data sets that are processed by machine learning.

As is known in the art, a massive dataset, also referred to as a large-scale dataset or big dataset, is a collection of data that is exceptionally large in size and complexity. These datasets typically exceed the capacity of traditional data processing and analysis tools, requiring specialized approaches and infrastructure to handle and extract insights from them effectively.

The term "massive" is relative and can vary depending on the context and available resources. The size of a massive dataset can range from terabytes (1012 bytes) to petabytes (1015 bytes) or even exabytes (1018 bytes) and beyond. Massive datasets can arise from various sources and domains, including scientific research, social media, e-commerce, financial transactions, sensor networks, genomics, astronomy, and more. They often contain a high volume of records, measurements, or observations, along with diverse data types such as text, images, videos, time series, graphs, or unstructured data.

Working with massive datasets poses several challenges, including storage, processing, analysis, and scalability. Traditional methods and tools may not be sufficient to handle these datasets efficiently. Specialized technologies and techniques, such as distributed computing, parallel processing, cloud computing, and big data frameworks (e.g., Apache Hadoop, Apache Spark), are often employed to manage and process the data at scale.

The analysis of massive datasets aims to extract meaningful insights, patterns, correlations, or trends from the vast amount of available data. This process involves data preprocessing, cleansing, transformation, statistical analysis, machine learning, data visualization, and other techniques tailored to handle the specific challenges of large-scale data. The insights derived from massive datasets can have significant implications in various domains, including scientific discoveries, business intelligence, personalized recommendations, predictive analytics, fraud detection, and infrastructure optimization. It's worth noting that the term "massive dataset" is often used interchangeably with terms like "big data" or "large-scale data." While there is no strict definition for these terms, they generally refer to datasets that exceed the capabilities of conventional data processing methods and require specialized approaches for storage, management, and analysis.

As is known in the art, machine learning (ML) is a subfield of artificial intelligence (AI) that focuses on the development of algorithms and models that enable computers to learn from and make predictions or decisions based on data, without being explicitly programmed. It involves the use of statistical techniques and computational algorithms to identify patterns, extract insights, and make predictions or decisions from the available data.

Machine learning algorithms are designed to automatically learn and improve from experience or examples, allowing them to adapt to new data and make accurate predictions or decisions. These algorithms can be broadly categorized into three main types:

Supervised Learning: In supervised learning, the machine learning algorithm learns from a labeled dataset, where each data instance is associated with a known target or outcome. The algorithm learns to generalize from the labeled examples and make predictions on new, unseen data. Examples of supervised learning algorithms include linear regression, decision trees, support vector machines (SVM), and neural networks.

Unsupervised Learning: In unsupervised learning, the machine learning algorithm explores the underlying structure or patterns in the dataset without explicit labels or targets. It aims to discover hidden patterns, clusters, or associations in the data. Unsupervised learning algorithms include clustering algorithms (e.g., k-means, hierarchical clustering) and dimensionality reduction techniques (e.g., principal component analysis, t-SNE).

Reinforcement Learning: Reinforcement learning involves an agent that learns to interact with an environment and make decisions based on trial and error. The agent learns through feedback in the form of rewards or penalties, guiding it to optimize its actions and maximize its cumulative reward over time. Reinforcement learning algorithms are commonly used in robotics, gaming, and control systems.

Machine learning algorithms and models play a crucial role in processing massive datasets. As datasets grow in size, traditional data processing and analysis methods may become impractical or infeasible. Machine learning offers scalable and automated approaches to handle and extract insights from massive datasets.

Machine learning algorithms can handle large-scale datasets by leveraging distributed computing and parallel processing techniques. Technologies like Apache Spark, Hadoop, and GPU acceleration enable the efficient processing and analysis of massive datasets. Machine learning models can be trained on subsets of the data in parallel or distributed across multiple computing resources to accelerate the learning process. Furthermore, machine learning techniques are designed to identify patterns, relationships, and dependencies in the data, allowing them to capture complex interactions and make predictions or decisions based on the patterns learned from the massive dataset. By learning from the data, machine learning models can handle the high dimensionality, variability, and complexity often present in massive datasets.

Such defined signal norms (e.g., defined signal norms 228) may be compartmentalized by e.g., gender, race, age, location, device type, device class, seasonality, time of day, etc. Specifically, medical statistics may vary depending upon various factors (including gender, race, age, location, device type, device class, seasonality, and time of day), wherein these factors can influence health outcomes, disease prevalence, treatment response, and other medical parameters.

For example and with respect to such factors:

Gender: Biological differences between males and females can lead to variations in health conditions, disease incidence, treatment responses, and outcomes. For example, certain diseases or conditions may predominantly affect one gender more than the other.

Race: Different racial and ethnic groups can exhibit variations in disease prevalence, genetic factors, response to treatments, and healthcare disparities. These differences can contribute to variations in medical statistics among different racial and ethnic populations.

Age: Medical statistics often vary across different age groups. Certain diseases or conditions may be more common or have different manifestations in specific age brackets, such as pediatric or geriatric populations.

Location: Geographical location can impact medical statistics due to differences in environmental factors, access to healthcare, lifestyle choices, genetic variations, and regional disease patterns. For example, certain diseases may be more prevalent in specific regions or countries.

Device Type and Device Class: In medical research and statistics, different types and classes of devices can have varying performance, efficacy, safety profiles, and outcomes. The characteristics and use of specific medical devices can influence medical statistics related to their effectiveness, complications, and patient outcomes.

Seasonality: Some medical conditions or diseases exhibit seasonal patterns. For instance, respiratory illnesses like influenza may be more prevalent during certain seasons. Seasonal variations can affect medical statistics related to disease incidence, hospitalizations, and mortality rates.

Time of Day: Physiological parameters and disease symptoms can vary throughout the day. For example, blood pressure and heart rate can fluctuate depending on circadian rhythms. Time of day can influence medical statistics related to monitoring vital signs or evaluating symptoms at different time points.

Further, this list of factors is not intended to be exhaustive, and there may be other factors specific to certain medical conditions or studies that can contribute to variations in medical statistics. Additionally, there may be a historical component to such defined signal norms (e.g., defined signal norms 228), wherein historical norms across different recent timespans have varying implications (i.e. last 15 mins vs. last 6 hours). For example, the historical norm for a patient admitted for extreme hypertension may have a very high systolic/diastolic pressure readings when the patient is first admitted . . . but may have much lower systolic/diastolic pressure readings the following day or week.

Information process 10 may investigate 354 the outliers (e.g., outliers 230) to determine if an issue exists with the device (e.g., one or more of first vendor devices 202 and/or one or more of second vendor devices 206). For example, information process 10 may investigate 354 the outliers (e.g., outliers 230) to determine if: the outliers (e.g., outliers 230) are inaccurate (e.g., due to a malfunctioning device); the outliers (e.g., outliers 230) are accurate but the patient (e.g., patient 232) is not experiencing an issue (e.g., due to the patients "norms" being outside of societal "norms"); and the outliers (e.g., outliers 230) are accurate and the patient (e.g., patient 232) is experiencing an issue.

For example and when investigating 354 the outliers (e.g., outliers 230) to determine if an issue exists with the device (e.g., one or more of first vendor devices 202 and/or one or more of second vendor devices 206), information process 10 may physically investigate 356 the outliers (e.g., outliers 230). For example, information process 10 may request that e.g., a nurse assigned to patient 232 physically investigate 356 the outliers (e.g., outliers 230) by visiting the room of patient 232 to e.g., confirm the proper operation of the device (e.g., one or more of first vendor devices 202 and/or one or more of second vendor devices 206) and/or to confirm that the patient (e.g., patient 232) is not experiencing a medical issue (e.g., a low/high heart rate and/or a low/high respiratory rate).

Additionally/alternatively and when investigating 354 the outliers (e.g., outliers 230) to determine if an issue exists with the device (e.g., one or more of first vendor devices 202 and/or one or more of second vendor devices 206), information process 10 may examine 358 other data signals from the device (e.g., one or more of first vendor devices 202 and/or one or more of second vendor devices 206). Often times, when a patient is experiencing a medical issue, multiple events may occur. For example, if the patient (e.g., patient 232) is experiencing a respiratory medical issue, a reduced heart rate may be accompanied by an elevated respiratory rate or a reduced blood gas saturation. So in the event that the outlier for patient 232 is a reduced heart rate, information process 10 may examine 358 other data signals (e.g., respiratory rate and/or blood gas saturation) from the device (e.g., one or more of first vendor devices 202 and/or one or more of second vendor devices 206) to determine if an issue exists. Therefore, if the other data signals (e.g., respiratory rate and/or blood gas saturation) from the device are normal, information process 10 may determine that an issue does not exist (e.g., patient 322 is not having a medical issue).

Information process 10 may adjust 360 outlier definition criteria to eliminate the outlier (e.g., outliers 230) if an issue does not exist. As discussed above, if the patient (e.g., patient 232) is a seasoned athlete of exceptional health, their "normal" heartrate may be 50-55 beats per minute and their "normal" respiratory rate may be 9-11 breaths per minute. Accordingly and in such a situation, the individual "norms" of the patient (e.g., patient 232) would consistently be outliers (e.g., outliers 230) if the societal heartrate norms and respiratory rate norms were applied to patient 232. Accordingly, information process 10 may adjust 360 outlier definition criteria to eliminate the outlier (e.g., outliers 230) if an issue does not exist, wherein this outlier definition criteria may include signal thresholds.

As discussed above, while the defined signal norms (e.g., defined signal norms 228) for a heart rate is 60-100 beats per minute and a respiratory rate is 12-20 breaths per minute, information process 10 may adjust 360 outlier definition criteria to eliminate the outlier (e.g., outliers 230) if an issue does not exist.

For example and when adjusting 360 the outlier definition criteria, information process 10 may define 362 bespoke outlier definition criteria for the device (e.g., one or more of first vendor devices 202 and/or one or more of second vendor devices 206). Continuing with the above-stated example, being the "normal" heartrate of patient 232 is 50-55 beats per minute and the "normal" respiratory rate is 9-11 breaths per minute, information process 10 may adjust 360 the lower range of the heart rate to 48 beats per minute and may adjust 360 the lower range of the respiratory rate to 8 breaths per minute . . . , thus eliminating the outlier (e.g., outliers 230).

Conversely and if an issue does exist with patient 232, information process 10 may address 364 the issue. Accordingly and if patient 232 is in respiratory distress, information process 10 may e.g., notify a doctor, make an emergency announcement, notify medical staff, etc.

Establishing Norms for a Device:

The following discussion concerns the manner in which information process 10 may be utilized to establish norms for a specific patient over a defined period of time. For example and when onboarding a patient within a hospital, generalized norms (as discussed above) may be utilized. However and as is often the case, societal norms may not be applicable to a specific individual. So while societal norms may be initially utilized, they may prove to be inapplicable over time on an individual basis.

Figure 5:
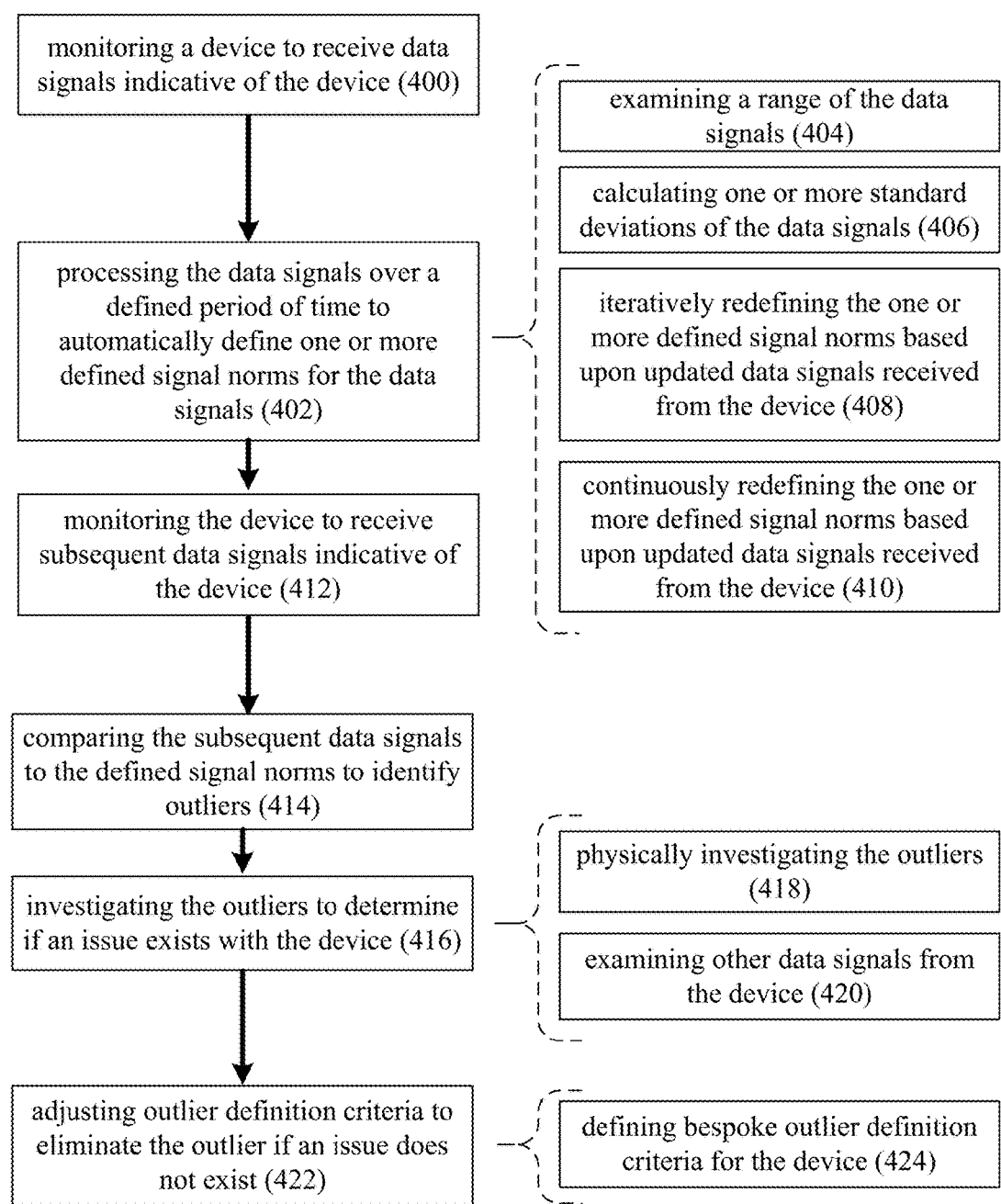
FIG. 5 is another flowchart of the information process of FIG. 1 according to an embodiment of the present disclosure.

Referring also to FIG. 5 and as discussed above, information process 10 may monitor 400 a device (e.g., one or more of first vendor devices 202 and/or one or more of second vendor devices 206) to receive data signals (e.g., one or more of data signals 200 and/or one or more of data signals 204) indicative of the device (e.g., one or more of first vendor devices 202 and/or one or more of second vendor devices 206), wherein the data signals (e.g., one or more of data signals 200 and/or one or more of data signals 204) may concern one or more details of the device (e.g., one or more of first vendor devices 202 and/or one or more of second vendor devices 206) and/or uses of the device (e.g., one or more of first vendor devices 202 and/or one or more of second vendor devices 206).

As discussed above, the device (e.g., one or more of first vendor devices 202 and/or one or more of second vendor devices 206) may include one or more of: a medical device, a process control device, a networking device, a computing device, a manufacturing device, an agricultural device, an energy/refining device, an aerospace device, a forestry device, and a defense device. Further and as discussed above, the device (e.g., one or more of first vendor devices 202 and/or one or more of second vendor devices 206) may include one or more sub devices (e.g., sub devices 224, 226).

Information process 10 may process 402 the data signals (e.g., one or more of data signals 200 and/or one or more of data signals 204) over a defined period of time to automatically define one or more defined signal norms for the data signals (e.g., one or more of data signals 200 and/or one or more of data signals 204). As discussed above, when onboarding a patient (e.g., patient 232) within a hospital, generalized norms (e.g., societal norms) may be utilized. However and as also discussed above, these generalized norms (e.g., societal norms) are often inapplicable with respect specific patients. Accordingly, information process 10 may process 402 these data signals (e.g., one or more of data signals 200 and/or one or more of data signals 204) over a defined period of time (e.g., several minutes, several hours, several days, etc.) so that information process 10 may automatically define one or more defined signal norms (e.g., defined signal norms 228) for the data signals (e.g., one or more of data signals 200 and/or one or more of data signals 204)

When processing 402 the data signals (e.g., one or more of data signals 200 and/or one or more of data signals 204) over a defined period of time (e.g., several minutes, several hours, several days, etc.) to automatically define one or more defined signal norms (e.g., defined signal norms 228) for the data signals (e.g., one or more of data signals 200 and/or one or more of data signals 204), information process 10 may: examine 404 a range of the data signals (e.g., one or more of data signals 200 and/or one or more of data signals 204).

Continuing with the above stated example, assume that the defined signal norms (e.g., defined signal norms 228) for a heart rate is 60-100 beats per minute and a respiratory rate is 12-20 breaths per minute. Accordingly and when onboarding patient 232 into the hospital, such "societal" norms may be used. However, information process 10 may process 402 the data signals (e.g., one or more of data signals 200 and/or one or more of data signals 204) over a defined period of time (e.g., several minutes, several hours, several days, etc.) so that information process 10 may automatically define one or more defined signal norms (e.g., defined signal norms 228) for the data signals (e.g., one or more of data signals 200 and/or one or more of data signals 204).

As discussed above, if the patient (e.g., patient 232) is a seasoned athlete of exceptional health, their "normal" heart-rate may be 50-55 beats per minute and their "normal" respiratory rate may be 9-11 breaths per minute. Accordingly, the use of "societal" norms with respect to the data signals (e.g., one or more of data signals 200 and/or one or more of data signals 204) may result in an abundance of "false" alarms being issued by the device (e.g., one or more of first vendor devices 202 and/or one or more of second vendor devices 206) due to the appearance that patient 232 has a very low heart rate of 50-55 beats per minute (when the "societal" norm is 60-100) and a very low respiratory rate of 9-11 breaths per minute (when the societal norm is 12-20). Accordingly, information process 10 may examine 404 a range of the data signals (e.g., one or more of data signals 200 and/or one or more of data signals 204) and identify that patient 232 has the following data signal ranges: heart rate of 50-55 beats per minute (even though the "societal" norm is 60-100); and a respiratory rate of 9-11 breaths per minute (even though the societal norm is 12-20).

Further and when processing 402 the data signals (e.g., one or more of data signals 200 and/or one or more of data signals 204) over a defined period of time (e.g., several minutes, several hours, several days, etc.) to automatically define one or more defined signal norms (e.g., defined signal norms 228) for the data signals (e.g., one or more of data signals 200 and/or one or more of data signals 204), information process 10 may calculate 406 one or more standard deviations of the data signals (e.g., one or more of data signals 200 and/or one or more of data signals 204).

Standard deviation is a statistical measure that quantifies the amount of variation or dispersion in a dataset. It provides a numerical value that indicates how spread out the data points are from the mean (average) of the dataset. When considering a data range, the standard deviation can provide insights into the variability within that range. It helps assess the extent to which data points deviate from the mean value within the given range.

To calculate the standard deviation within a data range, you would typically follow these steps:
Calculate the mean (average) of the data within the range.
Subtract the mean from each data point within the range.
Square each of the differences obtained in step 2.
Calculate the average (mean) of the squared differences.
Take the square root of the average obtained in step 4.

The resulting value is the standard deviation within the specified data range. It represents the average amount by which data points deviate from the mean within that particular range. A larger standard deviation indicates greater variability or dispersion, meaning the data points within the range are more spread out from the mean. Conversely, a smaller standard deviation suggests less variation and a tighter clustering of data points around the mean within the range.

Additionally and when processing 402 the data signals (e.g., one or more of data signals 200 and/or one or more of data signals 204) over a defined period of time (e.g., several minutes, several hours, several days, etc.) to automatically define one or more defined signal norms (e.g., defined signal norms 228) for the data signals (e.g., one or more of data signals 200 and/or one or more of data signals 204), information process 10 may: iteratively redefine 408 the one or more defined signal norms (e.g., defined signal norms 228) based upon updated data signals (e.g., one or more of data signals 200 and/or one or more of data signals 204) received from the device (e.g., one or more of first vendor devices 202 and/or one or more of second vendor devices 206). For example, information process 10 may iteratively redefine 408 (e.g., every 10 seconds, or every one minute, or every few minutes, etc.) the defined signal norms (e.g., defined signal norms 228) based upon updated data signals (e.g., one or more of data signals 200 and/or one or more of data signals 204) received from the device (e.g., one or more of first vendor devices 202 and/or one or more of second vendor devices 206). In the configuration, the compute requirements of information process 10 may be reduced at the expense of reduced performance.

Further and when processing 402 the data signals (e.g., one or more of data signals 200 and/or one or more of data signals 204) over a defined period of time (e.g., several minutes, several hours, several days, etc.) to automatically define one or more defined signal norms (e.g., defined signal norms 228) for the data signals (e.g., one or more of data signals 200 and/or one or more of data signals 204), information process 10 may: continuously redefine 410 the one or more defined signal norms based upon updated data signals (e.g., one or more of data signals 200 and/or one or more of data signals 204) received from the device (e.g., one or more of first vendor devices 202 and/or one or more of second vendor devices 206). For example, information process 10 may continuously redefine 410 (e.g., every few milliseconds, every time new data is received, etc.) the defined signal norms (e.g., defined signal norms 228) based upon updated data signals (e.g., one or more of data signals 200 and/or one or more of data signals 204) received from the device (e.g., one or more of first vendor devices 202 and/or one or more of second vendor devices 206). In the configuration, the performance of information process 10 may be increased at the expense of increased compute requirements.

Information process 10 may monitor 412 the device (e.g., one or more of first vendor devices 202 and/or one or more of second vendor devices 206) to receive subsequent data signals (e.g., data signals 234) indicative of the device (e.g., one or more of first vendor devices 202 and/or one or more of second vendor devices 206), wherein information process 10 may compare 414 the subsequent data signals (e.g., data signals 234) to the defined signal norms (e.g., defined signal norms 228) to identify outliers (e.g., outliers 230).

As discussed above, information process 10 may investigate 416 the outliers (e.g., outliers 230) to determine if an issue exists with the device (e.g., one or more of first vendor devices 202 and/or one or more of second vendor devices 206), wherein investigating 416 the outliers (e.g., outliers 230) to determine if an issue exists with the device (e.g., one or more of first vendor devices 202 and/or one or more of second vendor devices 206) may include physically investigating 418 the outliers (e.g., outliers 230); and/or examining 420 other data signals from the device (e.g., one or more of first vendor devices 202 and/or one or more of second vendor devices 206).

As discussed above, information process 10 may adjust 422 outlier definition criteria to eliminate the outlier (e.g., outliers 230) if an issue does not exist. For example and when adjusting 422 the outlier definition criteria, information process 10 may define 424 bespoke outlier definition criteria for the device (e.g., one or more of first vendor devices 202 and/or one or more of second vendor devices 206). Conversely and if an issue does exist with patient 232, information process 10 may address by e.g., notifying a doctor, making an emergency announcement, notifying medical staff, etc.

Centralized Threshold Adjustment:

The following discussion concerns the manner in which information process 10 may enable the centralized management of the thresholds, wherein these thresholds may be used by devices (e.g., one or more of first vendor devices 202 and/or one or more of second vendor devices 206) to establish norms for the patient being monitored. As discussed above, oftentimes generalized norms are not applicable to specific patients. And being these norms/thresholds are used to generate alarms, inapplicable norms/thresholds many result in an abundance of "false" alarms being issued by the device (e.g., one or more of first vendor devices 202 and/or one or more of second vendor devices 206). Accordingly, information process 10 may enable the centralized management of such thresholds.

Figure 6:
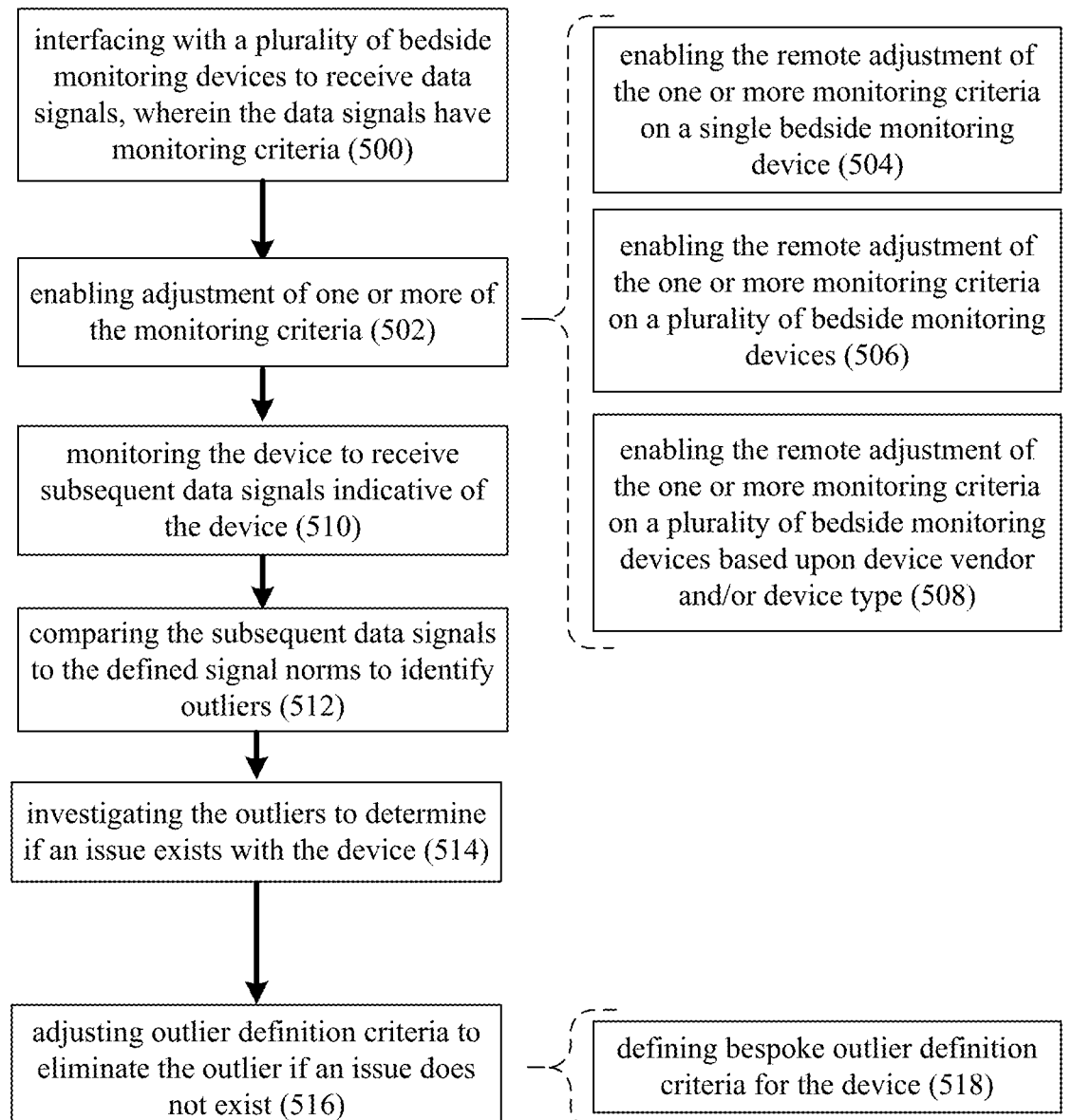
FIG. 6 is another flowchart of the information process of FIG. 1 according to an embodiment of the present disclosure.

Referring also to FIG. 6, information process 10 may interface 500 with a plurality of bedside monitoring devices (e.g., one or more of first vendor devices 202 and/or one or more of second vendor devices 206) to receive data signals (e.g., one or more of data signals 200 and/or one or more of data signals 204). These data signals (e.g., one or more of data signals 200 and/or one or more of data signals 204) may have monitoring criteria, wherein the monitoring criteria may include one or more thresholds.

As discussed above, examples of such monitoring criteria/thresholds may include defined signal norms (e.g., defined signal norms 228). These defined signal norms (e.g., defined signal norms 228) may include user-defined signal norms and/or machine-defined signal norms. For example and with respect to user-defined signal norms, such user-defined signal norms may be the result of (in this example) medical studies, medical books, insurance charts, medical records, etc. Further and with respect to machine-defined signal norms, such machine-defined signal norms may be defined via massive data sets that are processed by machine learning. Accordingly, such monitoring criteria (e.g., defined signal norms 228), may include user-defined monitoring criteria and/or machine-defined monitoring criteria.

As also discussed above, such monitoring criteria (e.g., defined signal norms 228) may be compartmentalized by e.g., gender, race, age, location, device type, device class, seasonality, time of day, etc. Specifically, medical statistics may vary depending upon various factors (including gender, race, age, location, device type, device class, seasonality, and time of day), wherein these factors can influence health outcomes, disease prevalence, treatment response, and other medical parameters.

As also discussed above, such data signals (e.g., one or more of data signals 200 and/or one or more of data signals 204) may concern one or more details of the plurality of bedside monitoring devices (e.g., one or more of first vendor devices 202 and/or one or more of second vendor devices 206) and/or uses of the plurality of bedside monitoring devices (e.g., one or more of first vendor devices 202 and/or one or more of second vendor devices 206).

Device Details: One or more details of the device (e.g., one or more of first vendor devices 202 and/or one or more of second vendor devices 206) may concern one or more readings, signals and/or alarms that are provided by the device and concern (in the example) the vital signs of a patient.

Device Uses: One or more uses of the device (e.g., one or more of first vendor devices 202 and/or one or more of second vendor devices 206) may concern the manner in which the device is being used (e.g., what is the device doing, what is the device being used for, who is the device assigned/connected to, etc.).

As also discussed above, the plurality of bedside monitoring devices (e.g., one or more of first vendor devices 202 and/or one or more of second vendor devices 206) may span a plurality of vendors, wherein (as discussed above) information process 10 may enable such multiple-vendor devices to communicate.

Information process 10 may enable 502 adjustment of one or more of the monitoring criteria (e.g., defined signal norms 228). For example, information process 10 may enable 502 adjustment of one or more of the monitoring criteria (e.g., defined signal norms 228) by a user (e.g., user 236) via a computing device (e.g., computing device 238). Examples of user 236 may include but are not limited to a medical professional, such as a nurse, nurse supervisor, medical technician, physician's assistant, physician, etc. Examples of the computing device (e.g., computing device 238) may include but are not limited to a nurse's workstation, a tablet computer, a laptop computer, a desktop computer, a smart phone, etc.

As discussed above, the defined signal norms (e.g., defined signal norms 228) for a heart rate may be 60-100 beats per minute and for a respiratory rate may be 12-20 breaths per minute. Accordingly, information process 10 may enable 502 adjustment of one or more of the monitoring criteria (e.g., namely defined signal norms of 60-100 beats per minute for a heart rate and 12-20 breaths per minute for a respiratory rate) by the user (e.g., user 236) via a computing device (e.g., computing device 238). Additionally/alternatively, information process 10 may enable 502 adjustment of one or more of the monitoring criteria (e.g., namely defined signal norms of 60-100 beats per minute for a heart rate and 12-20 breaths per minute for a respiratory rate) by the user (e.g., user 236) by providing the user (e.g., user 236) with instructions (e.g., graphical and/or text-based) concerning how to manually adjust the one or more of the monitoring criteria (e.g., namely defined signal norms of 60-100 beats per minute for a heart rate and 12-20 breaths per minute for a respiratory rate) via e.g., a user interface (not shown) included within the plurality of bedside monitoring devices (e.g., one or more of first vendor devices 202 and/or one or more of second vendor devices 206).

When enabling 502 the adjustment of one or more of these monitoring criteria (e.g., defined signal norms 228), information process 10 may: enable 504 the remote adjustment of the one or more monitoring criteria (e.g., defined signal norms 228) on a single bedside monitoring device (e.g., one or more of first vendor devices 202 and/or one or more of second vendor devices 206).

As discussed above, "societal" defined signal norms (e.g., defined signal norms 228) may not work for everyone. So while the defined signal norms (e.g., defined signal norms 228) for a heart rate may be 60-100 beats per minute and a respiratory rate may be 12-20 breaths per minute; if a patient (e.g., patient 232) is a seasoned athlete of exceptional health, their "normal" heartrate may be 50-55 beats per minute and their "normal" respiratory rate may be 9-11 breaths per minute. Accordingly, information process 10 may: enable 504 the remote adjustment of the one or more monitoring criteria (e.g., defined signal norms 228) on a single bedside monitoring device (e.g., the single bedside device associated with patient 232) so that the monitoring criteria for the heart rate of patient 232 may be adjusted downward from 60-100 beats per minute to 50-55 beats per minute and the monitoring criteria for the respiratory rate may be adjusted downward from 12-20 breaths per minute to 9-11 breaths per minute, wherein such adjustment may be made by the user (e.g., user 236) via the computing device (e.g., computing device 238).

When enabling 502 the adjustment of one or more of these monitoring criteria (e.g., defined signal norms 228), information process 10 may: enable 506 the remote adjustment of the one or more monitoring criteria (e.g., defined signal norms 228) on a plurality of bedside monitoring devices (e.g., one or more of first vendor devices 202 and/or one or more of second vendor devices 206).

For example, assume that the "societal" defined signal norms (e.g., defined signal norms 228) are not working for the majority of people within e.g., a hospital, a unit, a ward, a clinic, etc. For example, assume that a large portion of the people within the hospital, the unit, the ward, the clinic, etc. have a heart rate that is slightly over 100 (e.g., 101-105 beats per minute), resulting in the generation of a considerable number of false alarms. Accordingly, information process 10 may enable 506 the remote adjustment of the one or more monitoring criteria (e.g., defined signal norms 228) on a plurality of bedside monitoring devices (e.g., some or all of the devices within the hospital, the unit, the ward, the clinic, etc.) so that the monitoring criteria for the heart rate of patients within the hospital, the unit, the ward, the clinic, etc. may be adjusted upward from 60-100 beats per minute to 60-110 beats per minute, wherein such adjustment may be made by the user (e.g., user 236) via the computing device (e.g., computing device 238).

When enabling 502 the adjustment of one or more of these monitoring criteria (e.g., defined signal norms 228), information process 10 may: enable 508 the remote adjustment of the one or more monitoring criteria (e.g., defined signal norms 228) on a plurality of bedside monitoring devices (e.g., one or more of first vendor devices 202 and/or one or more of second vendor devices 206) based upon device vendor and/or device type.

For example, assume that the default defined signal norms (e.g., defined signal norms 228) concerning heart rate are 60-100 beats per minute (for devices made by Company A), while the default defined signal norms (e.g., defined signal norms 228) concerning heart rate are 70-90 beats per minute (for devices made by Company B). Assume that the default defined signal norms (e.g., defined signal norms 228) for Company A (i.e., a heart rate are 60-100 beats per minute) appear to be working properly, as it is not triggering a high level of false alarms. However, the default defined signal norms (e.g., defined signal norms 228) for Company B (i.e., a heart rate are 70-90 beats per minute) appear to not be working properly, as it is triggering a high level of false alarms. Accordingly, information process 10 may enable 508 the remote adjustment of the one or more monitoring criteria (e.g., defined signal norms 228) on a plurality of bedside monitoring devices (e.g., the bedside devices manufactured by Company B) so that the heart rate monitoring criteria for the bedside devices manufactured by Company B may be adjusted from 70-90 beats per minute to 60-100 beats per minute, wherein such adjustment may be made by the user (e.g., user 236) via the computing device (e.g., computing device 238).

Information process 10 may monitor 510 the device (e.g., one or more of first vendor devices 202 and/or one or more of second vendor devices 206) to receive subsequent data signals (e.g., data signals 234) indicative of the device (e.g., one or more of first vendor devices 202 and/or one or more of second vendor devices 206), wherein information process 10 may compare 512 the subsequent data signals (e.g., data signals 234) to the defined signal norms (e.g., defined signal norms 228) to identify outliers (e.g., outliers 230).

As discussed above, information process 10 may investigate 514 the outliers (e.g., outliers 230) to determine if an issue exists with the device (e.g., one or more of first vendor devices 202 and/or one or more of second vendor devices 206), wherein investigating 514 the outliers (e.g., outliers 230) to determine if an issue exists with the device (e.g., one or more of first vendor devices 202 and/or one or more of second vendor devices 206) may include physically investigating the outliers (e.g., outliers 230); and/or examining other data signals from the device (e.g., one or more of first vendor devices 202 and/or one or more of second vendor devices 206).

As discussed above, information process 10 may adjust 516 outlier definition criteria to eliminate the outlier (e.g., outliers 230) if an issue does not exist. For example and when adjusting 516 the outlier definition criteria, information process 10 may define 518 bespoke outlier definition criteria for the device (e.g., one or more of first vendor devices 202 and/or one or more of second vendor devices 206). Conversely and if an issue does exist with patient 232, information process 10 may address by e.g., notifying a doctor, making an emergency announcement, notifying medical staff, etc.

Automated Device Personalization:

The following discussion concerns the manner in which information process 10 may enable the customization of a bedside monitoring device (e.g., one or more of first vendor devices 202 and/or one or more of second vendor devices 206) based upon patient information obtained from a medical record (e.g., an EMR and/or an EHR). As discussed above, oftentimes generalized norms are not applicable to specific patients. And being these norms are used to generate alarms, inapplicable norms many result in an abundance of "false" alarms being issued by the device (e.g., one or more of first vendor devices 202 and/or one or more of second vendor devices 206). Accordingly, information process 10 may enable the setting of such norms based upon patient information to mitigate such false alarms.

Figure 7:
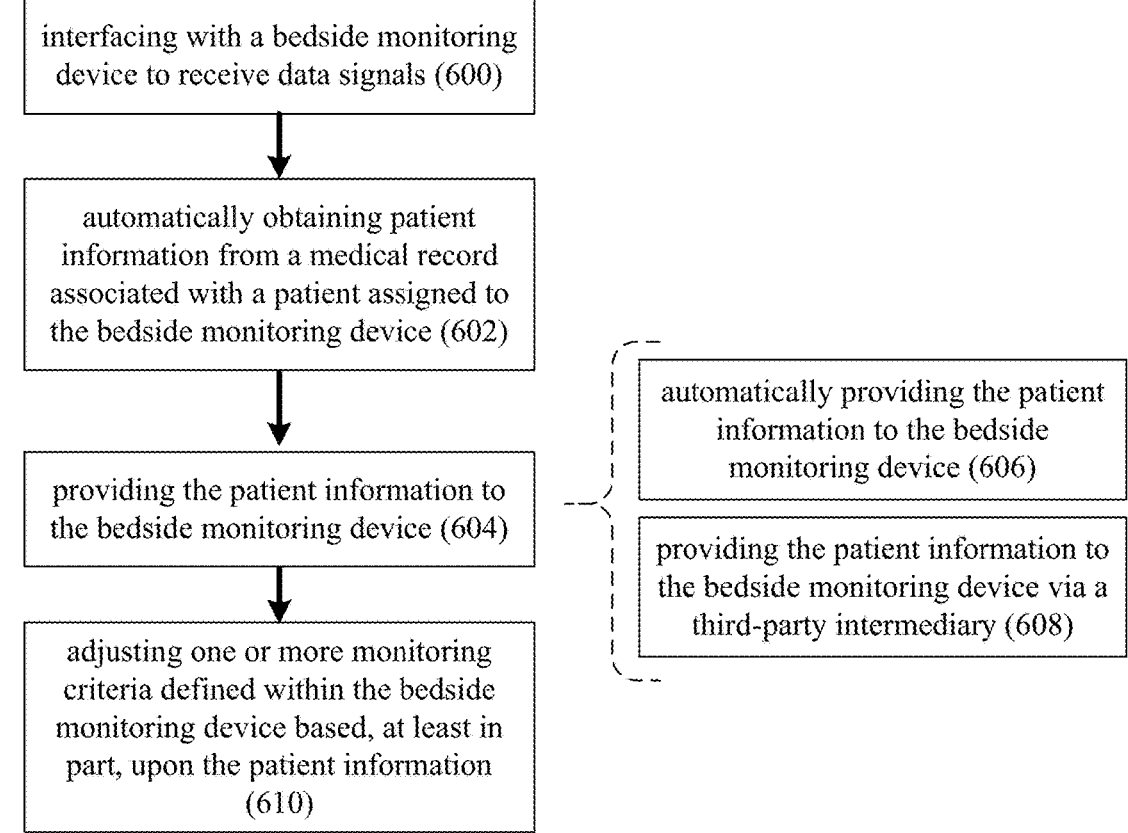
FIG. 7 is another flowchart of the information process of FIG. 1 according to an embodiment of the present disclosure.

Referring also to FIG. 7, information process 10 may interface 600 with a bedside monitoring device (e.g., one or more of first vendor devices 202 and/or one or more of second vendor devices 206) to receive data signals (e.g., one or more of data signals 200 and/or one or more of data signals 204).

As also discussed above, such data signals (e.g., one or more of data signals 200 and/or one or more of data signals 204) may concern one or more details of the bedside monitoring device (e.g., one or more of first vendor devices 202 and/or one or more of second vendor devices 206) and/or uses of the bedside monitoring devices (e.g., one or more of first vendor devices 202 and/or one or more of second vendor devices 206).

Device Details: One or more details of the device (e.g., one or more of first vendor devices 202 and/or one or more of second vendor devices 206) may concern one or more readings, signals and/or alarms that are provided by the device and concern (in the example) the vital signs of a patient.

Device Uses: One or more uses of the device (e.g., one or more of first vendor devices 202 and/or one or more of second vendor devices 206) may concern the manner in which the device is being used (e.g., what is the device doing, what is the device being used for, who is the device assigned/connected to, etc.).

Further and as discussed above, the bedside monitoring device (e.g., one or more of first vendor devices 202 and/or one or more of second vendor devices 206) may include one or more bedside monitoring sub devices (e.g., sub devices 224, 226).

Information process 10 may automatically obtain 602 patient information (e.g., patient information 240) from a medical record (e.g., patient record 242) associated with a patient (e.g., patient 232) assigned to the bedside monitoring device (e.g., one or more of first vendor devices 202 and/or one or more of second vendor devices 206).

The patient information (e.g., patient information 240) may include but is not limited to one or more of: a patient name, a patient demographic (e.g., age, gender, income level, race, employment, location, homeownership, and level of education), a medical history of the patient, a medication history of the patient, caregiver assignment history (e.g., what medical professionals are assigned to the patient) and patient assignment history (e.g., what room is assigned to the patient).

Examples of the medical record (e.g., patient record 242) may include but are not limited to one or more of an EMR and an EHR.

EHR stands for Electronic Health Record. An EHR is a digital version of a patient's paper medical records, containing comprehensive and organized information about an individual's health and medical history. It is designed to be accessible, updated, and shared securely among authorized healthcare providers and organizations.

Key features of an EHR include:

Digital Health Information: EHRs contain a wide range of health-related information, including patient demographics, medical history, diagnoses, medications, allergies, laboratory results, imaging reports, immunization records, and more. These records are stored electronically, making them easily accessible and searchable.

Comprehensive View: EHRs provide a holistic and longitudinal view of a patient's health. They capture information from various healthcare providers and settings, enabling authorized users to access and review a patient's complete medical history, facilitating better care coordination and continuity.

Data Entry and Updates: EHRs allow healthcare providers to enter and update patient information electronically. This includes clinical notes, examination findings, treatment plans, progress notes, and other relevant data. EHR systems often include templates and forms to assist in efficient data entry.

Interoperability: EHRs support the exchange and sharing of health information across different healthcare settings and systems. Interoperability enables seamless communication and collaboration among healthcare providers, facilitating coordinated care, referrals, and transitions between different care settings.

Decision Support: EHRs often include decision support tools, such as clinical guidelines, alerts, reminders, and drug interaction checks. These features assist healthcare providers in making informed decisions, improving patient safety, and adhering to evidence-based practices.

Privacy and Security: EHRs prioritize the security and privacy of patient information. They employ stringent safeguards to protect against unauthorized access, data breaches, and ensure compliance with relevant privacy regulations, such as the Health Insurance Portability and Accountability Act (HIPAA) in the United States.

The adoption of EHRs aims to enhance patient care, improve efficiency, reduce medical errors, support evidence-based practices, and facilitate health information exchange. It allows healthcare providers to access accurate and up-to-date patient information at the point of care, leading to better-informed decisions and improved patient outcomes.

EMR stands for Electronic Medical Record. An EMR is a digital version of a patient's medical records that is maintained within a healthcare provider's own system or network. It is similar to an Electronic Health Record (EHR), but with a narrower scope as it primarily focuses on the medical information specific to a single healthcare organization or practice.

Here are some key aspects of an EMR:

Digital Storage: EMRs store patient health information electronically within a specific healthcare organization's database or network. They replace traditional paper-based medical charts and records, making information more accessible and easily retrievable.

Medical Information: EMRs primarily contain medical and clinical information, including diagnoses, treatments, medications, medical procedures, laboratory and imaging results, progress notes, and other relevant data specific to the healthcare provider's practice.

Organization-Specific: Unlike EHRs, which are designed to be interoperable and shared across different healthcare settings, EMRs are typically limited to a specific healthcare organization or practice. They are customized to fit the workflows and requirements of the particular healthcare provider using them.

Data Entry and Updates: Healthcare providers enter patient information directly into the EMR system using electronic forms, templates, or structured data entry. EMRs support efficient data entry and updates, including capturing patient demographics, medical history, examination findings, and treatment plans.

Clinical Decision Support: EMRs often include clinical decision support features, such as drug interaction checks, alerts for potential contraindications or allergies, reminders for preventive care, and clinical guidelines. These tools assist healthcare providers in making informed decisions and improving patient care.

Privacy and Security: EMRs prioritize the privacy and security of patient information, implementing measures to protect against unauthorized access, data breaches, and compliance with relevant privacy regulations, such as HIPAA in the United States.

EMRs are primarily used within a single healthcare organization or practice to manage patient records, streamline clinical workflows, and support patient care. While they may not have the same level of interoperability as EHRs, efforts are being made to enhance data exchange and integration between different systems to promote better care coordination and continuity across healthcare settings.

Accordingly, assume that patient 232 (i.e., John Smith) is admitted to the hospital and is in Bed A in Room 203. Accordingly and once admitted, information process 10 may automatically obtain 602 patient information 240 from patient record 242 associated with patient 232 (i.e., John Smith) assigned to the bedside monitoring device (e.g., one or more of first vendor devices 202 and/or one or more of second vendor devices 206). As discussed above, this patient information (e.g., patient information 240) may include but is not limited to one or more of: a patient name, a patient demographic (e.g., age, gender, income level, race, employment, location, homeownership, and level of education), a medical history of the patient, a medication history of the patient, caregiver assignment history (e.g., what medical professionals are assigned to the patient) and patient assignment history (e.g., what room is assigned to the patient).

Once obtained 602, information process 10 may provide 604 the patient information (e.g., patient information 240) to the bedside monitoring device (e.g., one or more of first vendor devices 202 and/or one or more of second vendor devices 206). For example, information process 10 may provide 604 patient information 240 to the bedside monitoring device (e.g., one or more of first vendor devices 202 and/or one or more of second vendor devices 206) that identifies the name of patient 232, the nurse assigned to patient 232, the doctor assigned to patient 232, the admission date of patient 232, the anticipated discharge date of patient 232, the average blood pressure of patient 232, the average respiratory rate of patient 232, the average blood gas level of patient 232, etc.

When providing 604 the patient information (e.g., patient information 240) to the bedside monitoring device (e.g., one or more of first vendor devices 202 and/or one or more of second vendor devices 206), information process 10 may: automatically provide 606 the patient information (e.g., patient information 240) to the bedside monitoring device (e.g., one or more of first vendor devices 202 and/or one or more of second vendor devices 206). For example, information process 10 may automatically provide 606 the patient information (e.g., patient information 240) directly to the bedside monitoring device (e.g., one or more of first vendor devices 202 and/or one or more of second vendor devices 206) in an automated fashion without the need for third party assistance/intervention.

When providing 604 the patient information to the bedside monitoring device (e.g., one or more of first vendor devices 202 and/or one or more of second vendor devices 206), information process 10 may: provide 608 the patient information (e.g., patient information 240) to the bedside monitoring device (e.g., one or more of first vendor devices 202 and/or one or more of second vendor devices 206) via a third-party intermediary (e.g., third-party intermediary 244). For example, information process 10 may: provide 608 the patient information (e.g., patient information 240) indirectly to the bedside monitoring device (e.g., one or more of first vendor devices 202 and/or one or more of second vendor devices 206), wherein the patient information 240 is first provided to third-party intermediary 244 (e.g., a hospital administrator or medical device professional) and third-party intermediary 244 subsequently provides the patient information 240 to the bedside monitoring device (e.g., one or more of first vendor devices 202 and/or one or more of second vendor devices 206).

Information process 10 may adjust 610 one or more monitoring criteria defined within the bedside monitoring device (e.g., one or more of first vendor devices 202 and/or one or more of second vendor devices 206) based, at least in part, upon the patient information (e.g., patient information 240).

As discussed above, examples of such monitoring criteria may include defined signal norms (e.g., defined signal norms 228) and/or one or more signal thresholds. Assume that the default defined signal norms (e.g., defined signal norms 228) concerning heart rate is 60-100 beats per minute. Further assume that the patient (e.g., patient 232) is a seasoned athlete of exceptional health and their "normal" heartrate is defined within patient information 240 as 50-55 beats per minute. Accordingly, information process 10 may adjust 610 the monitoring criteria for heart rate (as defined within the bedside monitoring device) downward from 60-100 beats per minute to e.g., 45-60 beats per minute based, at least in part, upon patient information 240.

Environment Baseline Setting:

The following discussion concerns the manner in which information process 10 may help to battle alarm fatigue . . . the detrimental effect of false alarms within medical facilities. False alarms are a significant concern within hospitals, as they can lead to alarm fatigue, decreased patient safety, and increased healthcare provider burden. The prevalence of false alarms can vary depending upon multiple factors, including the specific hospital, the type of medical devices used, and the clinical setting.

Studies have shown that the rate of false alarms in hospitals can be alarmingly high. For example, research conducted in intensive care units (ICUs) has reported false alarm rates ranging from 72% to 99%, indicating that the majority of alarms in these settings are false positives.

Several factors contribute to the occurrence of false alarms in hospitals:

Inadequate Alarm Parameters: Alarm systems may be set with default or suboptimal alarm thresholds, leading to alarms that trigger unnecessarily. This can be due to alarm settings being too sensitive or not properly adjusted to patient-specific conditions.

Device Malfunctions or Technical Issues: Faulty equipment or technical issues with medical devices can result in false alarms. For example, electrode or sensor detachment, poor signal quality, or software glitches can generate false positive alarms.

Lack of Contextual Information: Alarms may lack the necessary contextual information to help healthcare providers accurately interpret their significance. For instance, alarms may not consider the patient's clinical condition, medications, or concurrent therapies, leading to false alarms that do not require immediate action.

Inefficient Alarm Management: Healthcare providers may be overwhelmed by the sheer number of alarms, making it challenging to respond promptly and appropriately. This can lead to alarm fatigue, where healthcare providers become desensitized or ignore alarms due to their frequency, potentially compromising patient safety.

Addressing false alarms is a priority for healthcare organizations and device manufacturers. Efforts are being made to improve alarm management systems, enhance alarm customization options, implement better alarm algorithms, and provide more contextual information to reduce false positives and improve the accuracy and relevance of alarms. Additionally, initiatives focusing on standardization, education, and guidelines are being developed to promote best practices in alarm management and mitigate the impact of false alarms on patient care. Accordingly and as will be discussed below, information process 10 may be configured to monitor a medical environment to determine the prevalence and severity of the alarm situation within the monitored medical environment.

Figure 8:
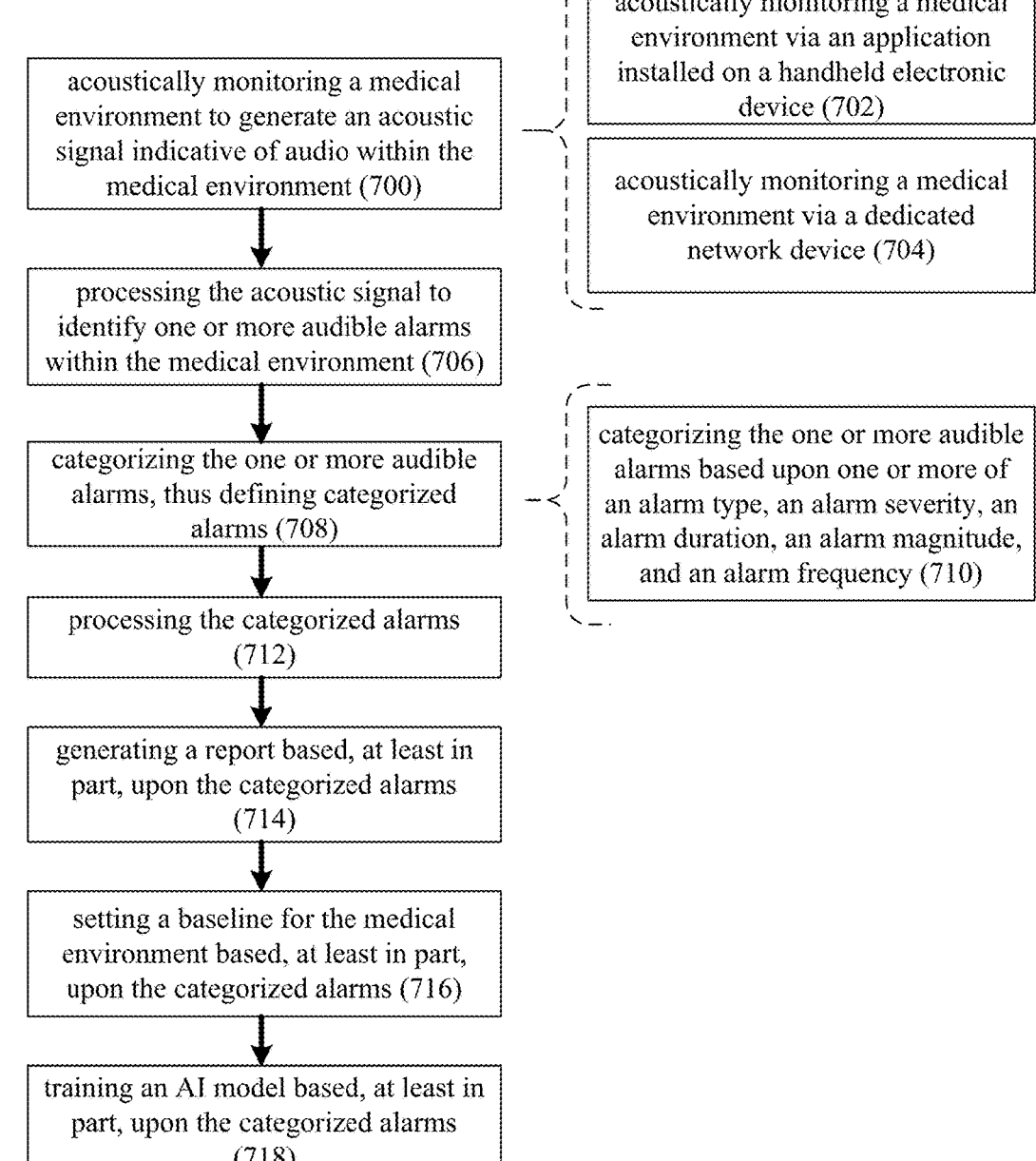
FIG. 8 is another flowchart of the information process of FIG. 1 according to an embodiment of the present disclosure.

Referring also to FIG. 8, information process 10 may acoustically monitor 700 a medical environment (e.g., hospital 246 . . . or a portion thereof) to generate an acoustic signal (e.g., acoustic signal 248) indicative of audio within the medical environment (e.g., hospital 246 . . . or a portion thereof).

When acoustically monitoring 700 a medical environment (e.g., hospital 246 . . . or a portion thereof) to generate an acoustic signal (e.g., acoustic signal 248) indicative of audio within the medical environment (e.g., hospital 246 . . . or a portion thereof), information process 10 may acoustically monitor 702 a medical environment (e.g., hospital 246 . . . or a portion thereof) via an application (e.g., application 250) installed on a handheld electronic device (e.g., handheld electronic device 252), examples of which may include but are not limited to a smart phone, a tablet computer, a wireless dedicated device, etc.).

Additionally/alternatively and when acoustically monitoring 700 a medical environment (e.g., hospital 246 . . . or a portion thereof) to generate an acoustic signal (e.g., acoustic signal 248) indicative of audio within the medical environment (e.g., hospital 246 . . . or a portion thereof), information process 10 may acoustically monitor 704 a medical environment (e.g., hospital 246 . . . or a portion thereof) via a dedicated network device (e.g., dedicated network device 252), an example of which may include but is not limited to a wall-mounted microphone.

Generally speaking, information process 10 acoustically monitors 700 the medical environment (e.g., hospital 246 . . . or a portion thereof) to generate acoustic signal 248 indicative of audio within the medical environment (e.g., hospital 246 . . . or a portion thereof) so that the quantity and quality of the alarms within the medical environment (e.g., hospital 246 . . . or a portion thereof) may be detected and determined. Accordingly, information process 10 may process 706 the acoustic signal (e.g., acoustic signal 248) to identify one or more audible alarms (e.g., audible alarms 256, 258, 260, 262) within the medical environment (e.g., hospital 246 . . . or a portion thereof).

Information process 10 may categorize 708 the one or more audible alarms (e.g., audible alarms 256, 258, 260, 262), thus defining categorized alarms (e.g., categorized alarms 264). For example and when categorizing 708 the one or more audible alarms (e.g., audible alarms 256, 258, 260, 262), information process 10 may: categorize 710 the one or more audible alarms (e.g., audible alarms 256, 258, 260, 262) based upon one or more of an alarm type, an alarm severity, an alarm duration, an alarm magnitude, and an alarm frequency.

Specifically, the alarms generated by the bedside monitoring devices (e.g., one or more of first vendor devices 202 and/or one or more of second vendor devices 206) may vary in volume, frequency, pattern and duration based upon one or more of an alarm type, an alarm severity, an alarm duration, an alarm magnitude, and an alarm frequency. Accordingly, information process 10 may be configured to categorize 710 audible alarms 256, 258, 260, 262 based upon an alarm type, an alarm severity, an alarm duration, an alarm magnitude, and an alarm frequency Information process 10 may process 712 the categorized alarms (e.g., categorized alarms 264) and generate 714 a report (e.g., report 266) based, at least in part, upon the categorized alarms (e.g., categorized alarms 264). For example, report 266 may identify the quantity and quality of audible alarms 256, 258, 260, 262 and present them within report 266 in accordance with one or more of alarm type, an alarm severity, an alarm duration, an alarm magnitude, and an alarm frequency.

Further, information process 10 may set 716 a baseline for the medical environment (e.g., hospital 246 . . . or a portion thereof) based, at least in part, upon the categorized alarms (e.g., categorized alarms 264). For example, the information defined within report 266 for the medical environment (e.g., hospital 246 . . . or a portion thereof) may be compared to other medical environments to determine how the medical environment (e.g., hospital 246 . . . or a portion thereof) compares with these other medical environments so that such a baseline may be established. For example, report 266 may identify the medical environment (e.g., hospital 246 . . . or a portion thereof) as e.g., being:

XX % worse (or better) than the average medical environment with respect to false alarms;

YY % worse (or better) than the average medical environment with respect to critical alarms; and ZZ % worse (or better) than the average medical environment with respect to total alarms.

Accordingly and through the use of such a report (e.g., report 266), the medical environment (e.g., hospital 246 . . . or a portion thereof) may be able to see what areas they are good in, as well as the areas in which they can improve (thus establishing a baseline). And by addressing the areas that need improvement, staff retention may be improved by e.g., reducing alarm fatigue.

Information process 10 may train 718 an AI model (e.g., AI model 268) based, at least in part, upon the categorized alarms (e.g., categorized alarms 264). For example, data set 270 may be generated and AI model 268 may be trained based upon data set 270. Data set 270 may include e.g., categorized alarms from the medical environment (e.g., hospital 246 . . . or a portion thereof) and from other medical environments (not shown), wherein AI model 268 may be trained by processing data set 270 to extract patterns hidden within data set 270.

Machine learning models extract patterns from a dataset through a process called training. During training, the model learns to recognize patterns and relationships within the data by adjusting its internal parameters or weights. The general steps involved in pattern extraction by a machine learning model are as follows:

Data Preparation: The dataset is preprocessed and prepared to ensure its quality and suitability for training. This may involve tasks such as data cleaning, normalization, feature selection, and splitting the dataset into training and testing subsets.

Model Selection: The appropriate machine learning model is selected based on the nature of the problem and the characteristics of the dataset. Different types of models, such as decision trees, neural networks, support vector machines, or random forests, can be used depending on the problem and the data.

Model Training: The selected model is trained using the training dataset. During this phase, the model iteratively adjusts its internal parameters based on the input data and the desired output. It tries to find the optimal settings that minimize the difference between the predicted output and the actual output in the training data.

Pattern Extraction: As the model iteratively adjusts its parameters, it learns to recognize patterns and relationships present in the data. The model identifies features or combinations of features that are most relevant for predicting the target variable or making accurate classifications. These patterns can be simple or complex and can involve various features or variables within the dataset.

Evaluation and Validation: Once the model is trained, it is evaluated using the testing dataset to assess its performance and generalization ability. The model's ability to extract patterns effectively is measured by evaluating its accuracy, precision, recall, F1 score, or other appropriate metrics based on the specific problem domain.

Application and Prediction: After training and validation, the trained model can be used to make predictions or classify new, unseen data based on the patterns it learned from the training dataset. The model applies the extracted patterns to new input data to generate predictions or classify instances based on the trained relationships.

It's important to note that the success of pattern extraction depends on several factors, such as the quality and representativeness of the training data, the choice of appropriate features, the selection of an appropriate model, and the careful tuning of model parameters. The process of extracting patterns from data is at the core of machine learning, enabling models to learn from examples and make predictions or classifications on new data.

Accordingly, by training 718 AI model 268 based, at least in part, upon categorized alarms 264, various patterns may be extracted concerning e.g., average alarms counts/types and how they relate to patient demographics, hospital locations, staffing levels, staff attrition levels, staff satisfaction levels, etc.

Clustering Alarms to Define an Incident:

The following discussion concerns the manner in which information process 10 may define the occurrence of a group of alarms as the occurrence of an incident. Generally speaking, while the individual occurrence of any of the group of alarms may not be a concern, the occurrence of the entire group of alarms may be indicative of a bigger problem (i.e., hence the occurrence of an incident).

Figure 9:
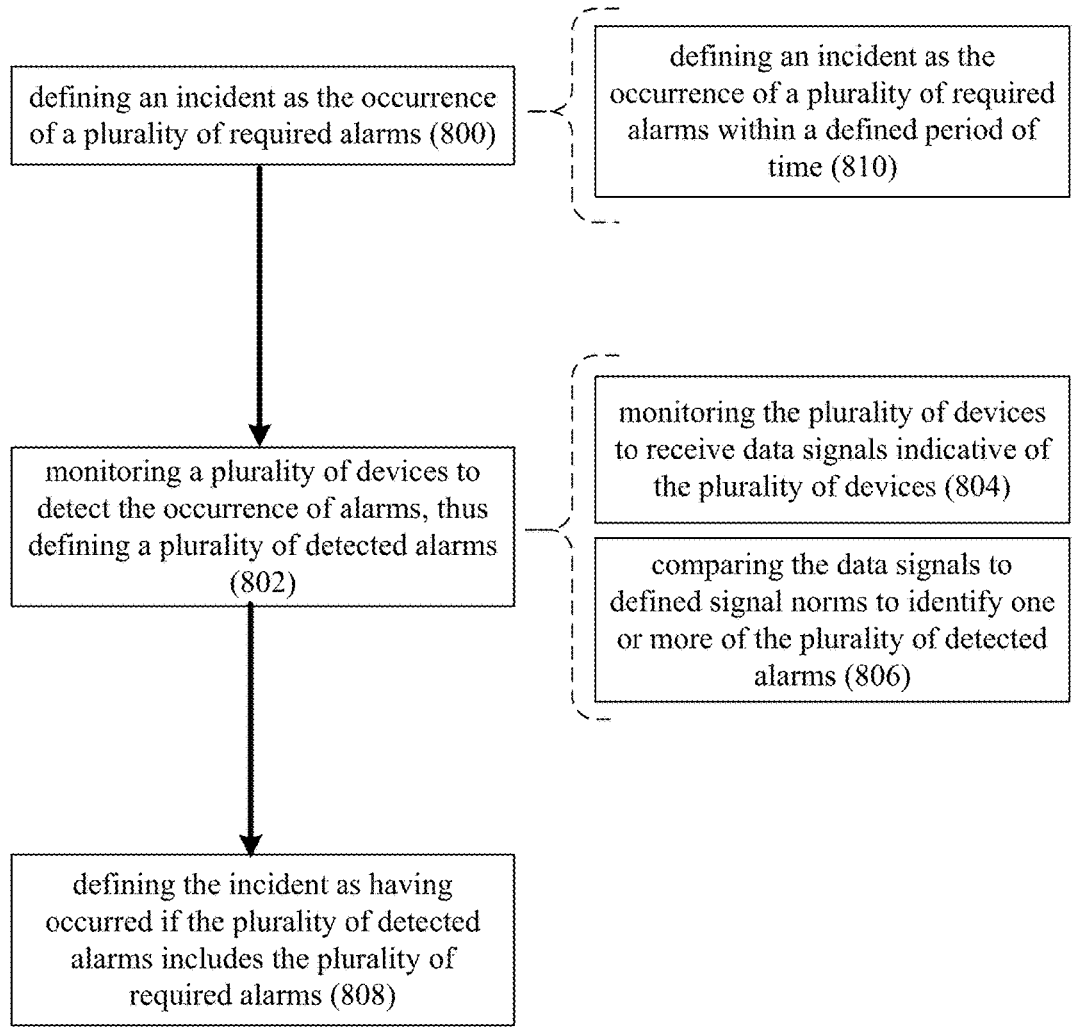
FIG. 9 is another flowchart of the information process of FIG. 1 according to an embodiment of the present disclosure.

Referring also to FIG. 9, information process 10 may define 800 an incident (e.g., incident 272) as the occurrence of a plurality of required alarms. For example, assume that the incident of heart failure may be defined 800 as the occurrence of: low blood pressure, a rapid heart rate, and a low blood oxygen level. While the occurrence of any of these individual alarms may not be indicative of a more serious issue, when a person is experiencing all three of these issues (e.g., low blood pressure, a rapid heart rate, and a low blood oxygen level), that person may be experiencing heart failure. Accordingly, information process 10 may define 800 incident 272 (e.g., heart failure) as the occurrence of low blood pressure, a rapid heart rate, and a low blood oxygen level).

As discussed above, information process 10 may monitor 802 a plurality of devices (e.g., one or more of first vendor devices 202 and/or one or more of second vendor devices 206) to detect the occurrence of alarms. As discussed above, the plurality of devices (e.g., one or more of first vendor devices 202 and/or one or more of second vendor devices 206) may include one or more of: a medical device, a process control device, a networking device, a computing device, a manufacturing device, an agricultural device, an energy/refining device, an aerospace device, a forestry device, and a defense device. Further, the plurality of devices (e.g., one or more of first vendor devices 202 and/or one or more of second vendor devices 206) may be geographically proximate or geographically dispersed. For example, the plurality of devices (e.g., one or more of first vendor devices 202 and/or one or more of second vendor devices 206) may be within one unit of a hospital, spread across an entire hospital, spread across a group of hospitals, spread across a state, or spread across a country.

For this example, assume that the bedside devices (e.g., one or more of first vendor devices 202 and/or one or more of second vendor devices 206) that are monitoring patient 232 generate three alarms (e.g., alarms 274, 276, 278). Being information process 10 is monitoring 802 such devices (e.g., one or more of first vendor devices 202 and/or one or more of second vendor devices 206), information process 10 will detect the occurrence of the alarms, thus defining a plurality of detected alarms (e.g., alarms 274, 276, 278).

For this example, assume that:

Detected alarm 274 indicates that patient 232 has low blood pressure;

Detected alarm 276 indicates that patient 232 has a rapid heart rate; and

Detected alarm 278 indicates that patient 232 has low oxygen levels in their blood.

When monitoring 802 a plurality of devices (e.g., one or more of first vendor devices 202 and/or one or more of second vendor devices 206) to detect the occurrence of alarms, information process 10 may: monitor 804 the plurality of devices (e.g., one or more of first vendor devices 202 and/or one or more of second vendor devices 206) to receive data signals (e.g., data signals 200 and/or data signals 204) indicative of the plurality of devices (e.g., one or more of first vendor devices 202 and/or one or more of second vendor devices 206).

As also discussed above, such data signals (e.g., one or more of data signals 200 and/or one or more of data signals 204) may concern one or more details of the plurality of devices (e.g., one or more of first vendor devices 202 and/or one or more of second vendor devices 206) and/or uses of the plurality of devices (e.g., one or more of first vendor devices 202 and/or one or more of second vendor devices 206).

Device Details: One or more details of the device (e.g., one or more of first vendor devices 202 and/or one or more of second vendor devices 206) may concern one or more readings, signals and/or alarms that are provided by the device and concern (in the example) the vital signs of a patient.

Device Uses: One or more uses of the device (e.g., one or more of first vendor devices 202 and/or one or more of second vendor devices 206) may concern the manner in which the device is being used (e.g., what is the device doing, what is the device being used for, who is the device assigned/connected to, etc.).

When monitoring 802 a plurality of devices (e.g., one or more of first vendor devices 202 and/or one or more of second vendor devices 206) to detect the occurrence of alarms, information process 10 may: compare 806 the data signals (e.g., data signals 200 and/or data signals 204) to defined signal norms to identify one or more of the plurality of detected alarms (e.g., alarms 274, 276, 278).

As discussed above, examples of such defined signal norms (e.g., defined signal norms 228) may include user-defined signal norms and/or machine-defined signal norms. For example and with respect to user-defined signal norms, such user-defined signal norms may be the result of (in this example) medical studies, medical books, insurance charts, medical records, etc. Further and with respect to machine-defined signal norms, such machine-defined signal norms may be defined via massive data sets that are processed by machine learning.

As also discussed above, such defined signal norms (e.g., defined signal norms 228) may be compartmentalized by e.g., gender, race, age, location, device type, device class, seasonality, time of day, etc. Specifically, medical statistics may vary depending upon various factors (including gender, race, age, location, device type, device class, seasonality, and time of day), wherein these factors can influence health outcomes, disease prevalence, treatment response, and other medical parameters.

Information process 10 may define 808 the incident (e.g., incident 272) as having occurred if the plurality of detected alarms (e.g., alarms 274, 276, 278) includes the plurality of required alarms (e.g., a low blood pressure alarm, a rapid heart rate alarm, and a low blood oxygen level alarm).

As stated above and for this example:

Detected alarm 274 indicates that patient 232 has low blood pressure;

Detected alarm 276 indicates that patient 232 has a rapid heart rate; and

Detected alarm 278 indicates that patient 232 has low oxygen levels in their blood.

Accordingly, information process 10 may define 808 incident 272 (e.g., a heart failure incident) as having occurred since detected alarm 274 indicates that patient 232 has low blood pressure; detected alarm 276 indicates that patient 232 has a rapid heart rate; and detected alarm 278 indicates that patient 232 has low oxygen levels in their blood.

Oftentimes, the occurrence of a plurality of alarms is only significant if such alarms occurred in a temporarily-proximate fashion. For example, a low blood pressure alarm, followed by a rapid heart rate alarm a week later (when the low blood pressure alarm no longer exists), followed by a low blood oxygen level alarm a week later (when the low blood pressure alarm and the rapid heart rate alarm no longer exist) is probably NOT indicative of incident 272 (e.g., a heart failure incident). Accordingly and when defining 800 an incident (e.g., a heart failure incident) as the occurrence of a plurality of required alarms (e.g., a low blood pressure alarm, a rapid heart rate alarm, and a low blood oxygen level alarm), information process 10 may define 810 the incident (e.g., a heart failure incident) as the occurrence of a plurality of required alarms (e.g., a low blood pressure alarm, a rapid heart rate alarm, and a low blood oxygen level alarm) within a defined period of time.

Predicting an Incident:

As discussed above, information process 10 may define the occurrence of a group of alarms as the occurrence of an incident. The following discussion concerns the manner in which information process 10 may predict the occurrence of an incident when a portion of the group of alarms that defines such an incident has occurred.

Figure 10:
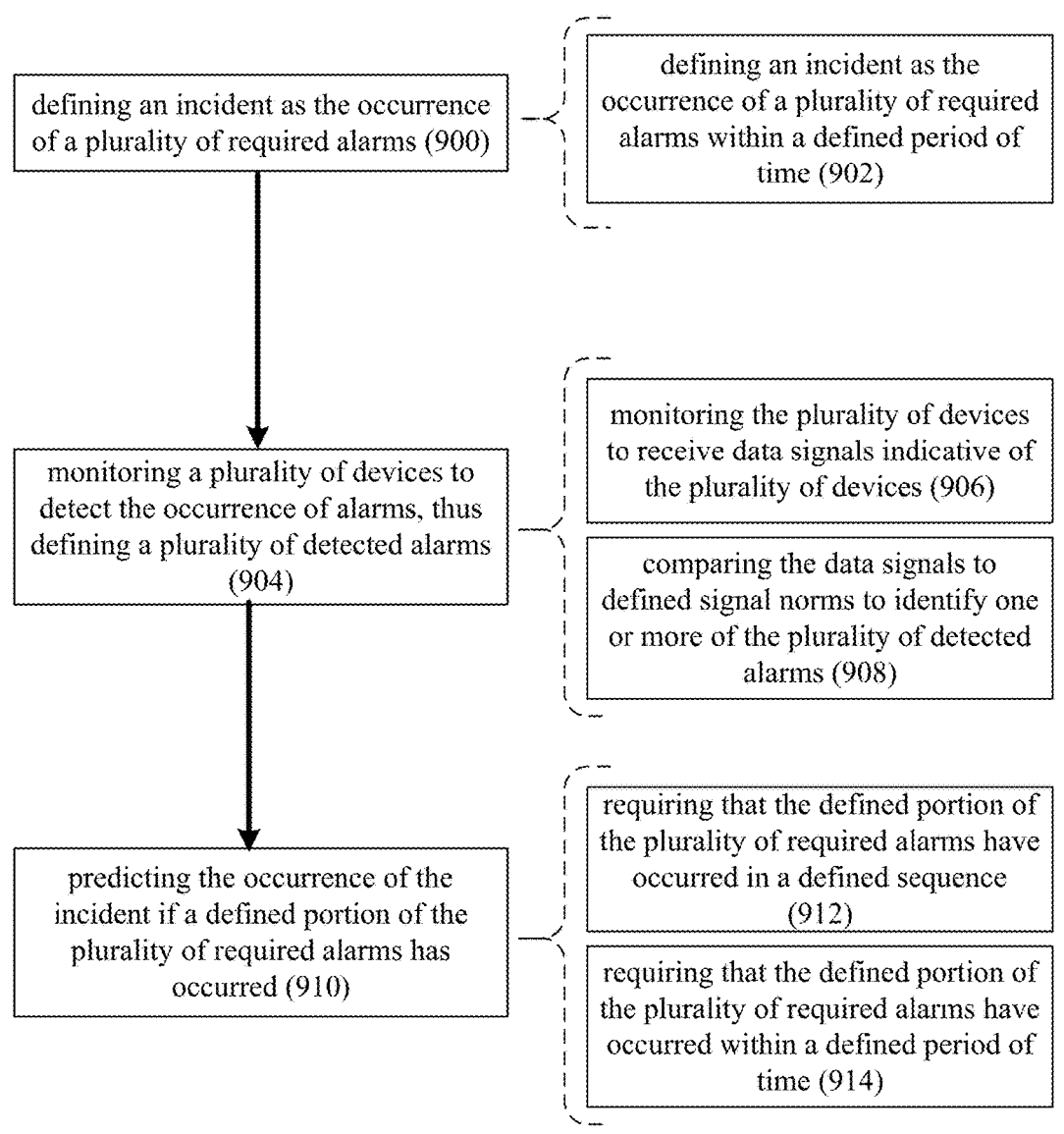
FIG. 10 is another flowchart of the information process of FIG. 1 according to an embodiment of the present disclosure.

Referring also to FIG. 10 and as discussed above, information process 10 may define 900 an incident (e.g., incident 272) as the occurrence of a plurality of required alarms, wherein the incident of heart failure may be defined 900 as the occurrence of: low blood pressure, a rapid heart rate, and a low blood oxygen level. As also discussed above, when defining 900 an incident (e.g., a heart failure incident) as the occurrence of a plurality of required alarms (e.g., a low blood pressure alarm, a rapid heart rate alarm, and a low blood oxygen level alarm), information process 10 may define 902 the incident (e.g., a heart failure incident) as the occurrence of a plurality of required alarms (e.g., a low blood pressure alarm, a rapid heart rate alarm, and a low blood oxygen level alarm) within a defined period of time.

Further and as discussed above, information process 10 may monitor 904 a plurality of devices (e.g., one or more of first vendor devices 202 and/or one or more of second vendor devices 206) to detect the occurrence of alarms. As also discussed above, the plurality of devices (e.g., one or more of first vendor devices 202 and/or one or more of second vendor devices 206) may include one or more of: a medical device, a process control device, a networking device, a computing device, a manufacturing device, an agricultural device, an energy/refining device, an aerospace device, a forestry device, and a defense device. Further and as discussed above, the plurality of devices (e.g., one or more of first vendor devices 202 and/or one or more of second vendor devices 206) may be geographically proximate or geographically dispersed (e.g., within one unit of a hospital, spread across an entire hospital, spread across a group of hospitals, spread across a state, or spread across a country).

As discussed above, when monitoring 904 a plurality of devices (e.g., one or more of first vendor devices 202 and/or one or more of second vendor devices 206) to detect the occurrence of alarms, information process 10 may: monitor 906 the plurality of devices (e.g., one or more of first vendor devices 202 and/or one or more of second vendor devices 206) to receive data signals (e.g., data signals 200 and/or data signals 204) indicative of the plurality of devices (e.g., one or more of first vendor devices 202 and/or one or more of second vendor devices 206).

As also discussed above, such data signals (e.g., one or more of data signals 200 and/or one or more of data signals 204) may concern one or more details of the plurality of devices (e.g., one or more of first vendor devices 202 and/or one or more of second vendor devices 206) and/or uses of the plurality of devices (e.g., one or more of first vendor devices 202 and/or one or more of second vendor devices 206).

As also discussed above, when monitoring 904 a plurality of devices (e.g., one or more of first vendor devices 202 and/or one or more of second vendor devices 206) to detect the occurrence of alarms, information process 10 may: compare 908 the data signals (e.g., data signals 200 and/or data signals 204) to defined signal norms to identify one or more of the plurality of detected alarms (e.g., alarms 274, 276, 278).

As discussed above, examples of such defined signal norms (e.g., defined signal norms 228) may include user-defined signal norms and/or machine-defined signal norms. For example and with respect to user-defined signal norms, such user-defined signal norms may be the result of (in this example) medical studies, medical books, insurance charts, medical records, etc. Further and with respect to machine-defined signal norms, such machine-defined signal norms may be defined via massive data sets that are processed by machine learning.

As also discussed above, such defined signal norms (e.g., defined signal norms 228) may be compartmentalized by e.g., gender, race, age, location, device type, device class, seasonality, time of day, etc. Specifically, medical statistics may vary depending upon various factors (including gender, race, age, location, device type, device class, seasonality, and time of day), wherein these factors can influence health outcomes, disease prevalence, treatment response, and other medical parameters.

Information process 10 may predict 910 the occurrence of the incident (e.g., incident 272) if a defined portion of the plurality of required alarms (e.g., a low blood pressure alarm, a rapid heart rate alarm, and a low blood oxygen level alarm) has occurred. For example, if a patient is experiencing e.g., low blood pressure and a rapid heart rate, information process 10 may predict 910 the occurrence of incident 272 (e.g., heart failure), as a defined portion (e.g., ⅔rds) of the plurality of required alarms (e.g., a low blood pressure alarm, a rapid heart rate alarm, and a low blood oxygen level alarm) have occurred (and information process 10 is anticipating that the patient will soon be experiencing low blood oxygen levels).

For example and when predicting 910 the occurrence of the incident (e.g., incident 272) if a defined portion (e.g., ⅔rds) of the plurality of required alarms (e.g., a low blood pressure alarm, a rapid heart rate alarm, and a low blood oxygen level alarm) has occurred, information process 10 may: require 912 that the defined portion (e.g., ⅔rds) of the plurality of required alarms (e.g., a low blood pressure alarm, a rapid heart rate alarm, and a low blood oxygen level alarm) have occurred in a defined sequence.

As discussed above, low blood pressure, a rapid heart rate, and a low blood oxygen level are the three events that define the occurrence of heart failure (e.g., incident 272). However, the sequence in which these events occur may be important to making a prediction of heart failure. For example, history may show that low blood pressure and a rapid heart rate will likely result in a low blood oxygen level shortly thereafter; thus enabling information process 10 to predict 910 the occurrence of incident 272 (e.g., heart failure), anticipating that the patient will soon be experiencing low blood oxygen levels. However, history may show that a low blood oxygen level and low blood pressure may not result in a rapid heart rate shortly thereafter; thus preventing information process 10 from predicting 910 the occurrence of incident 272 (e.g., heart failure), anticipating that the patient will not soon be experiencing a rapid heart rate.

Further and when predicting 910 the occurrence of the incident (e.g., incident 272) if a defined portion (e.g., ⅔rds) of the plurality of required alarms (e.g., a low blood pressure alarm, a rapid heart rate alarm, and a low blood oxygen level alarm) has occurred, information process 10 may: require 914 that the defined portion (e.g., ⅔rds) of the plurality of required alarms (e.g., a low blood pressure alarm, a rapid heart rate alarm, and a low blood oxygen level alarm) have occurred within a defined period of time. As discussed above, the occurrence of a plurality of alarms is only significant if such alarms occurred in a temporarily-proximate fashion. For example, a low blood pressure alarm, followed by a rapid heart rate alarm a week later (when the low blood pressure alarm no longer exists), followed by a low blood oxygen level alarm a week later (when the low blood pressure alarm and the rapid heart rate alarm no longer exist) is probably NOT indicative of incident 272 (e.g., a heart failure incident). Accordingly and when predicting 910 the occurrence of the incident (e.g., incident 272) if a defined portion (e.g., ⅔rds) of the plurality of required alarms (e.g., a low blood pressure alarm, a rapid heart rate alarm, and a low blood oxygen level alarm) has occurred, information process 10 may: require 914 that the defined portion (e.g., ⅔rds) of the plurality of required alarms (e.g., a low blood pressure alarm, a rapid heart rate alarm, and a low blood oxygen level alarm) have occurred within a defined period of time.

The defined portion (e.g., ⅔rds) of the plurality of required alarms (e.g., a low blood pressure alarm, a rapid heart rate alarm, and a low blood oxygen level alarm) may be defined via massive data sets that are processed by machine learning. As discussed above, information process 10 may train an AI model (e.g., AI model 268) based, at least in part, upon the categorized alarms (e.g., categorized alarms 264). For example, data set 270 may be generated and AI model 268 may be trained based upon data set 270. Data set 270 may include e.g., categorized alarms from the medical environment (e.g., hospital 246 . . . or a portion thereof) and from other medical environments (not shown), wherein AI model 268 may be trained by processing data set 270 to extract patterns hidden within data set 270.

Machine learning models extract patterns from a dataset through a process called training. During training, the model learns to recognize patterns and relationships within the data by adjusting its internal parameters or weights. Accordingly, by training AI model 268 based, at least in part, upon categorized alarms 264, various patterns may be extracted concerning e.g., average alarms counts/types and how they relate to patient demographics, hospital locations, staffing levels, staff attrition levels, staff satisfaction levels, etc.

Clustering Incidents to Define an Event:

As discussed above, information process 10 may define the occurrence of a group of alarms as the occurrence of an incident. Generally speaking, while the individual occurrence of any of the group of alarms may not be a concern, the occurrence of the entire group of alarms may be indicative of a bigger problem (i.e., hence the occurrence of an incident). Further and as will be discussed below, information process 10 may define the occurrence of a group of incidents as the occurrence of an event. Generally speaking, while the individual occurrence of any of the group of incidents may not be a concern, the occurrence of the entire group of incidents may be indicative of a bigger problem (i.e., hence the occurrence of an event).

Figure 11:
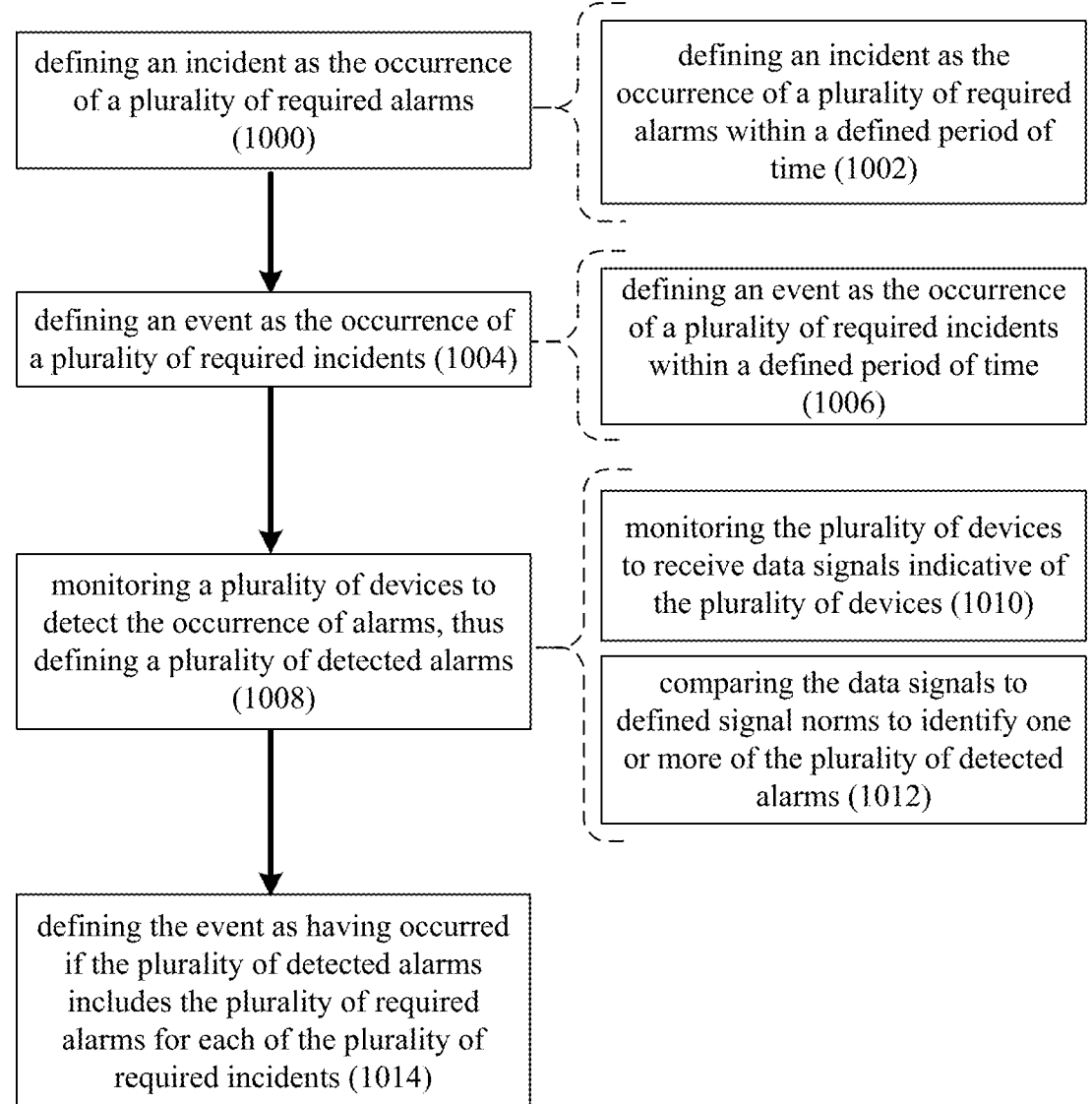
FIG. 11 is another flowchart of the information process of FIG. 1 according to an embodiment of the present disclosure.

Referring also to FIG. 11 and as discussed above, information process 10 may define 1000 an incident (e.g., incident 272) as the occurrence of a plurality of required alarms, wherein the incident of heart failure may be defined 1000 as the occurrence of: low blood pressure, a rapid heart rate, and a low blood oxygen level. As also discussed above, when defining 1000 an incident (e.g., a heart failure incident) as the occurrence of a plurality of required alarms (e.g., a low blood pressure alarm, a rapid heart rate alarm, and a low blood oxygen level alarm), information process 10 may define 1002 the incident (e.g., a heart failure incident) as the occurrence of a plurality of required alarms (e.g., a low blood pressure alarm, a rapid heart rate alarm, and a low blood oxygen level alarm) within a defined period of time.

Information process 10 may define 1004 an event (e.g., event 280) as the occurrence of a plurality of required incidents. For example, the occurrence of incidents 272, 282, 284 may be indicative of the occurrence of an event (e.g., event 280). For example, incident 272 is deemed to have occurred if three alarms (e.g., alarms 274, 276, 278) have occurred. And similarly, information process 10 may deem incidents 282, 284 to have occurred if a plurality of alarms (not shown) associated with each of incidents 282, 284 have occurred. Assume for this example that the plurality of alarms (not shown) associated with incident 282 concern the functioning of the kidneys and, therefore, incident 282 may indicate renal failure. Further assume for this example that the plurality of alarms (not shown) associated with incident 284 concern the functioning of the respiratory system and, therefore, incident 284 may indicate respiratory failure. Accordingly, when incidents 272, 282, 284 (namely heart failure, renal failure and respiratory failure) have occurred, information process 10 may deem the occurrence of such incidents to be indicative of the occurrence of event 280 (namely systemic organ failure).

Further, while incidents 272, 282, 284 are described above as being different incidents that result in event 280, this is for illustrative purposes only, as other configurations are possible and are considered to be within the scope of this disclosure. For example, assume that each of incidents 272, 282, 284 is the same (e.g., ricin poisoning). Accordingly, if three ricin incidents occur, event 280 may be a terrorist attack.

When defining 1004 an event (e.g., event 280) as the occurrence of a plurality of required incidents (e.g., incidents 272, 282, 284), information process 10 may: define 1006 an event (e.g., event 280) as the occurrence of a plurality of required incidents (e.g., incidents 272, 282, 284) within a defined period of time.

Oftentimes, the occurrence of a plurality of incidents is only significant if such incidents occurred in a temporarily-proximate fashion. For example, a heart failure incident, followed by a renal failure incident a week later (when the heart failure incident no longer exists), followed by a respiratory failure incident a week later (when the heart failure incident and the renal failure incident no longer exist) is probably NOT indicative of event 280 (e.g., a systemic organ failure event). Accordingly and when defining 1004 an event (e.g., event 280) as the occurrence of a plurality of required incidents (e.g., a heart failure incident, a renal failure incident and a respiratory failure incident), information process 10 may: define 1006 the event (e.g., a systemic organ failure event) as the occurrence of a plurality of required incidents (e.g., a heart failure incident, a renal failure incident and a respiratory failure incident) within a defined period of time As discussed above, information process 10 may monitor 1008 a plurality of devices (e.g., one or more of first vendor devices 202 and/or one or more of second vendor devices 206) to detect the occurrence of alarms. As discussed above, the plurality of devices (e.g., one or more of first vendor devices 202 and/or one or more of second vendor devices 206) may include one or more of: a medical device, a process control device, a networking device, a computing device, a manufacturing device, an agricultural device, an energy/refining device, an aerospace device, a forestry device, and a defense device. Further, the plurality of devices (e.g., one or more of first vendor devices 202 and/or one or more of second vendor devices 206) may be geographically proximate or geographically dispersed. For example, the plurality of devices (e.g., one or more of first vendor devices 202 and/or one or more of second vendor devices 206) may be within one unit of a hospital, spread across an entire hospital, spread across a group of hospitals, spread across a state, or spread across a country.

When monitoring 1008 a plurality of devices (e.g., one or more of first vendor devices 202 and/or one or more of second vendor devices 206) to detect the occurrence of alarms, information process 10 may: monitor 1010 the plurality of devices (e.g., one or more of first vendor devices 202 and/or one or more of second vendor devices 206) to receive data signals (e.g., data signals 200 and/or data signals 204) indicative of the plurality of devices (e.g., one or more of first vendor devices 202 and/or one or more of second vendor devices 206).

As also discussed above, such data signals (e.g., one or more of data signals 200 and/or one or more of data signals 204) may concern one or more details of the plurality of devices (e.g., one or more of first vendor devices 202 and/or one or more of second vendor devices 206) and/or uses of the plurality of devices (e.g., one or more of first vendor devices 202 and/or one or more of second vendor devices 206).

When monitoring 1008 a plurality of devices (e.g., one or more of first vendor devices 202 and/or one or more of second vendor devices 206) to detect the occurrence of alarms, information process 10 may: compare 1012 the data signals (e.g., data signals 200 and/or data signals 204) to defined signal norms to identify one or more of the plurality of detected alarms (e.g., alarms 274, 276, 278).

As discussed above, examples of such defined signal norms (e.g., defined signal norms 228) may include user-defined signal norms and/or machine-defined signal norms. For example and with respect to user-defined signal norms, such user-defined signal norms may be the result of (in this example) medical studies, medical books, insurance charts, medical records, etc. Further and with respect to machine-defined signal norms, such machine-defined signal norms may be defined via massive data sets that are processed by machine learning.

As also discussed above, such defined signal norms (e.g., defined signal norms 228) may be compartmentalized by e.g., gender, race, age, location, device type, device class, seasonality, time of day, etc. Specifically, medical statistics may vary depending upon various factors (including gender, race, age, location, device type, device class, seasonality, and time of day), wherein these factors can influence health outcomes, disease prevalence, treatment response, and other medical parameters.

As discussed above, information process 10 may define 1004 an event (e.g., event 280) as the occurrence of a plurality of required incidents. Assume for this example that the plurality of alarms (not shown) associated with incident 282 concern the functioning of the kidneys and, therefore, incident 282 may indicate renal failure. Further assume for this example that the plurality of alarms (not shown) associated with incident 284 concern the functioning of the respiratory system and, therefore, incident 284 may indicate respiratory failure. Accordingly, when incidents 272, 282, 284 (namely heart failure, renal failure and respiratory failure) have occurred, information process 10 may deem the occurrence of such incidents to be indicative of the occurrence of event 280 (namely systemic organ failure).

Accordingly, information process 10 may define 1014 the event (e.g., event 280) as having occurred if the plurality of detected alarms (which were detected while monitoring 1008 the plurality of devices) includes the plurality of required alarms for each of the plurality of required incidents (e.g., incidents 272, 282, 284). So if each of incidents 272, 282, 284 requires a plurality of alarms to have occurred . . . and if the plurality of detected alarms includes the sum of the plurality of required alarms associated with each of incidents 272, 282, 284, information process 10 may define 1014 the event (e.g., event 280) as having occurred. Threshold Management:

The following discussion concerns the manner in which information process 10 may help to battle alarm fatigue by processing detected alarms to determine their authenticity and making the necessary adjustments (e.g., to monitoring criteria) to reduce the quantity of inauthentic alarms.

Referring also to FIG. 12 and as discussed above, information process 10 may monitor 1100 a bedside monitoring device (e.g., one or more of first vendor devices 202 and/or one or more of second vendor devices 206) to detect the occurrence of alarms (e.g., alarms 274, 276, 278). As discussed above, the device (e.g., one or more of first vendor devices 202 and/or one or more of second vendor devices 206) may include one or more sub devices (e.g., sub devices 224, 226).

As discussed above, studies have shown that the rate of false alarms in hospitals can be alarmingly high. For example, research conducted in intensive care units (ICUs) has reported false alarm rates ranging from 72% to 99%, indicating that the majority of alarms in these settings are false positives. Several factors contribute to the occurrence of false alarms in hospitals:

Inadequate Alarm Parameters: Alarm systems may be set with default or suboptimal alarm thresholds, leading to alarms that trigger unnecessarily. This can be due to alarm settings being too sensitive or not properly adjusted to patient-specific conditions.

Device Malfunctions or Technical Issues: Faulty equipment or technical issues with medical devices can result in false alarms. For example, electrode or sensor detachment, poor signal quality, or software glitches can generate false positive alarms.

Lack of Contextual Information: Alarms may lack the necessary contextual information to help healthcare providers accurately interpret their significance. For instance, alarms may not consider the patient's clinical condition, medications, or concurrent therapies, leading to false alarms that do not require immediate action.

Inefficient Alarm Management: Healthcare providers may be overwhelmed by the sheer number of alarms, making it challenging to respond promptly and appropriately. This can lead to alarm fatigue, where healthcare providers become desensitized or ignore alarms due to their frequency, potentially compromising patient safety.

As alarms are detected during the above-described monitoring 1100 operation, information process 10 may process 1102 the detected alarms (e.g., alarms 274, 276, 278) to determine their authenticity.

For example and when processing 1102 the detected alarms (e.g., alarms 274, 276, 278) to determine their authenticity, information process 10 may: define 1104 volume information for the detected alarms (e.g., alarms 274, 276, 278); and/or utilize 1106 the volume information to determine the authenticity of the detected alarms (e.g., alarms 274, 276, 278).

Volume: This signal measure indicates the amount of vital sign sample measurements with respect to the thresholds, e.g., the percentage of samples across the last 30 minutes and 240 minutes where vital measure level is within 90% of the threshold level. When the volume metric is high, i.e., greater than 0.8 across a 30-minute look-back and 0.5 across a 240-minute look-back, it means a high volume of measures in recent history as compared to a longer span of recent history are near the threshold and the condition is met for updating a threshold in the non-conservative direction (i.e., increasing the upper or decreasing the lower). When the volume metric is low, it means a low sample count of measures in recent history and satisfies the condition to update a threshold in the conservative direction (i.e., decreasing the upper threshold or increasing the lower).

Additionally and when processing 1102 the detected alarms (e.g., alarms 274, 276, 278) to determine their authenticity, information process 10 may: define 1108 volatility information for the detected alarms (e.g., alarms 274, 276, 278); and/or utilize 1110 the volatility information to determine the authenticity of the detected alarms (e.g., alarms 274, 276, 278).

Volatility: The next signal measure involves the level of erratic or volatile behavior. By comparing the variance of the signal over the most recent short history, e.g., last 30 minutes, to the variance of the signal over the most recent history over a longer span of time, e.g., last 240 minutes, we can deduce whether the signal is volatile or non-volatile. When the variance over the last 30 minutes, for example, exceeds that of the last 240 minutes then we can deduce the signal is too volatile for threshold adjustment. Conversely, when the opposite is true the signal is stable and this second condition is met for threshold adjustment.

Further and when processing 1102 the detected alarms (e.g., alarms 274, 276, 278) to determine their authenticity, information process 10 may: define 1112 bias information for the detected alarms (e.g., alarms 274, 276, 278); and/or utilize 1114 the bias information to determine the authenticity of the detected alarms (e.g., alarms 274, 276, 278).

Bias: This next measure involves understanding the shifting behavior of the signal, or time-varying bias. By measuring the instantaneous first derivative of the signal with respect to time, aka the time rate of change of the signal, aka the signal "velocity", we can understand when the signal is shifting and which direction. For example, when a high percentage of samples across the most recent history, e.g., last 30 or 60 minutes, with non-zero instantaneous velocity, we can deduce the signal is likely to be biased. When not found to be biased, this third condition is met for threshold adjustment.

Additionally and when processing 1102 the detected alarms (e.g., alarms 274, 276, 278) to determine their authenticity, information process 10 may: define 1116 persistence information for the detected alarms (e.g., alarms 274, 276, 278); and/or utilize 1118 the persistence information to determine the authenticity of the detected alarms (e.g., alarms 274, 276, 278).

Persistence: To understand whether the signal is persistent or non-persistent (i.e., shifting), we compute the integral (i.e., area under the curve) of the difference between the average velocity (or slope) of the signal across the most recent 30 minutes and the average velocity (or slope) of the signal across the most recent 240 minutes. When the 30-minute slope exceeds the 240 minute slope (i.e., the integral is positive), then the signal is said to be persistent (i.e., not shifting overall) and appropriate for threshold update.

Further and when processing 1102 the detected alarms (e.g., alarms 274, 276, 278) to determine their authenticity, information process 10 may: define 1120 stationary information for the detected alarms (e.g., alarms 274, 276, 278); and/or utilize 1122 the stationary information to determine the authenticity of the detected alarms (e.g., alarms 274, 276, 278).

Stationary: Lastly, measuring whether the signal is unchanged over a timespan is important for understanding whether statistics are changing or not. The signal needs to show stationarity across recent history, e.g., the Augmented Dickey-Fuller test is satisfied across a high percentage of samples in recent history.

While the above discussion concerns volume information, volatility information, bias information, persistence information, and stationary information, this is for illustrative purposes only and is not intended to be a limitation, as other configurations are possible and are considered to be within the scope of this disclosure, examples of which may include but are not limited to: pulse pressure (systolic blood pressure-diastolic), mean arterial pressure, shock index (HR/ systolic blood pressure), and external interventions that are perturbations to effect the condition and behavior of the device (e.g., one or more of first vendor devices 202 and/or one or more of second vendor devices 206), such as e.g. medications (the time since, the rate, the total amount) are important to consider here when deciding whether an adjustment to the threshold can be safely performed. If a detected alarms (e.g., one or more of alarms 274, 276, 278) is determined to be non-authentic (in any of the fashions discussed above), information process 10 may adjust 1124 one or more monitoring criteria that was instrumental in producing the non-authentic detected alarms (e.g., one or more of alarms 274, 276, 278).

As discussed above, examples of such monitoring criteria may include defined signal norms (e.g., defined signal norms 228) and/or one or more signal thresholds. Assume as discussed above that the defined signal norms (e.g., defined signal norms 228) concerning heart rate is 60-100 beats per minute. Accordingly, the defined signal norm for heart rate has a lower threshold of 60 and an upper threshold of 100.

Accordingly and when adjusting 1124 one or more monitoring criteria that was instrumental in producing the non-authentic detected alarms (e.g., one or more of alarms 274, 276, 278), information process 10 may: define 1126 bespoke monitoring criteria for the bedside monitoring device (e.g., one or more of first vendor devices 202 and/or one or more of second vendor devices 206). As discussed above, while the defined signal norms (e.g., defined signal norms 228) for a heart rate is 60-100 beats per minute; if the patient (e.g., patient 232) is a seasoned athlete of exceptional health, their "normal" heartrate may be 50-55 beats per minute. Accordingly and in such a situation, information process 10 may: define 1126 bespoke monitoring criteria (e.g., 50-55 beats per minute) for the bedside monitoring device (e.g., one or more of first vendor devices 202 and/or one or more of second vendor devices 206) that is monitoring patient 232.

If a detected alarms (e.g., one or more of alarms 274, 276, 278) is determined to be authentic, information process 10 may effectuate 1128 an appropriate medical response (e.g., notify a doctor, make an emergency announcement, notify medical staff, etc.). to the authentic detected alarms (e.g., one or more of alarms 274, 276, 278).

Operations Health UX:

The following discussion concerns the manner in which information process 10 may render an Operations Health user experience that enables a user to visually monitor the operations within one or more medical institutions.

UX stands for User Experience. It refers to the overall experience and satisfaction that a user has when interacting with a product, system, or service. UX encompasses various elements, including usability, accessibility, ease of use, efficiency, and overall user satisfaction. UX design involves understanding the users' needs, preferences, and goals and designing the product or system in a way that optimizes their experience. It aims to create intuitive, user-friendly, and enjoyable interactions that meet the users' expectations and enhance their overall satisfaction.

Some key aspects of UX design include:

User Research: Gathering insights about the target users through methods such as interviews, surveys, and observations to understand their behaviors, needs, and pain points.

Information Architecture: Organizing and structuring the information within a product or system to facilitate easy navigation and findability. This involves designing menus, categories, and hierarchies to ensure users can locate information or perform tasks efficiently.

Interaction Design: Designing the interactive elements and user interfaces of a product or system. This involves creating intuitive interfaces, designing clear and meaningful feedback for user actions, and considering the overall flow and sequence of user interactions.

Visual Design: Enhancing the visual appeal of the product or system by considering color schemes, typography, iconography, and other visual elements. Visual design aims to create a visually pleasing and cohesive user interface that supports the overall user experience.

Usability Testing: Conducting user testing sessions to evaluate the usability and effectiveness of a product or system. Usability testing helps identify areas of improvement and ensures that the design aligns with the users' expectations and needs.

The goal of UX design is to create products or systems that are intuitive, efficient, and enjoyable for users to interact with. It involves considering the users' needs, goals, and context of use to provide meaningful and satisfying experiences. By prioritizing user experience, organizations can enhance customer satisfaction, increase engagement, and build long-term user loyalty.

Referring also to FIGS. 13A-13D, information process 10 may gather 1200 information from a datasource (e.g., datasource 54, FIG. 1) concerning one or more medical professionals (e.g., user 236) within one or more medical institutions (e.g., hospital 246 . . . or a portion thereof), thus defining gathered information (e.g., gathered information 56).

As discussed above, examples of such medical professionals (e.g., user 236) may include but are not limited to any people (e.g., a nurse, nurse supervisor, medical technician, physician's assistant, physician, etc.) that work for and/or are employed by the one or more medical institutions (e.g., hospital 246 . . . or a portion thereof).

Datasource 54 may include any device that is capable of storing information concerning the one or more medical professionals (e.g., user 236) of the one or more medical institutions (e.g., hospital 246 . . . or a portion thereof), examples of which may include but are not limited to an employment database, a spreadsheet, a storage device, etc.

Generally speaking, gathered information 56 may concern, at least in part, the wellbeing of one or more medical staff (e.g., nurses, nurse supervisors, medical technicians, physician's assistants, physicians, etc.) of the one or more medical institutions (e.g., hospital 246 . . . or a portion thereof).

The wellbeing of one or more medical staff (e.g., nurses, nurse supervisors, medical technicians, physician's assistants, physicians, etc.) may concerns one or more of:

the attrition potential of the one or more medical staff (e.g., nurses, nurse supervisors, medical technicians, physician's assistants, physicians, etc.), namely what is the likelihood of a particular staff member leaving the one or more medical institutions (e.g., hospital 246 . . . or a portion thereof);

the fatigue level of the one or more medical staff (e.g., nurses, nurse supervisors, medical technicians, physician's assistants, physicians, etc.), namely how fatigued (generally) or how alarm fatigued (specifically) is a particular staff member of the one or more medical institutions (e.g., hospital 246 . . . or a portion thereof);

the patient-loading of the one or more medical staff (e.g., nurses, nurse supervisors, medical technicians, physician's assistants, physicians, etc.), namely what is the level of patient loading of a particular staff member of the one or more medical institutions (e.g., hospital 246 . . . or a portion thereof); and the alarm-loading of the one or more medical staff (e.g., nurses, nurse supervisors, medical technicians, physician's assistants, physicians, etc.), namely what is the level of alarm loading of a particular staff member of the one or more medical institutions (e.g., hospital 246 . . . or a portion thereof).

The wellbeing of the one or more medical staff (e.g., nurses, nurse supervisors, medical technicians, physician's assistants, physicians, etc.) may be based, at least in part, upon the quantity and/or authenticity of the alarms (e.g., one or more of alarms 274, 276, 278) to which the one or more medical staff (e.g., nurses, nurse supervisors, medical technicians, physician's assistants, physicians, etc.) were subjected. As discussed above, as alarms are detected during the above-described monitoring operation, information process 10 may process the detected alarms (e.g., alarms 274, 276, 278) to determine their authenticity, wherein such authenticity may be determined by examining e.g., volume information, volatility information, bias information, persistence information, and stationary information Information process 10 may enable 1202 a user (e.g., user 236) to select a viewing lens from a plurality of available viewing lenses (e.g., plurality of lens 286) through which to display the gathered information (e.g., gathered information 56), thus defining a selected viewing lens. The plurality of available viewing lenses (e.g., plurality of lens 286) may include one or more of:

Macro Level Viewing Lens 288: a lens that displays a portion of gathered information 56 that concerns the wellbeing of the medical staff (e.g., a nurse, a nurse supervisor, a medical technician, a physician's assistant, a physician, etc.) at any facility within the one or more medical institutions (e.g., hospital 246 . . . or a portion thereof).

Figure 13B:
FIGS. 13B-13D are diagrammatic views of a portion of an Operations Health UX rendered by the information process of FIG. 1 according to an embodiment of the present disclosure.

Facility Level Viewing Lens 290: a lens that displays a portion of gathered information 56 that concerns the wellbeing of the medical staff (e.g., a nurse, a nurse supervisor, a medical technician, a physician's assistant, a physician, etc.) at a particular facility within the one or more medical institutions (e.g., hospital 246 . . . or a portion thereof), as illustrated in FIG. 13B.

Figure 13C:
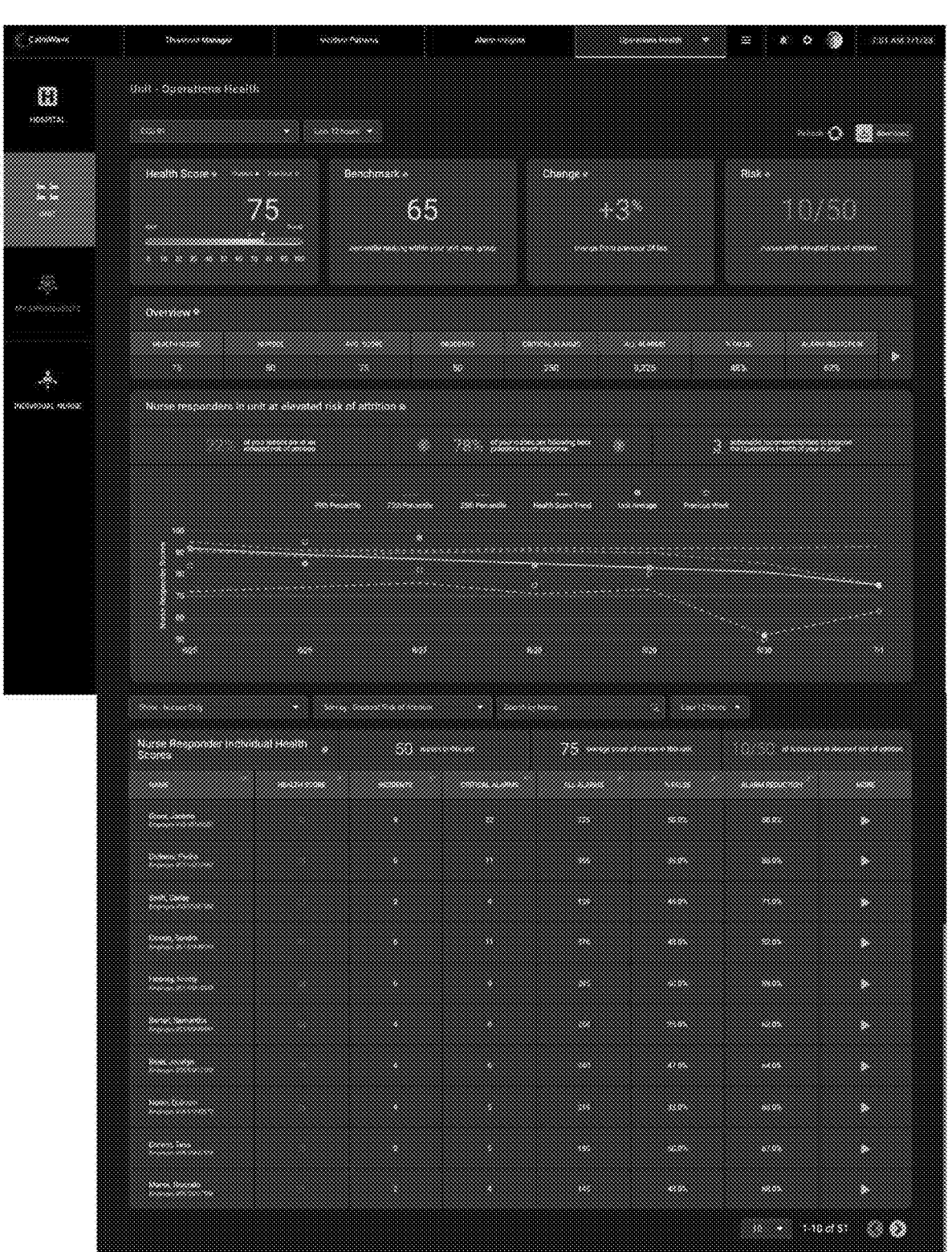

Unit Level Viewing Lens 292: a lens that displays a portion of gathered information 56 that concerns the wellbeing of the medical staff (e.g., a nurse, a nurse supervisor, a medical technician, a physician's assistant, a physician, etc.) at a particular unit of the one or more medical institutions (e.g., hospital 246 . . . or a portion thereof), as illustrated in FIG. 13C.

Cohort Level Viewing Lens 294: a lens that displays a portion of gathered information 56 that concerns the wellbeing of a selected group of medical staff (e.g., a nurse, a nurse supervisor, a medical technician, a physician's assistant, a physician, etc.) at the one or more medical institutions (e.g., hospital 246 . . . or a portion thereof).

Figure 13D:

Individual Level Viewing Lens 296: a lens that displays a portion of gathered information 56 that concerns the wellbeing of a particular medical staff (e.g., a nurse, a nurse supervisor, a medical technician, a physician's assistant, a physician, etc.) within the one or more medical institutions (e.g., hospital 246 . . . or a portion thereof), as illustrated in FIG. 13D.

Information process 10 may render 1204 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296).

When rendering 1204 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296), information process 10 may: graphically indicate 1206 information concerning the wellbeing of at least a portion of the one or more medical staff (e.g., nurses, nurse supervisors, medical technicians, physician's assistants, physicians, etc.) of the one or more medical institutions (e.g., hospital 246 . . . or a portion thereof).

When rendering 1204 at least a portion of the gathered information (e.g., gathered information 56) based, at least in part, upon the selected viewing lens, information process 10 may: provide 1208 time-based information concerning the wellbeing of at least a portion of the one or more medical staff (e.g., nurses, nurse supervisors, medical technicians, physician's assistants, physicians, etc.) of the one or more medical institutions (e.g., hospital 246 . . . or a portion thereof).

Incident Patterns UX:

The following discussion concerns the manner in which information process 10 may render an Incident Patterns user experience that enables a user to visually monitor the operations within one or more medical institutions.

Referring also to FIG. 14A-14D, information process 10 may gather 1300 information from a datasource (e.g., datasource 54, FIG. 1) concerning one or more incidents (e.g., incident 272) within one or more medical institutions (e.g., hospital 246 . . . or a portion thereof), thus defining gathered information (e.g., gathered information 56).

As discussed above, such incidents (e.g., incident 272) may be defined, at least in part, by one or more alarms (e.g., one or more of alarms 274, 276, 278) occurring within the one or more medical institutions (e.g., hospital 246 . . . or a portion thereof).

As discussed above, one or more alarms (e.g., one or more of alarms 274, 276, 278) may be originated, at least in part, on one or more devices (e.g., one or more of first vendor devices 202 and/or one or more of second vendor devices 206) within the one or more medical institutions (e.g., hospital 246 . . . or a portion thereof).

As discussed above, the one or more alarms (e.g., one or more of alarms 274, 276, 278) may be based, at least in part, upon one or more thresholds (e.g., a lower threshold of 60 and an upper threshold of 100 for the defined signal norm for a heart rate) of the one or more devices (e.g., one or more of first vendor devices 202 and/or one or more of second vendor devices 206) within the one or more medical institutions (e.g., hospital 246 . . . or a portion thereof).

Datasource 54 may include any device that is capable of storing information concerning such incidents (e.g., incident 272), examples of which may include but are not limited to an incident database, a spreadsheet, a storage device, etc.

Generally speaking, gathered information 56 may concern, at least in part, one or more incidents (e.g., incident 272) that occurred within the one or more medical institutions (e.g., hospital 246 . . . or a portion thereof).

Information process 10 may enable 1302 a user (e.g., user 236) to select a viewing lens from a plurality of available viewing lenses (e.g., plurality of lens 286) through which to display the gathered information (e.g., gathered information 56), thus defining a selected viewing lens. The plurality of available viewing lenses (e.g., plurality of lens 286) may include one or more of:

Macro Level Viewing Lens 288: a lens that displays a portion of gathered information 56 that concerns the incidents at any facility within the one or more medical institutions (e.g., hospital 246 . . . or a portion thereof).

Figure 14A:
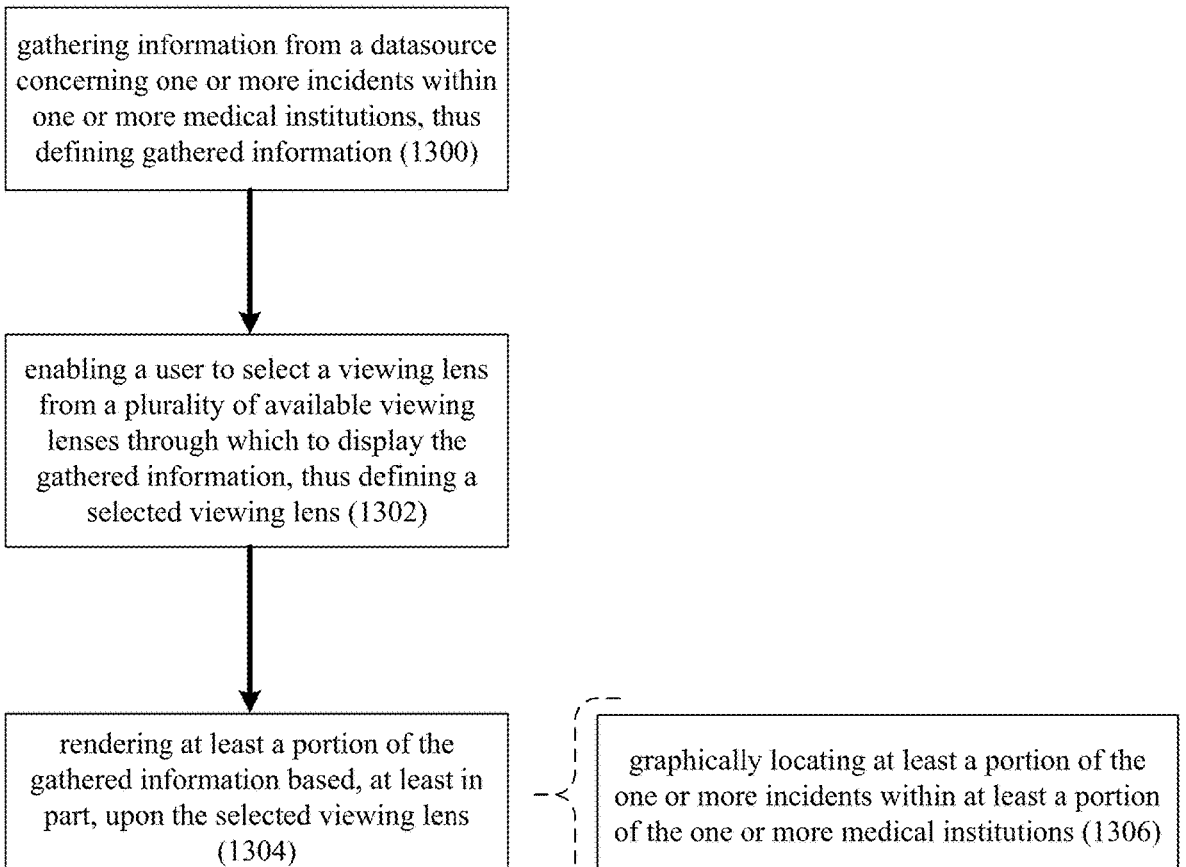
FIG. 14A is another flowchart of the information process of FIG. 1 according to an embodiment of the present disclosure.
Figure 14B:
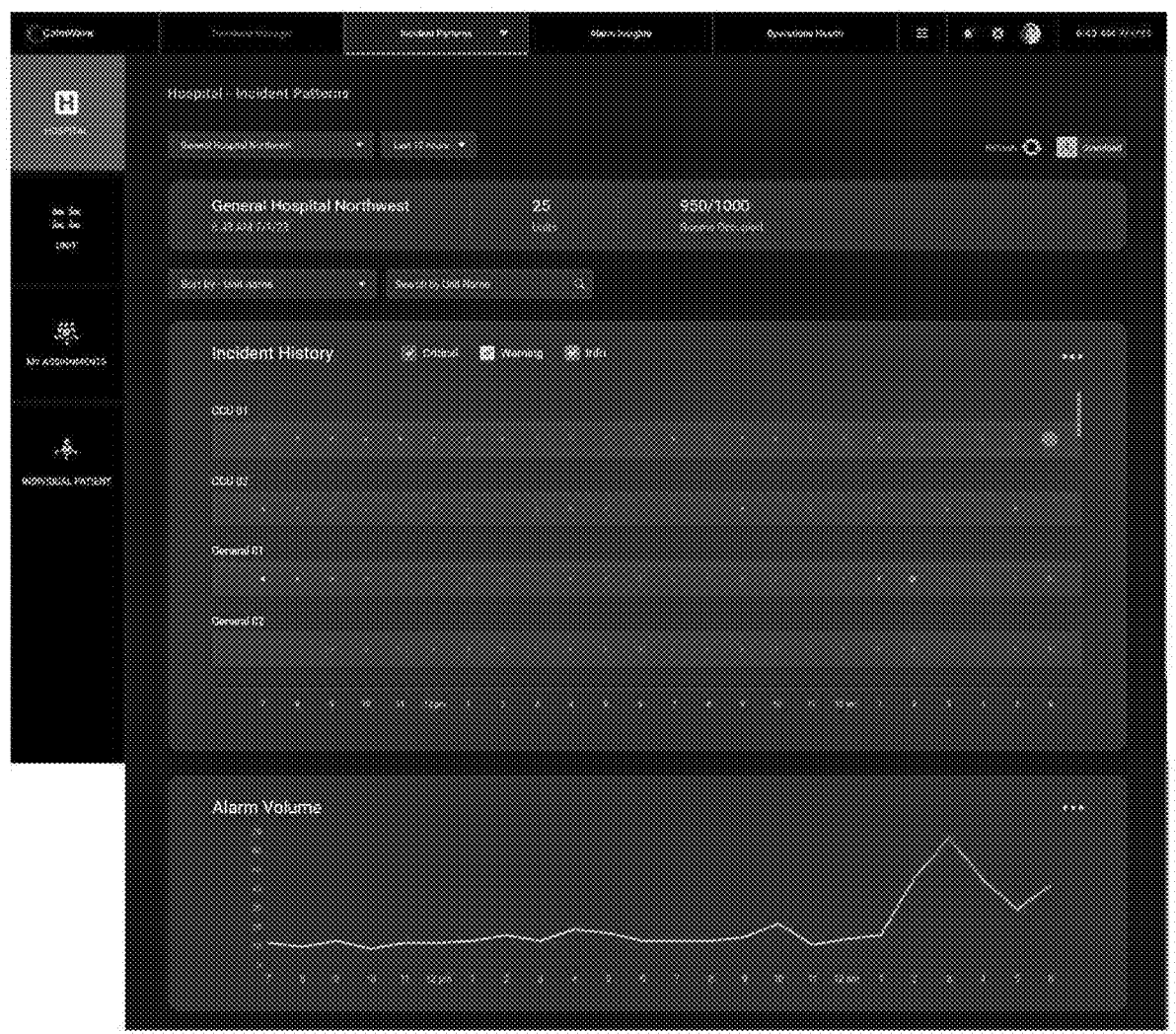
FIGS. 14B-14D are diagrammatic views of a portion of an Incident Patterns UX rendered by the information process of FIG. 1 according to an embodiment of the present disclosure.

Facility Level Viewing Lens 290: a lens that displays a portion of gathered information 56 that concerns the incidents at a particular facility within the one or more medical institutions (e.g., hospital 246 . . . or a portion thereof), as illustrated in FIG. 14B.

Figure 14C:
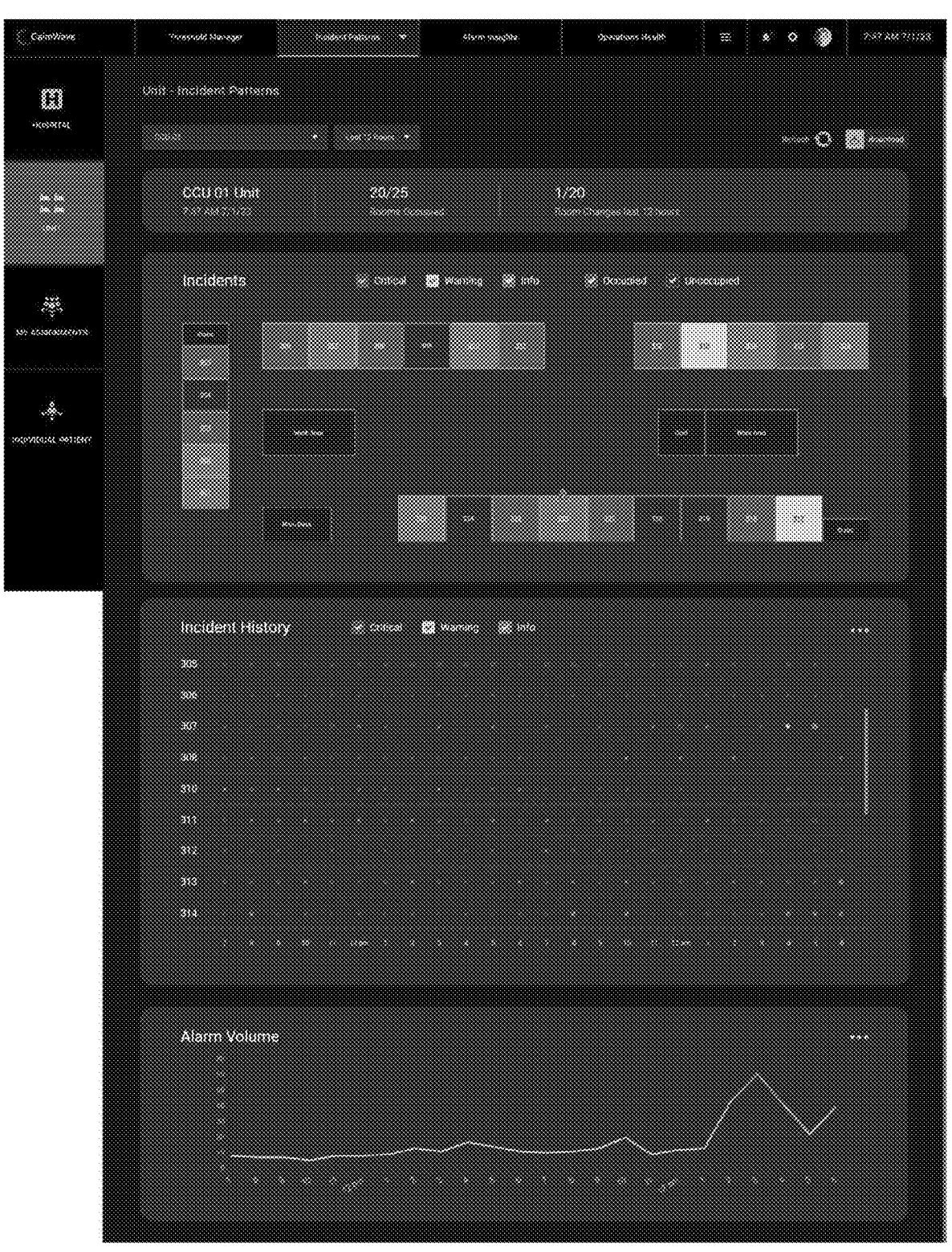

Unit Level Viewing Lens 292: a lens that displays a portion of gathered information 56 that concerns the incidents at a particular unit of the one or more medical institutions (e.g., hospital 246 . . . or a portion thereof), as illustrated in FIG. 14C.

Cohort Level Viewing Lens 294: a lens that displays a portion of gathered information 56 that concerns the incidents of a selected group of patients at the one or more medical institutions (e.g., hospital 246 . . . or a portion thereof).

Figure 14D:
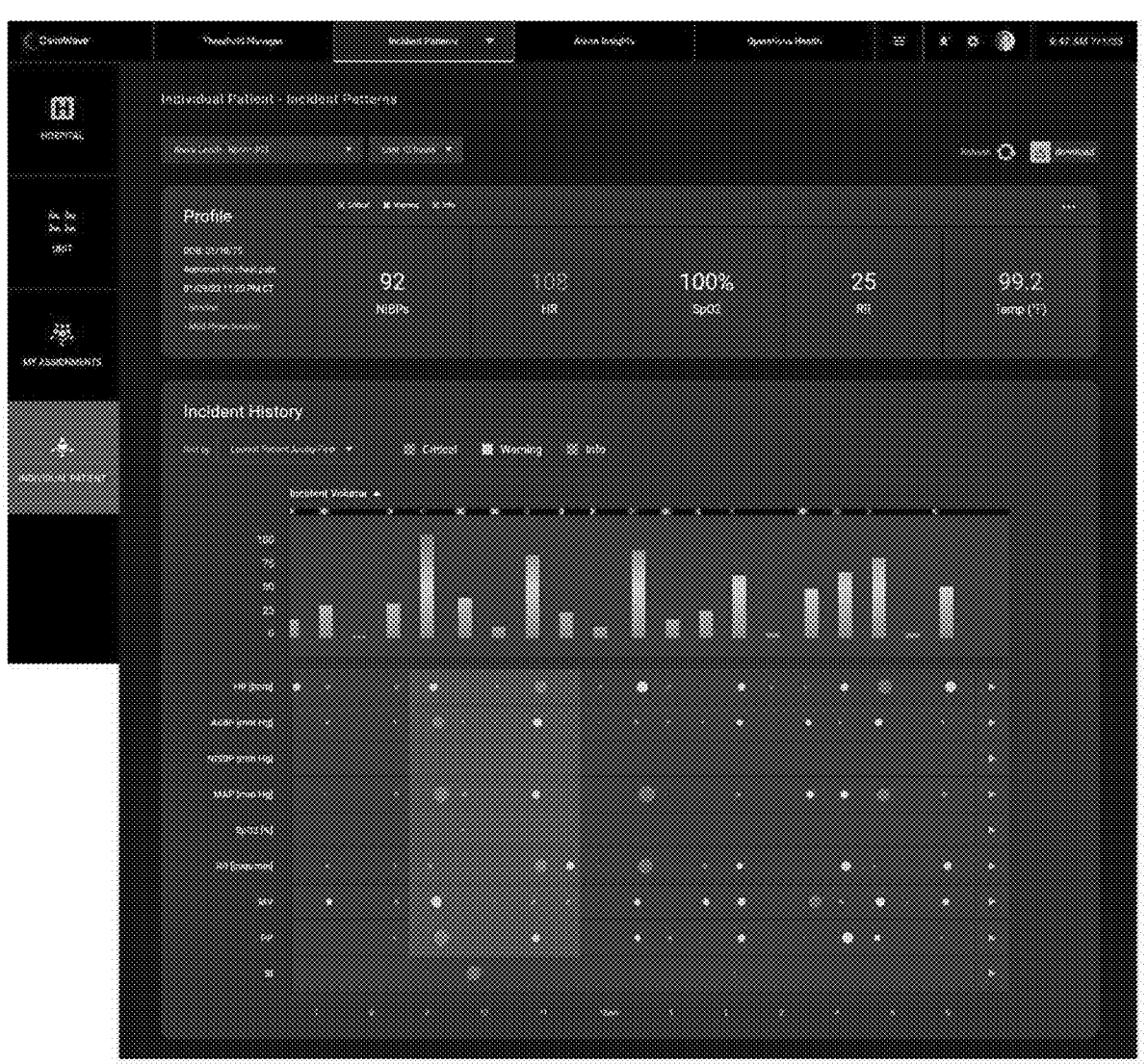

Individual Level Viewing Lens 296: a lens that displays a portion of gathered information 56 that concerns the incidents of a particular patient within the one or more medical institutions (e.g., hospital 246 . . . or a portion thereof), as illustrated in FIG. 14D.

Information process 10 may render 1304 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296).

When rendering 1304 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296), information process 10 may: graphically locate 1306 at least a portion of the one or more incidents (e.g., incident 272) within at least a portion of the one or more medical institutions (e.g., hospital 246 . . . or a portion thereof).

Information process 10 may enable 1308 a user (e.g., user 236) to adjust the one or more thresholds (e.g., a lower threshold of 60 and an upper threshold of 100 for the defined signal norm for a heart rate) of the one or more devices (e.g., one or more of first vendor devices 202 and/or one or more of second vendor devices 206) within the one or more medical institutions (e.g., hospital 246 . . . or a portion thereof).

Threshold Manager UX:

The following discussion concerns the manner in which information process 10 may render a Threshold Manager user experience that enables a user to visually monitor the operations within one or more medical institutions.

Referring also to FIG. 15A-15D, information process 10 may gather 1400 information from a datasource (e.g., datasource 54, FIG. 1) concerning one or more thresholds (e.g., a lower threshold of 60 and an upper threshold of 100 for the defined signal norm for a heart rate) within one or more medical institutions (e.g., hospital 246 . . . or a portion thereof), thus defining gathered information (e.g., gathered information 56).

As discussed above, such thresholds (e.g., a lower threshold of 60 and an upper threshold of 100 for the defined signal norm for a heart rate) may be defined, at least in part, within the one or more devices (e.g., one or more of first vendor devices 202 and/or one or more of second vendor devices 206) within the one or more medical institutions (e.g., hospital 246 . . . or a portion thereof).

Datasource 54 may include any device that is capable of storing information concerning such thresholds (e.g., a lower threshold of 60 and an upper threshold of 100 for the defined signal norm for a heart rate), examples of which may include but are not limited to an incident database, a spreadsheet, a storage device, etc.

Generally speaking, gathered information 56 may concern, at least in part, one or more thresholds of one or more devices within the one or more medical institutions.

Information process 10 may enable 1402 a user (e.g., user 236) to select a viewing lens from a plurality of available viewing lenses (e.g., plurality of lens 286) through which to display the gathered information (e.g., gathered information 56), thus defining a selected viewing lens. The plurality of available viewing lenses (e.g., plurality of lens 286) may include one or more of:

Macro Level Viewing Lens 288: a lens that displays a portion of gathered information 56 that concerns the thresholds at any facility within the one or more medical institutions (e.g., hospital 246 . . . or a portion thereof).

Facility Level Viewing Lens 290: a lens that displays a portion of gathered information 56 that concerns the thresholds at a particular facility within the one or more medical institutions (e.g., hospital 246 . . . or a portion thereof).

Figure 15A:
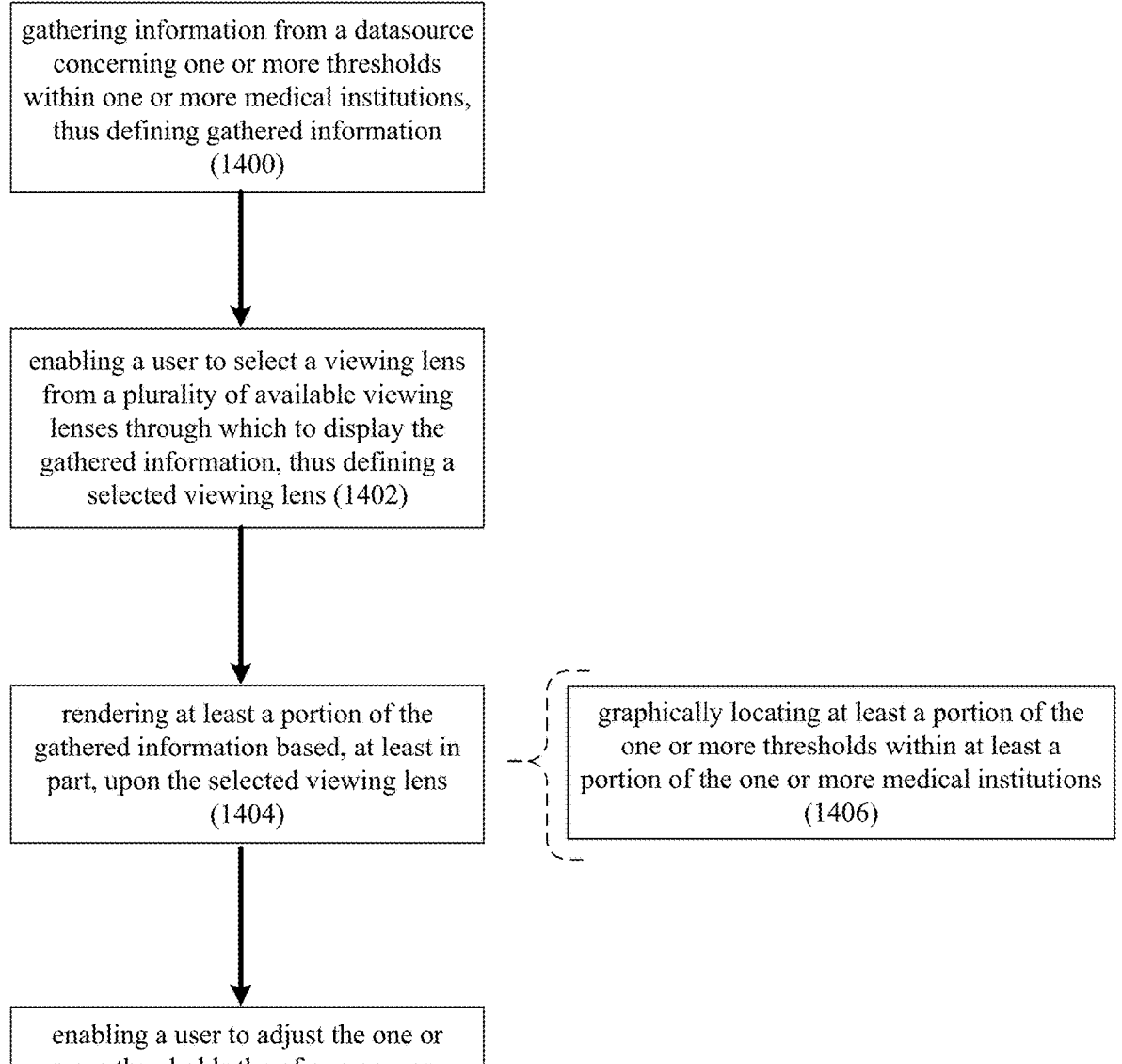
FIG. 15A is another flowchart of the information process of FIG. 1 according to an embodiment of the present disclosure.
Figure 15B:
FIGS. 15B-15D are diagrammatic views of a portion of a Threshold Manager UX rendered by the information process of FIG. 1 according to an embodiment of the present disclosure.
Figure 15C:
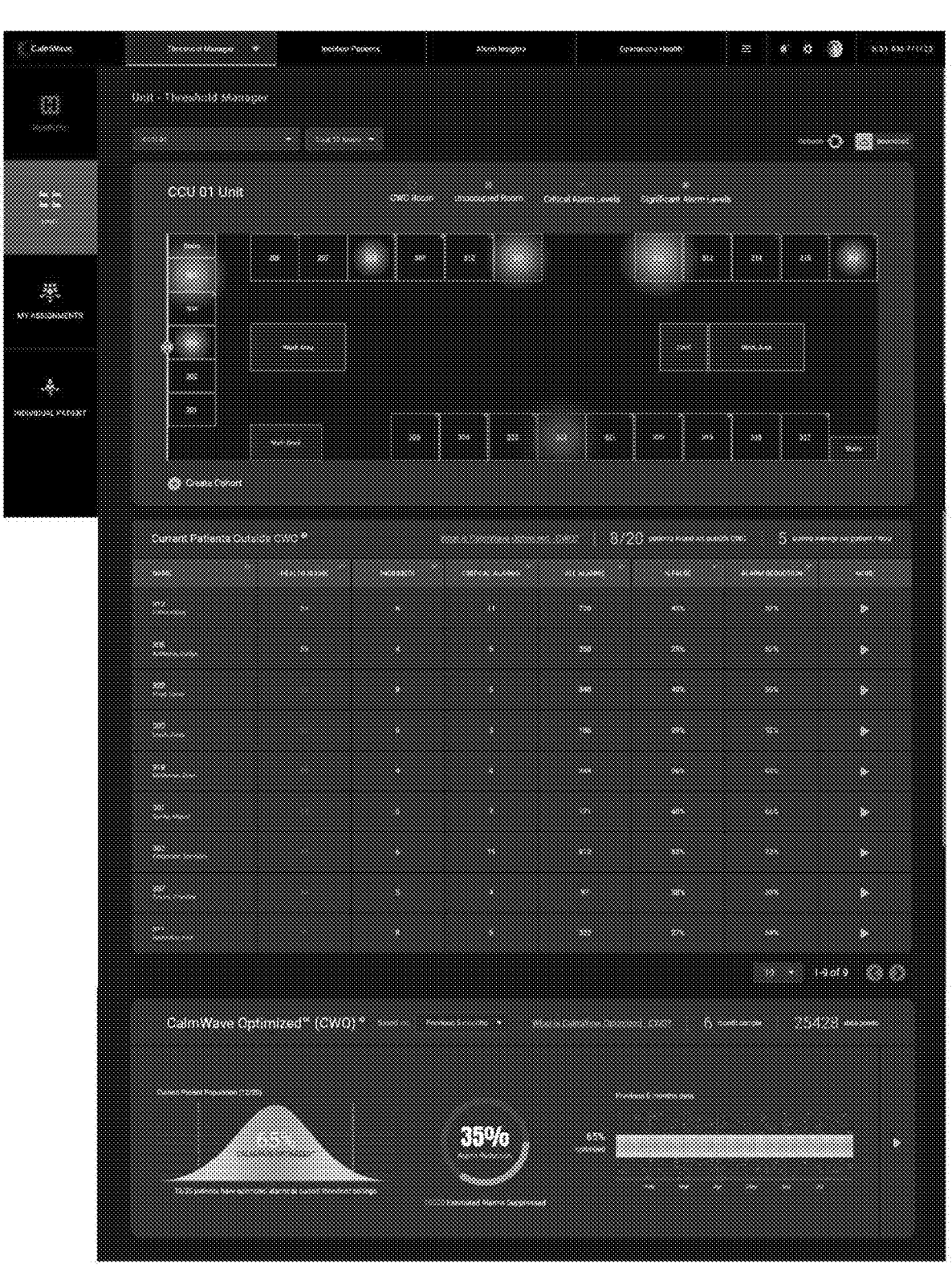

Unit Level Viewing Lens 292: a lens that displays a portion of gathered information 56 that concerns the thresholds at a particular unit of the one or more medical institutions (e.g., hospital 246 . . . or a portion thereof), as illustrated in FIGS. 15B-15C.

Cohort Level Viewing Lens 294: a lens that displays a portion of gathered information 56 that concerns the thresholds of a selected group of patients at the one or more medical institutions (e.g., hospital 246 . . . or a portion thereof).

Figure 15D:
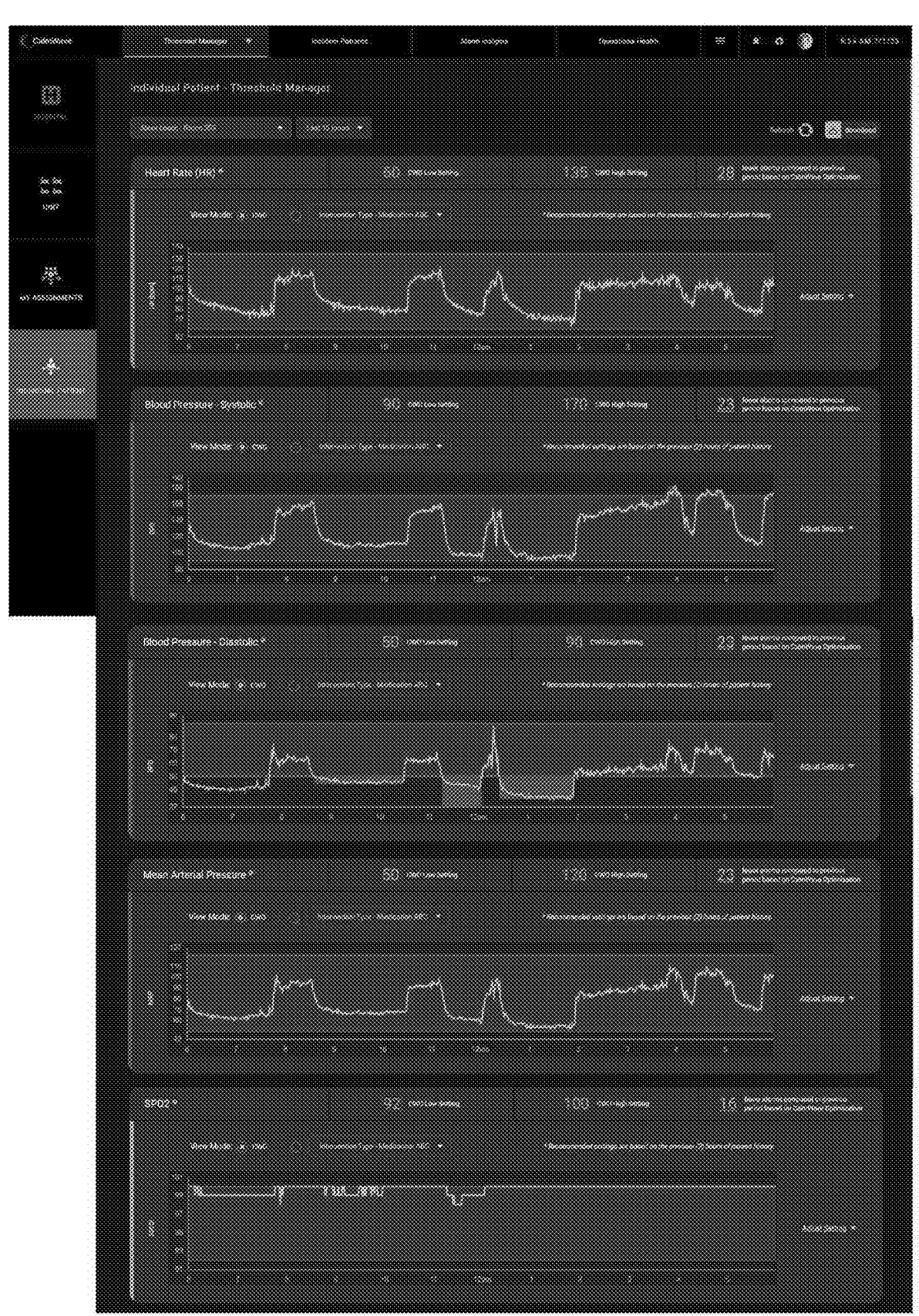

Individual Level Viewing Lens 296: a lens that displays a portion of gathered information 56 that concerns the thresholds of a particular patient within the one or more medical institutions (e.g., hospital 246 . . . or a portion thereof), as illustrated in FIG. 15D.

Information process 10 may render 1404 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296).

When rendering 1404 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296), information process 10 may: graphically locate 1406 at least a portion of the one or more thresholds within at least a portion of the one or more medical institutions (e.g., hospital 246 . . . or a portion thereof).

Information process 10 may enable 1408 a (e.g., user 236) to adjust the one or more thresholds (e.g., a lower threshold of 60 and an upper threshold of 100 for the defined signal norm for a heart rate) of the one or more devices (e.g., one or more of first vendor devices 202 and/or one or more of second vendor devices 206) within the one or more medical institutions (e.g., hospital 246 . . . or a portion thereof).

Of particular interest is FIGS. 15B-15C, which show two representations of the same information. Specifically, FIG. 15B shows the thresholds and the level at which these thresholds are currently being exceeded (i.e., bigger and/or darker indicators are indicative of more serious alarms) within the medical facility. FIG. 15C shows the same area within the medical facility but illustrates what the levels would be like if information process 10 was utilized to adjust the thresholds to a level that would reduce false alarms.

Alarm Insights UX:

The following discussion concerns the manner in which information process 10 may render an Alarm Insights user experience that enables a user to visually monitor the operations within one or more medical institutions.

Figure 16B:
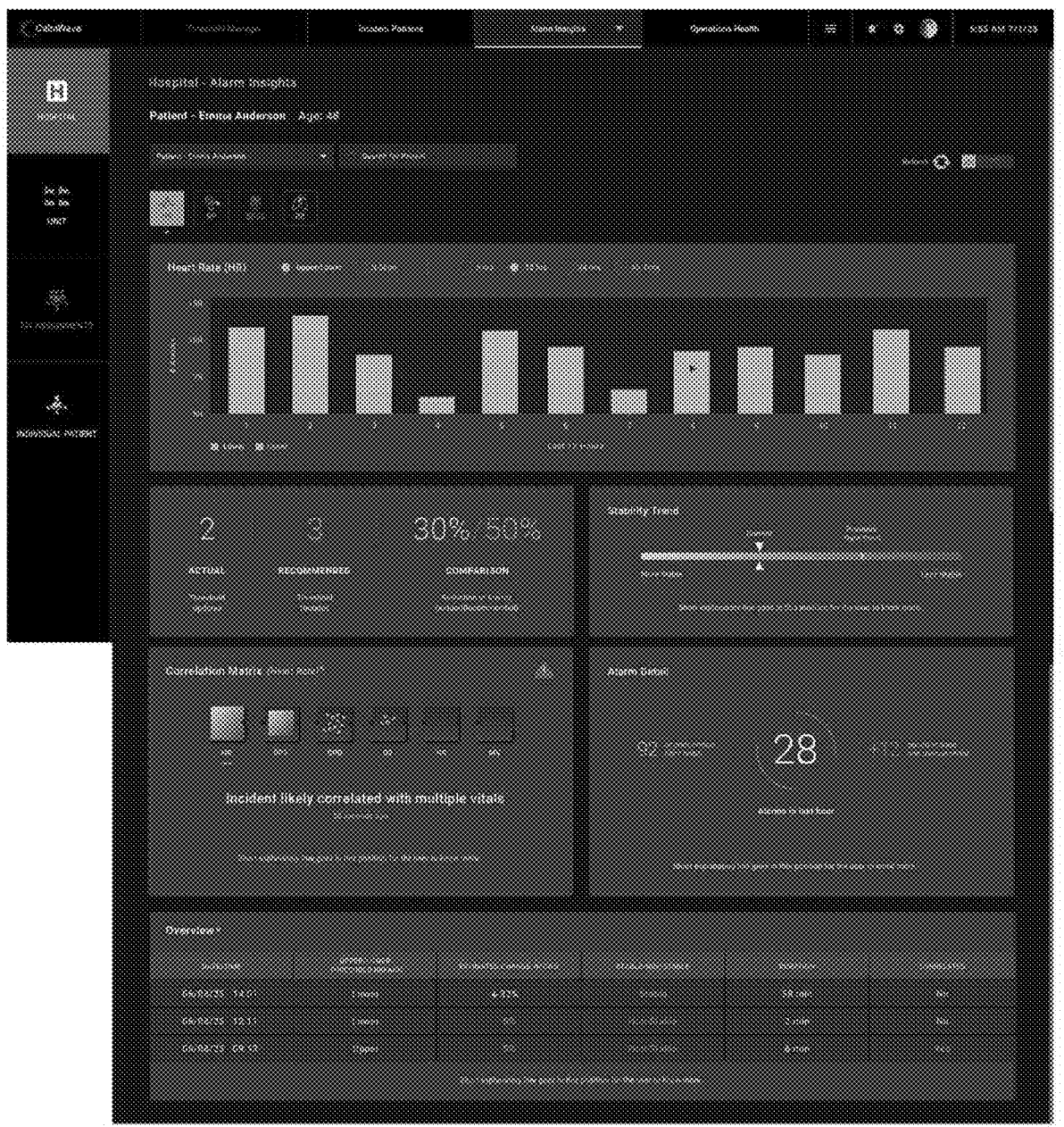
FIG. 16B is a diagrammatic view of a portion of an Alarm Insights UX rendered by the information process of FIG. 1 according to an embodiment of the present disclosure.

Referring also to FIG. 16A-16B, information process 10 may gather 1500 information from a datasource (e.g., data-source 54, FIG. 1) concerning one or more alarms (e.g., alarms 274, 276, 278) within one or more medical institutions (e.g., hospital 246 . . . or a portion thereof), thus defining gathered information (e.g., gathered information 56).

As discussed above, such alarms (e.g., alarms 274, 276, 278) may be based, at least in part, upon one or more thresholds (e.g., a lower threshold of 60 and an upper threshold of 100 for the defined signal norm for a heart rate) and originated, at least in part, on the one or more devices (e.g., one or more of first vendor devices 202 and/or one or more of second vendor devices 206) within the one or more medical institutions (e.g., hospital 246 . . . or a portion thereof).

Datasource 54 may include any device that is capable of storing information concerning such alarms (e.g., alarms 274, 276, 278), examples of which may include but are not limited to an incident database, a spreadsheet, a storage device, etc.

Generally speaking, gathered information 56 may concern, at least in part, one or more alarms (e.g., one or more of alarms 274, 276, 278) that occurred within the one or more medical institutions (e.g., hospital 246 . . . or a portion thereof).

Information process 10 may enable 1502 a user (e.g., user 236) to select a viewing lens from a plurality of available viewing lenses (e.g., plurality of lens 286) through which to display the gathered information (e.g., gathered information 56), thus defining a selected viewing lens. The plurality of available viewing lenses (e.g., plurality of lens 286) may include one or more of:

Macro Level Viewing Lens 288: a lens that displays a portion of gathered information 56 that concerns the alarms at any facility within the one or more medical institutions (e.g., hospital 246 . . . or a portion thereof).

Facility Level Viewing Lens 290: a lens that displays a portion of gathered information 56 that concerns the alarms at a particular facility within the one or more medical institutions (e.g., hospital 246 . . . or a portion thereof), as illustrated in FIG. 16B.

Unit Level Viewing Lens 292: a lens that displays a portion of gathered information 56 that concerns the alarms at a particular unit of the one or more medical institutions (e.g., hospital 246 . . . or a portion thereof).

Cohort Level Viewing Lens 294: a lens that displays a portion of gathered information 56 that concerns a selected group of alarms at the one or more medical institutions (e.g., hospital 246 . . . or a portion thereof).

Individual Level Viewing Lens 296: a lens that displays a portion of gathered information 56 that concerns a single alarm within the one or more medical institutions (e.g., hospital 246 . . . or a portion thereof).

Information process 10 may render 1504 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296).

When rendering 1504 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296), information process 10 may: graphically indicate 1506 information concerning the one or more alarms (e.g., one or more of alarms 274, 276, 278) within one or more medical institutions (e.g., hospital 246 . . . or a portion thereof).

When rendering 1504 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296), information process 10 may: provide 1508 information concerning the quantity of authentic alarms identified and inauthentic alarms avoided.

Multi-Lens UX:

The following discussion concerns the manner in which information process 10 may allow a user to gather and view information is a UX from any type of organization (e.g., a medical organization, a process control organization, a networking organization, a computing organization, a manufacturing organization, an agricultural organization, an energy/refining organization, an aerospace organization, a forestry organization, and a defense organization).

Figure 17A:
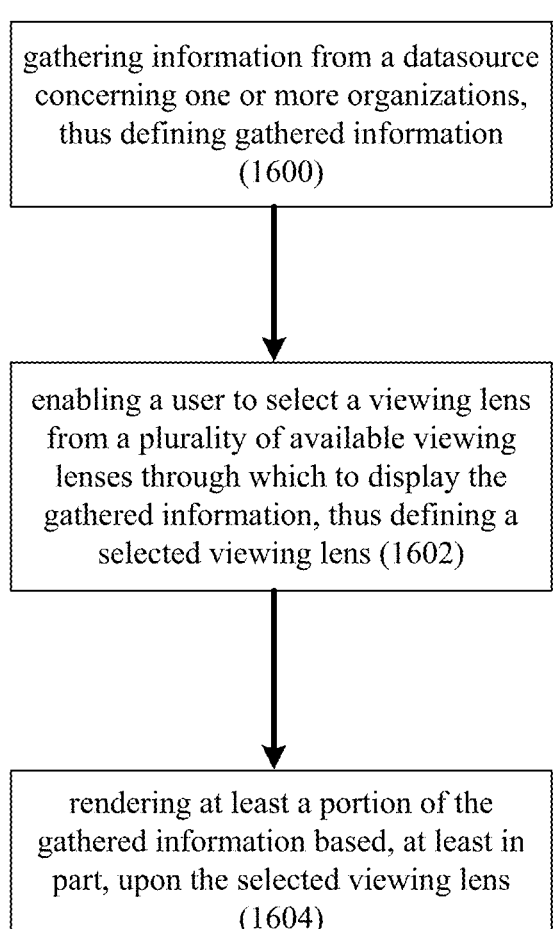
FIG. 17A is another flowchart of the information process of FIG. 1 according to an embodiment of the present disclosure.

Accordingly and referring also to FIG. 17A, information process 10 may gather 1600 information from a datasource (e.g., datasource 54, FIG. 1) concerning one or more organizations, thus defining gathered information (e.g., gathered information 56). Datasource 54 may include any device that is capable of storing gathered information 56, examples of which may include but are not limited to an incident database, a spreadsheet, a storage device, etc.

The information (e.g., gathered information 56) may concern, at least in part, the wellbeing of one or more staff of the one or more organizations; one or more incidents that occurred within the one or more organizations; one or more thresholds of one or more devices within the one or more organizations; and one or more alarms that occurred within the one or more organizations.

Generally speaking, gathered information 56 may concern, at least in part, any information about the one or more organizations, examples of which may include but are not limited to:

Corporate/Company Information: Information concerning the corporate structure of the organization.

Employment Information: Information concerning the employment practices and employment structure of the organization.

Employee/Staff Information: Information concerning the employees/staff of the organization, such as number of employees, types of employees, and benefits provided to employees.

Shareholder Information: Information concerning the shareholders, equity structure, and equity type of the organization.

Owner Information: Information concerning the owners/majority shareholders of the organization.

Event Information: Information concerning events within the organization, such as turnover events, attrition events, advertising campaigns, legal events, active lawsuits and historical lawsuits.

Tax Information: Information concerning the tax structure, tax status, tax filings of the organization.

Product/Service Information: Information concerning the products and/or services offered by the organization.

Production Information: Information concerning the production levels/production targets of the organization.

Sales Information: Information concerning the sales levels/sale targets of the organization.

Historical Information: Information concerning the history of the organization.

Location Information: Information concerning the domestic locations and foreign locations of the organization.

Information process 10 may enable 1602 a user (e.g., user 236) to select a viewing lens from a plurality of available viewing lenses (e.g., plurality of lens 286) through which to display the gathered information (e.g., gathered information 56), thus defining a selected viewing lens. The plurality of available viewing lenses (e.g., plurality of lens 286) may include one or more of:

Macro Level Viewing Lens 288: a lens that displays a portion of gathered information 56 that concerns information at any facility within the one or more organizations.

Facility Level Viewing Lens 290: a lens that displays a portion of gathered information 56 that concerns information at a particular facility within the one or more organizations.

Unit Level Viewing Lens 292: a lens that displays a portion of gathered information 56 that concerns information at a particular portion (unit/subsidiary/entity) of the one or more organizations).

Cohort Level Viewing Lens 294: a lens that displays a portion of gathered information 56 that concerns information for selected group/sub-portion at the one or more organizations.

Individual Level Viewing Lens 296: a lens that displays a portion of gathered information 56 that concerns a small item of information concerning a single employee, a single corporate event, a single tax filing, a sales of a single product within a single region, etc.

Information process 10 may render 1604 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296).

Incident Summary:

The following discussion concerns the manner in which information process 10 may monitor a plurality of data signals concerning a patient to identify discrete events concerning the patient, wherein information process 10 may summarize these discrete events so that a practitioner may quickly be informed as to what is going on with the patient.

Figure 18A:
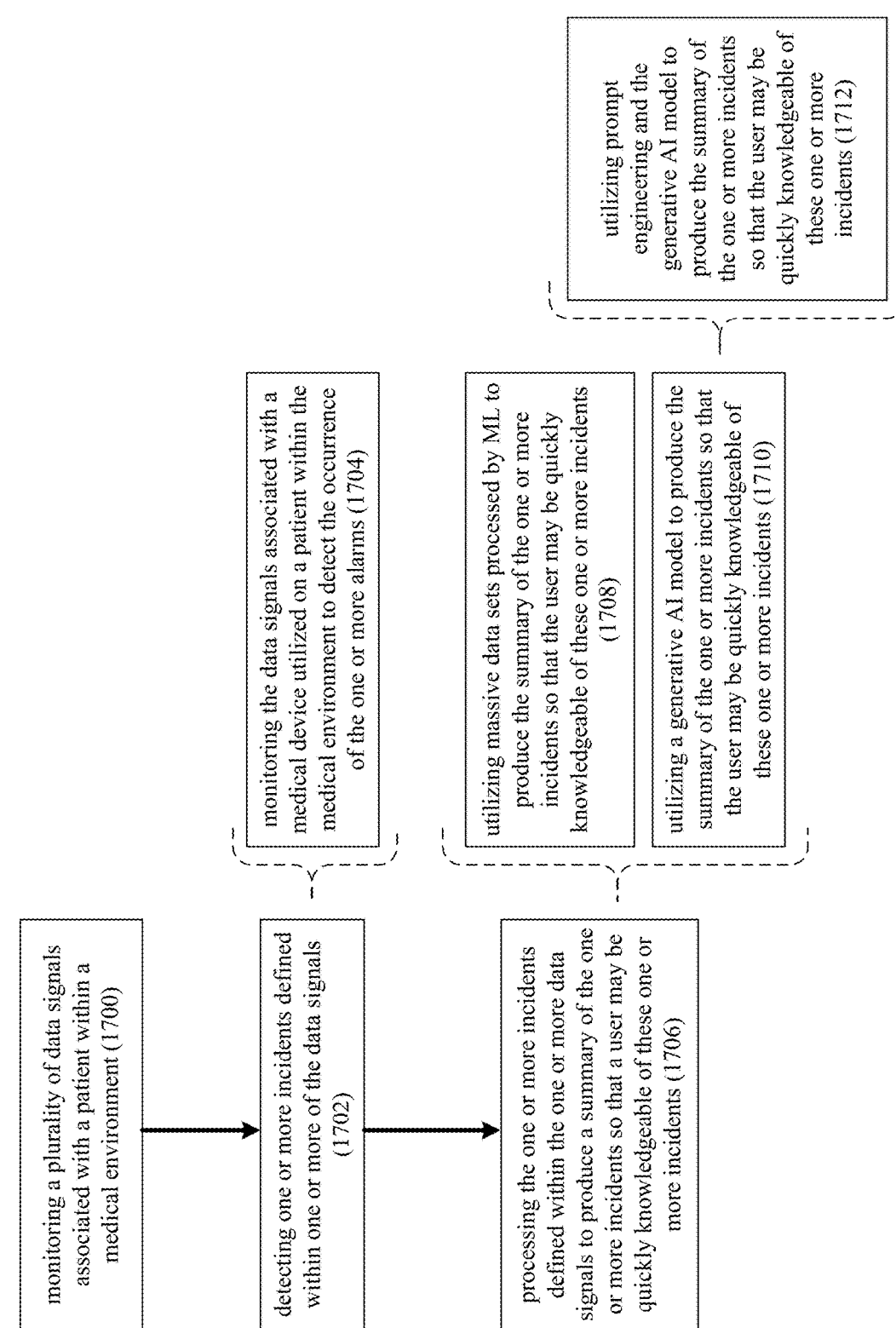
FIG. 18A is another flowchart of the information process of FIG. 1 according to an embodiment of the present disclosure.
Figure 18B:
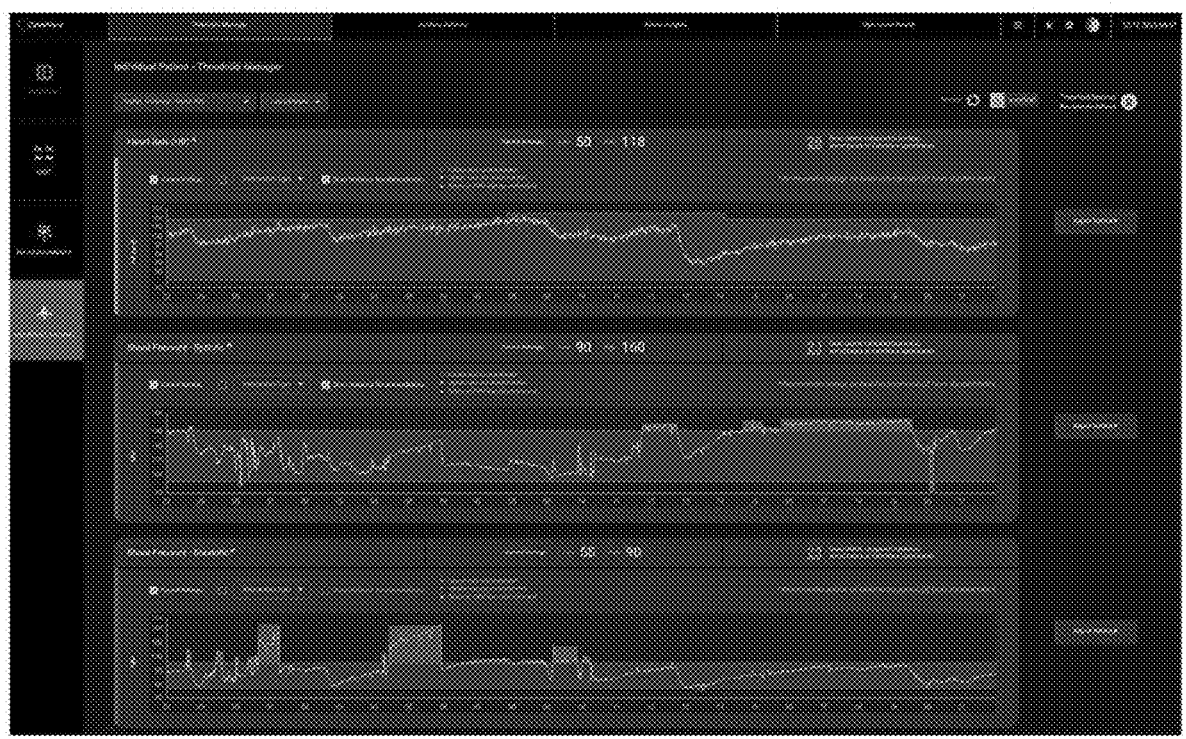
FIG. 18B-18C are diagrammatic views of display screens/windows rendered by the information process of FIG. 1 according to an embodiment of the present disclosure.
Figure 18C:
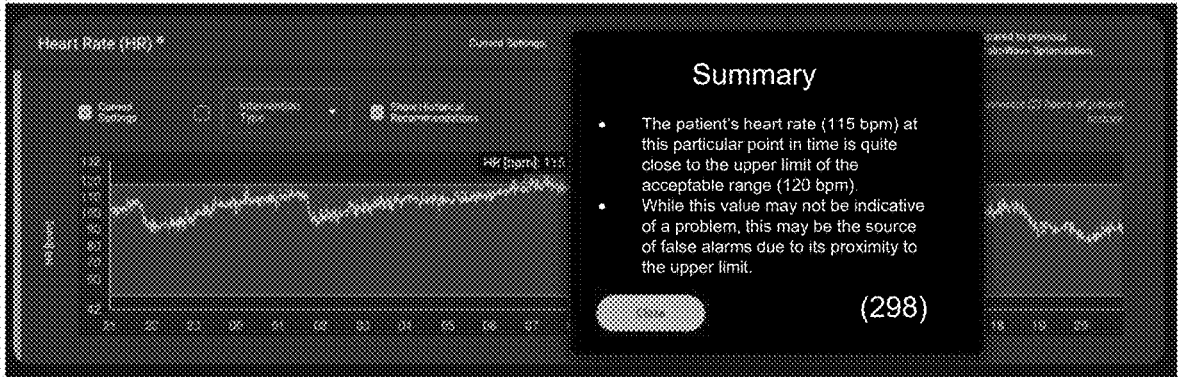

Referring also to FIGS. 18A-18C, information process 10 may monitor 1700 a plurality of data signals (e.g., data signals 200 and/or data signals 204) associated with a patient (e.g., patient 232) within a medical environment (e.g., hospital 246 . . . or a portion thereof).

Examples of this plurality of data signals (e.g., data signals 200 and/or data signals 204) may include but are not limited to one or more of the following:

One or more data signals (e.g., data signals 200 and/or data signals 204) associated with a medical device (e.g., first vendor device 202, second vendor device 204) utilized on a patient (e.g., patient 232) within the medical environment (e.g., hospital 246 . . . or a portion thereof). For example, medical devices may monitor patient 232 and provide the data signals (e.g., data signals 200 and/or data signals 204) to information process 10. These data signals (e.g., data signals 200 and/or data signals 204) may generally concern one or more details of the medical device (e.g., first vendor device 202, second vendor device 204) and/or uses of the medical device (e.g., first vendor device 202, second vendor device 204), examples of which may include:

1. Device Details: One or more details of the medical device (e.g., one or more of first vendor devices 202 and/or one or more of second vendor devices 206) may concern one or more readings, signals and/or alarms provided by the device.

2. Device Uses: One or more uses of the medical device (e.g., one or more of first vendor devices 202 and/or one or more of second vendor devices 206) may concern the manner in which the device is being used (e.g., what is the device doing, what is the device being used for, who is the device assigned/connected to, etc.).

One or more data signals (e.g., data signals 200 and/or data signals 204) associated with drugs administered to the patient (e.g., patient 232) within the medical environment (e.g., hospital 246 . . . or a portion thereof). For example, the drug administration history of patient 232 may be digitized and provided to information process 10 as the data signals (e.g., data signals 200 and/or data signals 204).

One or more data signals (e.g., data signals 200 and/or data signals 204) associated with lab work performed on the patient (e.g., patient 232) within the medical environment (e.g., hospital 246 . . . or a portion thereof). For example, the lab history of patient 232 may be digitized and provided to information process 10 as the data signals (e.g., data signals 200 and/or data signals 204).

One or more data signals (e.g., data signals 200 and/or data signals 204) associated with clinical assessments performed on the patient (e.g., patient 232) within the medical environment (e.g., hospital 246 . . . or a portion thereof). For example, the clinical assessment history of patient 232 may be digitized and provided to information process 10 as the data signals (e.g., data signals 200 and/or data signals 204).

One or more data signals (e.g., data signals 200 and/or data signals 204) associated with clinical procedures performed on the patient (e.g., patient 232) within the medical environment (e.g., hospital 246 . . . or a portion thereof). For example, the clinical procedure history of patient 232 may be digitized and provided to information process 10 as the data signals (e.g., data signals 200 and/or data signals 204).

One or more data signals (e.g., data signals 200 and/or data signals 204) associated with electronic health records and/or electronic medical records of the patient (e.g., patient 232) within the medical environment (e.g., hospital 246 . . . or a portion thereof). For example, the electronic health records and/or electronic medical records of patient 232 may be provided to information process 10 as the data signals (e.g., data signals 200 and/or data signals 204).

One or more data signals (e.g., data signals 200 and/or data signals 204) associated with a medical history of the patient (e.g., patient 232) within the medical environment (e.g., hospital 246 . . . or a portion thereof). For example, the medical history of patient 232 may be digitized and provided to information process 10 as the data signals (e.g., data signals 200 and/or data signals 204).

Information process 10 may detect 1702 one or more incidents (e.g., incidents 272, 282, 284) defined within one or more of the data signals (e.g., data signals 200 and/or data signals 204). For example and when detecting 1702 one or more incidents (e.g., incidents 272, 282, 284) defined within one or more of the data signals (e.g., data signals 200 and/or data signals 204), information process 10 may monitor 1704 the data signals (e.g., data signals 200 and/or data signals 204) associated with a medical device (e.g., first vendor device 202, second vendor device 204) utilized on a patient (e.g., patient 232) within the medical environment (e.g., hospital 246 . . . or a portion thereof) to detect the occurrence of the one or more alarms (e.g., alarms 274, 276, 278).

These medical devices (e.g., first vendor device 202, second vendor device 204) may include one or more sub-medical devices. For example, it is foreseeable that e.g., a blood pressure monitoring system may have one or more sub-systems (e.g., a wirelessly coupled blood pressure monitoring cuff).

An incident may include (i.e., may be defined as) the occurrence of one or more alarms (e.g., alarms 274, 276, 278). For example, assume that the incident of heart failure may be defined as the occurrence of: low blood pressure, a rapid heart rate, and a low blood oxygen level. While the occurrence of any of these individual alarms may not be indicative of a more serious issue, when a person is experiencing all three of these issues (e.g., low blood pressure, a rapid heart rate, and a low blood oxygen level), that person may be experiencing heart failure.

For this example, assume that the bedside devices (e.g., one or more of first vendor devices 202 and/or one or more of second vendor devices 206) that are monitoring patient 232 generate three alarms (e.g., alarms 274, 276, 278), wherein:

alarm 274 indicates that patient 232 has low blood pressure;

alarm 276 indicates that patient 232 has a rapid heart rate; and alarm 278 indicates that patient 232 has low oxygen levels in their blood.

Accordingly, information process 10 may consider the occurrence of these three alarms (e.g., alarms 274, 276, 278) to be indicative of a heart failure incident (e.g., incident 272).

Further, the occurrence of a plurality of incidents may be significant if such incidents occurred in a temporarily-proximate fashion. For example, a heart failure incident (e.g., incident 272), followed by a renal failure incident (e.g., incident 282) a week later (when heart failure incident 272 no longer exists), followed by a respiratory incident (e.g., incident 284) a week later (when heart failure incident 272 and renal failure incident 282 no longer exist) is probably NOT indicative of event 280 (e.g., a systemic organ failure event). Accordingly and if an event (e.g., event 280) is defined as the occurrence of a plurality of required incidents (e.g., a heart failure incident, a renal failure incident and a respiratory failure incident), information process 10 may: define the event (e.g., systemic organ failure event 280) as the occurrence of a plurality of required incidents (e.g., a heart failure incident, a renal failure incident and a respiratory failure incident) within a defined period of time (e.g., simultaneously, within an hour, within a day, etc.).

Information process 10 may process 1706 the one or more incidents (e.g., incidents 272, 282, 284) defined within the one or more data signals (e.g., data signals 200 and/or data signals 204) to produce a summary (e.g., summary 298) of the one or more incidents (e.g., incidents 272, 282, 284) so that a user (e.g., user 236) may be quickly knowledgeable of these one or more incidents (e.g., incidents 272, 282, 284). As discussed above, examples of user 236 may include but are not limited to a medical professional, such as a nurse, nurse supervisor, medical technician, physician's assistant, physician, etc.

For example and referring also to FIG. 18B, information process 10 may render a user interface that will enable a user (e.g., user 236) to view their patient (e.g., patient 232) over a defined period of time (e.g., the last 24 hours). The user (e.g., user 236) may see trends within data signals (e.g., heart rate in this particular case) to get a holistic view of the condition of the patient (e.g., patient 232) over this recent history.

The square markers along each of the vital sign time signatures may indicate incidents across this timeline when information process 10 recommends an alarm limit update, based on the patient (e.g., patient 232) and various specific measures. Some boxes may indicate past alarm limit updates to avoid non-medically actionable alarms, while other boxes may indicate past alarm limit updates in the conservative direction so as to avoid missing medically actionable alarms, and still other boxes may indicate past occurrences where information process 10 deemed it not safe to adjust alarm limits and, therefore, no action required.

One or more of these boxes may be selected (e.g., with a mouse click) by the user (e.g., user 236) so that information process 10 may provide supplemental information concerning the box (or boxes) selected. For example, information process 10 may provide a summary of one or more of these boxes in the event that the user (e.g., user 236) selects a specific box. Therefore and as shown in FIG. 18C, when the box at time 07:00 is selected for this patient (e.g., patient 232), information process 10 may render a summary window (e.g., summary 298) for this box that states the following:

The patient's heart rate (115 bpm) at this particular point in time is quite close to the upper limit of the acceptable range (120 bpm).

While this value may not be indicative of a problem, this may be the source of false alarms due to its proximity to the upper limit.

When processing 1706 the one or more incidents (e.g., incidents 272, 282, 284) defined within the one or more data signals (e.g., data signals 200 and/or data signals 204) to produce a summary (e.g., summary 298) of the one or more incidents (e.g., incidents 272, 282, 284) so that a user (e.g., user 236) may be quickly knowledgeable of these one or more incidents (e.g., incidents 272, 282, 284), information process 10 may utilize 1708 massive data sets processed by ML to produce the summary (e.g., summary 298) of the one or more incidents (e.g., incidents 272, 282, 284) so that the user (e.g., user 236) may be quickly knowledgeable of these one or more incidents (e.g., incidents 272, 282, 284).

As discussed above, a massive dataset, also referred to as a large-scale dataset or big dataset, is a collection of data that is exceptionally large in size and complexity. These datasets typically exceed the capacity of traditional data processing and analysis tools, requiring specialized approaches and infrastructure to handle and extract insights from them effectively.

The term "massive" is relative and can vary depending on the context and available resources. The size of a massive dataset can range from terabytes (1012 bytes) to petabytes (1015 bytes) or even exabytes (1018 bytes) and beyond. Massive datasets can arise from various sources and domains, including scientific research, social media, e-commerce, financial transactions, sensor networks, genomics, astronomy, and more. They often contain a high volume of records, measurements, or observations, along with diverse data types such as text, images, videos, time series, graphs, or unstructured data.

Working with massive datasets poses several challenges, including storage, processing, analysis, and scalability. Traditional methods and tools may not be sufficient to handle these datasets efficiently. Specialized technologies and techniques, such as distributed computing, parallel processing, cloud computing, and big data frameworks (e.g., Apache Hadoop, Apache Spark), are often employed to manage and process the data at scale.

The analysis of massive datasets aims to extract meaningful insights, patterns, correlations, or trends from the vast amount of available data. This process involves data preprocessing, cleansing, transformation, statistical analysis, machine learning, data visualization, and other techniques tailored to handle the specific challenges of large-scale data. The insights derived from massive datasets can have significant implications in various domains, including scientific discoveries, business intelligence, personalized recommendations, predictive analytics, fraud detection, and infrastructure optimization. It's worth noting that the term "massive dataset" is often used interchangeably with terms like "big data" or "large-scale data." While there is no strict definition for these terms, they generally refer to datasets that exceed the capabilities of conventional data processing methods and require specialized approaches for storage, management, and analysis.

As discussed above, machine learning (ML) is a subfield of artificial intelligence (AI) that focuses on the development of algorithms and models that enable computers to learn from and make predictions or decisions based on data, without being explicitly programmed. It involves the use of statistical techniques and computational algorithms to identify patterns, extract insights, and make predictions or decisions from the available data.

Machine learning algorithms are designed to automatically learn and improve from experience or examples, allowing them to adapt to new data and make accurate predictions or decisions. These algorithms can be broadly categorized into three main types:

Supervised Learning: In supervised learning, the machine learning algorithm learns from a labeled dataset, where each data instance is associated with a known target or outcome. The algorithm learns to generalize from the labeled examples and make predictions on new, unseen data. Examples of supervised learning algorithms include linear regression, decision trees, support vector machines (SVM), and neural networks.

Unsupervised Learning: In unsupervised learning, the machine learning algorithm explores the underlying structure or patterns in the dataset without explicit labels or targets. It aims to discover hidden patterns, clusters, or associations in the data. Unsupervised learning algorithms include clustering algorithms (e.g., k-means, hierarchical clustering) and dimensionality reduction techniques (e.g., principal component analysis, t-SNE).

Reinforcement Learning: Reinforcement learning involves an agent that learns to interact with an environment and make decisions based on trial and error. The agent learns through feedback in the form of rewards or penalties, guiding it to optimize its actions and maximize its cumulative reward over time. Reinforcement learning algorithms are commonly used in robotics, gaming, and control systems.

Machine learning algorithms and models play a crucial role in processing massive datasets. As datasets grow in size, traditional data processing and analysis methods may become impractical or infeasible. Machine learning offers scalable and automated approaches to handle and extract insights from massive datasets.

Machine learning algorithms can handle large-scale datasets by leveraging distributed computing and parallel processing techniques. Technologies like Apache Spark, Hadoop, and GPU acceleration enable the efficient processing and analysis of massive datasets. Machine learning models can be trained on subsets of the data in parallel or distributed across multiple computing resources to accelerate the learning process. Furthermore, machine learning techniques are designed to identify patterns, relationships, and dependencies in the data, allowing them to capture complex interactions and make predictions or decisions based on the patterns learned from the massive dataset. By learning from the data, machine learning models can handle the high dimensionality, variability, and complexity often present in massive datasets.

When processing 1706 the one or more incidents (e.g., incidents 272, 282, 284) defined within the one or more data signals (e.g., data signals 200 and/or data signals 204) to produce a summary (e.g., summary 298) of the one or more incidents (e.g., incidents 272, 282, 284) so that a user (e.g., user 236) may be quickly knowledgeable of these one or more incidents (e.g., incidents 272, 282, 284), information process 10 may utilize 1710 a generative AI model to produce the summary (e.g., summary 298) of the one or more incidents (e.g., incidents 272, 282, 284) so that the user (e.g., user 236) may be quickly knowledgeable of these one or more incidents (e.g., incidents 272, 282, 284).

As is known in the art, Generative AI refers to artificial intelligence systems that create new content, such as text, images, audio, or video, based on patterns and data they have been trained on. In the medical space, generative AI can be a transformative tool for generating content like summaries and reports concerning a patient's condition. For instance, it can analyze electronic health records (EHRs), lab results, imaging studies, and clinical notes to produce concise and accurate patient summaries. These summaries can highlight key medical history, current medications, allergies, recent test results, and other pertinent information, providing healthcare providers with a quick and comprehensive overview of a patient's condition. This can be particularly useful in emergency situations where time is of the essence.

Moreover, generative AI can create detailed medical reports by synthesizing data from various sources, ensuring that all relevant information is included and presented in a structured format. This can enhance the efficiency of healthcare providers by reducing the time spent on administrative tasks, allowing them to focus more on direct patient care. For example, AI can generate discharge summaries that encapsulate the patient's hospital stay, including diagnoses, treatments administered, and follow-up instructions. These reports can be customized to meet the specific needs of different healthcare providers, ensuring that each professional receives the most relevant information.

In addition to aiding healthcare providers, generative AI can generate personalized health reports for patients. These reports can explain the patient's conditions, treatment plans, and follow-up instructions in easily understandable language, improving communication and ensuring that the reader is well-informed about the patient. For chronic disease management, AI can create progress reports that track a patient's health metrics over time, providing insights into the effectiveness of treatments and helping to adjust care plans as needed.

Furthermore, AI can support clinical decision-making by generating predictive reports based on patient data. For instance, it can identify patients at high risk for certain conditions, such as heart disease or diabetes, by analyzing patterns in their medical history and current health metrics. These predictive insights can prompt early interventions and personalized treatment plans, potentially improving patient outcomes.

When utilizing 1710 a generative AI model to produce the summary (e.g., summary 298) of the one or more incidents (e.g., incidents 272, 282, 284) so that the user (e.g., user 236) may be quickly knowledgeable of these one or more incidents (e.g., incidents 272, 282, 284), information process 10 may utilize 1712 prompt engineering and the generative AI model to produce the summary (e.g., summary 298) of the one or more incidents (e.g., incidents 272, 282, 284) so that the user (e.g., user 236) may be quickly knowledgeable of these one or more incidents (e.g., incidents 272, 282, 284).

Prompt engineering is the practice of designing and crafting prompts to guide generative AI models in producing specific and desired outputs. By carefully formulating prompts, users can influence the AI to generate more accurate, relevant, and high-quality content tailored to their needs. This involves providing clear and detailed instructions, setting the context, and sometimes using templates or examples to guide the AI in following a specific structure or format. For instance, framing the prompt as a series of questions can help the AI focus on particular aspects of the content, ensuring comprehensive coverage of the topic. Iterative refinement, where the prompt is adjusted based on the initial output, can further enhance the quality of the generated content. Highlighting or emphasizing certain keywords within the prompt can direct the AI to prioritize specific information or themes. Additionally, setting constraints and boundaries, such as word limits or format guidelines, helps control the length and organization of the output. In the medical space, prompt engineering can be used to create concise patient summaries by specifying the inclusion of past diagnoses, current medications, recent lab results, and allergies. It can generate detailed discharge reports by outlining the necessary sections, such as diagnosis, treatment, prescribed medications, follow-up instructions, and lifestyle recommendations. Research summaries can be crafted by asking the AI to provide a structured overview of a study's objective, methodology, results, and conclusions. Predictive health insights can be generated by directing the AI to analyze a patient's medical history, lifestyle factors, and test results, and then provide actionable recommendations for reducing risk. Through these carefully crafted prompts, prompt engineering ensures that the AI produces high-quality content that meets specific requirements, enhancing its utility and impact in various applications, including the medical field.

Incident Recommendations:

The following discussion concerns the manner in which information process 10 may monitor a plurality of data signals concerning a patient to identify discrete events concerning the patient, wherein information process 10 may make a recommendation to a practitioner based upon these discrete events.

Figure 19B:
FIG. 19B-19C are diagrammatic views of display screens/windows rendered by the information process of FIG. 1 according to an embodiment of the present disclosure.
Figure 19C:
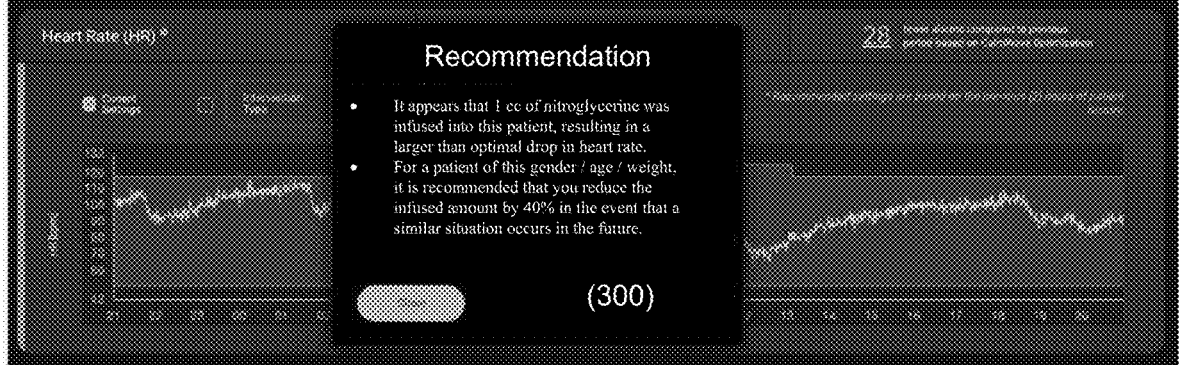

Referring also to FIGS. 19A-19C, information process 10 may monitor 1800 a plurality of data signals (e.g., data signals 200 and/or data signals 204) associated with a patient (e.g., patient 232) within a medical environment (e.g., hospital 246 . . . or a portion thereof).

As discussed above, examples of this plurality of data signals (e.g., data signals 200 and/or data signals 204) may include but are not limited to one or more of the following:

One or more data signals (e.g., data signals 200 and/or data signals 204) associated with a medical device (e.g., first vendor device 202, second vendor device 204) utilized on a patient (e.g., patient 232) within the medical environment (e.g., hospital 246 . . . or a portion thereof). For example, medical devices may monitor patient 232 and provide the data signals (e.g., data signals 200 and/or data signals 204) to information process 10. These data signals (e.g., data signals 200 and/or data signals 204) may generally concern one or more details of the medical device (e.g., first vendor device 202, second vendor device 204) and/or uses of the medical device (e.g., first vendor device 202, second vendor device 204), examples of which may include:

3. Device Details: One or more details of the medical device (e.g., one or more of first vendor devices 202 and/or one or more of second vendor devices 206) may concern one or more readings, signals and/or alarms provided by the device.

4. Device Uses: One or more uses of the medical device (e.g., one or more of first vendor devices 202 and/or one or more of second vendor devices 206) may concern the manner in which the device is being used (e.g., what is the device doing, what is the device being used for, who is the device assigned/connected to, etc.).

One or more data signals (e.g., data signals 200 and/or data signals 204) associated with drugs administered to the patient (e.g., patient 232) within the medical environment (e.g., hospital 246 . . . or a portion thereof). For example, the drug administration history of patient 232 may be digitized and provided to information process 10 as the data signals (e.g., data signals 200 and/or data signals 204).

One or more data signals (e.g., data signals 200 and/or data signals 204) associated with lab work performed on the patient (e.g., patient 232) within the medical environment (e.g., hospital 246 . . . or a portion thereof). For example, the lab history of patient 232 may be digitized and provided to information process 10 as the data signals (e.g., data signals 200 and/or data signals 204).

One or more data signals (e.g., data signals 200 and/or data signals 204) associated with clinical assessments performed on the patient (e.g., patient 232) within the medical environment (e.g., hospital 246 . . . or a portion thereof). For example, the clinical assessment history of patient 232 may be digitized and provided to information process 10 as the data signals (e.g., data signals 200 and/or data signals 204).

One or more data signals (e.g., data signals 200 and/or data signals 204) associated with clinical procedures performed on the patient (e.g., patient 232) within the medical environment (e.g., hospital 246 . . . or a portion thereof). For example, the clinical procedure history of patient 232 may be digitized and provided to information process 10 as the data signals (e.g., data signals 200 and/or data signals 204).

One or more data signals (e.g., data signals 200 and/or data signals 204) associated with electronic health records and/or electronic medical records of the patient (e.g., patient 232) within the medical environment (e.g., hospital 246 . . . or a portion thereof). For example, the electronic health records and/or electronic medical records of patient 232 may be provided to information process 10 as the data signals (e.g., data signals 200 and/or data signals 204).

One or more data signals (e.g., data signals 200 and/or data signals 204) associated with a medical history of the patient (e.g., patient 232) within the medical environment (e.g., hospital 246 . . . or a portion thereof). For example, the medical history of patient 232 may be digitized and provided to information process 10 as the data signals (e.g., data signals 200 and/or data signals 204).

Information process 10 may detect 1802 one or more incidents (e.g., incidents 272, 282, 284) defined within one or more of the data signals (e.g., data signals 200 and/or data signals 204).

As discussed above, an incident may include the occurrence of one or more alarms (e.g., alarms 274, 276, 278), wherein one or more incidents (e.g., incidents 272, 282, 284) may define an event (e.g., event 280).

For example and when detecting 1802 one or more incidents (e.g., incidents 272, 282, 284) defined within one or more of the data signals (e.g., data signals 200 and/or data signals 204), information process 10 may monitor 1804 the data signals (e.g., data signals 200 and/or data signals 204) associated with a medical device (e.g., first vendor device 202, second vendor device 204) utilized on a patient (e.g., patient 232) within the medical environment (e.g., hospital 246 . . . or a portion thereof) to detect the occurrence of the one or more alarms (e.g., alarms 274, 276, 278).

As discussed above, these medical devices (e.g., first vendor device 202, second vendor device 204) may include one or more sub-medical devices. For example, it is foreseeable that e.g., a blood pressure monitoring system may have one or more sub-systems (e.g., a wirelessly coupled blood pressure monitoring cuff).

Information process 10 may process 1806 the one or more incidents (e.g., incidents 272, 282, 284) defined within the one or more data signals (e.g., data signals 200 and/or data signals 204) to produce a recommendation based upon the one or more incidents (e.g., incidents 272, 282, 284) so that a user (e.g., user 236) may gain more insight into these one or more incidents (e.g., incidents 272, 282, 284). As discussed above, examples of user 236 may include but are not limited to a medical professional, such as a nurse, nurse supervisor, medical technician, physician's assistant, physician, etc.

As discussed above and referring also to FIG. 19B, information process 10 may render a user interface that will enable a user (e.g., user 236) to view their patient (e.g., patient 232) over a defined period of time (e.g., the last 24 hours). The user (e.g., user 236) may see trends within data signals (e.g., heart rate in this particular case) to get a holistic view of the condition of the patient (e.g., patient 232) over this recent history.

As discussed above, the square markers along each of the vital sign time signatures may indicate incidents across this timeline when information process 10 recommends an alarm limit update, based on the patient (e.g., patient 232) and various specific measures. Some boxes may indicate past alarm limit updates to avoid non-medically actionable alarms, while other boxes may indicate past alarm limit updates in the conservative direction so as to avoid missing medically actionable alarms, and still other boxes may indicate past occurrences where information process 10 deemed it not safe to adjust alarm limits and, therefore, no action required.

One or more of these boxes may be selected (e.g., with a mouse click) by the user (e.g., user 236) so that information process 10 may provide supplemental information concerning the box (or boxes) selected. For example, information process 10 may provide a recommendation concerning one or more of these boxes in the event that the user (e.g., user 236) selects a specific box. Assume for this example that a patient (e.g., patient 232) experienced a rapid heart rate increase (incident 1), wherein a drug (e.g., nitroglycerine) was administered (incident 2). The drug (e.g., nitroglycerine) lowered the heart rate of the patient (e.g., patient 232) to a lower than normal range (incident 3), wherein another drug (e.g., epinephrine) was administered (incident 4) to raise the heart rate of the patient (e.g., patient 232) back into a normal range (incident 5). Information process 10 may enable a user (e.g., user 236) to see this rapid chain of events/incidents in the history of the patient (e.g., patient 232). Therefore and as shown in FIG. 19C, the user (e.g., user 236) may select (e.g., with a mouse click) this group of events/incidents and information process 10 may render a recommendation window (e.g., recommendations window 300) for this box that states the following:

It appears that 1 cc of nitroglycerine was infused into this patient, resulting in a larger than optimal drop in heart rate For a patient of this gender/age/weight, it is recommended that you reduce the infused amount by 40% in the event that a similar situation occurs in the future When processing 1806 the one or more incidents (e.g., incidents 272, 282, 284) defined within the one or more data signals (e.g., data signals 200 and/or data signals 204) to produce a recommendation based upon the one or more incidents (e.g., incidents 272, 282, 284) so that a user (e.g., user 236) may gain more insight into these one or more incidents (e.g., incidents 272, 282, 284), information process 10 may utilize 1808 massive data sets processed by ML to produce the recommendation based upon the one or more incidents (e.g., incidents 272, 282, 284) so that the user (e.g., user 236) may gain more insight into these one or more incidents (e.g., incidents 272, 282, 284). As discussed above, examples of user 236 may include but are not limited to a medical professional, such as a nurse, nurse supervisor, medical technician, physician's assistant, physician, etc.

As discussed above, a massive dataset, also referred to as a large-scale dataset or big dataset, is a collection of data that is exceptionally large in size and complexity. These datasets typically exceed the capacity of traditional data processing and analysis tools, requiring specialized approaches and infrastructure to handle and extract insights from them effectively.

When processing 1806 the one or more incidents (e.g., incidents 272, 282, 284) defined within the one or more data signals (e.g., data signals 200 and/or data signals 204) to produce a recommendation based upon the one or more incidents (e.g., incidents 272, 282, 284) so that a user (e.g., user 236) may gain more insight into these one or more incidents (e.g., incidents 272, 282, 284), information process 10 may utilize 1810 a generative AI model to produce the recommendation based upon the one or more incidents (e.g., incidents 272, 282, 284) so that the user (e.g., user 236) may gain more insight into these one or more incidents (e.g., incidents 272, 282, 284).

As discussed above, generative AI refers to artificial intelligence systems that create new content, such as text, images, audio, or video, based on patterns and data they have been trained on. In the medical space, generative AI can be a transformative tool for generating content like summaries and reports concerning a patient's condition.

When utilizing 1810 a generative AI model to produce the recommendation based upon the one or more incidents (e.g., incidents 272, 282, 284) so that the user (e.g., user 236) may gain more insight into these one or more incidents (e.g., incidents 272, 282, 284), information process 10 may utilize 1812 prompt engineering and the generative AI model to produce the recommendation based upon the one or more incidents (e.g., incidents 272, 282, 284) so that the user (e.g., user 236) may gain more insight into these one or more incidents (e.g., incidents 272, 282, 284).

As discussed above, prompt engineering is the practice of designing and crafting prompts to guide generative AI models in producing specific and desired outputs. By carefully formulating prompts, users can influence the AI to generate more accurate, relevant, and high-quality content tailored to their needs. This involves providing clear and detailed instructions, setting the context, and sometimes using templates or examples to guide the AI in following a specific structure or format.

User-Proposed Change Feedback:

The following discussion concerns the manner in which information process 10 may monitor for changes (e.g., changing a range limit, changing an alarm buffer, turning on a feature, etc.) that are proposed by a clinician. In the event that such a proposed change is detected, information process 10 will vet the proposed change and opine on whether the proposed change is recommended (from a safety/efficacy point of view), providing a justification/explanation as to why the proposed change should/should not be done.

Figure 20A:
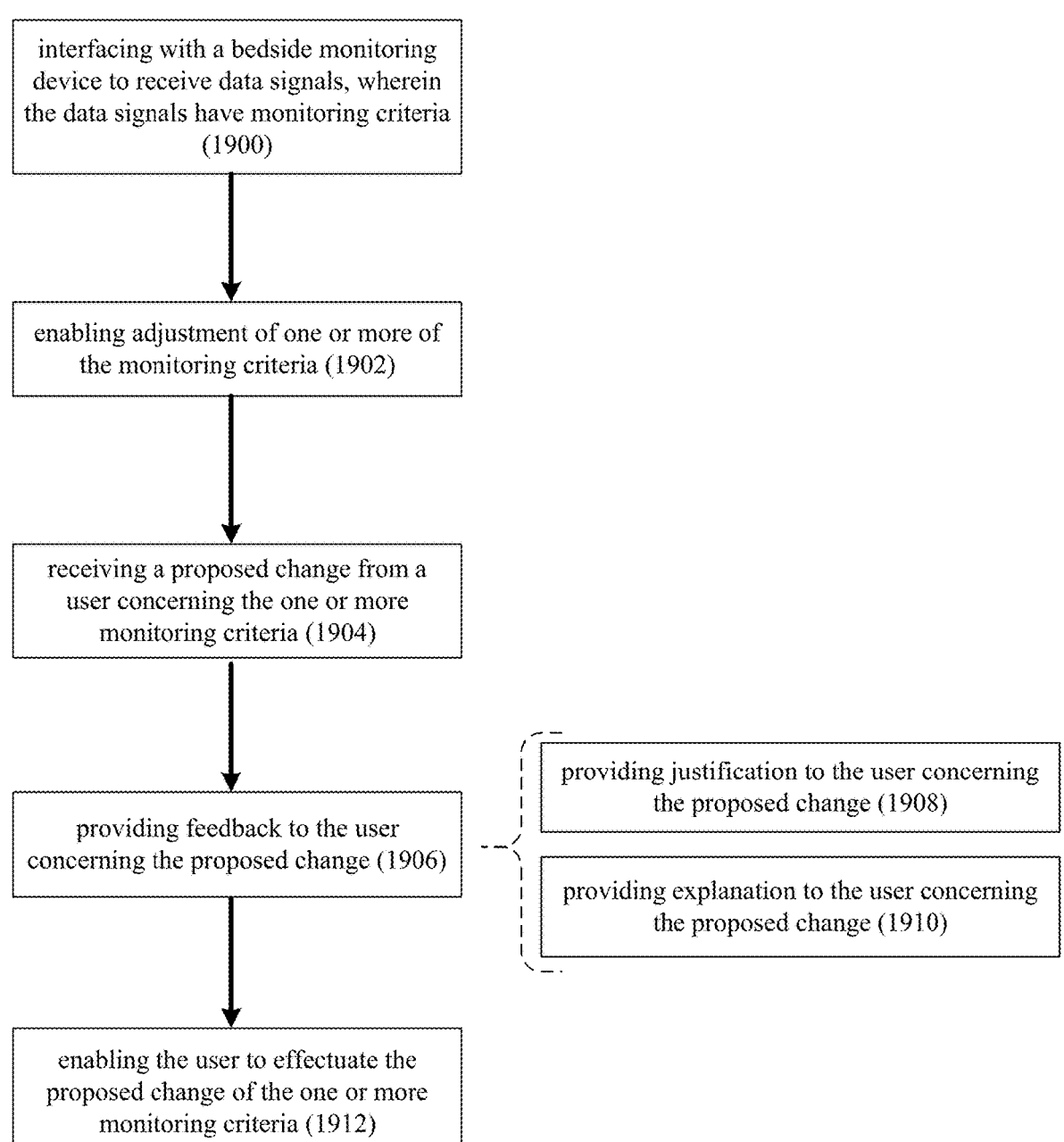
FIG. 20A is another flowchart of the information process of FIG. 1 according to an embodiment of the present disclosure.

Referring also to FIGS. 20A-20B, information process 10 may interface 1900 with a bedside monitoring device (e.g., first vendor device 202, second vendor device 204) to receive data signals (e.g., data signals 200 and/or data signals 204). These data signals (e.g., one or more of data signals 200 and/or one or more of data signals 204) may have monitoring criteria, wherein the monitoring criteria may include one or more thresholds.

As discussed above, these medical devices (e.g., first vendor device 202, second vendor device 204) may include one or more sub-medical devices. For example, it is foreseeable that e.g., a blood pressure monitoring system may have one or more sub-systems (e.g., a wirelessly coupled blood pressure monitoring cuff).

As discussed above, examples of such monitoring criteria/thresholds may include defined signal norms (e.g., defined signal norms 228). These defined signal norms (e.g., defined signal norms 228) may include user-defined signal norms and/or machine-defined signal norms. For example and with respect to user-defined signal norms, such user-defined signal norms may be the result of (in this example) medical studies, medical books, insurance charts, medical records, etc. Further and with respect to machine-defined signal norms, such machine-defined signal norms may be defined via massive data sets that are processed by machine learning. As discussed above, a massive dataset, also referred to as a large-scale dataset or big dataset, is a collection of data that is exceptionally large in size and complexity. These datasets typically exceed the capacity of traditional data processing and analysis tools, requiring specialized approaches and infrastructure to handle and extract insights from them effectively. Accordingly, such monitoring criteria (e.g., defined signal norms 228), may include user-defined monitoring criteria and/or machine-defined monitoring criteria.

As discussed above, examples of this plurality of data signals (e.g., data signals 200 and/or data signals 204) may include but are not limited to one or more of the following:

One or more data signals (e.g., data signals 200 and/or data signals 204) associated with a medical device (e.g., first vendor device 202, second vendor device 204) utilized on a patient (e.g., patient 232) within the medical environment (e.g., hospital 246 . . . or a portion thereof). For example, medical devices may monitor patient 232 and provide the data signals (e.g., data signals 200 and/or data signals 204) to information process 10. These data signals (e.g., data signals 200 and/or data signals 204) may generally concern one or more details of the medical device (e.g., first vendor device 202, second vendor device 204) and/or uses of the medical device (e.g., first vendor device 202, second vendor device 204), examples of which may include:

5. Device Details: One or more details of the medical device (e.g., one or more of first vendor devices 202 and/or one or more of second vendor devices 206) may concern one or more readings, signals and/or alarms provided by the device.

6. Device Uses: One or more uses of the medical device (e.g., one or more of first vendor devices 202 and/or one or more of second vendor devices 206) may concern the manner in which the device is being used (e.g., what is the device doing, what is the device being used for, who is the device assigned/connected to, etc.).

Information process 10 may enable 1902 adjustment of one or more of the monitoring criteria (e.g., defined signal norms 228). As discussed above, information process 10 may enable 1902 adjustment of one or more of the monitoring criteria (e.g., defined signal norms 228) by a user (e.g., user 236) via a computing device (e.g., computing device 238). Examples of user 236 may include but are not limited to a medical professional, such as a nurse, nurse supervisor, medical technician, physician's assistant, physician, etc. Examples of the computing device (e.g., computing device 238) may include but are not limited to a nurse's workstation, a tablet computer, a laptop computer, a desktop computer, a smart phone, etc.

As discussed above, the defined signal norms (e.g., defined signal norms 228) for a heart rate may be 60-100 beats per minute and for a respiratory rate may be 12-20 breaths per minute. Accordingly, information process 10 may enable 2002 adjustment of one or more of the monitoring criteria (e.g., namely defined signal norms of 60-100 beats per minute for a heart rate and 12-20 breaths per minute for a respiratory rate) by the user (e.g., user 236) via a computing device (e.g., computing device 238).

Assume for this example that the user (e.g., user 236) initiates such a change via the computing device (e.g., computing device 238). Accordingly, information process 10 may receive 1904 a proposed change (e.g., proposed change 302) from the user (e.g., user 236) concerning the one or more monitoring criteria (e.g., defined signal norms 228).

Once received, information process 10 may provide 1906 feedback to the user (e.g., user 236) concerning the proposed change (e.g., proposed change 302), wherein providing 1906 feedback to the user (e.g., user 236) concerning the proposed change (e.g., proposed change 302) may include one or more of: providing 1908 justification to the user (e.g., user 236) concerning the proposed change (e.g., proposed change 302) and/or providing 1910 explanation to the user (e.g., user 236) concerning the proposed change (e.g., proposed change 302).

Upon receiving the proposed change (e.g., proposed change 302) and as shown in FIG. 20B, information process 10 may render a feedback window (e.g., feedback window 304) that provides the above-described feedback (e.g., the above-described justification and/or the above-described explanation concerning why the proposed change should or should not be done. For this particular example, information process 10 is recommending that the proposed change (e.g., proposed change 302) should not be implemented.

Information process 10 may enable 2012 the user (e.g., user 236) to effectuate the proposed change (e.g., proposed change 302) of the one or more monitoring criteria (e.g., defined signal norms 228). For example, if the recommendation was positive or the user (e.g., user 236) was not concerned with the issues raised by information process 10 (in this particular example), the user (e.g., user 236) may select the "Implement Change" button included within the feedback window (e.g., feedback window 304).

System-Proposed Change Justification:

The following discussion concerns the manner in which information process 10 may explain why a system-proposed change (e.g., changing a range limit, changing an alarm transient buffer, turning on a feature, etc.) is recommended (from a safety and an efficacy point of view), providing justification and/or explanation concerning the same.

Figure 21A:
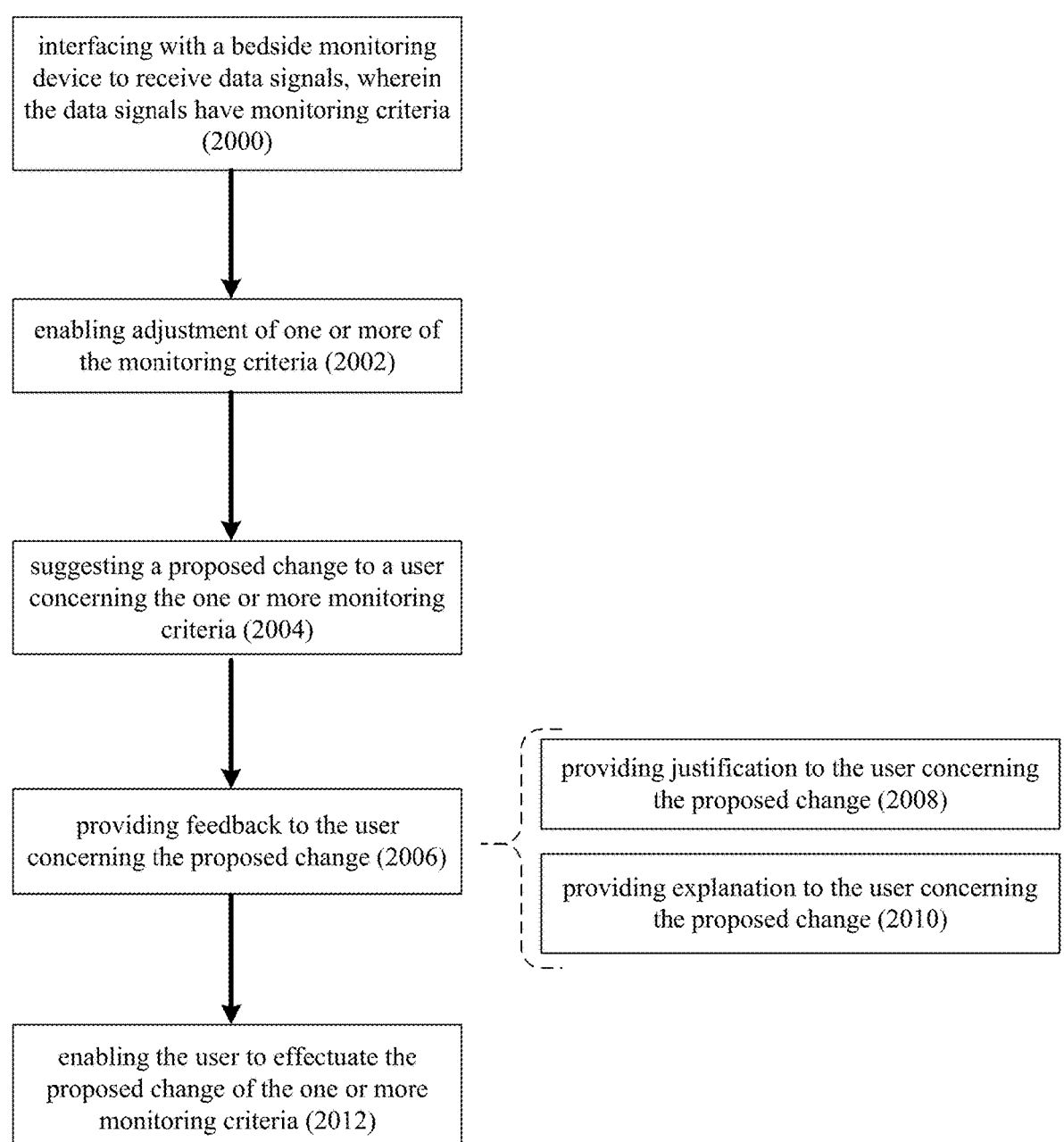
FIG. 21A is another flowchart of the information process of FIG. 1 according to an embodiment of the present disclosure.
Figure 21B:
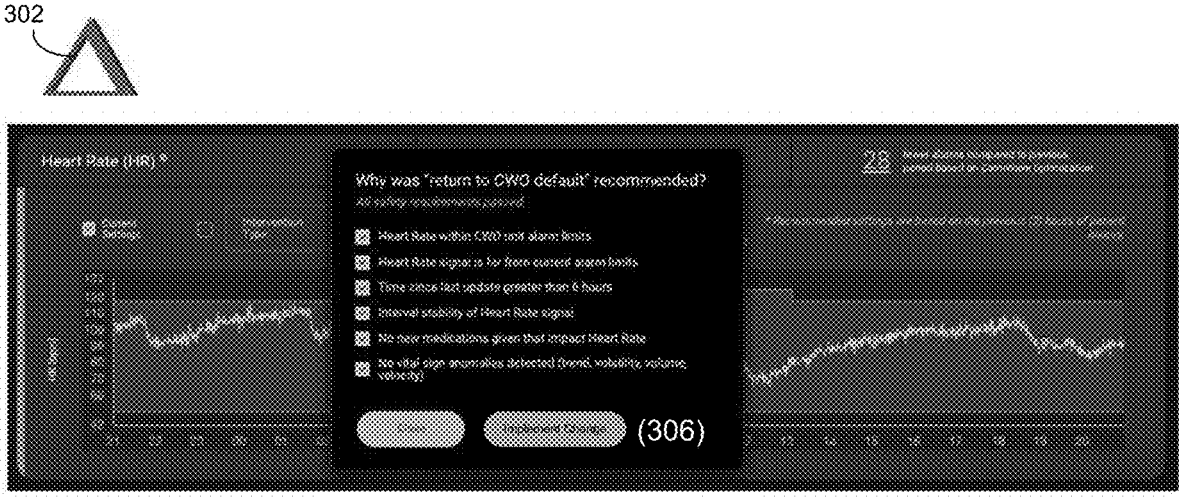
FIG. 21B is a diagrammatic view of a display screen/window rendered by the information process of FIG. 1 according to an embodiment of the present disclosure.
Figure 22A:
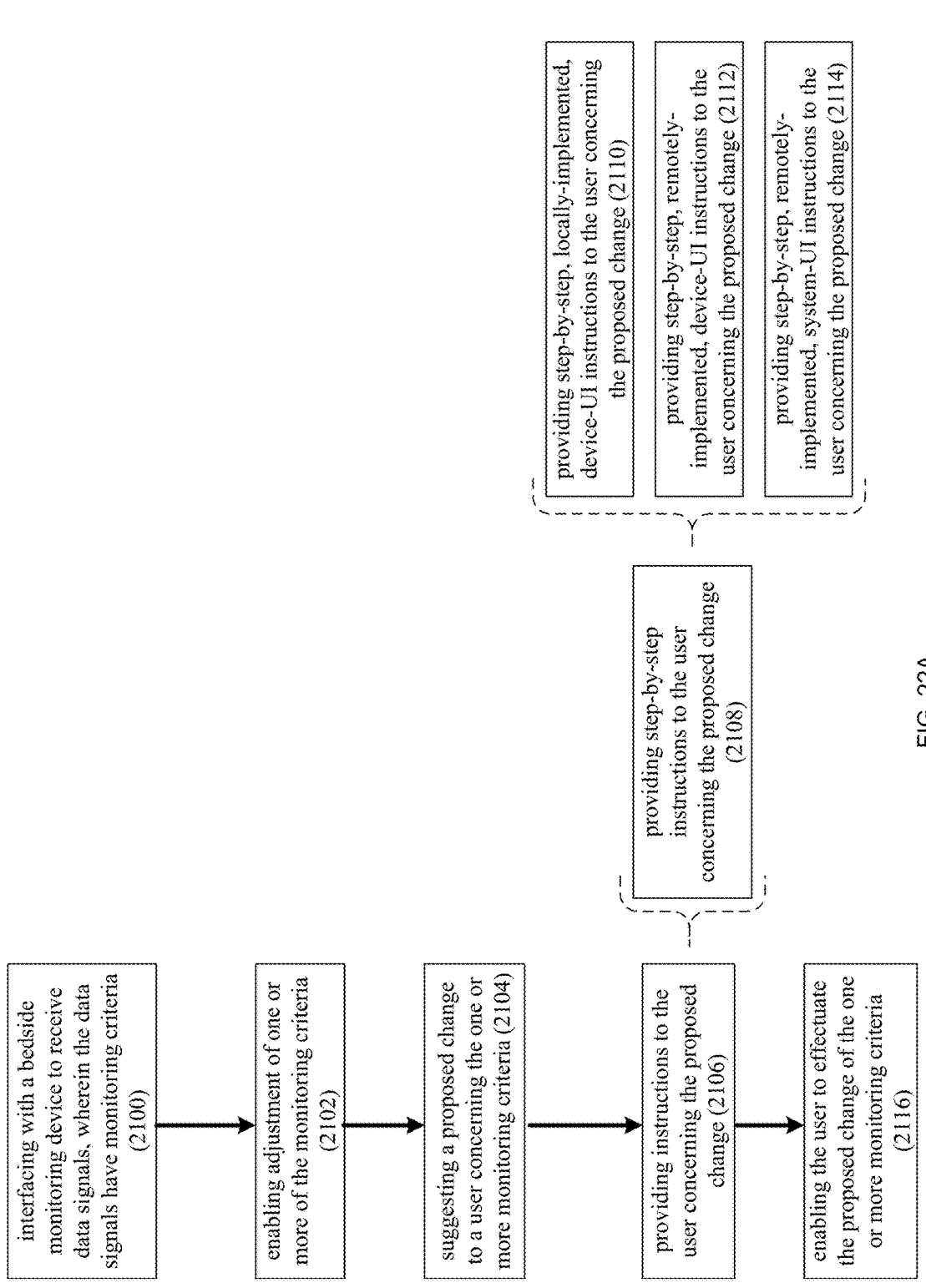
FIG. 22A is another flowchart of the information process of FIG. 1 according to an embodiment of the present disclosure.

Referring also to FIGS. 21A-21B, information process 10 may interface 2000 with a bedside monitoring device (e.g., first vendor device 202, second vendor device 204) to receive data signals (e.g., data signals 200 and/or data signals 204). These data signals (e.g., one or more of data signals 200 and/or one or more of data signals 204) may have monitoring criteria, wherein the monitoring criteria may include one or more thresholds.

As discussed above, these medical devices (e.g., first vendor device 202, second vendor device 204) may include one or more sub-medical devices. For example, it is foreseeable that e.g., a blood pressure monitoring system may have one or more sub-systems (e.g., a wirelessly coupled blood pressure monitoring cuff).

As discussed above, examples of such monitoring criteria/thresholds may include defined signal norms (e.g., defined signal norms 228). These defined signal norms (e.g., defined signal norms 228) may include user-defined signal norms and/or machine-defined signal norms. For example and with respect to user-defined signal norms, such user-defined signal norms may be the result of (in this example) medical studies, medical books, insurance charts, medical records, etc. Further and with respect to machine-defined signal norms, such machine-defined signal norms may be defined via massive data sets that are processed by machine learning. As discussed above, a massive dataset, also referred to as a large-scale dataset or big dataset, is a collection of data that is exceptionally large in size and complexity. These datasets typically exceed the capacity of traditional data processing and analysis tools, requiring specialized approaches and infrastructure to handle and extract insights from them effectively. Accordingly, such monitoring criteria (e.g., defined signal norms 228), may include user-defined monitoring criteria and/or machine-defined monitoring criteria.

As discussed above, examples of this plurality of data signals (e.g., data signals 200 and/or data signals 204) may include but are not limited to one or more of the following:

One or more data signals (e.g., data signals 200 and/or data signals 204) associated with a medical device (e.g., first vendor device 202, second vendor device 204) utilized on a patient (e.g., patient 232) within the medical environment (e.g., hospital 246 . . . or a portion thereof). For example, medical devices may monitor patient 232 and provide the data signals (e.g., data signals 200 and/or data signals 204) to information process 10. These data signals (e.g., data signals 200 and/or data signals 204) may generally concern one or more details of the medical device (e.g., first vendor device 202, second vendor device 204) and/or uses of the medical device (e.g., first vendor device 202, second vendor device 204), examples of which may include:

7. Device Details: One or more details of the medical device (e.g., one or more of first vendor devices 202 and/or one or more of second vendor devices 206) may concern one or more readings, signals and/or alarms provided by the device.

8. Device Uses: One or more uses of the medical device (e.g., one or more of first vendor devices 202 and/or one or more of second vendor devices 206) may concern the manner in which the device is being used (e.g., what is the device doing, what is the device being used for, who is the device assigned/connected to, etc.).

Information process 10 may enable 2002 adjustment of one or more of the monitoring criteria (e.g., defined signal norms 228). As discussed above, information process 10 may enable 2002 adjustment of one or more of the monitoring criteria (e.g., defined signal norms 228) by a user (e.g., user 236) via a computing device (e.g., computing device 238). Examples of user 236 may include but are not limited to a medical professional, such as a nurse, nurse supervisor, medical technician, physician's assistant, physician, etc. Examples of the computing device (e.g., computing device 238) may include but are not limited to a nurse's workstation, a tablet computer, a laptop computer, a desktop computer, a smart phone, etc.

As discussed above, the defined signal norms (e.g., defined signal norms 228) for a heart rate may be 60-100 beats per minute and for a respiratory rate may be 12-20 breaths per minute. Accordingly, information process 10 may enable 2102 adjustment of one or more of the monitoring criteria (e.g., namely defined signal norms of 60-100 beats per minute for a heart rate and 12-20 breaths per minute for a respiratory rate) by the user (e.g., user 236) via a computing device (e.g., computing device 238).

Assume for this example that information process 10 suggests 2004 a proposed change (e.g., proposed change 302) to a user (e.g., user 236) concerning the one or more monitoring criteria (e.g., defined signal norms 228).

Information process 10 may provide 2006 feedback to the user (e.g., user 236) concerning the proposed change (e.g., proposed change 302), wherein providing 2006 feedback to the user (e.g., user 236) concerning the proposed change (e.g., proposed change 302) may include one or more of: providing 2008 justification to the user (e.g., user 236) concerning the proposed change (e.g., proposed change 302) and/or providing 2010 explanation to the user (e.g., user 236) concerning the proposed change (e.g., proposed change 302).

Specifically and as shown in FIG. 21B, information process 10 may render a feedback window (e.g., feedback window 306) that provides the above-described feedback (e.g., the above-described justification and/or the above-described explanation concerning why the proposed change should be done.

Information process 10 may enable 2012 the user (e.g., user 236) to effectuate the proposed change (e.g., proposed change 302) of the one or more monitoring criteria (e.g., defined signal norms 228). For example, if the user (e.g., user 236) agrees with the recommendation, the user (e.g., user 236) may select the "Implement Change" button included within the feedback window (e.g., feedback window 306).

System-Proposed Change Instructions:

The following discussion concerns the manner in which information process 10 may provide step-by-step instructions concerning how to effectuate change on a medical device in the event that a change is recommended. These step-by-step instructions may be instructions for making the changes by locally accessing the medical device's user interface, instructions for making the changes by remotely accessing the medical device's user interface, or instructions for making the changes via a common user interface that interfaces with the medical device in question (e.g., via an API).

Referring also to FIG. 22A-22D, information process 10 may interface 2100 with a bedside monitoring device (e.g., first vendor device 202, second vendor device 204) to receive data signals (e.g., data signals 200 and/or data signals 204). These data signals (e.g., one or more of data signals 200 and/or one or more of data signals 204) may have monitoring criteria, wherein the monitoring criteria may include one or more thresholds.

As discussed above, these medical devices (e.g., first vendor device 202, second vendor device 204) may include one or more sub-medical devices. For example, it is foreseeable that e.g., a blood pressure monitoring system may have one or more sub-systems (e.g., a wirelessly coupled blood pressure monitoring cuff).

As discussed above, examples of such monitoring criteria/thresholds may include defined signal norms (e.g., defined signal norms 228). These defined signal norms (e.g., defined signal norms 228) may include user-defined signal norms and/or machine-defined signal norms. For example and with respect to user-defined signal norms, such user-defined signal norms may be the result of (in this example) medical studies, medical books, insurance charts, medical records, etc. Further and with respect to machine-defined signal norms, such machine-defined signal norms may be defined via massive data sets that are processed by machine learning. As discussed above, a massive dataset, also referred to as a large-scale dataset or big dataset, is a collection of data that is exceptionally large in size and complexity. These datasets typically exceed the capacity of traditional data processing and analysis tools, requiring specialized approaches and infrastructure to handle and extract insights from them effectively. Accordingly, such monitoring criteria (e.g., defined signal norms 228), may include user-defined monitoring criteria and/or machine-defined monitoring criteria.

As discussed above, examples of this plurality of data signals (e.g., data signals 200 and/or data signals 204) may include but are not limited to one or more of the following:

One or more data signals (e.g., data signals 200 and/or data signals 204) associated with a medical device (e.g., first vendor device 202, second vendor device 204) utilized on a patient (e.g., patient 232) within the medical environment (e.g., hospital 246 . . . or a portion thereof). For example, medical devices may monitor patient 232 and provide the data signals (e.g., data signals 200 and/or data signals 204) to information process 10. These data signals (e.g., data signals 200 and/or data signals 204) may generally concern one or more details of the medical device (e.g., first vendor device 202, second vendor device 204) and/or uses of the medical device (e.g., first vendor device 202, second vendor device 204), examples of which may include:

9. Device Details: One or more details of the medical device (e.g., one or more of first vendor devices 202 and/or one or more of second vendor devices 206) may concern one or more readings, signals and/or alarms provided by the device.

10. Device Uses: One or more uses of the medical device (e.g., one or more of first vendor devices 202 and/or one or more of second vendor devices 206) may concern the manner in which the device is being used (e.g., what is the device doing, what is the device being used for, who is the device assigned/connected to, etc.).

Information process 10 may enable 2102 adjustment of one or more of the monitoring criteria (e.g., defined signal norms 228). As discussed above, information process 10 may enable 2102 adjustment of one or more of the monitoring criteria (e.g., defined signal norms 228) by a user (e.g., user 236) via a computing device (e.g., computing device 238). Examples of user 236 may include but are not limited to a medical professional, such as a nurse, nurse supervisor, medical technician, physician's assistant, physician, etc. Examples of the computing device (e.g., computing device 238) may include but are not limited to a nurse's workstation, a tablet computer, a laptop computer, a desktop computer, a smart phone, etc.

As discussed above, the defined signal norms (e.g., defined signal norms 228) for a heart rate may be 60-100 beats per minute and for a respiratory rate may be 12-20 breaths per minute. Accordingly, information process 10 may enable 2102 adjustment of one or more of the monitoring criteria (e.g., namely defined signal norms of 60-100 beats per minute for a heart rate and 12-20 breaths per minute for a respiratory rate) by the user (e.g., user 236) via a computing device (e.g., computing device 238).

Assume for this example that information process 10 suggests 2104 a proposed change (e.g., proposed change 302) to a user (e.g., user 236) concerning the one or more monitoring criteria (e.g., defined signal norms 228).

Further, information process 10 may provide 2106 instructions (e.g., instructions 304) to the user (e.g., user 236) concerning the proposed change (e.g., proposed change 302).

Specifically and in order to enable the user (e.g., user 236) to make the proposed change (e.g., proposed change 302), information process 10 may provide 2106 instructions (e.g., instructions 304) to the user (e.g., user 236) concerning the proposed change (e.g., proposed change 302). For example and when providing 2106 instructions to the user (e.g., user 236) concerning the proposed change (e.g., proposed change 302), information process 10 may provide 2108 step-by-step instructions (e.g., instructions 304) to the user (e.g., user 236) concerning the proposed change (e.g., proposed change 302).

For example, providing 2108 step-by-step instructions (e.g., instructions 304) to the user (e.g., user 236) concerning the proposed change (e.g., proposed change 302) may include one or more of the following:

Providing 2110 step-by-step, locally-implemented, device-UI instructions (e.g., instructions 304) to the user (e.g., user 236) concerning the proposed change (e.g., proposed change 302). For example and as shown in FIG. 22B, such instructions may be rendered on the computing device (e.g., computing device 238), examples of which may include but are not limited to a nurse's workstation, a tablet computer, a laptop computer, a desktop computer, a smart phone, etc. Such instructions explain to the user (e.g., user 236) how to effectuate the proposed change (e.g., proposed change 302) on a local device user interface of the bedside monitoring device (e.g., first vendor device 202, second vendor device 204).

Providing 2112 step-by-step, remotely-implemented, device-UI instructions (e.g., instructions 304) to the user (e.g., user 236) concerning the proposed change (e.g., proposed change 302). For example and as shown in FIG. 22C, such instructions may be rendered on the computing device (e.g., computing device 238), examples of which may include but are not limited to a nurse's workstation, a tablet computer, a laptop computer, a desktop computer, a smart phone, etc. Such instructions explain to the user (e.g., user 236) how to effectuate the proposed change (e.g., proposed change 302) on a remote device user interface of the bedside monitoring device (e.g., first vendor device 202, second vendor device 204).

Providing 2114 step-by-step, remotely-implemented, system-UI instructions (e.g., instructions 304) to the user (e.g., user 236) concerning the proposed change (e.g., proposed change 302). For example and as shown in FIG. 22D, such instructions may be rendered on the computing device (e.g., computing device 238), examples of which may include but are not limited to a nurse's workstation, a tablet computer, a laptop computer, a desktop computer, a smart phone, etc. Such instructions explain to the user (e.g., user 236) how to effectuate the proposed change (e.g., proposed change 302) on a remote device user interface of information process 10.

Information process 10 may enable 2116 the user (e.g., user 236) to effectuate the proposed change (e.g., proposed change 302) of the one or more monitoring criteria (e.g., defined signal norms 228). For example, the above-described instructions (e.g., instructions 304) may include an "Implement Change" button that the user (e.g., user 236) may select to effectuate the proposed change (e.g., proposed change 302).

Shift Change Report Generation:

The following discussion concerns the manner in which information process 10 may monitor a plurality of data signals over a defined period of time (e.g., the previous shift, multiple shifts, the entire stay of one or more patients, etc.). Information process 10 may then generate a shift change report for these one or more patients.

Figure 23A:
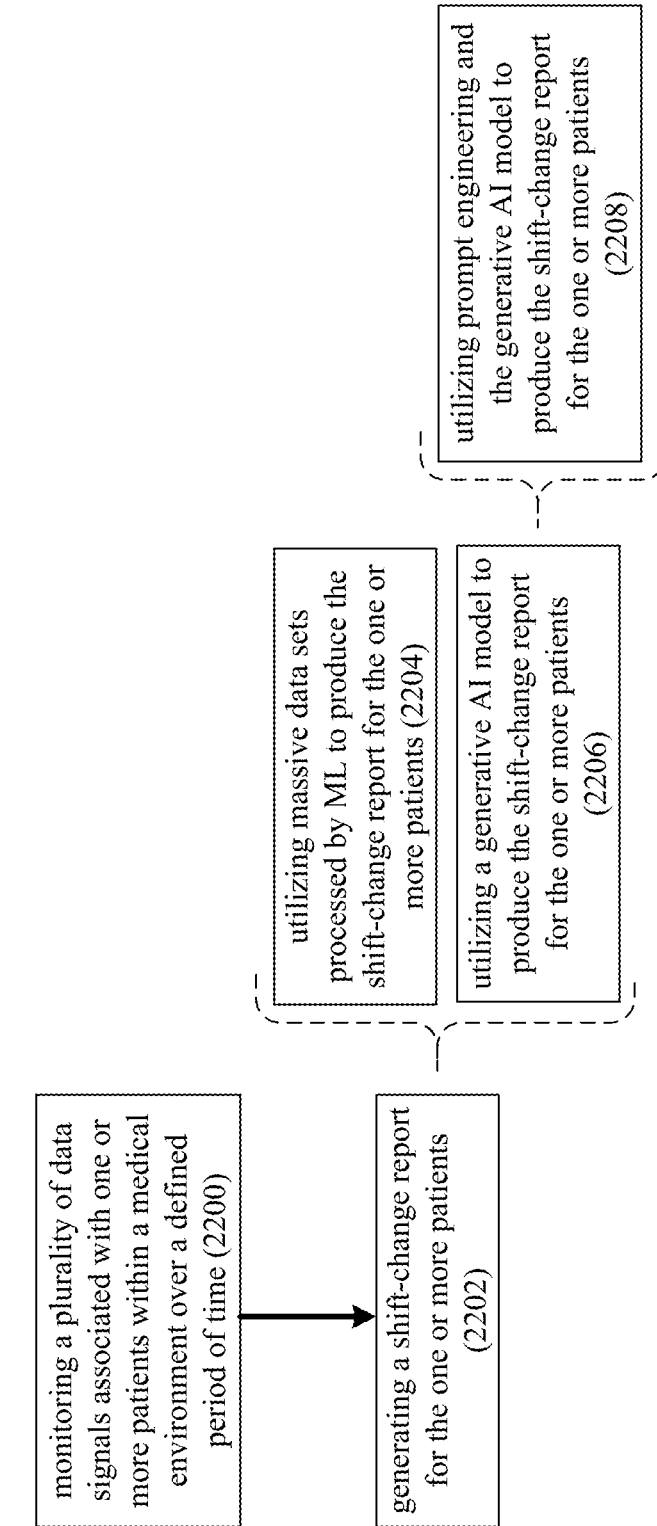
FIG. 23A is another flowchart of the information process of FIG. 1 according to an embodiment of the present disclosure.
Figure 23B:
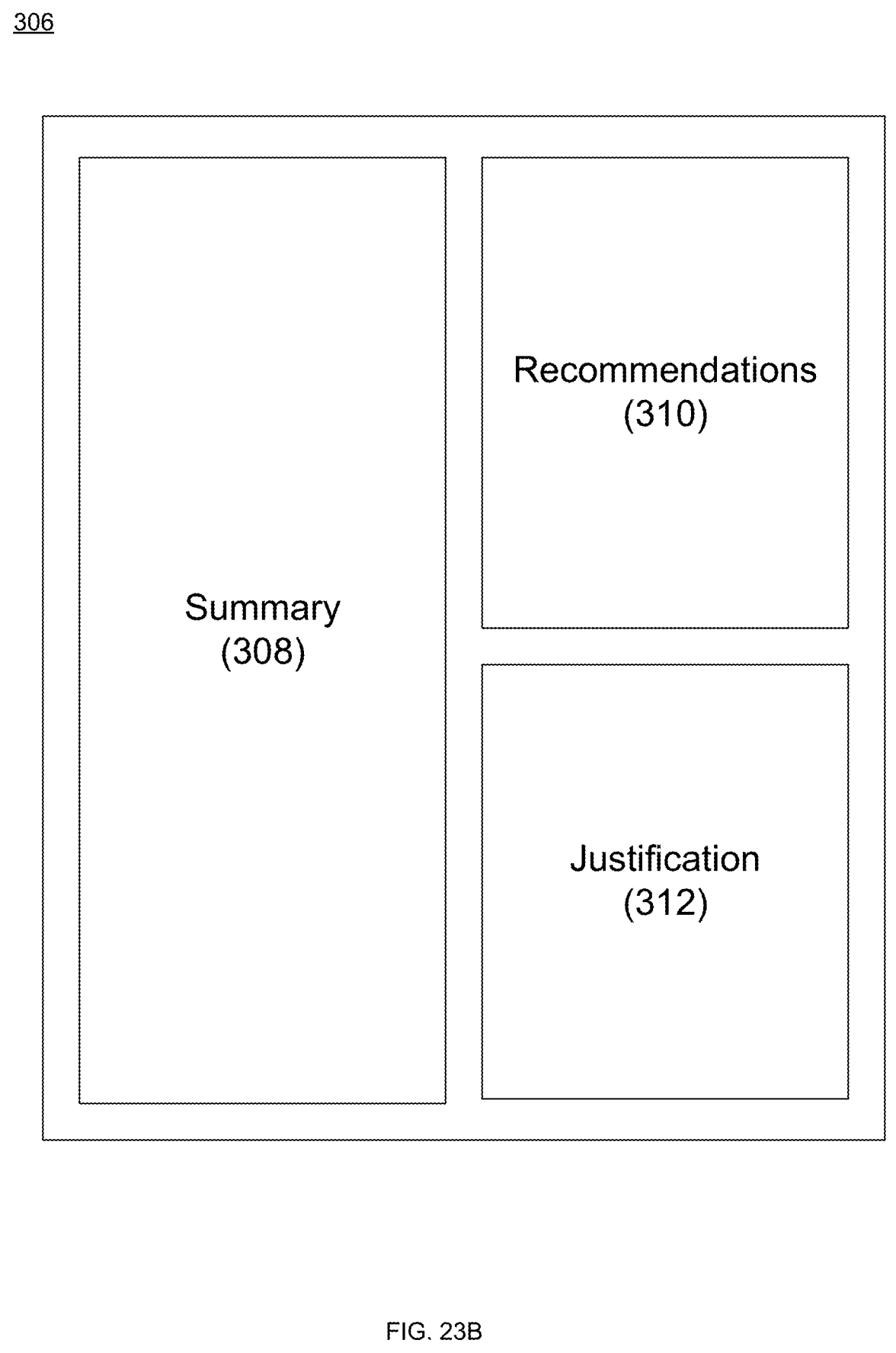

Referring also to FIGS. 23A-23B, information process 10 may monitor 2200 a plurality of data signals (e.g., data signals 200 and/or data signals 204) associated with one or more patients (e.g., patient 232) within a medical environment (e.g., hospital 246 . . . or a portion thereof) over a defined period of time.

As discussed above, examples of this plurality of data signals (e.g., data signals 200 and/or data signals 204) may include but are not limited to one or more of the following:

One or more data signals (e.g., data signals 200 and/or data signals 204) associated with a medical device (e.g., first vendor device 202, second vendor device 204) utilized on a patient (e.g., patient 232) within the medical environment (e.g., hospital 246 . . . or a portion thereof). For example, medical devices may monitor patient 232 and provide the data signals (e.g., data signals 200 and/or data signals 204) to information process 10. These data signals (e.g., data signals 200 and/or data signals 204) may generally concern one or more details of the medical device (e.g., first vendor device 202, second vendor device 204) and/or uses of the medical device (e.g., first vendor device 202, second vendor device 204), examples of which may include:

11. Device Details: One or more details of the medical device (e.g., one or more of first vendor devices 202 and/or one or more of second vendor devices 206) may concern one or more readings, signals and/or alarms provided by the device.

12. Device Uses: One or more uses of the medical device (e.g., one or more of first vendor devices 202 and/or one or more of second vendor devices 206) may concern the manner in which the device is being used (e.g., what is the device doing, what is the device being used for, who is the device assigned/connected to, etc.).

One or more data signals (e.g., data signals 200 and/or data signals 204) associated with drugs administered to the patient (e.g., patient 232) within the medical environment (e.g., hospital 246 . . . or a portion thereof). For example, the drug administration history of patient 232 may be digitized and provided to information process 10 as the data signals (e.g., data signals 200 and/or data signals 204).

One or more data signals (e.g., data signals 200 and/or data signals 204) associated with lab work performed on the patient (e.g., patient 232) within the medical environment (e.g., hospital 246 . . . or a portion thereof). For example, the lab history of patient 232 may be digitized and provided to information process 10 as the data signals (e.g., data signals 200 and/or data signals 204).

One or more data signals (e.g., data signals 200 and/or data signals 204) associated with clinical assessments performed on the patient (e.g., patient 232) within the medical environment (e.g., hospital 246 . . . or a portion thereof). For example, the clinical assessment history of patient 232 may be digitized and provided to information process 10 as the data signals (e.g., data signals 200 and/or data signals 204).

One or more data signals (e.g., data signals 200 and/or data signals 204) associated with clinical procedures performed on the patient (e.g., patient 232) within the medical environment (e.g., hospital 246 . . . or a portion thereof). For example, the clinical procedure history of patient 232 may be digitized and provided to information process 10 as the data signals (e.g., data signals 200 and/or data signals 204).

One or more data signals (e.g., data signals 200 and/or data signals 204) associated with electronic health records and/or electronic medical records of the patient (e.g., patient 232) within the medical environment (e.g., hospital 246 . . . or a portion thereof). For example, the electronic health records and/or electronic medical records of patient 232 may be provided to information process 10 as the data signals (e.g., data signals 200 and/or data signals 204).

One or more data signals (e.g., data signals 200 and/or data signals 204) associated with a medical history of the patient (e.g., patient 232) within the medical environment (e.g., hospital 246 . . . or a portion thereof). For example, the medical history of patient 232 may be digitized and provided to information process 10 as the data signals (e.g., data signals 200 and/or data signals 204).

As discussed above, these medical devices (e.g., first vendor device 202, second vendor device 204) may include one or more sub-medical devices. For example, it is foreseeable that e.g., a blood pressure monitoring system may have one or more sub-systems (e.g., a wirelessly coupled blood pressure monitoring cuff).

The one or more patients (e.g., patient 232) may include one or more of: a single patient (e.g., patient 232) within the medical environment (e.g., hospital 246 . . . or a portion thereof); a plurality of patients (e.g., patient 232) within the medical environment (e.g., hospital 246 . . . or a portion thereof); a unit within the medical environment (e.g., hospital 246 . . . or a portion thereof); and the medical environment (e.g., hospital 246 . . . or a portion thereof).

This defined period of time may include one or more of: a shift (e.g., 12 hours) within the medical environment (e.g., hospital 246 . . . or a portion thereof); a plurality of shifts (e.g., multiple 12 hours shifts) within the medical environment (e.g., hospital 246 . . . or a portion thereof); and a history of the one or more patients (e.g., patient 232) within the medical environment (e.g., hospital 246 . . . or a portion thereof), such as the entire stay of one or more patients.

Information process 10 may generate 2202 a shift-change report (e.g., report 306) for the one or more patients (e.g., patient 232). As shown in FIG. 23B, the shift-change report (e.g., report 306) may include one or more of: a summary (e.g., summary 308) of the medical history of the one or more patients (e.g., patient 232) over the defined period of time, a recommendation (e.g., recommendation 310) concerning the one or more patients (e.g., patient 232) based, at least in part, upon the history of the one or more patients (e.g., patient 232) over the defined period of time, and a justification (e.g., justification 312) for the recommendation for the one or more patients (e.g., patient 232).

Summary:

Summary 308 may be a concise yet comprehensive overview of the current status and recent medical history of one or more patients (e.g., patient 232), designed to ensure a smooth transition of care between outgoing and incoming healthcare providers. This summary typically includes essential information such as the patients' demographics, primary diagnosis, and a brief history of their current hospital stay. The summary typically outlines the key clinical events that have occurred during the previous shift, including any new symptoms, changes in vital signs, significant lab results, and interventions or treatments administered. Additionally, the summary may highlight any pending tests or procedures, specific care instructions, medication updates, and any critical issues that need immediate attention.

Recommendation:

Recommendation 310 may offer guidance and suggestions for the incoming team regarding the one or more patients (e.g., patient 232) ongoing care and management. This recommendation may include specific actions or observations that need to be prioritized during the next shift, such as monitoring for particular symptoms, adjusting medication dosages, or following up on pending lab results or diagnostic tests. It may also involve suggestions for interventions or treatments based on the patient's current status and response to previous care. Additionally, the recommendation section can highlight any potential complications to watch for and provide continuity in care strategies, ensuring that critical aspects of the patient's treatment plan are maintained.

Justification:

Justification 312 may explain the rationale behind the recommended actions for the incoming team. This justification may provide context and evidence supporting the recommendations, ensuring that the incoming team understands the reasoning and clinical judgment involved. For instance, if a specific medication adjustment is recommended, the justification might include details about the patient's recent lab results, observed side effects, or changes in symptoms that prompted this recommendation. Similarly, if close monitoring for particular symptoms is advised, the justification may outline any recent changes in the patient's condition or relevant medical history that necessitate this vigilance.

The shift-change report (e.g., report 266) may include one or more of: a digital shift-change report and a hardcopy shift-change report. In a medical environment, both digital and hardcopy shift-change reports (e.g., report 266) play crucial roles in ensuring smooth transitions between healthcare shifts, each offering unique benefits and drawbacks.

A digital shift-change report leverages technology to provide a comprehensive, real-time handover process. Digital systems allow for the instantaneous updating of patient information, ensuring that incoming staff have access to the most current data regarding patient status, medications, treatment plans, and any recent changes. Features such as searchable databases, integrated alerts, and multimedia attachments (e.g., images, test results) enhance the clarity and accessibility of information. Additionally, digital reports can be accessed remotely, allowing for preparation before arriving on shift and facilitating consultations with off-site specialists. These reports reduce the risk of lost or misplaced information and support streamlined workflows. However, the reliance on electronic devices and internet connectivity can pose challenges, especially in case of technical failures. Training is also required to ensure that all staff can effectively navigate and utilize the digital system.

Conversely, a hardcopy shift-change report involves physical documents that are generated and handed over. This traditional method is straightforward, requiring minimal technology and providing a tangible record that can be quickly referenced during patient rounds. Hardcopy reports are particularly valuable in environments with limited access to electronic devices or unstable internet connections. They are not subject to software malfunctions or cyber threats. However, the process of maintaining and updating these reports can be time-consuming and prone to human error, such as illegible handwriting, misplaced pages, or outdated information if changes occur after the report is generated. Furthermore, the inability to easily search through or analyze data can hinder the efficiency and thoroughness of the handover process.

When generating 2202 a shift-change report (e.g., report 266) for the one or more patients (e.g., patient 232), information process 10 may utilize 2204 massive data sets processed by ML to produce the shift-change report (e.g., report 266) for the one or more patients (e.g., patient 232).

As discussed above, a massive dataset, also referred to as a large-scale dataset or big dataset, is a collection of data that is exceptionally large in size and complexity. These datasets typically exceed the capacity of traditional data processing and analysis tools, requiring specialized approaches and infrastructure to handle and extract insights from them effectively.

When generating 2202 a shift-change report (e.g., report 266) for the one or more patients (e.g., patient 232), information process 10 may utilize 2206 a generative AI model to produce the shift-change report (e.g., report 266) for the one or more patients (e.g., patient 232).

As discussed above, generative AI refers to artificial intelligence systems that create new content, such as text, images, audio, or video, based on patterns and data they have been trained on. In the medical space, generative AI can be a transformative tool for generating content like summaries and reports concerning a patient's condition.

When utilizing 2206 a generative AI model to produce the shift-change report (e.g., report 266) for the one or more patients (e.g., patient 232), information process 10 may utilize 2208 prompt engineering and the generative AI model to produce the shift-change report (e.g., report 266) for the one or more patients (e.g., patient 232).

As discussed above, prompt engineering is the practice of designing and crafting prompts to guide generative AI models in producing specific and desired outputs. By carefully formulating prompts, users can influence the AI to generate more accurate, relevant, and high-quality content tailored to their needs. This involves providing clear and detailed instructions, setting the context, and sometimes using templates or examples to guide the AI in following a specific structure or format.

Rounding List Generation:

The following discussion concerns the manner in which information process 10 may monitor a plurality of data signals over a defined period of time (e.g., the previous shift, multiple shifts, the entire stay of one or more patients, etc.). Information process 10 may then generate an acuity score for the one or more patients and a rounding list for a medical professional (based upon these calculated acuity scores).

Figure 24A:
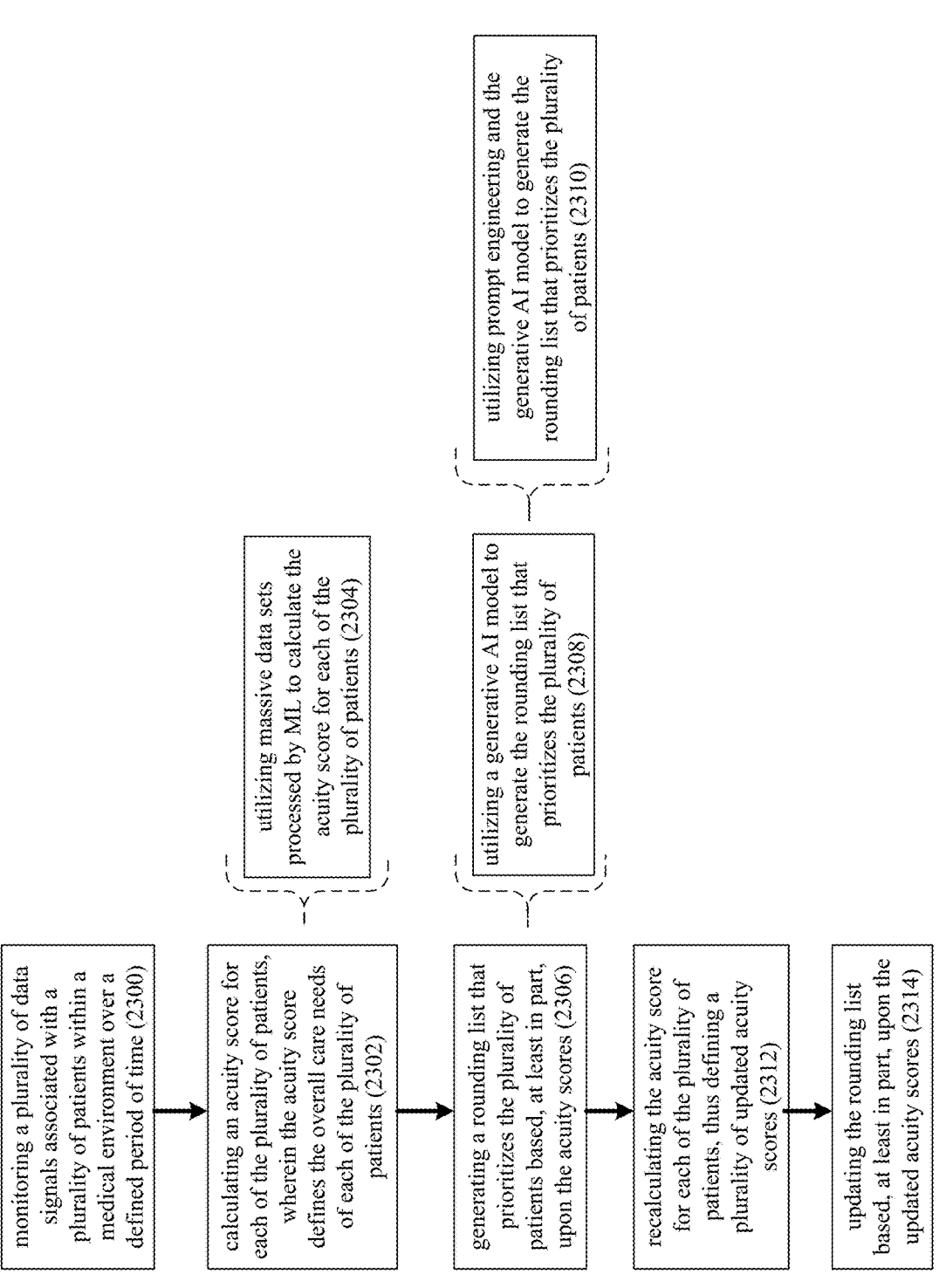
FIG. 24A is another flowchart of the information process of FIG. 1 according to an embodiment of the present disclosure.

Referring also to FIGS. 24A-24B, information process 10 may monitor 2300 a plurality of data signals (e.g., data signals 200 and/or data signals 204) associated with a plurality of patients (e.g., patient 232) within a medical environment (e.g., hospital 246 . . . or a portion thereof) over a defined period of time;

As discussed above, examples of this plurality of data signals (e.g., data signals 200 and/or data signals 204) may include but are not limited to one or more of the following:

One or more data signals (e.g., data signals 200 and/or data signals 204) associated with a medical device (e.g., first vendor device 202, second vendor device 204) utilized on a patient (e.g., patient 232) within the medical environment (e.g., hospital 246 . . . or a portion thereof). For example, medical devices may monitor patient 232 and provide the data signals (e.g., data signals 200 and/or data signals 204) to information process 10. These data signals (e.g., data signals 200 and/or data signals 204) may generally concern one or more details of the medical device (e.g., first vendor device 202, second vendor device 204) and/or uses of the medical device (e.g., first vendor device 202, second vendor device 204), examples of which may include:

13. Device Details: One or more details of the medical device (e.g., one or more of first vendor devices 202 and/or one or more of second vendor devices 206) may concern one or more readings, signals and/or alarms provided by the device.

14. Device Uses: One or more uses of the medical device (e.g., one or more of first vendor devices 202 and/or one or more of second vendor devices 206) may concern the manner in which the device is being used (e.g., what is the device doing, what is the device being used for, who is the device assigned/connected to, etc.).

One or more data signals (e.g., data signals 200 and/or data signals 204) associated with drugs administered to the patient (e.g., patient 232) within the medical environment (e.g., hospital 246 . . . or a portion thereof). For example, the drug administration history of patient 232 may be digitized and provided to information process 10 as the data signals (e.g., data signals 200 and/or data signals 204).

One or more data signals (e.g., data signals 200 and/or data signals 204) associated with lab work performed on the patient (e.g., patient 232) within the medical environment (e.g., hospital 246 . . . or a portion thereof). For example, the lab history of patient 232 may be digitized and provided to information process 10 as the data signals (e.g., data signals 200 and/or data signals 204).

One or more data signals (e.g., data signals 200 and/or data signals 204) associated with clinical assessments performed on the patient (e.g., patient 232) within the medical environment (e.g., hospital 246 . . . or a portion thereof). For example, the clinical assessment history of patient 232 may be digitized and provided to information process 10 as the data signals (e.g., data signals 200 and/or data signals 204).

One or more data signals (e.g., data signals 200 and/or data signals 204) associated with clinical procedures performed on the patient (e.g., patient 232) within the medical environment (e.g., hospital 246 . . . or a portion thereof). For example, the clinical procedure history of patient 232 may be digitized and provided to information process 10 as the data signals (e.g., data signals 200 and/or data signals 204).

One or more data signals (e.g., data signals 200 and/or data signals 204) associated with electronic health records and/or electronic medical records of the patient (e.g., patient 232) within the medical environment (e.g., hospital 246 . . . or a portion thereof). For example, the electronic health records and/or electronic medical records of patient 232 may be provided to information process 10 as the data signals (e.g., data signals 200 and/or data signals 204).

One or more data signals (e.g., data signals 200 and/or data signals 204) associated with a medical history of the patient (e.g., patient 232) within the medical environment (e.g., hospital 246 . . . or a portion thereof). For example, the medical history of patient 232 may be digitized and provided to information process 10 as the data signals (e.g., data signals 200 and/or data signals 204).

As discussed above, these medical devices (e.g., first vendor device 202, second vendor device 204) may include one or more sub-medical devices. For example, it is foreseeable that e.g., a blood pressure monitoring system may have one or more sub-systems (e.g., a wirelessly coupled blood pressure monitoring cuff).

The plurality of patients (e.g., patient 232) may includes one or more of: a plurality of patients (e.g., patient 232) assigned to an on-call nurse; a plurality of patients (e.g., patient 232) assigned to an on-call manager; and a plurality of patients (e.g., patient 232) assigned to an on-call physician.

As discussed above, this defined period of time may include one or more of: a shift (e.g., 12 hours) within the medical environment (e.g., hospital 246 . . . or a portion thereof); a plurality of shifts (e.g., multiple 12 hours shifts) within the medical environment (e.g., hospital 246 . . . or a portion thereof); and a history of the one or more patients (e.g., patient 232) within the medical environment (e.g., hospital 246 . . . or a portion thereof), such as the entire stay of one or more patients.

Information process 10 may calculate 2302 an acuity score for each of the plurality of patients (e.g., patient 232), wherein the acuity score defines the overall care needs of each of the plurality of patients (e.g., patient 232).

A patient acuity score is a numerical measure that quantifies the severity of a patient's condition and the level of care they require. Derived from various clinical data points such as vital signs, lab results, and clinical assessments, this score helps healthcare providers prioritize patient care and allocate resources effectively. For example, higher acuity scores indicate more severe conditions that necessitate more urgent medical attention. Systems like the Early Warning Score (EWS) use parameters such as heart rate, blood pressure, respiratory rate, and level of consciousness to calculate the score. Each parameter is scored based on its deviation from normal ranges, and the total score is the sum of these individual scores. In hospital settings, patient acuity scores are crucial for managing patient flow and ensuring optimal use of healthcare resources. In emergency departments, these scores aid in triaging patients, determining who needs immediate care versus those who can wait, thereby preventing overcrowding and ensuring critical patients are seen promptly. In intensive care units, acuity scores assist in monitoring patients' progress and adjusting care plans as needed, enabling proactive measures to prevent adverse outcomes. Acuity scores also play a vital role in nursing care planning by determining staffing levels based on the aggregate acuity of patients, ensuring balanced workloads and adequate patient attention. Beyond individual patient management, these scores provide data for quality assurance and performance evaluation, helping hospitals identify trends, measure outcomes, and implement evidence-based practices. Additionally, they contribute to research and policy-making by offering insights into patient populations, disease prevalence, and healthcare utilization patterns.

When calculating 2302 an acuity score for each of the plurality of patients (e.g., patient 232), information process 10 may utilize 2304 massive data sets processed by ML to calculate the acuity score for each of the plurality of patients (e.g., patient 232).

As discussed above, a massive dataset, also referred to as a large-scale dataset or big dataset, is a collection of data that is exceptionally large in size and complexity. These datasets typically exceed the capacity of traditional data processing and analysis tools, requiring specialized approaches and infrastructure to handle and extract insights from them effectively.

Information process 10 may generate 2306 a rounding list (e.g., rounding list 314) that prioritizes the plurality of patients (e.g., patient 232) based, at least in part, upon the acuity scores.

A rounding list (e.g., rounding list 314) in a medical environment is a detailed roster or schedule used by healthcare providers to systematically review and manage the care of patients during rounds. This list includes critical information about each patient, such as their name, room number, primary diagnosis, current treatment plans, vital signs, medication schedules, recent test results, and any specific care instructions or concerns. The rounding list helps ensure that all patients are seen and evaluated regularly, allowing the healthcare team to monitor progress, address issues promptly, and adjust treatment plans as needed.

During rounds, typically led by a physician or a senior healthcare professional, the rounding list serves as a guide to discuss each patient's condition with the medical team, including nurses, residents, and other specialists. It helps in coordinating care, improving communication among team members, and ensuring that no patient is overlooked. Additionally, the rounding list may include notes on pending tasks or follow-ups, ensuring continuity of care and facilitating the delegation of responsibilities.

Generally speaking and as shown in FIG. 24B, the rounding list (e.g., rounding list 314) may rank/prioritize patients based upon their acuity score, wherein patients that have higher overall care needs (e.g., patients that are more sick/more vulnerable/less healthy) may be placed higher/more frequently on the rounding list (e.g., rounding list 314) than patients that have lower overall care needs (e.g., patients that are less sick/less vulnerable/more healthy).

The rounding list (e.g., rounding list 314) may include one or more of: a digital rounding list and a hardcopy rounding list. In a medical environment, both digital and hardcopy rounding lists are vital tools for managing patient care during rounds, each offering distinct advantages and disadvantages.

A digital rounding list leverages technology to provide an efficient, real-time method of managing patient information. Digital systems allow for instantaneous updates, ensuring that the most current patient data, such as recent lab results, vital signs, and medication changes, are readily available. These lists can be accessed on various devices, including tablets, smartphones, and computers, providing flexibility and convenience for healthcare providers. Features such as searchable databases, integrated alerts for critical changes, and the ability to easily share information with the medical team enhance communication and coordination. Moreover, digital rounding lists can include multimedia elements like images and scanned documents, providing a comprehensive view of patient status. However, the reliance on electronic devices and internet connectivity can pose challenges, particularly during technical failures or in facilities with limited technological infrastructure. Additionally, there is a need for adequate training to ensure that all staff members can effectively use the digital system.

In contrast, a hardcopy rounding list involves printed documents that are manually updated and used during rounds. This traditional method is straightforward and familiar to many healthcare providers, requiring no electronic devices or connectivity, making it particularly useful in settings with limited access to technology. Hardcopy lists are less vulnerable to technical issues such as software malfunctions or power outages. They provide a tangible record that can be quickly referenced during patient rounds. However, hardcopy lists are more prone to errors, such as illegible handwriting, misplaced pages, and outdated information if changes occur after printing. The manual process of updating these lists can be time-consuming, and the inability to easily search or analyze data can hinder the efficiency of patient care management.

When generating 2306 a rounding list (e.g., rounding list 314) that prioritizes the plurality of patients (e.g., patient 232), information process 10 may utilize 2308 a generative AI model to generate the rounding list (e.g., rounding list 314) that prioritizes the plurality of patients (e.g., patient 232).

As discussed above, generative AI refers to artificial intelligence systems that create new content, such as text, images, audio, or video, based on patterns and data they have been trained on. In the medical space, generative AI can be a transformative tool for generating content like summaries and reports concerning a patient's condition.

When utilizing 2308 a generative AI model to generate the rounding list (e.g., rounding list 314) that prioritizes the plurality of patients (e.g., patient 232), information process 10 may utilize 2310 prompt engineering and the generative AI model to generate the rounding list (e.g., rounding list 314) that prioritizes the plurality of patients (e.g., patient 232).

As discussed above, prompt engineering is the practice of designing and crafting prompts to guide generative AI models in producing specific and desired outputs. By carefully formulating prompts, users can influence the AI to generate more accurate, relevant, and high-quality content tailored to their needs. This involves providing clear and detailed instructions, setting the context, and sometimes using templates or examples to guide the AI in following a specific structure or format.

In order to keep the rounding list (e.g., rounding list 314) current, information process 10 may recalculate 2312 the acuity score for each of the plurality of patients (e.g., patient 232). For example, these acuity scores may be recalculated e.g., continuously, every 15 minutes, every 30 minutes, every hour, etc., resulting in the generation of a plurality of updated acuity scores. Once calculated, information process 10 may update 2314 the rounding list (e.g., rounding list 314) based, at least in part, upon the updated acuity scores. For example and if the rounding list (e.g., rounding list 314) is a hardcopy rounding list, the rounding list (e.g., rounding list 314) may be reprinted and distributed to the appropriate medical professional (e.g., an on-call nurse, an on-call manager, an on-call physician, etc.). And if the rounding list (e.g., rounding list 314) is a digital rounding list, an updated rounding list may be wirelessly provided to the appropriate medical professional (e.g., an on-call nurse, an on-call manager, an on-call physician, etc.).

Urgent Care Notification:

The following discussion concerns the manner in which information process 10 may monitor a plurality of data signals to determine if an urgent care event is occurring. And if such an event is occurring, information process 10 may notify an on-call care member of the urgent care event so that the same can be addressed.

Referring also to FIG. 25A, information process 10 may monitor 2400 a plurality of data signals (e.g., data signals 200 and/or data signals 204) associated with a plurality of patients (e.g., patient 232) within a medical environment (e.g., hospital 246 . . . or a portion thereof).

As discussed above, examples of this plurality of data signals (e.g., data signals 200 and/or data signals 204) may include but are not limited to one or more of the following:

One or more data signals (e.g., data signals 200 and/or data signals 204) associated with a medical device (e.g., first vendor device 202, second vendor device 204) utilized on a patient (e.g., patient 232) within the medical environment (e.g., hospital 246 . . . or a portion thereof). For example, medical devices may monitor patient 232 and provide the data signals (e.g., data signals 200 and/or data signals 204) to information process 10. These data signals (e.g., data signals 200 and/or data signals 204) may generally concern one or more details of the medical device (e.g., first vendor device 202, second vendor device 204) and/or uses of the medical device (e.g., first vendor device 202, second vendor device 204), examples of which may include:

15. Device Details: One or more details of the medical device (e.g., one or more of first vendor devices 202 and/or one or more of second vendor devices 206) may concern one or more readings, signals and/or alarms provided by the device.

16. Device Uses: One or more uses of the medical device (e.g., one or more of first vendor devices 202 and/or one or more of second vendor devices 206) may concern the manner in which the device is being used (e.g., what is the device doing, what is the device being used for, who is the device assigned/connected to, etc.).

One or more data signals (e.g., data signals 200 and/or data signals 204) associated with drugs administered to the patient (e.g., patient 232) within the medical environment (e.g., hospital 246 . . . or a portion thereof). For example, the drug administration history of patient 232 may be digitized and provided to information process 10 as the data signals (e.g., data signals 200 and/or data signals 204).

One or more data signals (e.g., data signals 200 and/or data signals 204) associated with lab work performed on the patient (e.g., patient 232) within the medical environment (e.g., hospital 246 . . . or a portion thereof). For example, the lab history of patient 232 may be digitized and provided to information process 10 as the data signals (e.g., data signals 200 and/or data signals 204).

One or more data signals (e.g., data signals 200 and/or data signals 204) associated with clinical assessments performed on the patient (e.g., patient 232) within the medical environment (e.g., hospital 246 . . . or a portion thereof). For example, the clinical assessment history of patient 232 may be digitized and provided to information process 10 as the data signals (e.g., data signals 200 and/or data signals 204).

One or more data signals (e.g., data signals 200 and/or data signals 204) associated with clinical procedures performed on the patient (e.g., patient 232) within the medical environment (e.g., hospital 246 . . . or a portion thereof). For example, the clinical procedure history of a patient 232 may be digitized and provided to information process 10 as the data signals (e.g., data signals 200 and/or data signals 204).

One or more data signals (e.g., data signals 200 and/or data signals 204) associated with electronic health records and/or electronic medical records of the patient (e.g., patient 232) within the medical environment (e.g., hospital 246 . . . or a portion thereof). For example, the electronic health records and/or electronic medical records of patient 232 may be provided to information process 10 as the data signals (e.g., data signals 200 and/or data signals 204).

One or more data signals (e.g., data signals 200 and/or data signals 204) associated with a medical history of the patient (e.g., patient 232) within the medical environment (e.g., hospital 246 . . . or a portion thereof). For example, the medical history of patient 232 may be digitized and provided to information process 10 as the data signals (e.g., data signals 200 and/or data signals 204).

As discussed above, these medical devices (e.g., first vendor device 202, second vendor device 204) may include one or more sub-medical devices. For example, it is foreseeable that e.g., a blood pressure monitoring system may have one or more sub-systems (e.g., a wirelessly coupled blood pressure monitoring cuff).

Information process 10 may process 2402 the plurality of data signals (e.g., data signals 200 and/or data signals 204) to determine if one or more of the plurality of patients (e.g., patient 232) is experiencing an urgent care event.

Generally speaking, an urgent care event in a medical environment refers to a situation in which a patient requires immediate medical attention to prevent further complications, patient health deterioration and/or death. Examples of such urgent care events may include but are not limited to: a rapid change in heart rate, a rapid change in blood pressure, deterioration of respiratory function, deterioration of renal function, a drop of blood oxygen levels, a change in heart rhythm, etc.

When processing 2402 the plurality of data signals (e.g., data signals 200 and/or data signals 204) to determine if one or more of the plurality of patients (e.g., patient 232) is experiencing an urgent care event, information process 10 may detect 2404 one or more incidents (e.g., incidents 272, 282, 284) defined within the plurality of data signals (e.g., data signals 200 and/or data signals 204). As discussed above, an incident may include the occurrence of one or more alarms (e.g., alarms 274, 276, 278).

Accordingly and when detecting 2404 one or more incidents (e.g., incidents 272, 282, 284) defined within the plurality of data signals (e.g., data signals 200 and/or data signals 204), information process 10 may monitor 2406 one or more data signals (e.g., data signals 200 and/or data signals 204) associated with a medical device (e.g., first vendor device 202, second vendor device 204) utilized on a patient (e.g., patient 232) within the medical environment (e.g., hospital 246 . . . or a portion thereof) to detect the occurrence of the one or more alarms (e.g., alarms 274, 276, 278).

When processing 2402 the plurality of data signals (e.g., data signals 200 and/or data signals 204) to determine if one or more of the plurality of patients (e.g., patient 232) is experiencing an urgent care event, information process 10 may utilize 2408 massive data sets processed by ML to process the plurality of data signals (e.g., data signals 200 and/or data signals 204) to determine if one or more of the plurality of patients (e.g., patient 232) is experiencing an urgent care event.

As discussed above, a massive dataset, also referred to as a large-scale dataset or big dataset, is a collection of data that is exceptionally large in size and complexity. These datasets typically exceed the capacity of traditional data processing and analysis tools, requiring specialized approaches and infrastructure to handle and extract insights from them effectively.

If such an urgent care event is occurring, information process 10 may notify 2410 an on-call care member (e.g., on-call care member 316) so that the urgent care event can be addressed. Examples of such an on-call care member may include one or more of: an on-call nurse; an on-call manager; and an on-call physician.

An on-call nurse is a healthcare professional who is available to provide nursing care and support. This nurse remains on standby, ready to respond to medical needs or emergencies as they arise. On-call nurses may be required to assist with urgent patient care, administer medications, monitor patient conditions, or provide guidance to other healthcare staff during nights, weekends, or holidays. Their role is crucial in ensuring continuous and immediate care, particularly in settings like hospitals, nursing homes, or home health services, where patient needs can arise at any time.

An on-call manager in a medical environment is a professional responsible for overseeing the operational aspects of a healthcare facility. This manager is available to address administrative issues, coordinate staff activities, and ensure that the facility runs smoothly. They may handle situations such as staff shortages, urgent supply needs, or any operational emergencies that arise. The on-call manager acts as a critical link between the day-to-day operations and the senior management team, ensuring that any significant issues are promptly communicated and managed. Their availability ensures that the facility remains functional and that patient care is not disrupted by administrative or logistical challenges.

An on-call physician is a medical doctor who is available to provide medical consultation, diagnosis, and treatment. This physician is on standby to respond to urgent medical issues, offer guidance on patient care, and make critical decisions remotely or in person, depending on the situation's requirements. On-call physicians play a key role in managing acute medical conditions, providing continuity of care, and ensuring that patients receive timely and expert medical attention, especially during nights, weekends, or holidays.

Accordingly, the plurality of patients (e.g., patient 232) may include one or more of: a plurality of patients (e.g., patient 232) assigned to the on-call nurse; a plurality of patients (e.g., patient 232) assigned to the on-call manager; and a plurality of patients (e.g., patient 232) assigned to the on-call physician.

Such notification 2410 of the on-call care member (e.g., on-call care member 316) by information process 10 may occur in various ways, such as an audible notification directed to the on-call care member (e.g., on-call care member 316), a text-based notification directed to the on-call care member (e.g., on-call care member 316), a beeper-based notification directed to the on-call care member (e.g., on-call care member 316), etc.

Urgent Care Justification:

The following discussion concerns the manner in which information process 10 may monitor for the occurrence of an urgent care event. When an urgent event is occurring, the system may a) provide a summary of the urgent event, b) provide justifications as to why the event is an urgent care event, c) make recommendations for addressing the urgent care event.

Figure 26A:
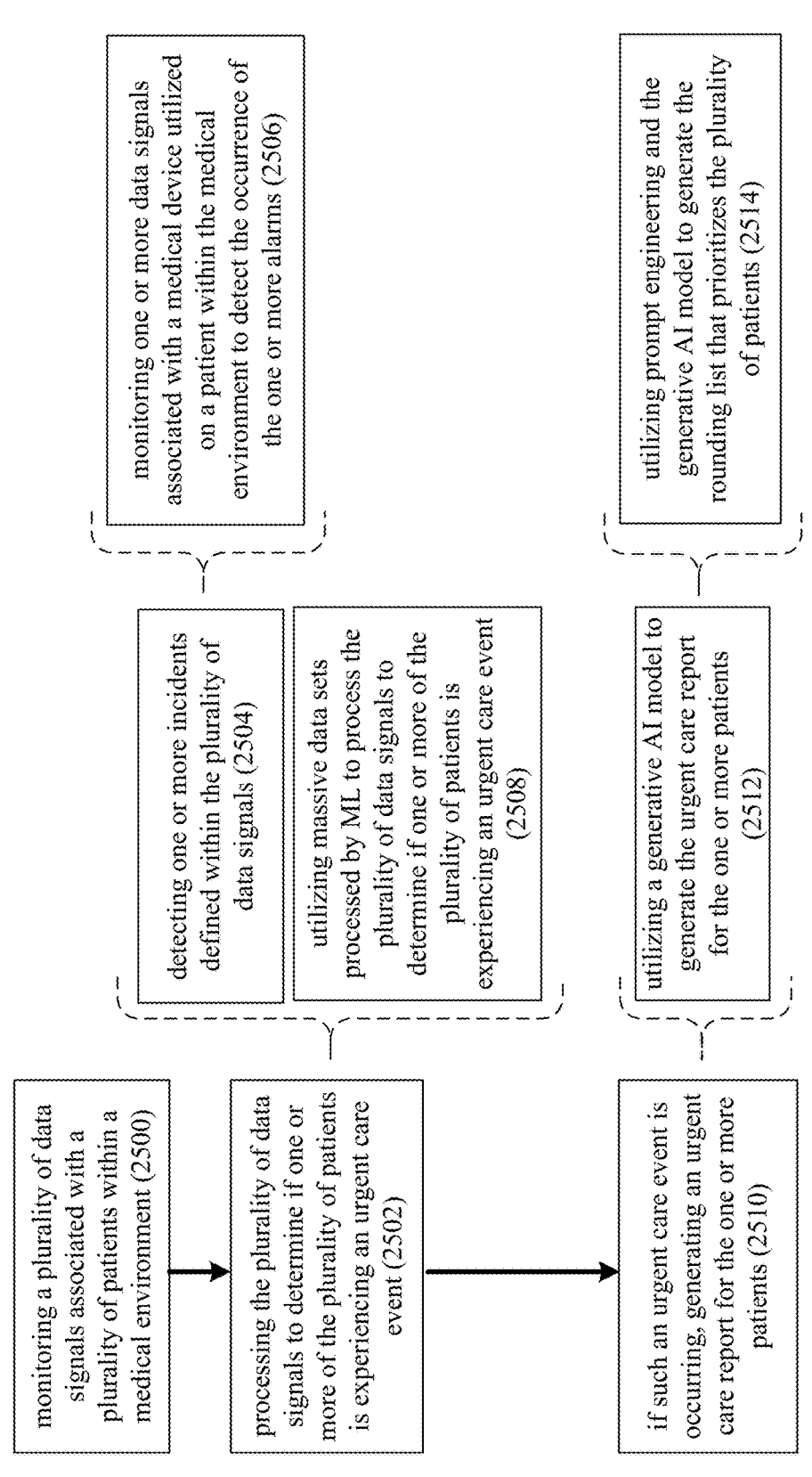
FIG. 26A is another flowchart of the information process of FIG. 1 according to an embodiment of the present disclosure.
Figure 26B:
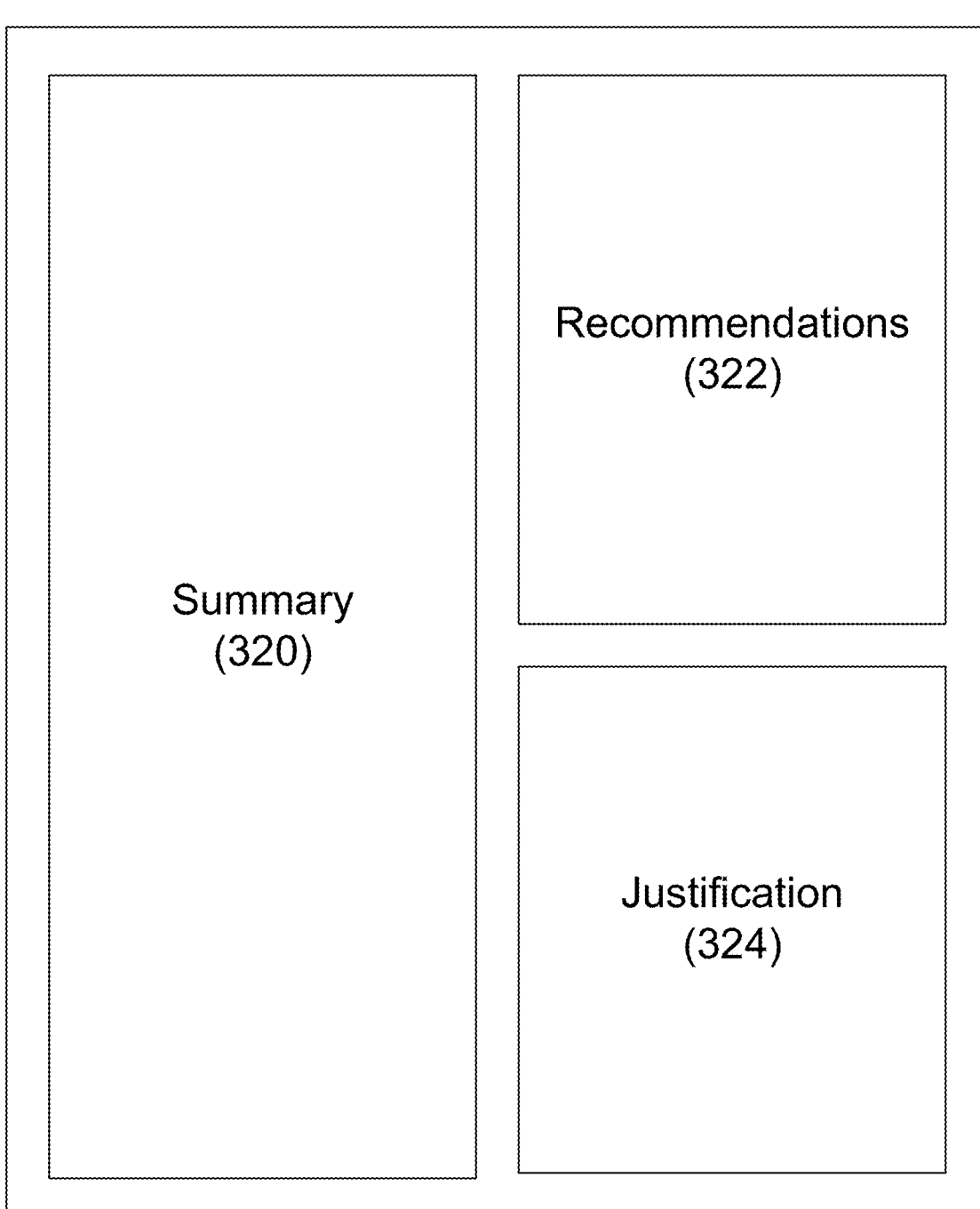
FIG. 26B is a diagrammatic view of a report rendered by the information process of FIG. 1 according to an embodiment of the present disclosure.

Referring also to FIG. 26A-26B, information process 10 may monitor 2500 a plurality of data signals (e.g., data signals 200 and/or data signals 204) associated with a plurality of patients (e.g., patient 232) within a medical environment (e.g., hospital 246 . . . or a portion thereof).

As discussed above, examples of this plurality of data signals (e.g., data signals 200 and/or data signals 204) may include but are not limited to one or more of the following:

One or more data signals (e.g., data signals 200 and/or data signals 204) associated with a medical device (e.g., first vendor device 202, second vendor device 204) utilized on a patient (e.g., patient 232) within the medical environment (e.g., hospital 246 . . . or a portion thereof). For example, medical devices may monitor patient 232 and provide the data signals (e.g., data signals 200 and/or data signals 204) to information process 10. These data signals (e.g., data signals 200 and/or data signals 204) may generally concern one or more details of the medical device (e.g., first vendor device 202, second vendor device 204) and/or uses of the medical device (e.g., first vendor device 202, second vendor device 204), examples of which may include:

17. Device Details: One or more details of the medical device (e.g., one or more of first vendor devices 202 and/or one or more of second vendor devices 206) may concern one or more readings, signals and/or alarms provided by the device.

18. Device Uses: One or more uses of the medical device (e.g., one or more of first vendor devices 202 and/or one or more of second vendor devices 206) may concern the manner in which the device is being used (e.g., what is the device doing, what is the device being used for, who is the device assigned/connected to, etc.).

One or more data signals (e.g., data signals 200 and/or data signals 204) associated with drugs administered to the patient (e.g., patient 232) within the medical environment (e.g., hospital 246 . . . or a portion thereof). For example, the drug administration history of patient 232 may be digitized and provided to information process 10 as the data signals (e.g., data signals 200 and/or data signals 204).

One or more data signals (e.g., data signals 200 and/or data signals 204) associated with lab work performed on the patient (e.g., patient 232) within the medical environment (e.g., hospital 246 . . . or a portion thereof). For example, the lab history of patient 232 may be digitized and provided to information process 10 as the data signals (e.g., data signals 200 and/or data signals 204).

One or more data signals (e.g., data signals 200 and/or data signals 204) associated with clinical assessments performed on the patient (e.g., patient 232) within the medical environment (e.g., hospital 246 . . . or a portion thereof). For example, the clinical assessment history of patient 232 may be digitized and provided to information process 10 as the data signals (e.g., data signals 200 and/or data signals 204).

One or more data signals (e.g., data signals 200 and/or data signals 204) associated with clinical procedures performed on the patient (e.g., patient 232) within the medical environment (e.g., hospital 246 . . . or a portion thereof). For example, the clinical procedure history of patient 232 may be digitized and provided to information process 10 as the data signals (e.g., data signals 200 and/or data signals 204).

One or more data signals (e.g., data signals 200 and/or data signals 204) associated with electronic health records and/or electronic medical records of the patient (e.g., patient 232) within the medical environment (e.g., hospital 246 . . . or a portion thereof). For example, the electronic health records and/or electronic medical records of patient 232 may be provided to information process 10 as the data signals (e.g., data signals 200 and/or data signals 204).

One or more data signals (e.g., data signals 200 and/or data signals 204) associated with a medical history of the patient (e.g., patient 232) within the medical environment (e.g., hospital 246 . . . or a portion thereof). For example, the medical history of patient 232 may be digitized and provided to information process 10 as the data signals (e.g., data signals 200 and/or data signals 204).

As discussed above, these medical devices (e.g., first vendor device 202, second vendor device 204) may include one or more sub-medical devices. For example, it is foreseeable that e.g., a blood pressure monitoring system may have one or more sub-systems (e.g., a wirelessly coupled blood pressure monitoring cuff).

Information process 10 may process 2502 the plurality of data signals (e.g., data signals 200 and/or data signals 204) to determine if one or more of the plurality of patients (e.g., patient 232) is experiencing an urgent care event.

As discussed above, an urgent care event in a medical environment refers to a situation in which a patient requires immediate medical attention to prevent further complications, patient health deterioration and/or death. Examples of such urgent care events may include but are not limited to: a rapid change in heart rate, a rapid change in blood pressure, deterioration of respiratory function, deterioration of renal function, a drop of blood oxygen levels, a change in heart rhythm, etc.

When processing 2502 the plurality of data signals (e.g., data signals 200 and/or data signals 204) to determine if one or more of the plurality of patients (e.g., patient 232) is experiencing an urgent care event, information process 10 may detect 2504 one or more incidents (e.g., incidents 272, 282, 284) defined within the plurality of data signals (e.g., data signals 200 and/or data signals 204). As discussed above, an incident may include the occurrence of one or more alarms (e.g., alarms 274, 276, 278).

Accordingly and when detecting 2504 one or more incidents (e.g., incidents 272, 282, 284) defined within the plurality of data signals (e.g., data signals 200 and/or data signals 204), information process 10 may monitor 2506 one or more data signals (e.g., data signals 200 and/or data signals 204) associated with a medical device (e.g., first vendor device 202, second vendor device 204) utilized on a patient (e.g., patient 232) within the medical environment (e.g., hospital 246 . . . or a portion thereof) to detect the occurrence of the one or more alarms (e.g., alarms 274, 276, 278).

When processing 2502 the plurality of data signals (e.g., data signals 200 and/or data signals 204) to determine if one or more of the plurality of patients (e.g., patient 232) is experiencing an urgent care event, information process 10 may utilize 2508 massive data sets processed by ML to process the plurality of data signals (e.g., data signals 200 and/or data signals 204) to determine if one or more of the plurality of patients (e.g., patient 232) is experiencing an urgent care event.

As discussed above, a massive dataset, also referred to as a large-scale dataset or big dataset, is a collection of data that is exceptionally large in size and complexity. These datasets typically exceed the capacity of traditional data processing and analysis tools, requiring specialized approaches and infrastructure to handle and extract insights from them effectively.

If such an urgent care event is occurring, information process 10 may generate 2510 an urgent care report (e.g., report 318) for the one or more patients (e.g., patient 232). As shown in FIG. 26B, the urgent care report (e.g., report 318) may include one or more of: a summary (e.g., summary 320) of the urgent care event of the one or more patients (e.g., patient 232), a justification (e.g., justification 322) as to why this is an urgent care event for the one or more patients (e.g., patient 232), and a recommendation (e.g., recommendation 324) for addressing the urgent care event of the one or more patients (e.g., patient 232).

Summary:

Summary 320 may be a concise and detailed account of the condition of the one or more patients (e.g., patient 232) and the medical attention they received. This summary typically includes the patient's symptoms/condition, the initial assessment and diagnosis, any tests or procedures performed, any treatments administered, and the patient's response to those treatments.

Recommendation:

Recommendation 322 may outline the suggested next steps for the patient's care with respect to addressing the urgent care event. This recommendation may include specific instructions for actions, such as appropriate urgent care, triage suggestions, diagnostic tests recommended, and/or starting or adjusting medications.

Justification:

Justification 324 may provide the reasoning and clinical rationale behind the medical decisions and recommendations concerning the one or more patients (e.g., patient 232). This section may explain why certain tests were ordered, why actions were suggested, why medications were recommended, why tests were suggested, etc. This justification may help ensure that all actions taken are medically appropriate and based on sound clinical judgment.

When generating 2510 an urgent care report (e.g., report 266) for the one or more patients (e.g., patient 232), information process 10 may utilize 2512 a generative AI model to generate the urgent care report (e.g., report 266) for the one or more patients (e.g., patient 232).

As discussed above, generative AI refers to artificial intelligence systems that create new content, such as text, images, audio, or video, based on patterns and data they have been trained on. In the medical space, generative AI can be a transformative tool for generating content like summaries and reports concerning a patient's condition.

When utilizing 2512 a generative AI model to generate the urgent care report (e.g., report 266) for the one or more patients (e.g., patient 232), information process 10 may utilize 2514 prompt engineering and the generative AI model to generate the rounding list that prioritizes the plurality of patients (e.g., patient 232).

As discussed above, prompt engineering is the practice of designing and crafting prompts to guide generative AI models in producing specific and desired outputs. By carefully formulating prompts, users can influence the AI to generate more accurate, relevant, and high-quality content tailored to their needs. This involves providing clear and detailed instructions, setting the context, and sometimes using templates or examples to guide the AI in following a specific structure or format.

Operations Management Report Generation:

The following discussion concerns the manner in which information process 10 may calculate an operations management score for all or a portion of a medical facility. The operations management score may be provided to a user, wherein the score is justified/explained.

Figure 27A:
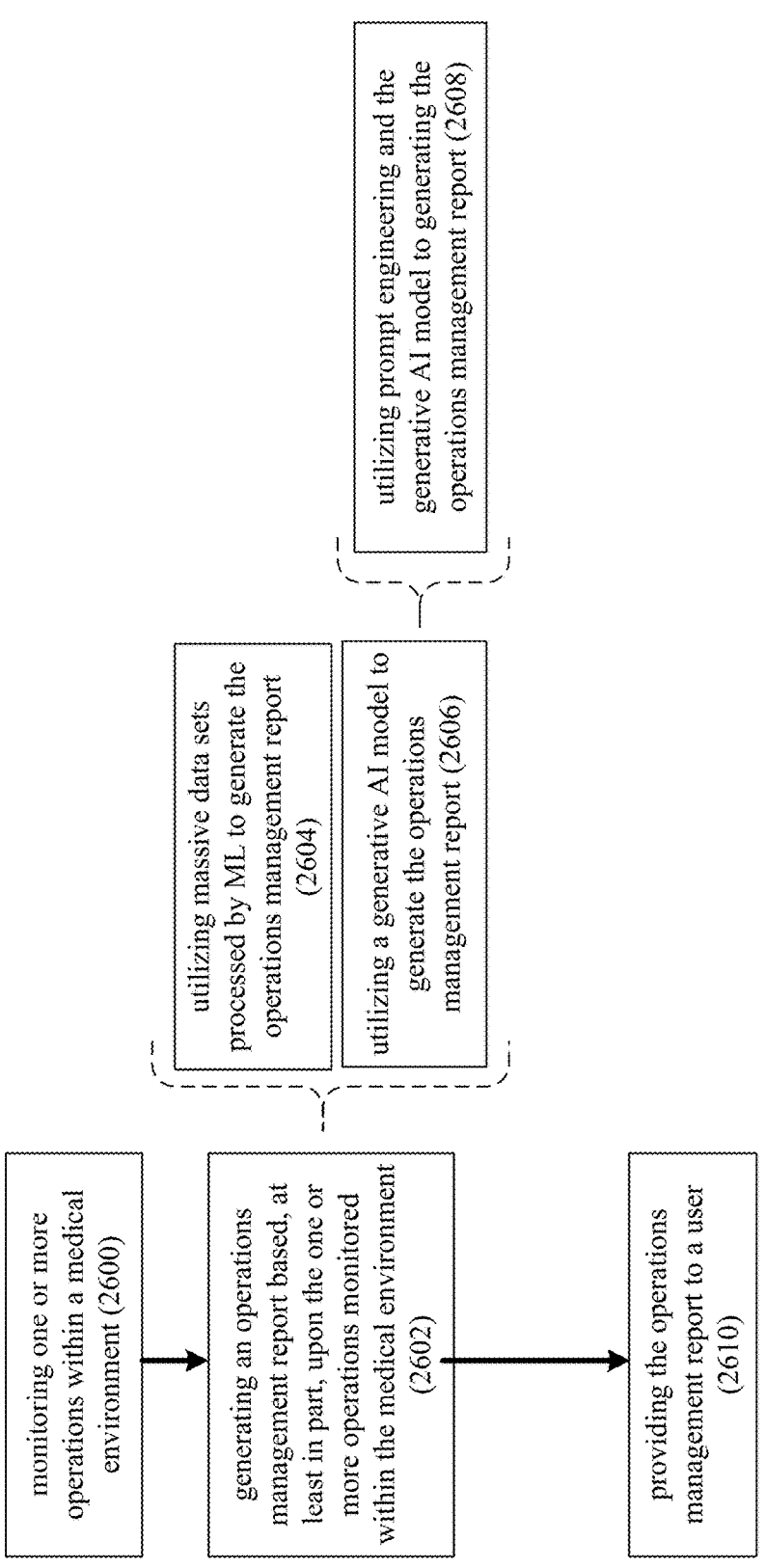
FIG. 27A is another flowchart of the information process of FIG. 1 according to an embodiment of the present disclosure.
Figure 27B:
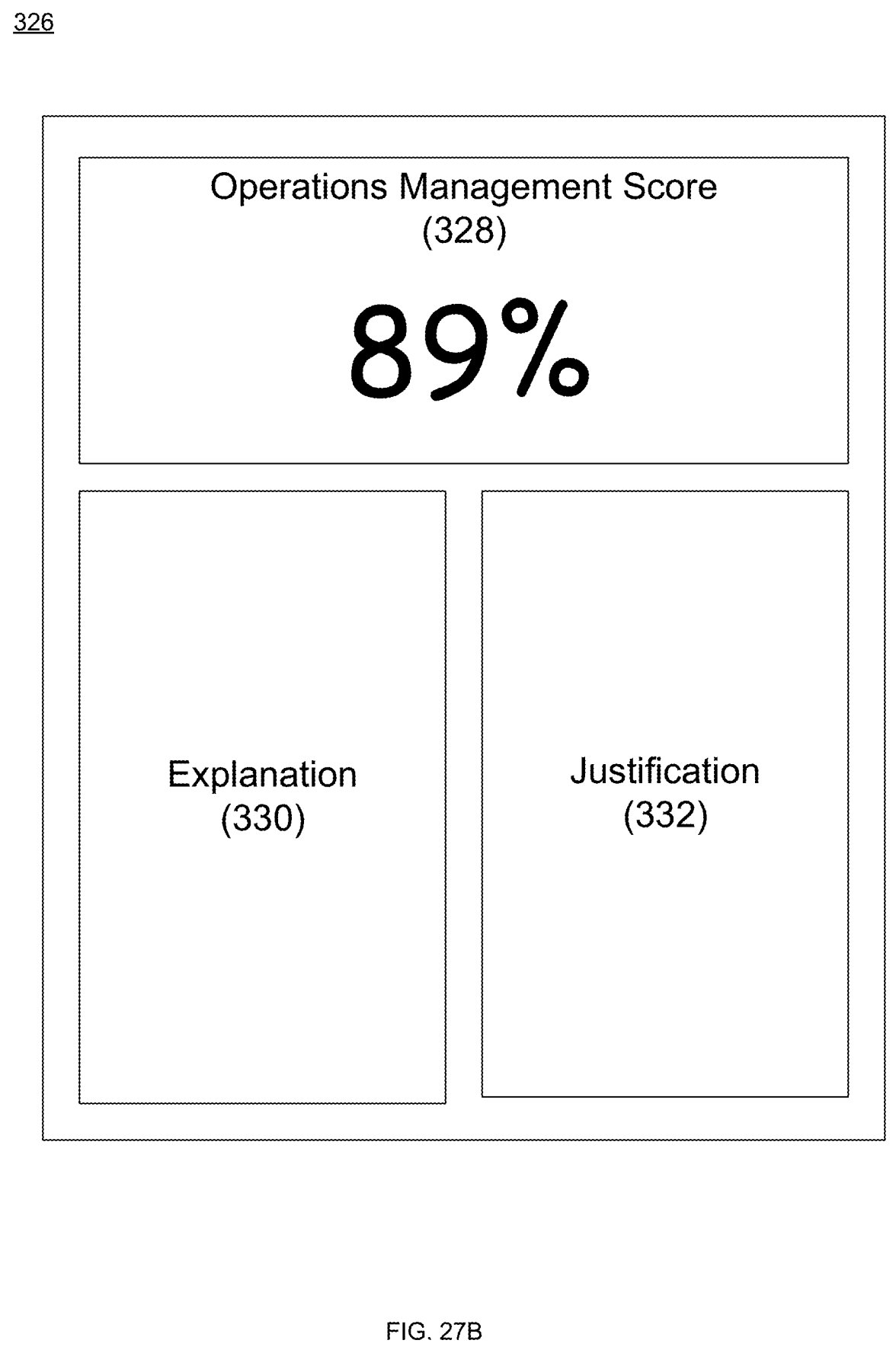

Referring also to FIGS. 27A-27B, information process 10 may monitor 2600 one or more operations within a medical environment (e.g., hospital 246 . . . or a portion thereof). When information process 10 is monitoring 2600 such operations within the medical environment (e.g., hospital 246 . . . or a portion thereof), the process of monitoring may occur automatically or manually. For example, it is foreseeable that some of the metrics that are utilized when monitoring the operations within the medical environment (e.g., hospital 246 . . . or a portion thereof) may be digital and, therefore, may be readily obtainable via one or more computing devices (not shown) coupled to network 14. Additionally/alternatively, it is foreseeable that some of the metrics that are utilized when monitoring the operations within the medical environment (e.g., hospital 246 . . . or a portion thereof) may be human defined and, therefore, may be manually entered into one or more computing devices (not shown) coupled to network 14.

Information process 10 may generate 2602 an operations management report (e.g., report 326) based, at least in part, upon the one or more operations monitored within the medical environment (e.g., hospital 246 . . . or a portion thereof).

For example and when generating 2602 an operations management report (e.g., report 326), information process 10 may utilize 2604 massive data sets processed by ML to generate the operations management report (e.g., report 326).

As discussed above, a massive dataset, also referred to as a large-scale dataset or big dataset, is a collection of data that is exceptionally large in size and complexity. These datasets typically exceed the capacity of traditional data processing and analysis tools, requiring specialized approaches and infrastructure to handle and extract insights from them effectively.

Further and when generating 2602 an operations management report (e.g., report 326), information process 10 may utilize 2606 a generative AI model to generate the operations management report (e.g., report 326).

As discussed above, generative AI refers to artificial intelligence systems that create new content, such as text, images, audio, or video, based on patterns and data they have been trained on. In the medical space, generative AI can be a transformative tool for generating content like summaries and reports concerning a patient's condition.

Additionally and when utilizing 2606 a generative AI model to generating the operations management report (e.g., report 326), information process 10 may utilize 2608 prompt engineering and the generative AI model to generate the operations management report (e.g., report 326).

As discussed above, prompt engineering is the practice of designing and crafting prompts to guide generative AI models in producing specific and desired outputs. By carefully formulating prompts, users can influence the AI to generate more accurate, relevant, and high-quality content tailored to their needs. This involves providing clear and detailed instructions, setting the context, and sometimes using templates or examples to guide the AI in following a specific structure or format.

The operations management report (e.g., report 326) may be based, at least in part, upon a patient acuity score.

A patient acuity score is a numerical measure that quantifies the severity of a patient's condition and the level of care they require. Derived from various clinical data points such as vital signs, lab results, and clinical assessments, this score helps healthcare providers prioritize patient care and allocate resources effectively. For example, higher acuity scores indicate more severe conditions that necessitate urgent medical attention. Systems like the Early Warning Score (EWS) use parameters such as heart rate, blood pressure, respiratory rate, and level of consciousness to calculate the score. Each parameter is scored based on its deviation from normal ranges, and the total score is the sum of these individual scores. In hospital settings, patient acuity scores are crucial for managing patient flow and ensuring optimal use of healthcare resources. In emergency departments, these scores aid in triaging patients, determining who needs immediate care versus those who can wait, thereby preventing overcrowding and ensuring critical patients are seen promptly. In intensive care units, acuity scores assist in monitoring patients' progress and adjusting care plans as needed, enabling proactive measures to prevent adverse outcomes. Acuity scores also play a vital role in nursing care planning by determining staffing levels based on the aggregate acuity of patients, ensuring balanced workloads and adequate patient attention. Beyond individual patient management, these scores provide data for quality assurance and performance evaluation, helping hospitals identify trends, measure outcomes, and implement evidence-based practices. Additionally, they contribute to research and policy-making by offering insights into patient populations, disease prevalence, and healthcare utilization patterns. Overall, patient acuity scores enhance clinical decision-making, optimize resource use, support nursing care planning, and contribute to quality improvement and research, ensuring patients receive the appropriate level of care at the right time.

The operations management report (e.g., report 326) may be based, at least in part, upon a caregiver proficiency score.

A caregiver proficiency score is a numerical measure that assesses the skills, competency, and performance of healthcare providers, including nurses, doctors, and other medical staff. This score is derived from various metrics such as clinical knowledge, technical skills, patient interaction, adherence to protocols, and overall effectiveness in delivering care. By evaluating these factors, the proficiency score helps healthcare institutions ensure that their staff meets the required standards of care and can effectively respond to patient needs. In practice, caregiver proficiency scores are calculated using a combination of objective data, such as patient outcomes and adherence to treatment guidelines, and subjective assessments, including peer reviews, patient feedback, and supervisor evaluations. For instance, a nurse's proficiency score might consider their ability to perform medical procedures accurately, communicate effectively with patients and families, and maintain up-to-date knowledge of best practices and protocols. These scores are crucial in several aspects of healthcare management. First, they aid in identifying areas where caregivers excel and areas needing improvement, guiding targeted training and professional development initiatives. High proficiency scores indicate a caregiver's readiness to handle complex cases and contribute positively to patient outcomes, while lower scores can highlight the need for additional support or training. Additionally, caregiver proficiency scores play a significant role in staffing decisions and workload distribution. By understanding the proficiency levels of their staff, healthcare managers can ensure that more experienced and skilled caregivers are assigned to patients with higher acuity levels, thereby optimizing patient care and safety. Furthermore, these scores contribute to performance evaluations and career advancement opportunities, rewarding high-performing caregivers and motivating continuous improvement.

The operations management report (e.g., report 326) may be based, at least in part, upon a caregiver employee attrition risk score.

A caregiver employee attrition risk score is a numerical measure used to predict the likelihood of healthcare staff, such as nurses, doctors, and other medical professionals, leaving their positions within an organization. This score is derived from various data points, including job satisfaction surveys, attendance records, performance evaluations, workload, tenure, engagement levels, and even personal circumstances. By analyzing these factors, healthcare institutions can identify employees at higher risk of attrition and implement strategies to retain valuable staff. In practice, attrition risk scores are calculated using predictive analytics and machine learning algorithms that assess the correlation between historical data and actual employee turnover. For instance, frequent absences, low job satisfaction ratings, and poor performance reviews are indicators that might contribute to a higher attrition risk score. Additionally, factors such as inadequate career growth opportunities, high stress levels, and work-life balance challenges can also elevate the risk. These scores are crucial for healthcare management as they provide actionable insights into workforce stability. By identifying employees at high risk of leaving, organizations can take proactive measures such as offering targeted support, career development programs, mentoring, and improved working conditions to address the underlying issues. This proactive approach helps reduce turnover rates, ensuring continuity of care and maintaining a stable, experienced workforce. Furthermore, understanding attrition risk scores allows healthcare institutions to plan better for staffing needs and allocate resources effectively. High attrition rates can lead to increased recruitment and training costs, as well as potential disruptions in patient care. By mitigating these risks, organizations can maintain higher levels of employee engagement, job satisfaction, and overall morale.

The operations management report (e.g., report 326) may be based, at least in part, upon a unit/facility operational efficiency score.

A medical unit or facility operational efficiency score is a numerical measure that evaluates the effectiveness and efficiency of healthcare operations within a specific medical unit or facility. This score is derived from a variety of performance metrics, including patient throughput, resource utilization, staff productivity, wait times, patient satisfaction, adherence to clinical guidelines, and financial performance. By assessing these factors, the operational efficiency score provides a comprehensive overview of how well a medical unit or facility is functioning. In practice, operational efficiency scores are calculated using data analytics tools that aggregate and analyze information from multiple sources. For example, patient throughput data might include the number of patients seen, average length of stay, and bed occupancy rates, while resource utilization metrics could assess the use of medical supplies, equipment, and staffing levels. Staff productivity measures might look at the ratio of patient care hours to administrative tasks, and patient satisfaction scores can be derived from surveys and feedback forms. Financial performance metrics might include cost per patient visit and revenue generation. These scores are critical for healthcare management as they help identify areas where operations can be improved. A high operational efficiency score indicates that a medical unit or facility is running smoothly, with optimal use of resources, timely patient care, and high levels of patient and staff satisfaction. Conversely, a low score highlights inefficiencies that may need to be addressed, such as long wait times, underutilized resources, or high operational costs. Understanding and improving operational efficiency scores enable healthcare facilities to enhance patient care, reduce waste, and lower costs. For instance, identifying bottlenecks in patient flow can lead to process improvements that shorten wait times and increase patient satisfaction. Similarly, optimizing resource allocation ensures that staff and equipment are used effectively, which can improve overall productivity and financial health.

The operations management report (e.g., report 326) may be based, at least in part, upon a benchmarking score.

A medical benchmarking score is a numerical measure used to evaluate and compare the performance of a healthcare provider, unit, or facility against established standards or best practices within the industry. This score is derived from a comprehensive analysis of various performance metrics, including clinical outcomes, patient safety, service efficiency, patient satisfaction, and financial health. By aggregating and analyzing these data points, a medical benchmarking score provides a clear and objective assessment of how well a healthcare entity performs relative to its peers. The calculation of a medical benchmarking score involves collecting data from multiple sources such as electronic health records, patient surveys, financial reports, and operational databases. Key performance indicators (KPIs) like mortality rates, readmission rates, infection rates, patient wait times, and treatment costs are often used. These metrics are then compared against industry benchmarks, which may be derived from national averages, top-performing institutions, or regulatory standards. Medical benchmarking scores are crucial for healthcare management as they highlight strengths and pinpoint areas needing improvement. A high benchmarking score signifies that the healthcare provider or facility is performing well across various metrics, meeting or exceeding industry standards. This can enhance the institution's reputation, attract more patients, and ensure higher quality care. Conversely, a low score can indicate deficiencies that require strategic interventions, such as staff training, process optimization, or investment in new technologies. Additionally, benchmarking scores facilitate continuous quality improvement by enabling healthcare providers to set realistic goals, track progress, and implement best practices from top-performing peers. They also support transparency and accountability by providing stakeholders, including patients, regulators, and insurers, with an objective measure of performance. By striving to improve their benchmarking scores, healthcare entities can achieve better patient outcomes, operational efficiencies, and financial stability, ultimately contributing to the overall improvement of the healthcare system.

Information process 10 may provide 2610 the operations management report (e.g., report 326) to a user (e.g., user 236). As shown in FIG. 27B, the operations management report (e.g., report 326) may include one or more of: an operations management score (e.g., operations management score 328), an explanation of the operations management score (e.g., explanation 330), and a justification for the operations management score (e.g., justification 332).

Operations Management Score:

Operations management score 328 is a quantitative measure used to evaluate the efficiency, effectiveness, and overall performance of a healthcare facility's operations. This score encompasses various aspects of hospital or clinic management, including patient flow, resource utilization, staff productivity, financial performance, and quality of care provided. By assessing these dimensions, the operations management score aims to provide a comprehensive overview of how well a medical facility is managed and identify areas for improvement.

Explanation:

Explanation 330 may explain the manner in which the operations management score is derived/calculated. The operations management score may be derived from a combination of key performance indicators (KPIs) and metrics that reflect different facets of a healthcare facility's operations. These indicators may include patient wait times, bed occupancy rates, average length of stay, staff-to-patient ratios, compliance with safety protocols, and patient satisfaction scores. Financial metrics such as cost per patient, revenue cycle efficiency, and budget adherence are also integral to the score. The data may be collected through various means, including electronic health records (EHRs), patient surveys, and financial reports, and then analyzed to produce the operations management score. This score may provide a snapshot of the facility's operational health, enabling administrators to make informed decisions and implement strategies for improvement.

Justification:

Justification 332 may provide actionable insights into the functioning of a medical facility. By consolidating multiple performance indicators into a single metric, it allows for a holistic assessment of operational efficiency and effectiveness. This score helps identify strengths and weaknesses in different areas, such as patient care processes, resource allocation, and financial management. For instance, if the score reveals prolonged patient wait times, administrators can investigate and address underlying issues such as staffing shortages or inefficient scheduling practices. Additionally, the operations management score can serve as a benchmark, enabling comparisons with industry standards or peer institutions, which can drive improvements and enhance overall healthcare quality.

The user (e.g., user 236) to which the operations management report (e.g., report 326) is provided 2610: may include one or more of: a manager of the medical environment (e.g., hospital 246 . . . or a portion thereof); a supervisor of the medical environment (e.g., hospital 246 . . . or a portion thereof); and an owner of the medical environment (e.g., hospital 246 . . . or a portion thereof).

A manager of the medical environment is a professional responsible for overseeing the day-to-day operations of a healthcare facility or department. Their role involves coordinating staff activities, ensuring compliance with healthcare regulations, managing budgets, and maintaining high standards of patient care. Managers in the medical environment play a crucial role in strategic planning and decision-making, implementing policies and procedures, and improving operational efficiency. They also act as a liaison between the healthcare staff and upper management, ensuring that communication flows smoothly and that the facility's goals and objectives are met. By effectively managing resources, addressing challenges, and fostering a positive work environment, they contribute significantly to the overall functioning and success of the medical facility.

A supervisor of the medical environment typically operates at a more granular level, directly overseeing the performance of a specific team or department within the healthcare facility. Supervisors ensure that staff members adhere to established protocols and standards, provide guidance and support, and address any issues that arise during their shifts. Their responsibilities include conducting performance evaluations, organizing staff schedules, and facilitating ongoing training and professional development. Supervisors play a key role in maintaining the quality of patient care by monitoring clinical activities and ensuring that all procedures are performed correctly and safely. Their hands-on approach allows them to promptly address any concerns and support their team in delivering effective and efficient care.

An owner of the medical environment holds the ultimate authority and responsibility for the healthcare facility. Whether an individual or a corporate entity, the owner is concerned with the overarching strategic direction, financial health, and long-term sustainability of the medical institution. Owners are typically involved in high-level decision-making processes, such as expansions, major investments, and partnerships. They may not be involved in the daily operations but will set the vision and goals for the facility, ensuring that it aligns with broader business objectives and market demands. Owners also bear the financial risks and rewards associated with the facility, making critical decisions that impact the institution's growth, reputation, and ability to provide quality healthcare services. Their leadership and investment are vital for the facility's development and success in a competitive healthcare landscape.

General

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a standalone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:

monitoring a plurality of data signals associated with a plurality of patients within a medical environment over a defined period of time, wherein the plurality of data signals include at least a first data signal from a first vendor device and a second data signal from a second vendor device;

normalizing the plurality of data signals to generate a plurality of homogenized signals so that the plurality of data signals can work together;

calculating an acuity score for each of the plurality of patients, wherein the acuity score defines the overall care needs of each of the plurality of patients, wherein calculating the acuity score includes defining one or more bespoke signal norms for one or more of the plurality of patients and comparing one or more of the plurality of data signals with the bespoke signal norms for the one or more of the plurality of patients;

generating a rounding list that prioritizes the plurality of patients based, at least in part, upon the acuity scores;

detecting one or more incidents defined within one or more of the plurality of data signals associated with the plurality of patients; and processing the one or more incidents defined within one or more of the plurality of data signals associated with the plurality of patients using a generative AI model to produce one or more recommendations.

2. The computer-implemented method of claim 1 wherein the defined period of time includes one or more of:

a shift within the medical environment;

a plurality of shifts within the medical environment; and a history of the one or more patients within the medical environment.

3. The computer-implemented method of claim 1 wherein the plurality of patients includes one or more of:

a plurality of patients assigned to an on-call nurse;

a plurality of patients assigned to an on-call manager; and a plurality of patients assigned to an on-call physician.

4. The computer-implemented method of claim 1 further comprising:

recalculating the acuity score for each of the plurality of patients, thus defining a plurality of updated acuity scores; and updating the rounding list based, at least in part, upon the updated acuity scores.

5. The computer-implemented method of claim 1 wherein calculating an acuity score for each of the plurality of patients includes:

utilizing massive data sets processed by ML to calculate the acuity score for each of the plurality of patients.

6. The computer-implemented method of claim 1 wherein generating a rounding list that prioritizes the plurality of patients includes:

utilizing a generative AI model to generate the rounding list that prioritizes the plurality of patients.

7. The computer-implemented method of claim 6 wherein utilizing a generative AI model to generate the rounding list that prioritizes the plurality of patients includes:

utilizing prompt engineering and the generative AI model to generate the rounding list that prioritizes the plurality of patients.

8. The computer-implemented method of claim 1 wherein the plurality of data signals include one or more of:

one or more data signals associated with a medical device utilized on a patient within the medical environment;

one or more data signals associated with drugs administered to the patient within the medical environment;

one or more data signals associated with lab work performed on the patient within the medical environment;

one or more data signals associated with clinical assessments performed on the patient within the medical environment;

one or more data signals associated with clinical procedures performed on the patient within the medical environment;

one or more data signals associated with electronic health records and/or electronic medical records of the patient within the medical environment; and one or more data signals associated with a medical history of the patient within the medical environment.

9. The computer-implemented method of claim 8 wherein the one or more data signals associated with a medical device utilized on a patient within the medical environment concern one or more details of the medical device and/or uses of the medical device.

10. The computer-implemented method of claim 8 wherein the medical device includes one or more sub-medical devices.

11. A computer program product residing on a computer readable medium having a plurality of instructions stored thereon which, when executed by a processor, cause the processor to perform operations comprising:

monitoring a plurality of data signals associated with a plurality of patients within a medical environment over a defined period of time, wherein the plurality of data signals include at least a first data signal from a first vendor device and a second data signal from a second vendor device;

normalizing the plurality of data signals to generate a plurality of homogenized signals so that the plurality of data signals can work together;

calculating an acuity score for each of the plurality of patients, wherein the acuity score defines the overall care needs of each of the plurality of patients, wherein calculating the acuity score includes defining one or more bespoke signal norms for one or more of the plurality of patients and comparing one or more of the plurality of data signals with the bespoke signal norms for the one or more of the plurality of patients;

generating a rounding list that prioritizes the plurality of patients based, at least in part, upon the acuity scores;

detecting one or more incidents defined within one or more of the plurality of data signals associated with the plurality of patients; and processing the one or more incidents defined within one or more of the plurality of data signals associated with the plurality of patients using a generative AI model to produce one or more recommendations.

12. The computer program product of claim 11 wherein the defined period of time includes one or more of:

a shift within the medical environment;

a plurality of shifts within the medical environment; and a history of the one or more patients within the medical environment.

13. The computer program product of claim 11 wherein the plurality of patients includes one or more of:

a plurality of patients assigned to an on-call nurse;

a plurality of patients assigned to an on-call manager; and a plurality of patients assigned to an on-call physician.

14. The computer program product of claim 11 further comprising:

recalculating the acuity score for each of the plurality of patients, thus defining a plurality of updated acuity scores; and updating the rounding list based, at least in part, upon the updated acuity scores.

15. The computer program product of claim 11 wherein calculating an acuity score for each of the plurality of patients includes:

utilizing massive data sets processed by ML to calculate the acuity score for each of the plurality of patients.

16. The computer program product of claim 11 wherein generating a rounding list that prioritizes the plurality of patients includes:

utilizing a generative AI model to generate the rounding list that prioritizes the plurality of patients.

17. The computer program product of claim 16 wherein utilizing a generative AI model to generate the rounding list that prioritizes the plurality of patients includes:

utilizing prompt engineering and the generative AI model to generate the rounding list that prioritizes the plurality of patients.

18. The computer program product of claim 11 wherein the plurality of data signals include one or more of:

one or more data signals associated with a medical device utilized on a patient within the medical environment;

one or more data signals associated with drugs administered to the patient within the medical environment;

one or more data signals associated with lab work performed on the patient within the medical environment;

one or more data signals associated with clinical assessments performed on the patient within the medical environment;

one or more data signals associated with clinical procedures performed on the patient within the medical environment;

one or more data signals associated with electronic health records and/or electronic medical records of the patient within the medical environment; and one or more data signals associated with a medical history of the patient within the medical environment.

19. The computer program product of claim 18 wherein the one or more data signals associated with a medical device utilized on a patient within the medical environment concern one or more details of the medical device and/or uses of the medical device.

20. The computer program product of claim 18 wherein the medical device includes one or more sub-medical devices.

21. A computing system including a processor and memory configured to perform operations comprising:

monitoring a plurality of data signals associated with a plurality of patients within a medical environment over a defined period of time, wherein the plurality of data signals include at least a first data signal from a first vendor device and a second data signal from a second vendor device;

normalizing the plurality of data signals to generate a plurality of homogenized signals so that the plurality of data signals can work together;

calculating an acuity score for each of the plurality of patients, wherein the acuity score defines the overall care needs of each of the plurality of patients, wherein calculating the acuity score includes defining one or more bespoke signal norms for one or more of the plurality of patients and comparing one or more of the plurality of data signals with the bespoke signal norms for the one or more of the plurality of patients;

generating a rounding list that prioritizes the plurality of patients based, at least in part, upon the acuity scores;

detecting one or more incidents defined within one or more of the plurality of data signals associated with the plurality of patients; and processing the one or more incidents defined within one or more of the plurality of data signals associated with the plurality of patients using a generative AI model to produce one or more recommendations.

22. The computing system of claim 21 wherein the defined period of time includes one or more of:

a shift within the medical environment;

a plurality of shifts within the medical environment; and a history of the one or more patients within the medical environment.

23. The computing system of claim 21 wherein the plurality of patients includes one or more of:

a plurality of patients assigned to an on-call nurse;

a plurality of patients assigned to an on-call manager; and a plurality of patients assigned to an on-call physician.

24. The computing system of claim 21 further comprising:

recalculating the acuity score for each of the plurality of patients, thus defining a plurality of updated acuity scores; and updating the rounding list based, at least in part, upon the updated acuity scores.

25. The computing system of claim 21 wherein calculating an acuity score for each of the plurality of patients includes:

utilizing massive data sets processed by ML to calculate the acuity score for each of the plurality of patients.

26. The computing system of claim 21 wherein generating a rounding list that prioritizes the plurality of patients includes:

utilizing a generative AI model to generate the rounding list that prioritizes the plurality of patients.

27. The computing system of claim 26 wherein utilizing a generative AI model to generate the rounding list that prioritizes the plurality of patients includes:

utilizing prompt engineering and the generative AI model to generate the rounding list that prioritizes the plurality of patients.

28. The computing system of claim 21 wherein the plurality of data signals include one or more of:

one or more data signals associated with a medical device utilized on a patient within the medical environment;

one or more data signals associated with drugs administered to the patient within the medical environment;

one or more data signals associated with lab work performed on the patient within the medical environment;

one or more data signals associated with clinical assessments performed on the patient within the medical environment;

one or more data signals associated with clinical procedures performed on the patient within the medical environment;

one or more data signals associated with electronic health records and/or electronic medical records of the patient within the medical environment; and one or more data signals associated with a medical history of the patient within the medical environment.

29. The computing system of claim 28 wherein the one or more data signals associated with a medical device utilized on a patient within the medical environment concern one or more details of the medical device and/or uses of the medical device.

30. The computing system of claim 28 wherein the medical device includes one or more sub-medical devices.

* * * * *